(12) United States Patent
Liao

(10) Patent No.: US 11,999,725 B2
(45) Date of Patent: Jun. 4, 2024

(54) HPK1 INHIBITORS, PREPARATION METHOD AND APPLICATION THEREOF

(71) Applicant: ZHUHAI YUFAN BIOTECHNOLOGIES CO., LTD, Guangdong (CN)

(72) Inventor: Xuebin Liao, Beijing (CN)

(73) Assignee: ZHUHAI YUFAN BIOTECHNOLOGIES CO., LTD., Guangdong (CN)

( * ) Notice: Subject to any disclaimer, the term of this patent is extended or adjusted under 35 U.S.C. 154(b) by 718 days.

(21) Appl. No.: 17/049,380

(22) PCT Filed: Apr. 19, 2019

(86) PCT No.: PCT/CN2019/083499
§ 371 (c)(1),
(2) Date: Oct. 21, 2020

(87) PCT Pub. No.: WO2019/206049
PCT Pub. Date: Oct. 31, 2019

(65) Prior Publication Data
US 2021/0276994 A1 Sep. 9, 2021

(30) Foreign Application Priority Data

| Apr. 25, 2018 | (CN) | 201810381425.X |
| Aug. 20, 2018 | (CN) | 201810945948.2 |
| Aug. 20, 2018 | (CN) | 201810946081.2 |

(51) Int. Cl.
| C07D 417/14 | (2006.01) |
| A61K 45/06 | (2006.01) |
| C07D 401/14 | (2006.01) |
| C07D 405/14 | (2006.01) |
| C07D 413/14 | (2006.01) |
| C07D 417/04 | (2006.01) |

(52) U.S. Cl.
CPC ............ C07D 417/14 (2013.01); A61K 45/06 (2013.01); C07D 401/14 (2013.01); C07D 405/14 (2013.01); C07D 413/14 (2013.01); C07D 417/04 (2013.01)

(58) Field of Classification Search
CPC .. C07D 417/14; C07D 401/14; C07D 405/14; C07D 413/14; C07D 417/04; A61K 45/06
USPC ........................................................ 514/218
See application file for complete search history.

(56) References Cited

U.S. PATENT DOCUMENTS

| 7,230,098 B2 | 6/2007 | Cui et al. |
| 2005/0009840 A1 | 1/2005 | Cui |
| 2006/0046991 A1 | 3/2006 | Cui |
| 2006/0178374 A1 | 8/2006 | Cui |
| 2014/0288086 A1 | 9/2014 | Cui et al. |
| 2016/0158360 A1 | 6/2016 | Hernandez |

FOREIGN PATENT DOCUMENTS

| CN | 101023064 | 8/2007 | |
| CN | 103265477 | 8/2013 | |
| CN | 103965161 | 8/2014 | |
| CN | 104650049 | 5/2015 | |
| EP | 2952510 | 12/2015 | |
| JP | 2006519232 | 8/2006 | |
| JP | 2008510790 | 4/2008 | |
| JP | 2008510792 | 4/2008 | |
| JP | 2013525476 | 6/2013 | |
| JP | 2016508490 | 3/2016 | |
| WO | 2006/021886 | 3/2006 | |
| WO | 2008053157 | 5/2008 | |
| WO | WO-2008053157 A1 * | 5/2008 | ........... C07D 401/04 |
| WO | 2011/138751 | 11/2011 | |
| WO | 2011138751 | 11/2011 | |
| WO | 2016/161145 | 10/2016 | |
| WO | 2018/049152 | 3/2018 | |

OTHER PUBLICATIONS

International Search Report for PCT/CN2019/083499 dated Jul. 18, 2019, 6 pages.
Written Opinion of the ISA for PCT/CN2019/083499 dated Jul. 18, 2019, 8 pages.
May-Dracka et al., "Investigating small molecules to inhibit germinal center kinase-like kinase (GL Potential therapy to modulate T cell dependent immunity", Bioorganic & Medicinal Chemistry Letters, Mar. 26, 2018, 8 pages.
Cui, et al., "Structure Based Drug Design of Crizotinib (PF-02341066), a Potent and Selective Dual (c-MET) Kinase and Anaplastic Lymphoma Kinase (ALK)", Journal of Medicinal Chemistry, American Chemical Society, Aug. 3, 2011, vol. 54, 22 pages.
Huang, et al., "Design of Potent and Selective Inhibitors to Overcome Clinical Anaplastic Lymphoma Kinase Mutations Resistant to Crizotinib", Journal of Medicinal Chemistry, Jan. 16, 2014, vol. 57, 18 pages.
Chen, "De novo design of novel selective COX-2 inhibitors: From virtual screening to pharmacophore analysis", Journal of the Taiwanese Institute of Chemical Engineers, Jan. 2009, vol. 40, Issue 1, 15 pages.
Lee, et al.: "3D-QSAR Studies on Chemical Features of 3-(benzo[d]oxazol-2-yl)pyridine-2-amines in the External Region of c-Met Active Site", Bulletin of the Korean Chemical Society, vol. 34, No. 12, Dec. 31, 2013 XP055331232, ISSN: 0253-2964, DOI: 10.5012/bkcs.2013.34.12.3553, 6 pages.

* cited by examiner

Primary Examiner — Kahsay Habte
(74) Attorney, Agent, or Firm — NIXON & VANDERHYE, PC

(57) ABSTRACT

Disclosed are HPK-1 inhibitors having a structure represented by Formula (X), pharmaceutical compositions comprising the HPK-1 inhibitors, methods of using the HPK-1 inhibitors, such as treating cancers, methods of preparing the HPK-1 inhibitors, and the synthetic intermediates.

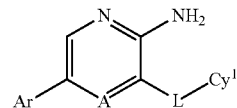

37 Claims, 1 Drawing Sheet

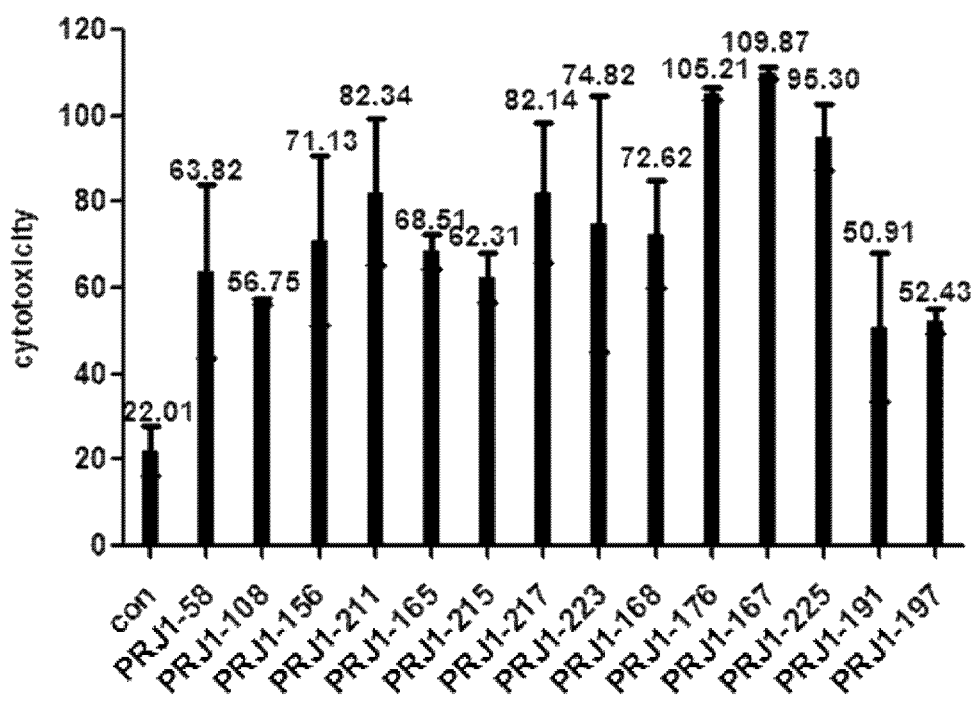

HPK1 INHIBITORS, PREPARATION METHOD AND APPLICATION THEREOF

CROSS REFERENCE TO RELATED APPLICATIONS

This application is the U.S. national phase of International Application No. PCT/CN2019/083499 filed Apr. 19, 2019 which designated the U.S. and claims priority priorities to Chinese Application Nos. 201810381425.X, filed on Apr. 25, 2018, 201810945948.2, filed on Aug. 20, 2018, and 201810946081.2, filed on Aug. 20, 2018, the content of each of which is incorporated herein by reference in its entirety.

TECHNICAL FIELD

The invention belongs to the technical field of medicine science, and particularly relates to HPK1 inhibitors and preparation method thereof.

BACKGROUND

Hematopoietic progenitor kinase 1 (HPK1) is involved in many signaling cascades, including growth factor signaling, MAPK signaling, cytokine signaling, apoptotic signaling, and antigen receptor signaling. HPK1 is a key functional activating factor of the JNK/SAPK signaling pathway. When activated, it selectively activates the MAPK signaling pathway of C-Jun N-terminal kinase (JNK).

HPK1, as a possible target for immunotherapy, which is activated by lymphocyte antigen receptors and inhibits AP-1, while AP-1 promotes cell proliferation, inhibits differentiation, and promotes tumor cell invasion during tumor formation and progression. Targeted disruption of HPK1 alleles confers T cells with an elevated Th1 cytokine production in response to TCR engagement.

S Sawasdikosol (HPK1 as a novel target for cancer immunotherapy, Immunol Res, 54 (2012), pp. 262-265) reported that HPK1 (−/−) T cells proliferate more rapidly than the haplotype-matched wild-type counterpart and are resistant to prostaglandin E2 (PGE 2)-mediated suppression. Most strikingly, mice that received adoptive transfer of HPK1 (−/−) T cells became resistant to lung tumor growth. Also, the loss of HPK1 from dendritic cells (DCs) endows them with superior antigen presentation ability, enabling HPK1 (−/−) DCs to elicit a more potent anti-tumor immune response when used as cancer vaccine. It is probable that blocking the HPK1 kinase activity with a small molecule inhibitor may activate the superior anti-tumor activity of both cell types, resulting in a synergistic amplification of anti-tumor potential. Given that HPK1 is not expressed in any major organs, it is less likely that an inhibitor of HPK1 kinase activity would cause any serious side effects.

Patent US2016158360A1 discloses compositions and methods for enhancing an immune response and treating cancer are provided. Compositions comprise PD-1 axis antagonists and HPK1 antagonists. HPK1 antagonists include compounds that inhibit the serine/threonine kinase activity of HPK1.

HPK1 plays a key role in the treatment of diseases, especially cancer, and the discovery of HPK1 small molecule inhibitors has become an important direction for anti-tumor drug research.

BRIEF DESCRIPTION OF DRAWINGS

FIG. 1 presents bar graphs showing that representative compounds of the present disclosure are effective in enhancing cytotoxicity of the tested Car-T cells. In FIG. 1, "con" refers to the control group. PRJ1-58 corresponds to compound A1, PRJ1-108 corresponds to compound A3, PRJ1-211 corresponds to compound A31, PRJ1-165 corresponds to compound A32, PRJ1-215 corresponds to compound A52, PRJ1-217 corresponds to compound A53, PRJ1-223 corresponds to compound A54, PRJ1-168 corresponds to compound A19, PRJ1-176 corresponds to compound A42, PRJ1-167 corresponds to compound A59, PRJ1-225 corresponds to compound A48, PRJ1-191 corresponds to compound A23, PRJ1-197 corresponds to compound A28.

DESCRIPTION

In one aspect, the present disclosure provides HPK1 inhibitors and preparation method thereof. In one aspect, disclosed herein is a use of HPK1 inhibitors for the prevention and/or treatment of cancer. In other aspect, the present disclosure provides a use of HPK1 inhibitors in cancer immunotherapy. In some embodiments, the present disclosure provides a use of HPK1 inhibitors in the preparation of a medicament for preventing and/or treating cancer.

Formula X

In some embodiments, the present invention provides a compound of Formula X, or a pharmaceutically acceptable salt thereof:

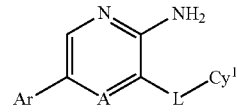

Formula X

Wherein: A is N or CH;

Ar is an optionally substituted aryl or heteroaryl; preferably, an optionally substituted 5 or 6 membered heteroaryl containing 1-4 (1, 2, 3, or 4) ring heteroatoms independently selected from O, S, and N;

L is a linker of formula $J^1$-$J^2$-$J^3$, wherein each of $J^1$, $J^2$, and $J^3$ is independently null, O, S, SO, $SO_2$, C=O, NH, optionally substituted $C_{1-4}$ alkylene, provided that L does not contain O—O, O—N, S—S, N—S, O—S, or N—N bond, and at most one of $J^1$, $J^2$, and $J^3$ is SO, $SO_2$, or C=O; and $Cy^1$ is an optionally substituted aryl or heteroaryl; preferably an optionally substituted phenyl or an optionally substituted 5 or 6 membered heteroaryl containing 1-4 (1, 2, 3, or 4) ring heteroatoms independently selected from O, S, and N.

Typically, A in Formula X is CH. However, in some embodiments, A in Formula X can also be N.

Ar in Formula X is typically an optionally substituted phenyl or an optionally substituted 5- or 6-membered heteroaryl. The 5 or 6 membered heteroaryl, as applicable, typically contains 1-4 (1, 2, 3, or 4) ring heteroatoms, more preferably, 1-3 ring heteroatoms, independently selected from O, S, and N. For example, in some embodiments, Ar is an optionally substituted thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl. It should be understood that, when applicable, two adjacent substituents of Ar can form an optionally substituted cycloalkyl, heterocyclyl, aryl, or heteroaryl ring. It should also be understood that any of the attaching points of the 5- or 6-membered heteroaryl can be used to attach to the pyridine or pyrazine core in Formula X. For example, as shown herein, both 2-thiazolyl,

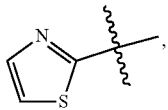 [SMILES: *c1nccs1]

and 5-thiazolyl,

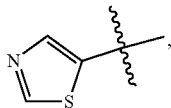 [SMILES: *c1cncs1]

are suitable, wherein the thiazolyl ring can be further substituted with 1 or 2 substituents as described herein. Other 5- or 6-membered heteroaryl should be understood similarly. In some embodiments, Ar is thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, which is optionally substituted with one or more substituents (e.g., 1-3 as valence permits) independently selected from alkyl, alkenyl, alkynyl, cycloalkyl, heterocyclyl, aryl, heteroaryl, —O—$R^{100}$, —$NR^{101}R^{102}$, —C(=O)—$R^{103}$, —$NR^{101}$—C(=O)—$R^{103}$, —$NR^{101}$—$SO_2$—$R^{14}$, —$SO_2$—$R^{104}$, —$NR^{101}$—$POR^{105}R^{106}$, —$POR^{105}R^{106}$, —$SR^{107}$, halogen, and —CN, wherein each $R^{100}$ is independently selected from hydrogen, an oxygen protecting group, alkyl, alkenyl, alkynyl, cycloalkyl, heterocyclyl, aryl, and heteroaryl;

each $R^{101}$ or $R^{102}$ is independently selected from hydrogen, a nitrogen protecting group, alkyl, alkenyl, alkynyl, cycloalkyl, heterocyclyl, aryl, and heteroaryl;

each $R^{103}$ is independently selected from hydrogen, alkyl, alkenyl, alkynyl, cycloalkyl, heterocyclyl, aryl, heteroaryl, —O—$R^{100}$, and —$NR^{101}R^{102}$;

each $R^{104}$ is independently selected from hydrogen, alkyl, alkenyl, alkynyl, cycloalkyl, heterocyclyl, aryl, heteroaryl, —O—$R^{100}$, and —$NR^{101}R^{102}$;

each $R^{105}$ or $R^{106}$ is independently selected from hydrogen, alkyl, alkenyl, alkynyl, cycloalkyl, heterocyclyl, aryl, heteroaryl, —O—$R^{100}$, and —$NR^{101}R^{102}$; each $R^{107}$ is independently selected from hydrogen, a thiol protecting group, alkyl, alkenyl, alkynyl, cycloalkyl, heterocyclyl, aryl, and heteroaryl;

wherein each of the alkyl, alkenyl, alkynyl, cycloalkyl, heterocyclyl, aryl, and heteroaryl is optionally substituted, e.g., with one or more (e.g., 1-5 as valence permits) substituents each independently selected from 1) $C_{1-7}$ alkyl (e.g., $C_{1-4}$ alkyl) optionally substituted with 1-3 substituents each independently selected from halogen (e.g., F), oxo, —OH or protected OH, optionally substituted $C_{1-4}$ alkoxy, —$NH_2$ or protected $NH_2$, —N($C_{0-4}$ alkyl)($C_{0-4}$ alkyl), optionally substituted $C_{3-6}$ cycloalkyl, optionally substituted phenyl, optionally substituted 5- or 6-membered heteroaryl, and optionally substituted 4-8 membered heterocyclyl; 2) halogen; 3) —OH or protected OH; 4) optionally substituted $C_{1-4}$ alkoxy; 5) —$NH_2$ or protected $NH_2$; 6) —N($C_{0-4}$ alkyl)($C_{0-4}$ alkyl), wherein the alkyl is optionally substituted; 7) optionally substituted $C_{3-6}$ cycloalkyl; 8) optionally substituted phenyl; 9) optionally substituted 5- or 6-membered heteroaryl; and 10) optionally substituted 4-8 membered heterocyclyl. As used herein, for groups such as —N($C_{0-4}$ alkyl)($C_{0-4}$ alkyl), the two $C_{0-4}$ alkyl are independently selected and can be the same or different.

Typically, Ar in formula X is a substituted aryl or heteroaryl, which is substituted with at least one substituent, e.g., as described herein. In some embodiments, Ar in formula X is thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, which is substituted with one substituent. To illustrate, when Ar is 5-thiazolyl substituted with one substituent, Formula X can have a Formula X-1,

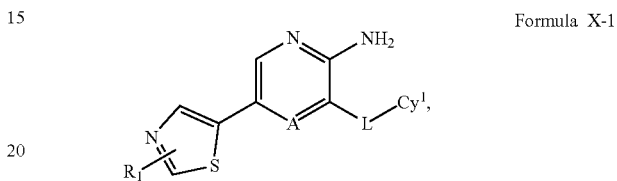

Formula X-1 wherein $R_1$ is the one substituent. The one substituent can be attached to any available position. However, in some preferred embodiments, the one substituent is attached to a position not ortho to the pyrinine or pyrazine core in Formula X. For example, in Formula X-1, the preferred position for the one substituent is the 2-position of the thiazolyl:

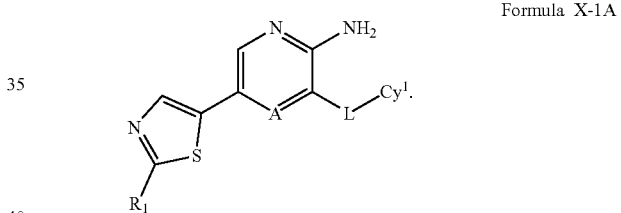

Formula X-1A

In some embodiments, the one substituent can be an optionally substituted heterocycle (e.g., optionally substituted 4-8 membered heterocyclyl). In some embodiments, the one substituent can be a $C_{1-7}$ alkyl (e.g., $C_{1-4}$ alkyl) optionally substituted with 1-3 substituents each independently selected from halogen (e.g., F), oxo, —OH or protected OH, optionally substituted $C_{1-4}$ alkoxy, —$NH_2$ or protected $NH_2$, —N($C_{0-4}$ alkyl)($C_{0-4}$ alkyl), optionally substituted $C_{3-6}$ cycloalkyl, optionally substituted phenyl, optionally substituted 5- or 6-membered heteroaryl, and optionally substituted 4-8 membered heterocyclyl. For example, in some embodiments, the one substituent can be a $C_{1-7}$ alkyl (e.g., $C_{1-4}$ alkyl) such as methyl or isopropyl. In some embodiments, the one substituent can be an optionally substituted cycloalkyl (e.g., $C_{3-6}$ cycloalkyl, such as cyproyl, cyclobutyl, cyclopentyl, or cyclohexyl). In some embodiments, the one substituent can be a —O—$R^{100}$, wherein $R^{100}$ is defined herein, for example, the one substituent can be —OPh. In some embodiments, the one substituent can be —$SO_2$—$R^{104}$ or —$SR^{107}$, wherein $R^{104}$ and $R^{107}$ are defined herein. For example, in some embodiments, the one substituent can be —$SO_2$-Me or SMe.

In some embodiments, the one substituent is an optionally substituted 4-10 membered heterocyclic ring containing 1-4 (1, 2, 3, or 4) ring heteroatoms, more preferably, 1-3 ring heteroatoms, independently selected from S, O, and N, wherein the S and N are optionally oxidized. In some embodiments, the 4-10 membered heterocyclic ring can be optionally substituted with 1-5 substituents each independently 1) an optionally substituted 5 or 6-membered heterocyclic ring containing 1 or 2 ring heteroatoms independently selected from S, O, and N, wherein the S and N are optionally oxidized; 2) $C_{1-7}$ alkyl (e.g., $C_{1-4}$ alkyl) optionally substituted with 1-3 substituents each independently selected from halogen (e.g., F), oxo, —OH or protected OH, optionally substituted $C_{1-4}$ alkoxy, —$NH_2$ or protected $NH_2$, —$N(C_{0-4}$ alkyl)($C_{0-4}$ alkyl), optionally substituted $C_{3-6}$ cycloalkyl, optionally substituted phenyl, optionally substituted 5- or 6-membered heteroaryl, and optionally substituted 4-8 membered heterocyclyl; 3) an optionally substituted cycloalkyl (e.g., $C_{3-6}$ cycloalkyl); 4) halogen (e.g., F); 5) oxo; or 6) a nitrogen protecting group as applicable.

In some preferred embodiments, the one substituent is an optionally substituted 5 or 6-membered heterocyclic ring containing 1 or 2 ring heteroatoms independently selected from S, O, and N, wherein the S and N are optionally oxidized. In some embodiments, the 5 or 6-membered heterocyclic ring is optionally substituted with 1-5 substituents each independently 1) an optionally substituted 5 or 6-membered heterocyclic ring containing 1 or 2 ring heteroatoms independently selected from S, O, and N, wherein the S and N are optionally oxidized; 2) $C_{1-7}$ alkyl (e.g., $C_{1-4}$ alkyl) optionally substituted with 1-3 substituents each independently selected from halogen (e.g., F), oxo, —OH or protected OH, optionally substituted $C_{1-4}$ alkoxy, —$NH_2$ or protected $NH_2$, —$N(C_{0-4}$ alkyl)($C_{0-4}$ alkyl), optionally substituted $C_{3-6}$ cycloalkyl, optionally substituted phenyl, optionally substituted 5- or 6-membered heteroaryl, and optionally substituted 4-8 membered heterocyclyl; 3) an optionally substituted cycloalkyl (e.g., $C_{3-6}$ cycloalkyl); 4) halogen (e.g., F); 5) oxo; or 6) a nitrogen protecting group as applicable. In some embodiments, the 5 or 6-membered heterocyclic ring is optionally substituted with 1-3 substituents each independently selected from 1) halogen; 2) $C_{1-7}$ alkyl (e.g., $C_{1-4}$ alkyl) optionally substituted with 1-3 fluorine; and 3) 5 or 6-membered heterocyclic ring containing 1 or 2 ring heteroatoms independently selected from S, O, and N, wherein the S and N are optionally oxidized, which is optionally substituted with 1-3 substituents each independently selected from halogen (e.g., F) and $C_{1-7}$ alkyl (e.g., $C_{1-4}$ alkyl) optionally substituted with 1-3 fluorine. In some embodiments, the optionally substituted 5 or 6-membered heterocyclic ring is a ring selected from:

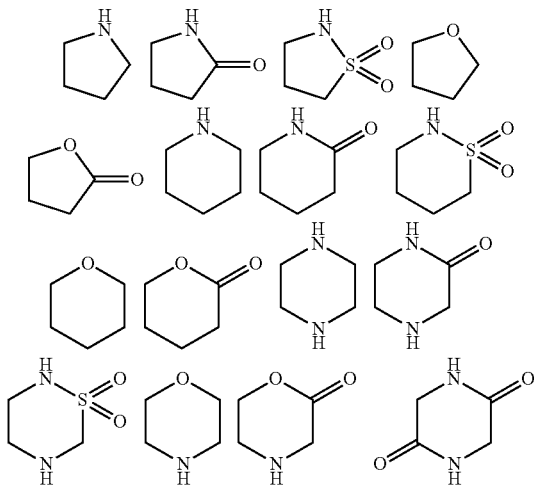

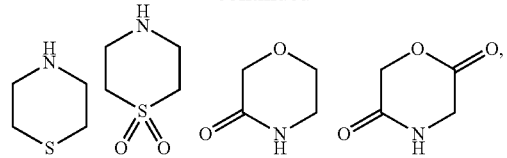

which is optionally substituted (e.g., as described herein), for example, unsubstituted or substituted with 1-3 substituents each independently selected from halogen (e.g., F) and $C_{1-7}$ alkyl (e.g., $C_{1-4}$ alkyl) optionally substituted with 1-3 fluorine. In some embodiments, the 5 or 6-membered heterocyclic ring is a ring selected from:

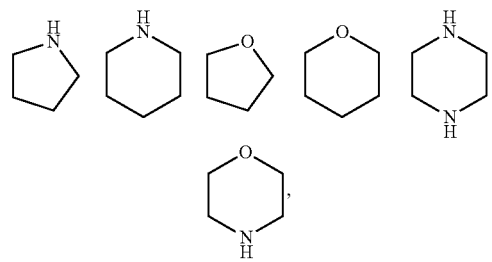

which is optionally substituted (e.g., as described herein), for example, unsubstituted or substituted with 1-3 substituents each independently selected from halogen (e.g., F) and $C_{1-7}$ alkyl (e.g., $C_{1-4}$ alkyl) optionally substituted with 1-3 fluorine. The 5 or 6-membered heterocyclic ring can be attached to the Ar in Formula X via any attaching point, such as a carbon or nitrogen attaching point. To illustrate, using 2-piperidinyl-5-thiazolyl as an example of Ar, in some embodiments, the compound of Formula X can be represented by Formula X-2:

Formula X-2

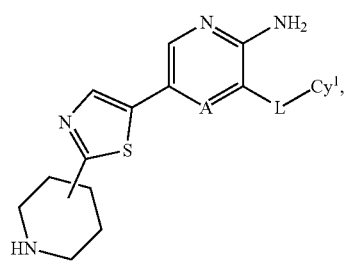

wherein the piperidinyl can be further substituted as described herein, for example, with one or more methyl groups on the ring, including on the nitrogen atom. Other substituents for Ar, such as the 5 or 6-membered heterocyclic ring described herein, should be understood similarly.

In some embodiments, Ar in Formula X is thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, which is substituted with two substituents, wherein one substituent is any of the suitable substituents described above, and the other substituent is selected from halogen, $C_{1-7}$ alkyl (e.g., $C_{1-4}$ alkyl), $NH_2$ and protected $NH_2$. Preferably, the substituent ortho to the pyridine or pyrazine core in Formula X, if exist, is selected from halogen, $C_{1-7}$ alkyl (e.g., $C_{1-4}$ alkyl), $NH_2$ and protected $NH_2$. Using 5-thiazolyl as an example, when the 5-thiazolyl is said to be substituted with two substituents, i.e., both $R_0$ and $R_1$ are not hydrogen in Formula X-1B,

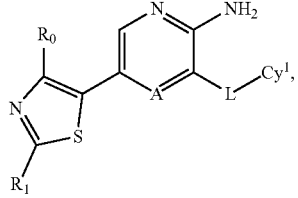

Formula X-1B then it is preferred that $R_0$ is halogen (e.g., F, Cl), $C_{1-7}$ alkyl (e.g., $C_{1-4}$ alkyl), $NH_2$ and protected $NH_2$, and $R_1$ is a substituent described herein (e.g., the one substituent discussed above). In some embodiments, Ar in Formula X is thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, which is substituted with one or two substituents, wherein one substituent is selected from

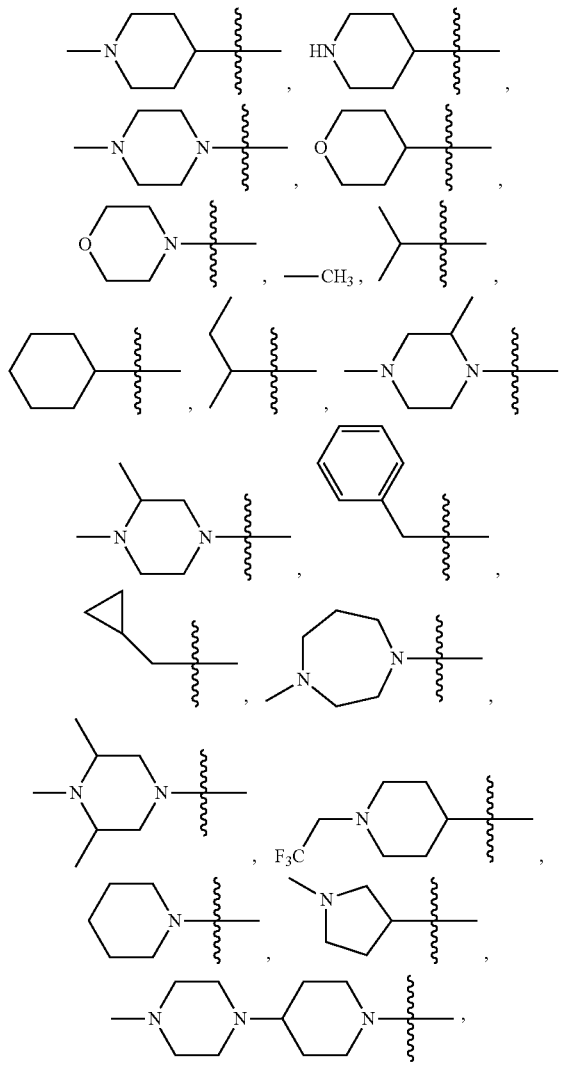

and the other substituent, when exist, is selected from halogen (e.g., F, Cl), methyl, ethyl, $NH_2$, or protected $NH_2$.

In some embodiments, Ar in Formula X (including any of the subformulae described herein such as Formula X-1, X-2, etc.) is:

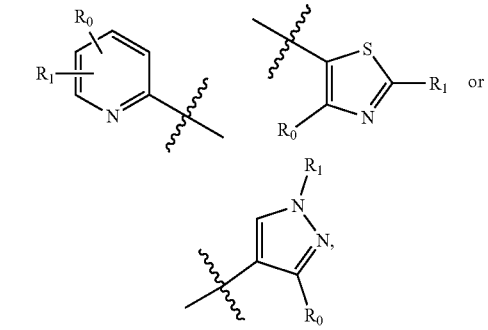

wherein $R_1$ is selected from

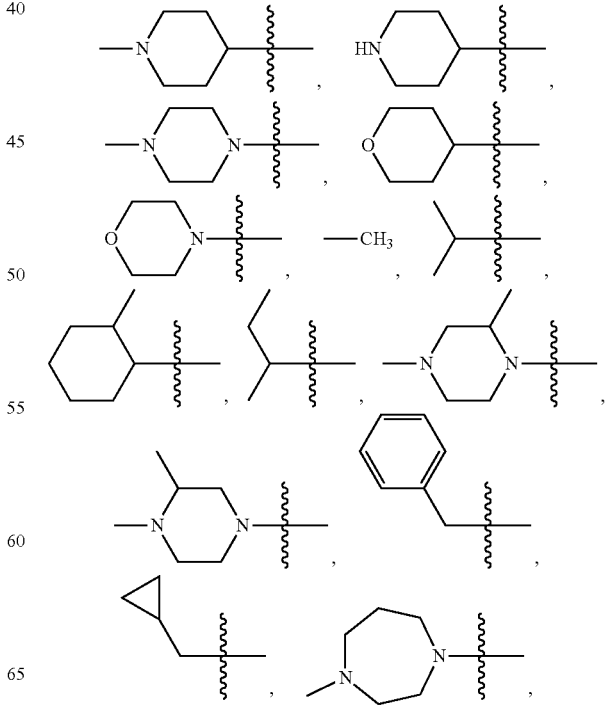

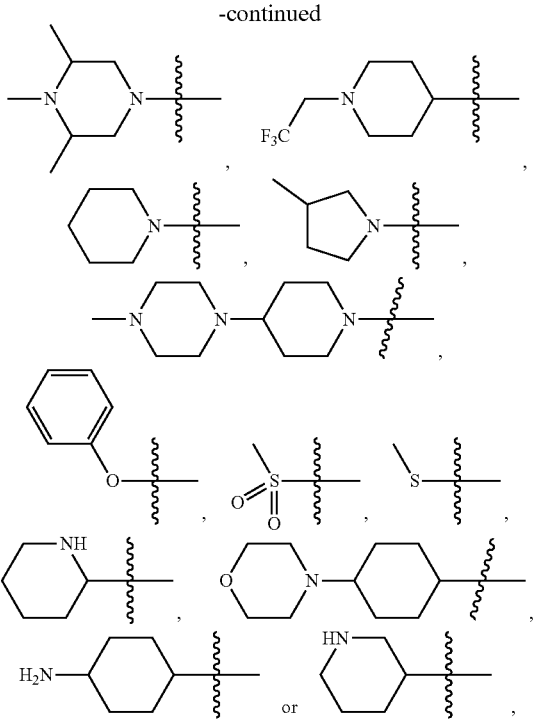

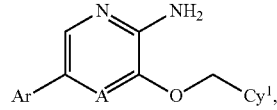

Formula X-3 wherein the variables A, Ar, and $Cy^1$ are defined and preferred herein.

$Cy^1$ in Formula X is typically a 5- or 6-membered aryl or heteroaryl, preferably a 6-membered aryl or heteroaryl. When $Cy^1$ in Formula X is a 5- or 6-membered heteroaryl, it typically has 1-4 (e.g., 1, 2, 3, or 4) ring heteroatoms, more preferably, 1-3 ring heteroatoms, independently selected from N, S, and O. For example, in some embodiments, $Cy^1$ is an optionally substituted phenyl or pyridinyl, e.g., optionally substituted with 1-3 substituents each independently selected from halogen (e.g., F), optionally substituted alkyl, optionally substituted alkenyl, optionally substituted alkynyl, CN, OH, optionally substituted alkoxyl, optionally substituted cycloalkyl, optionally substituted cycloalkoxyl, optionally substituted aryl, optionally substituted heteroaryl, and optionally substituted heterocyclyl, wherein when applicable, two adjacent substituents can form an optionally substituted cycloalkyl, heterocyclyl, aryl, or heteroaryl ring. In some embodiments, $Cy^1$ is a phenyl or pyridinyl substituted with 1 or 2 substituents, wherein one of the substituents is an optionally substituted alkyne; preferably, the alkyne is meta to the linker L, and has a formula of —C≡C—$R_{10}$, wherein $R_{10}$ is selected from H, optionally substituted $C_{1-5}$ alkyl, optionally substituted $C_{3-10}$ cycloalkyl, or

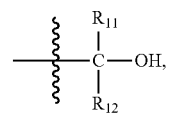

wherein $R_{11}$ and $R_{12}$ are each independently selected from hydrogen, optionally substituted alkyl, optionally substituted alkenyl, optionally substituted alkynyl, optionally substituted cycloalkyl, optionally substituted heterocyclyl, optionally substituted aryl, and optionally substituted heteroaryl, or $R_{11}$ and $R_{12}$ together form an optionally substituted cycloalkyl or an optionally substituted heterocyclyl.

In some preferred embodiments, $Cy^1$ can be a phenyl or pyridinyl substituted with an alkyne. For example, in some embodiments, $Cy^1$ can be a phenyl or pyridinyl substituted with one substituent, which is an optionally substituted alkyne. In some embodiments, $Cy^1$ is a phenyl or pyridinyl substituted with two substituents, wherein one of the substituents is an optionally substituted alkyne and the other of the substituents (preferably meta or para to the alkyne, as applicable) is selected from halogen (e.g., F or Cl), $C_{1-7}$ alkyl (e.g., $C_{1-4}$ alkyl) optionally substituted with one or more (preferably 1-3) substituents each independently selected from halogen, —OH, and $NH_2$, (e.g., $CF_3$, $CH_2OH$, $CH_2NH_2$, etc.), —CN, —OH, $C_{1-4}$ alkoxyl optionally substituted with 1-3 fluorine, $C_{3-6}$ cycloalkyl optionally substituted with 1 or 2 substituents each independently selected from F and $C_{1-7}$ alkyl (e.g., $C_{1-4}$ alkyl), and $C_{3-6}$ cycloalkoxyl optionally substituted with 1 or 2 substituents each independently selected from F and $C_{1-7}$ alkyl (e.g., $C_{1-4}$ alkyl).

and $R_0$ is selected from hydrogen, halogen (e.g., F, Cl), methyl, ethyl, $NH_2$, or protected $NH_2$, provided that in

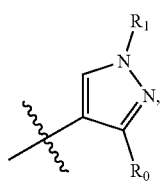

$R_1$ is not a moiety with an N, S, or O attaching point.

Various linker of formula $J^1$-$J^2$-$J^3$ can be used as L. In some embodiments, each of $J^1$, $J^2$, and $J^3$ can be independently null, O, S, SO, $SO_2$, C=O, NH, optionally substituted $C_{1-4}$ alkylene, provided that L does not contain O—O, O—N, S—S, N—S, O—S, or N—N bond, and at most one of $J^1$, $J^2$, and $J^3$ is SO, $SO_2$, or C=O. For example, in some embodiments, one of $J^1$, $J^2$, and $J^3$ can be null. In some embodiments, two of $J^1$, $J^2$, and $J^3$ can be null. In some embodiments, one of $J^1$, $J^2$, and $J^3$ can be O. In some embodiments, none of $J^1$, $J^2$, and $J^3$ is S, NH, SO, $SO_2$, or C=O. In some embodiments, one of $J^1$, $J^2$, and $J^3$ is SO, $SO_2$, or C=O. In some embodiments, one of $J^1$, $J^2$, and $J^3$ is NH. In some embodiments, one of $J^1$, $J^2$, and $J^3$ can be $C_{1-4}$ alkylene. Preferably, L in Formula X is a linker of —O—($C_{1-4}$ alkylene), —S—($C_{1-4}$ alkylene), or $C_{1-4}$ alkylene, wherein each of the $C_{1-4}$ alkylene is optionally substituted, for example, with 1-3 substituents selected from F, methyl or fluorine substituted methyl. In some embodiments, L is —O—($C_{1-4}$ alkylene), wherein the $C_{1-4}$ alkylene is unsubstituted. Preferably, L attaches to $Cy^1$ through a carbon atom. For example, in some preferred embodiments, L is —O—$CH_2$—, wherein the $CH_2$ is directly attached to $Cy^1$. To illustrate, in some embodiments, compounds of Formula X can be characterized as having Formula X-3:

Preferably, the position para to the linker L, as applicable, is unsubstituted. To clarify, as used herein, when $Cy^1$ is a 5-membered heteroaryl, there will be either an ortho or meta position, but no para position to the linker L.

In some specific embodiments, $Cy^1$ can be a phenyl or pyridinyl, substituted at a position meta to the linker L with an optionally substituted alkyne having the formula

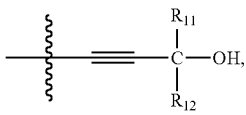

wherein $R_{11}$ and $R_{12}$ are each independently selected from hydrogen,

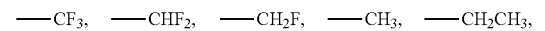

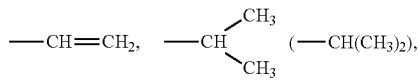

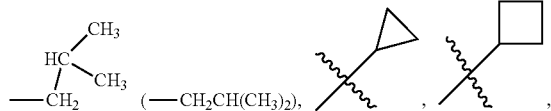

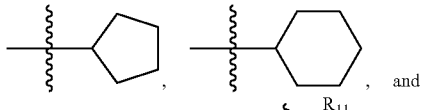

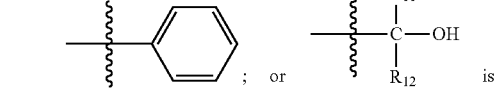

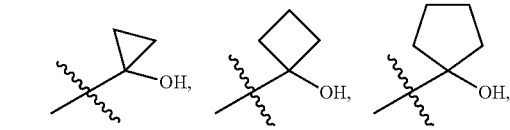

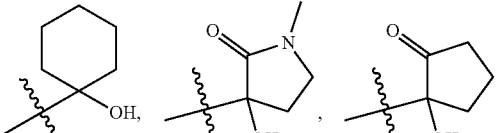

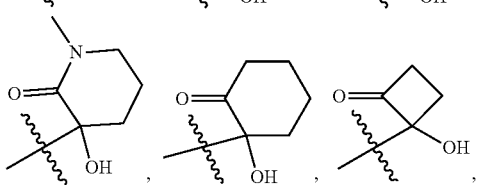

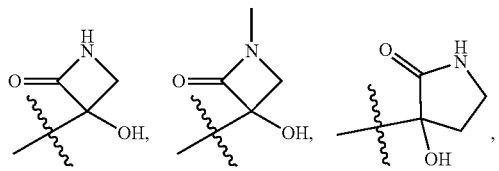

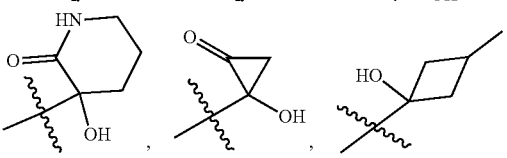

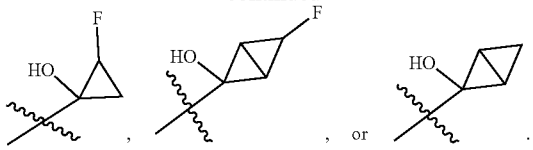 [SMILES: *C1(O)CC1F ; *C1(O)C2C(F)C21 ; *C1(O)C2CC21]

In some specific embodiments, $Cy^1$ can be a phenyl or pyridinyl, substituted at a position meta to the linker L with an optionally substituted alkyne having the formula

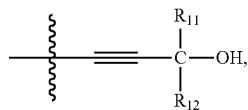

wherein $R_{11}$ and $R_{12}$ are both methyl. In some embodiments, $Cy^1$ can be a phenyl or pyridinyl, substituted at a position meta to the linker L, an optionally substituted alkyne having the formula

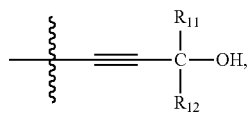

wherein

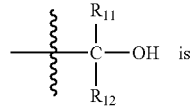 is

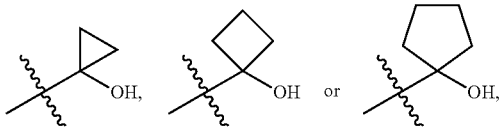

preferably

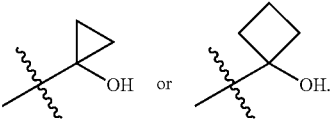 [SMILES: *C1(O)CC1 ; "or" ; *C1(O)CCC1]

Formula Y or Z

In some embodiments, the compound of Formula X can be characterized as having a Formula Y or Z:

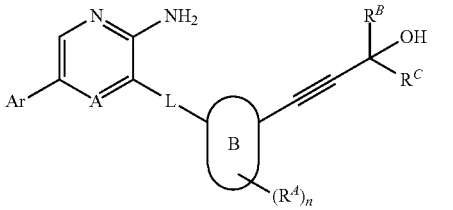

Formula Y

-continued

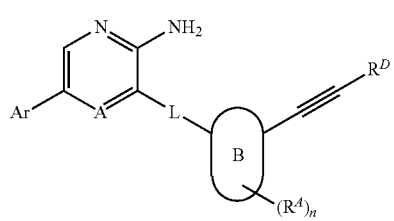

Formula Z wherein A, Ar, L are defined and preferred as in Formula X, ring B is an aryl or heteroaryl; preferably a phenyl or 5 or 6 membered heteroaryl containing 1-4 (1, 2, 3, or 4) ring heteroatoms independently selected from O, S, and N;

n is 0, 1, 2, or 3, as valance permits, each $R^A$ is independently selected from halogen (e.g., F), optionally substituted alkyl, optionally substituted alkenyl, optionally substituted alkynyl, CN, OH, optionally substituted alkoxyl, optionally substituted cycloalkyl, optionally substituted cycloalkoxyl, optionally substituted aryl, optionally substituted heteroaryl, and optionally substituted heterocyclyl, wherein when applicable, two adjacent $R^A$ can form an optionally substituted cycloalkyl, heterocyclyl, aryl, or heteroaryl ring, $R^B$ and $R^C$ are each independently selected from hydrogen, optionally substituted alkyl, optionally substituted alkenyl, optionally substituted alkynyl, optionally substituted cycloalkyl, optionally substituted heterocyclyl, optionally substituted aryl, and optionally substituted heteroaryl, or $R^B$ and $R^C$ together form an optionally substituted cycloalkyl or an optionally substituted heterocyclyl, wherein $R^D$ in Formula Z is hydrogen, optionally substituted $C_{1-5}$ alkyl, optionally substituted $C_{3-10}$ cycloalkyl, or optionally substituted 4-7 membered heterocyclyl, wherein the triple bond in Formula Y or Z is meta to the linker L. To avoid confusion, as used herein, when ring B is a 5-membered ring, the triple bond in formula Y is meta to the linker L as long as it is not ortho to the linker L.

In some specific embodiments, ring B in Formula Y or Z can be selected from:

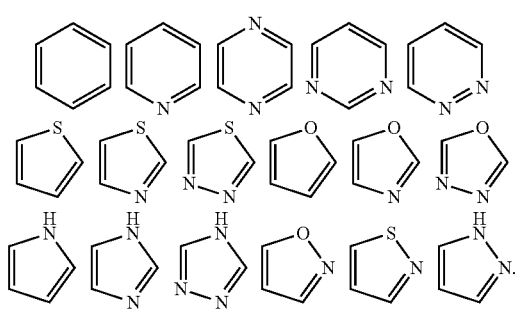

It should be understood that any of the available attaching points of the aryl or heteroaryl ring described herein can be used to connect with the linker L and the alkyne moiety in Formula Y or Z. Using pyridine as an example to illustrate, Formula Y with a pyridine as ring B can have any of the following formulae:

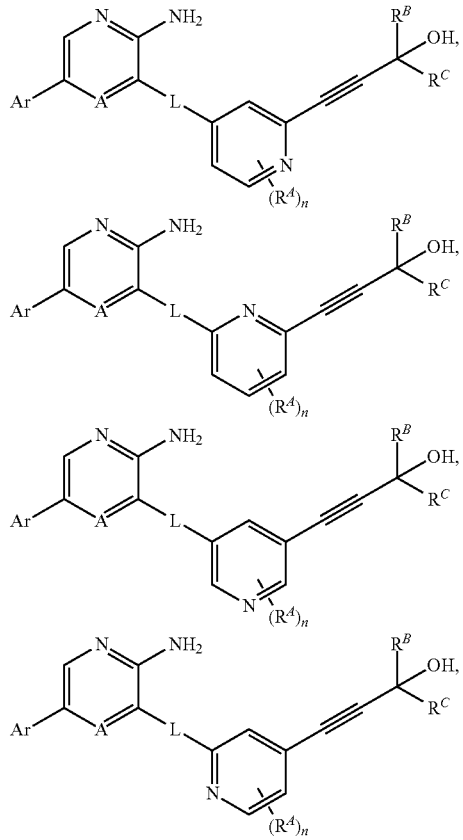

Other aryl or heteroaryl as ring B should be understood similarly.

In some embodiments, ring B in Formula Y or Z can also be a 5,5-bicyclic or 5,6-bicyclic heteroaryl ring.

In some specific embodiments, $R^B$ and $R^C$ in Formula Y can be independently selected from hydrogen,

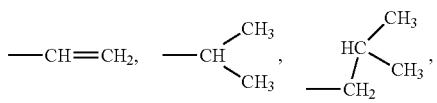

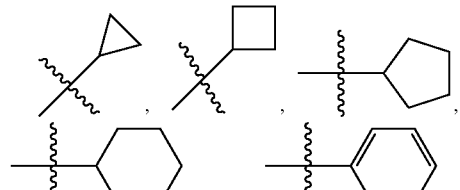

$R^B$ | $R^C$—OH is

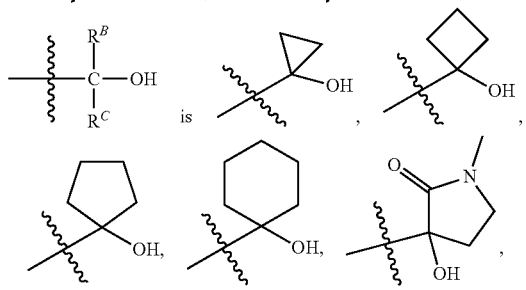

-continued

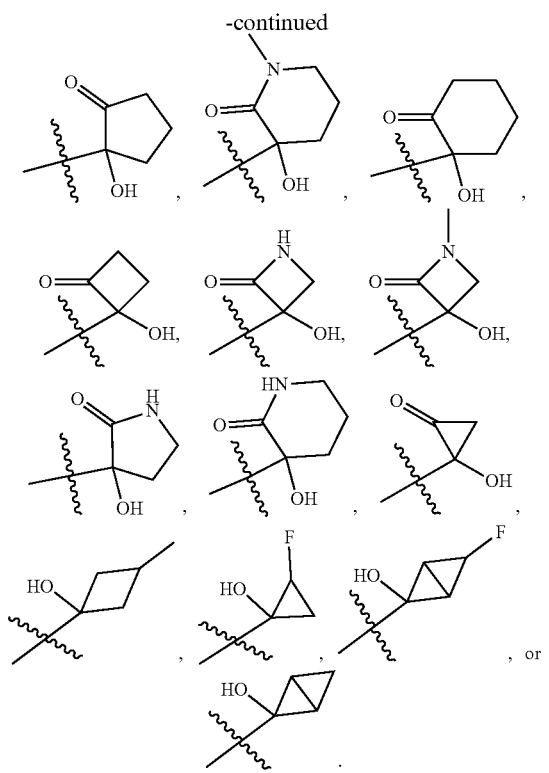

In some specific embodiments, $R^B$ and $R^C$ in Formula Y can be each methyl. In some embodiments,

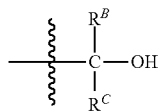

in Formula Y can be

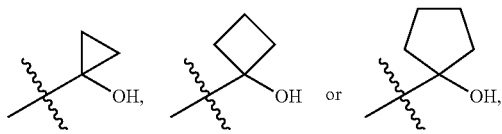 [SMILES: *C1(O)CC1 ; *C1(O)CCC1 ; "or" ; *C1(O)CCCC1]

preferably,

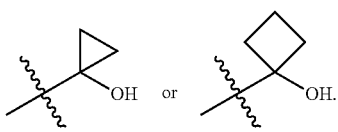 [SMILES: *C1(O)CC1 ; "or" ; *C1(O)CCC1]

In some embodiments, $R^D$ in Formula Z can be hydrogen,

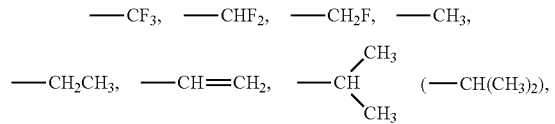

-continued

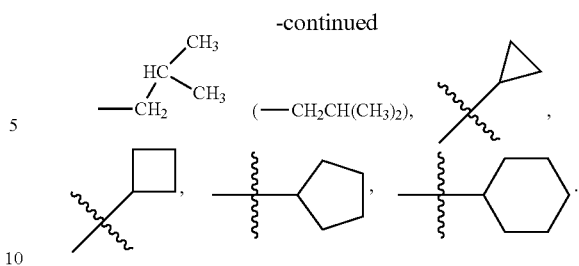

In some embodiments, n is 0, i.e., ring B is not further substituted.

In some embodiments, n is 1, and $R^A$ can be halogen (e.g., F or Cl), $C_{1-7}$ alkyl (e.g., $C_{1-4}$ alkyl) optionally substituted with one or more (preferably 1-3) substituents each independently selected from halogen, —OH, and $NH_2$, (e.g., $CF_3$, $CH_2OH$, $CH_2NH_2$, etc.), —CN, —OH, $C_{1-4}$ alkoxyl optionally substituted with 1-3 fluorine, $C_{3-6}$ cycloalkyl optionally substituted with 1 or 2 substituents each independently selected from F and $C_{1-7}$ alkyl (e.g., $C_{1-4}$ alkyl), and $C_{3-6}$ cycloalkoxyl optionally substituted with 1 or 2 substituents each independently selected from F and $C_{1-7}$ alkyl (e.g., $C_{1-4}$ alkyl).

In some embodiments, L in formula Y or Z is —O—$CH_2$—, with the $CH_2$ directly attached to ring B.

In some embodiments, the present disclosure also provides a compound selected from any of the compound A1 to A85, or a pharmaceutically acceptable salt thereof. Some compounds in the Examples section (Examples 1-23) are associated with two numbers, for example, Example 1 shows compound A1 also as compound 8. For clarity, compounds A1 to A85 include those compounds associated with two numbers, so long as one of the numbers is one of A1 to A85.

Formula I or II

In one aspect, the present invention provides a compound of formula (I):

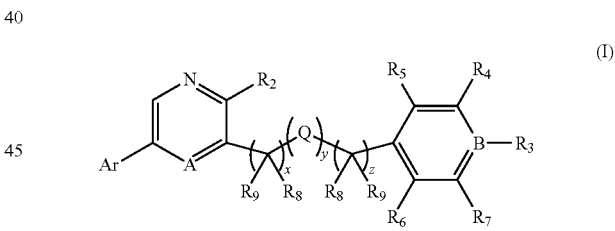

(I)

wherein, A is C or N; B is C or N.

Ar is a five-membered heteroaryl, six-membered heteroaryl or phenyl, wherein the five-membered heteroaryl is selected from furanyl, thienyl, pyrrolyl, pyrazolyl, imidazolyl, oxazolyl or thiazolyl; the six-membered heteroaryl is selected from pyridyl, pyridazinyl, pyrimidinyl or pyrazinyl, wherein the five-membered heteroaryl, six-membered heteroaryl or phenyl is optionally substituted with a group selected from —$SO_2$, —$SO_2N(C_{0-10}$ alkyl)($C_{0-10}$ alkyl), —N($C_{0-10}$ alkyl)$SO_2(C_{0-10}$ alkyl), —CON($C_{0-10}$ alkyl) ($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, $C_{0-10}$ linear/branched alkyl, —N($C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —$SO_2$, —$SO_2N(C_{0-10}$ alkyl)

(C₀₋₁₀ alkyl), —N(C₀₋₁₀ alkyl)SO₂(C₀₋₁₀ alkyl), —CON(C₀₋₁₀ alkyl)(C₀₋₁₀ alkyl), —N(C₀₋₁₀ alkyl)CO(C₀₋₁₀ alkyl), —N(C₀₋₁₀ alkyl)COO(C₀₋₁₀ alkyl), —OCON(C₀₋₁₀ alkyl)(C₀₋₁₀ alkyl), halogen, —CN, —OCH₂F, —OCHF₂, —OCF₃, —N(C₀₋₁₀ alkyl)(C₀₋₁₀ alkyl), —OC₀₋₁₀ alkyl, C₃₋₁₀ cycloalkyl, —O heterocyclyl, —N heteroaryl, —O heteroaryl or —S heteroaryl.

Preferably, at least one H on the five-membered heteroaryl, six-membered heteroaryl or phenyl is substituted with a group selected from the following: —SO₂, —SO₂NH₂, —NHSO₂, —CONH(C₀₋₁₀ alkyl), halogen, —CN, —OCF₃, —O heterocyclyl, —N heterocyclyl, C₁₋₁₀ linear/branched alkyl, —OC₀₋₁₀ alkyl, C₃₋₁₀ cycloalkyl, or —N(C₀₋₁₀ alkyl)(C₀₋₁₀ alkyl). More preferably, at least one H on the five-membered heteroaryl, six-membered heteroaryl or phenyl is substituted with a —O heterocyclyl or —N heterocyclyl.

In some preferred embodiments, Ar is thiazolyl, selenothiazolyl, imidazolyl, pyrazolyl or pyridyl.

In some preferred embodiments, Ar is

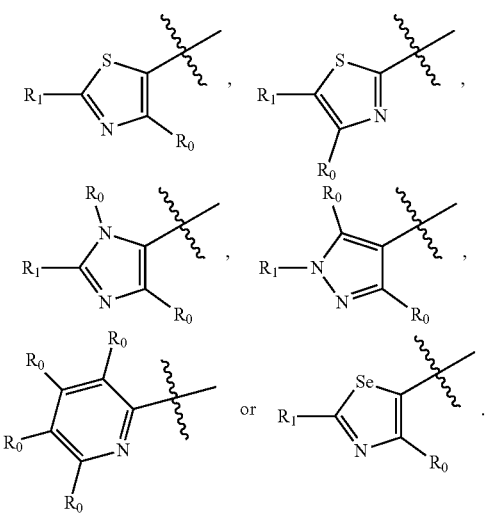

Q is O or S; x and z are integers from 0-6; y is 0 or 1.

Preferred, x and z are integers from 0-2, such as 0, 1 or 2.

In some preferred embodiments, the compound is formula (II):

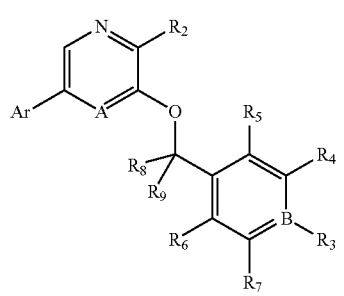

Preferably, the compound can have the following formulae:

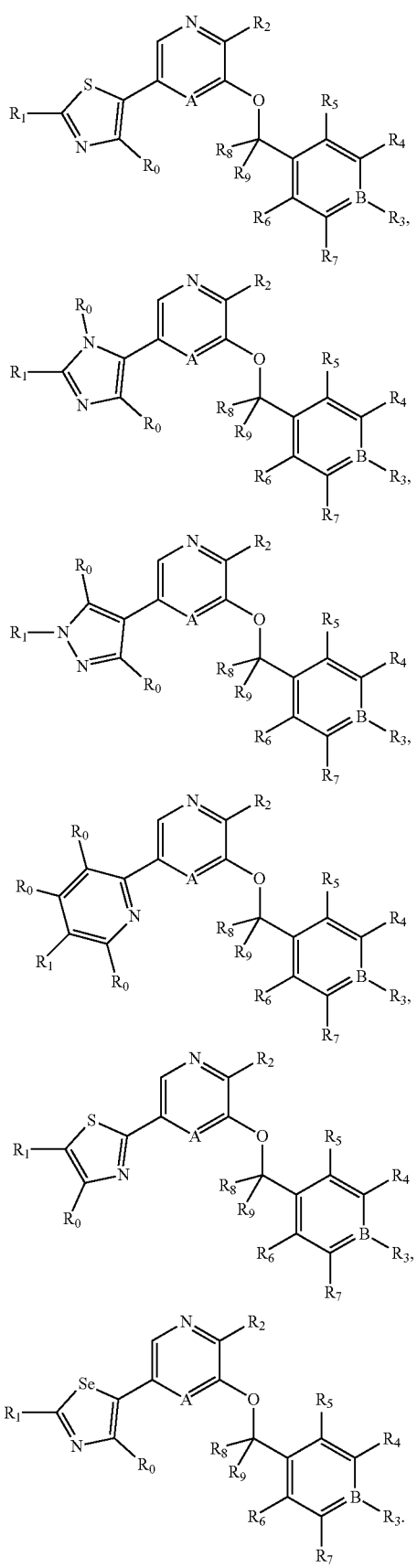

$R_0$ is independently selected from: —H, $C_{1-10}$ linear/branched alkyl, —N($C_{1-10}$ alkyl)($C_{0-10}$ alkyl), —$OC_{0-10}$ alkyl or $C_{3-10}$ cycloalkyl.

Preferably, $R_0$ is selected from $C_{1-5}$ linear/branched alkyl or —N($C_{0-10}$ alkyl)($C_{0-10}$ alkyl).

In some preferred embodiments, $R_0$ is —$CH_3$, —$CH_2CH_3$ or —$NH_2$.

$R_1$ is selected from: —H, —O heterocyclyl, —N heterocyclyl, $C_{1-10}$ linear/branched alkyl, $C_{3-10}$ cycloalkyl, —$OC_{0-10}$ alkyl, —N($C_{0-10}$ alkyl)($C_{0-10}$ alkyl), —$SO_2$ ($C_{0-10}$ alkyl), —O($C_{0-10}$ alkyl), —O-phenyl, —S($C_{0-10}$ alkyl), —N heteroaryl, —O heteroaryl or —S heteroaryl, wherein the H on the C or hetero atom is optionally substituted with one group selected from $C_{1-3}$ linear alkyl, —N($C_{0-10}$ alkyl)($C_{0-10}$ alkyl), —$CF_3$.

Preferably, $R_1$ is selected from: —O heterocyclyl, —N heterocyclyl, —$SO_2$ ($C_{0-3}$ alkyl), —O-phenyl, —S($C_{0-4}$ alkyl), $C_{3-6}$ cycloalkyl, $C_{3-5}$ linear/branched alkyl, wherein the H on the C or hetero atom is optionally substituted with —$CH_3$, —$NH_2$ or —$CF_3$.

In some preferred embodiments, $R_1$ is selected from the followings:

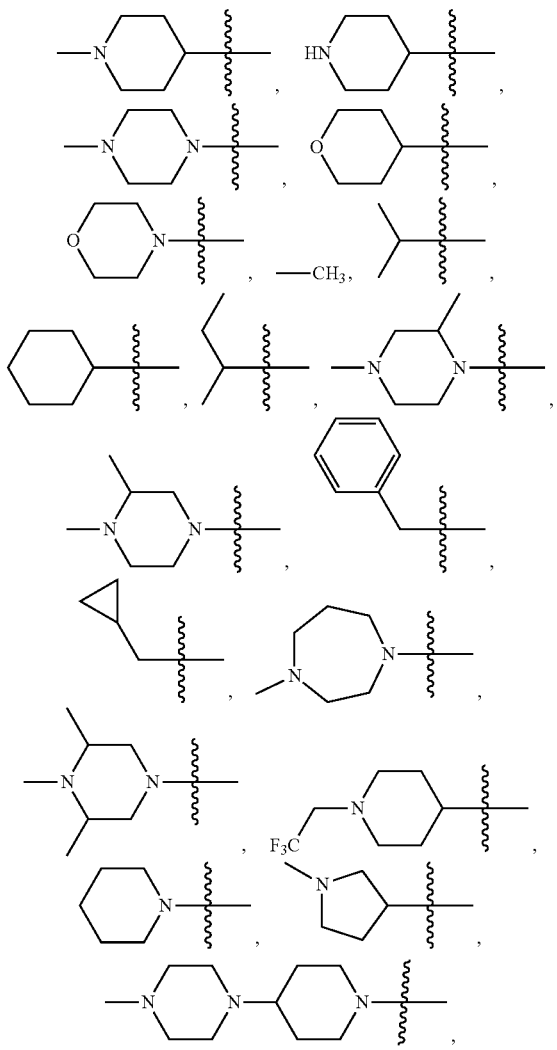

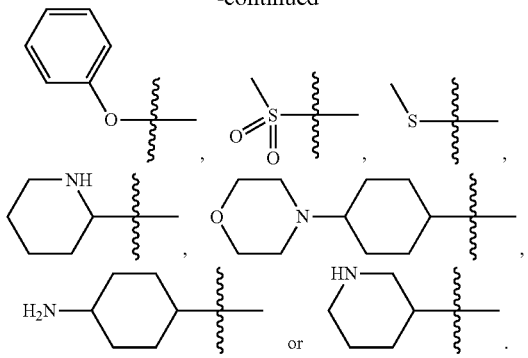

$R_2$ is selected from: —H, halogen, —$NO_2$, —CN, $C_{1-5}$ linear/branched alkyl, $C_{3-10}$ cycloalkyl, —N($C_{0-10}$ alkyl)($C_{0-10}$ alkyl), —$CF_3$, —$OCF_3$, —$OCHF_2$, —$OCH_2F$ or —$OC_{0-10}$ alkyl.

Preferably, $R_2$ is selected from: —$NO_2$, —N($C_{0-10}$ alkyl)($C_{0-10}$ alkyl), —$OCF_3$, or —$OC_{0-10}$ alkyl.

In some preferred embodiments, $R_2$ is —$NH_2$ or —$NO_2$.

When B is N, $R_3$ does not exist; when B is C, $R_3$ is selected from: —H, halogen, —$OC_{0-10}$ alkyl, $C_{1-10}$ linear/branched alkyl, —N($C_{0-10}$ alkyl)($C_{0-10}$ alkyl) or $C_{3-10}$ cycloalkyl.

Preferably, $R_3$ is selected from: —H, halogen, —$OC_{0-10}$ alkyl or $C_{0-10}$ linear/branched alkyl.

In some preferred embodiments, $R_3$ is —H, —F or —$OCH_3$.

$R_4$ is selected from: —H, halogen, —$OC_{0-10}$ alkyl, —CN, $C_{3-10}$ cycloalkyl, —C≡C—$R_{10}$, $C_{0-10}$ linear/branched alkyl, —N($C_{0-10}$ alkyl)($C_{0-10}$ alkyl), —O heterocyclyl or —N heterocyclyl.

Preferably, $R_4$ is selected from: —H, halogen, —$OC_{1-10}$ alkyl, —CN, $C_{3-10}$ cycloalkyl, —C≡C—$R_{10}$.

In some preferred embodiments, $R_4$ is selected from: —H, —F, —Cl, —$OCH_3$, —CN,

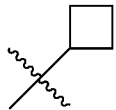

or —C≡C—$R_{10}$.

$R_{10}$ is selected from: H, $C_{1-5}$ linear/branched alkyl, $C_{3-10}$ cycloalkyl or

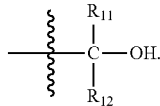

$R_{11}$, $R_{12}$ are independently selected from: —H, —$CF_3$, —$CHF_2H$, —$CH_2F$, $C_{1-10}$ linear/branched alkyl, —CH=C($C_{1-10}$ alkyl)($C_{0-10}$ alkyl), —C≡C($C_{1-10}$ alkyl), $C_{3-10}$ cycloalkyl, five-membered heteroaryl or six-membered heteroaryl, or $R_{11}$ and $R_{12}$ together with the atom(s) to which they are attached form a $C_{3-8}$ cycloalkyl, $C_{3-8}$ heterocyclyl containing O or S, $C_{4-9}$ fused cycloalkyl, $C_{3-7}$ lactam, $C_{3-7}$ lactone or $C_{3-7}$ cyclic ketone, wherein the H on the C is optionally substituted with alkyl or halogen.

Preferably, $R_{11}$, $R_{12}$ are independently selected from: —H, —CF$_3$, —CHF$_2$H, —CH$_2$F, $C_{1-10}$ linear/branched alkyl, —CH=C(C$_{0-10}$ alkyl)(C$_{0-10}$ alkyl), $C_{3-10}$ cycloalkyl or six-membered heteroaryl, or $R_{11}$ and $R_{12}$ together with the atom(s) to which they are attached form a $C_{3-8}$ cycloalkyl, $C_{4-7}$ fused cycloalkyl, $C_{3-7}$ lactam, $C_{3-7}$ lactone or $C_{3-7}$ cyclic ketone, wherein the H on the C is optionally substituted with alkyl or F.

Preferably, $R_{11}$, $R_{12}$ are independently selected from: —H, —CF$_3$, —CHF$_2$H, —CH$_2$F, $C_{1-5}$ linear/branched alkyl, —CH=CH(C$_{0-10}$ alkyl), $C_{3-10}$ cycloalkyl or six-membered heteroaryl, or $R_{11}$ and $R_{12}$ together with the atom(s) to which they are attached form a $C_{3-6}$ cycloalkyl, $C_{4-6}$ fused cycloalkyl, $C_{3-7}$ lactam, $C_{3-7}$ lactone or $C_{3-7}$ cyclic ketone, wherein the H on the C is optionally substituted with alkyl or F.

In some preferred embodiments, $R_{11}$, $R_{12}$ are independently selected from:

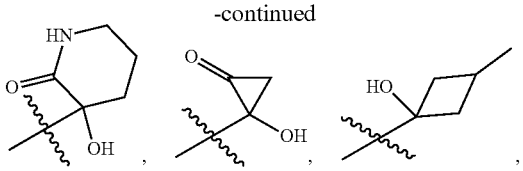

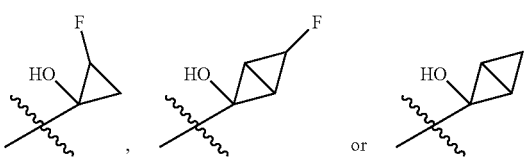

or $R_{11}$ and $R_{12}$ together with the atom(s) to which they are attached form:

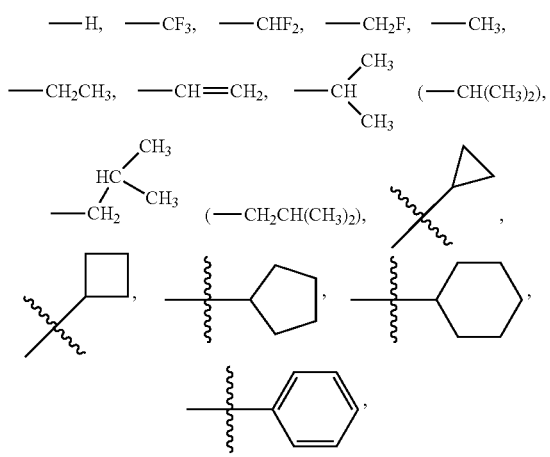

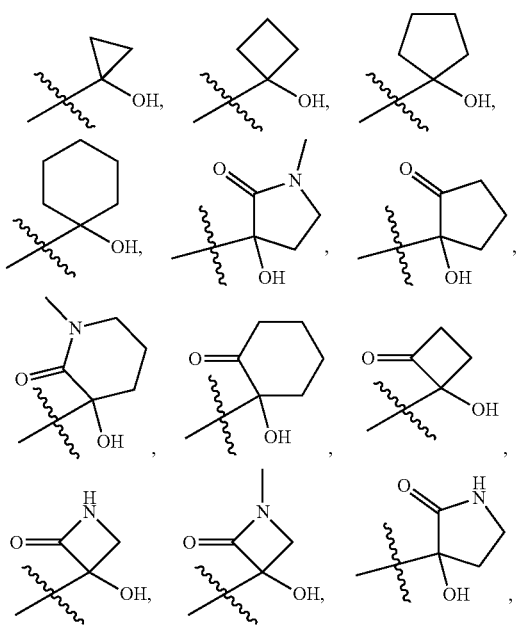

$R_5$, $R_6$, $R_7$ are independently selected from: —H, halogen, —CN, —OC$_{0-10}$ alkyl, C$_{0-10}$ linear/branched alkyl, —N(C$_{0-10}$ alkyl)(C$_{0-10}$ alkyl), $C_{3-10}$ cycloalkyl, —C≡C—$R_{10}$, —O heterocyclyl or —N heterocyclyl, or $R_6$ and $R_7$ together with the atom(s) to which they are attached form a $C_{3-8}$ cycloalkyl, $C_{3-8}$ heterocyclyl containing O or S, —N heteroaryl, —O heteroaryl, —S heteroaryl or phenyl, wherein the H on the C is optionally substituted with one or more of the following groups: —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, C$_{1-10}$ linear/branched alkyl, —N(C$_{0-10}$ alkyl)(C$_{0-10}$ alkyl), —OC$_{0-10}$ alkyl, $C_{3-10}$ cycloalkyl, —O heterocyclyl, —N heterocyclyl, —N heteroaryl, —O heteroaryl or —S heteroaryl.

Preferably, $R_5$, $R_6$, $R_7$ are independently selected from: —H, halogen, $C_{3-6}$ cycloalkyl, —OC$_{0-5}$ alkyl, $C_{1-5}$ linear/branched alkyl, $C_{1-5}$ linear/branched alkyl containing O or N, or $R_6$ and $R_7$ together with the atom(s) to which they are attached form a $C_{3-8}$ cycloalkyl, $C_{3-8}$ heterocyclyl containing O or S, wherein the H on the C is optionally substituted with F.

Preferably, $R_5$, $R_6$, $R_7$ are independently selected from: —H, halogen, —OC$_{0-3}$ alkyl, $C_{1-3}$ linear/branched alkyl, $C_{1-3}$ linear/branched alkyl containing N, or $R_6$ and $R_7$ together with the atom(s) to which they are attached form a $C_{3-8}$ cycloalkyl, $C_{3-8}$ heterocyclyl containing O, wherein the H on the C is optionally substituted with F.

In some preferred embodiments, $R_5$, $R_6$, $R_7$ are independently selected from —H, —F, —Cl, —CH$_3$, —CH$_2$NH$_2$, —CN or —OCH$_3$, or $R_6$ and $R_7$ together with the atom(s) to which they are attached form a five-membered cycloalkyl containing O.

$R_8$, $R_9$ are independently selected from: —H, halogen or $C_{1-10}$ linear/branched alkyl.

Preferably, $R_8$, $R_9$ are independently selected from: —H or C$_{0-10}$ linear/branched alkyl.

In some preferred embodiments, $R_8$, $R_9$ are independently selected from: —H or $C_{1-3}$ linear/branched alkyl.

In some preferred embodiments, $R_8$, $R_9$ are independently selected from —H or —CH$_3$.

Formula V

In one aspect, the present disclosed herein is a compound of formula (V):

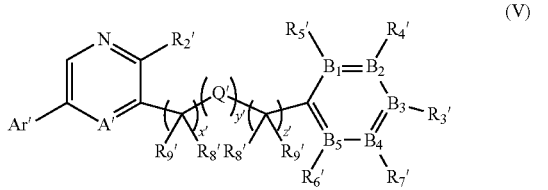

(V)

wherein, A' is C or N; $B_1$, $B_2$, $B_3$, $B_4$ or $B_5$ are independently selected from C or N.

Preferably, $B_1$, $B_2$, $B_3$, $B_4$ or $B_5$ is C, or at least one of $B_1$, $B_2$, $B_3$, $B_4$ or $B_5$ is N.

Preferably, when $B_2$ is C, at least one of $B_1$, $B_3$, $B_4$ or $B_5$ is N. In some embodiments, $B_2$ is C, $B_1$ is N, or $B_2$ is C, $B_3$ is N, or $B_2$ is C, $B_4$ is N, or $B_2$ is C, $B_5$ is N. In one embodiment, $B_2$ is C, $B_3$ and $B_4$ are N, or $B_3$ and $B_5$ are N.

Q' is O or S; x' and z' are integers from 0-6; y' is 0 or 1.

Preferably, x' and z' are integers from 0-2, such as 0, 1 or 2.

Ar' is five-membered heteroaryl, six-membered heteroaryl or phenyl, wherein the five-membered heteroaryl is selected from furanyl, thienyl, pyrrolyl, pyrazolyl, imidazolyl, oxazolyl or thiazolyl; the six-membered heteroaryl is selected from pyridyl, pyridazinyl, pyrimidinyl or pyrazinyl; wherein the H on the five-membered heteroaryl, six-membered heteroaryl or phenyl can be substituted with a group selected from —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{0-10}$ linear/branched alkyl, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —O heteroaryl or —S heteroaryl.

Preferably, at least one H on the five-membered heteroaryl, six-membered heteroaryl or phenyl is substituted with a group selected from: —$SO_2$, —$SO_2NH_2$, —$NHSO_2$, —$CONH(C_{0-10}$ alkyl), halogen, —CN, —$OCF_3$, —O heterocyclyl, —N heterocyclyl, $C_{1-10}$ linear/branched alkyl, —$OC_{0-10}$ alkyl, $C_{3-10}$ cycloalkyl, or —$N(C_{0-10}$ alkyl)($C_{0-10}$ alkyl). More preferably, at least one H on the five-membered heteroaryl, six-membered heteroaryl or phenyl is substituted with —O heterocyclyl or —N heterocyclyl.

In some preferred embodiments, Ar' is thiazolyl, selenothiazolyl, imidazolyl, pyrazolyl or pyridyl.

In some preferred embodiments, Ar' is

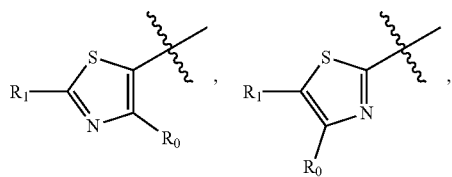

-continued

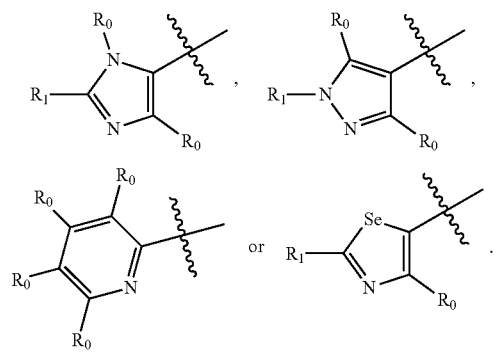

Preferably, the compound has a formula selected from the following:

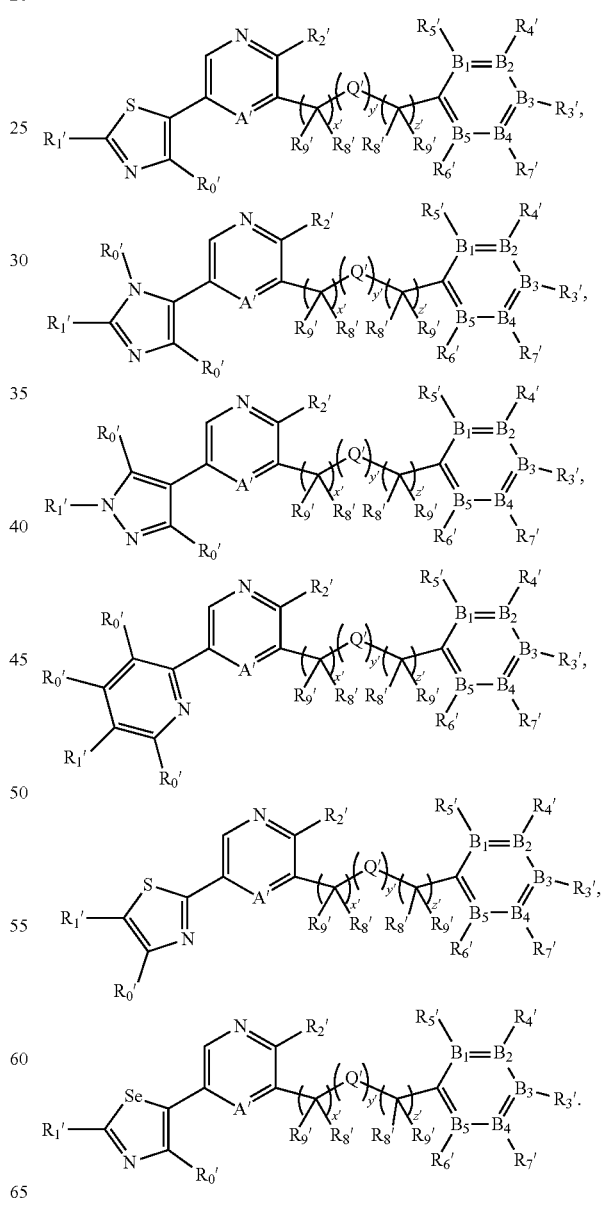

Preferably, the compound has the following formula:

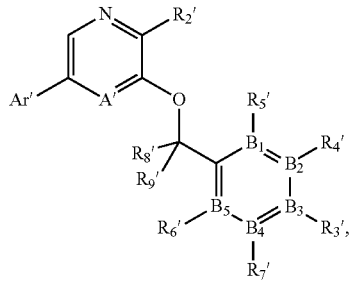

Preferably, the compound has one of the following formulae:

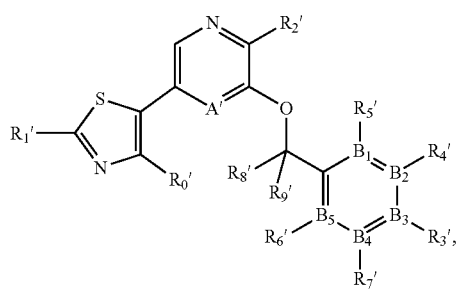

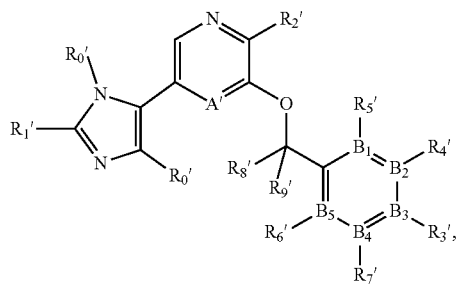

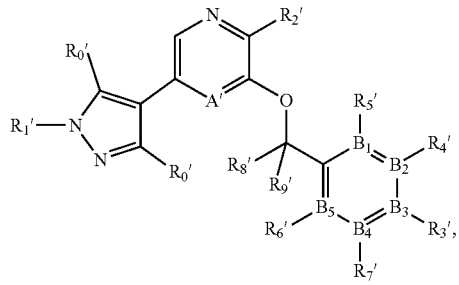

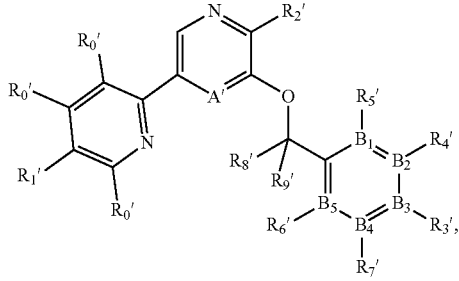

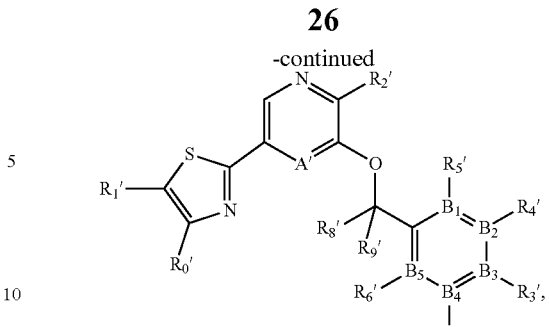

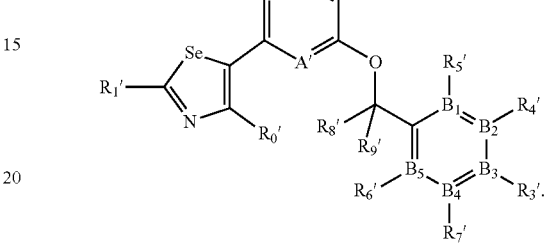

$R_0'$ is selected from: —H, $C_{1-10}$ linear/branched alkyl, —N($C_{0-10}$ alkyl)($C_{0-10}$ alkyl), —O$C_{0-10}$ alkyl or $C_{3-10}$ cycloalkyl.

Preferably, $R_0'$ is selected from: $C_{1-5}$ linear/branched alkyl or —N($C_{0-10}$ alkyl)($C_{0-10}$ alkyl).

In some preferred embodiments, $R_0'$ is —CH$_3$, —CH$_2$CH$_3$ or —NH$_2$.

$R_1'$ is selected from: —H, —O heterocyclyl, —N heterocyclyl, $C_{1-10}$ linear/branched alkyl, $C_{3-10}$ cycloalkyl, —O$C_{0-10}$ alkyl, —N($C_{0-10}$ alkyl)($C_{0-10}$ alkyl), —SO$_2$($C_{0-10}$ alkyl), —O($C_{0-10}$ alkyl), —O-phenyl, —S($C_{0-10}$ alkyl), —N heteroaryl, —O heteroaryl or —S heteroaryl, wherein the H on the C or hetero atom is optionally substituted with one group selected from $C_{1-3}$ linear alkyl, —N($C_{0-10}$ alkyl)($C_{0-10}$ alkyl), —CF$_3$.

Preferably, $R_1'$ is selected from: —O heterocyclyl, —N heterocyclyl, —SO$_2$ ($C_{0-3}$ alkyl), —O-phenyl, —S($C_{0-4}$ alkyl), $C_{3-6}$ cycloalkyl, $C_{3-5}$ linear/branched alkyl, wherein the H on the C or hetero atom is optionally substituted with —CH$_3$, —NH$_2$ or —CF$_3$.

In some preferred embodiments, $R_1'$ is selected from the followings:

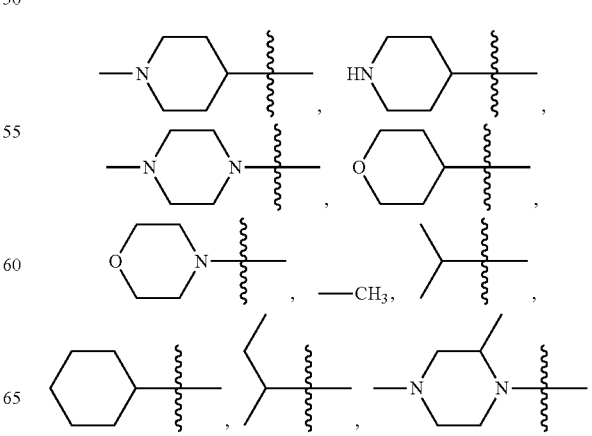

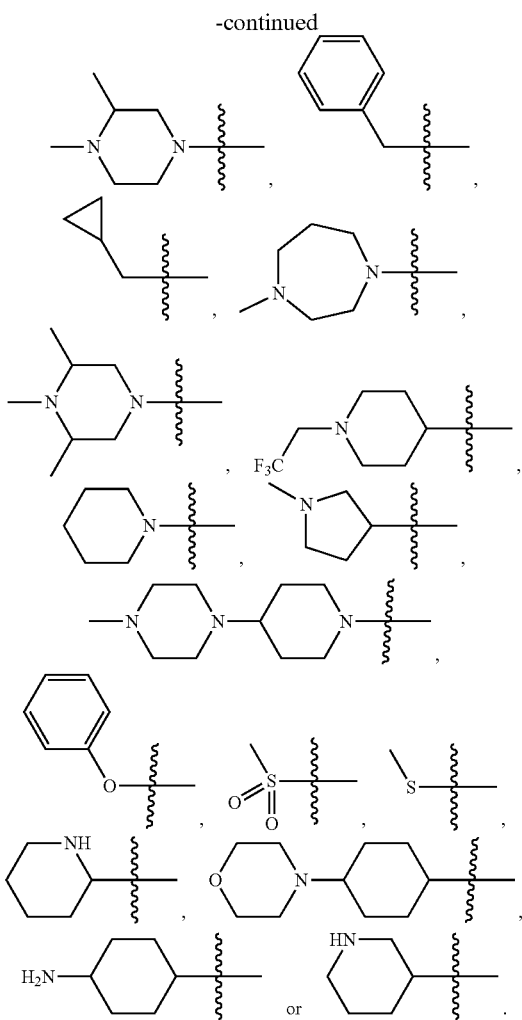

When $R_0'$ is adjacent to $R_1'$, $R_0'$ and $R_1'$ together with the atom(s) to which they are attached form a $C_{3-8}$ cycloalkyl, $C_{3-8}$ heterocyclyl containing 0 or S, —N heteroaryl, —O heteroaryl, —S heteroaryl or phenyl.

$R_2'$ is selected from: —H, halogen, —NO$_2$, —CN, $C_{1-5}$ linear/branched alkyl, $C_{3-10}$ cycloalkyl, —N($C_{0-10}$ alkyl)($C_{0-10}$ alkyl), —CF$_3$, —OCF$_3$, —OCHF$_2$, —OCH$_2$F or —OC$_{0-10}$ alkyl.

Preferably, $R_2'$ is selected from: —NO$_2$, —N($C_{0-10}$ alkyl)($C_{0-10}$ alkyl), —OCF$_3$, or —OC$_{0-10}$ alkyl.

In some preferred embodiments, $R_2'$ is —NH$_2$ or —NO$_2$.

When $B_1$, $B_2$, $B_3$, $B_4$ or $B_5$ is N, $R_3'$, $R_4'$, $R_5'$, $R_6'$ or $R_7'$ does not exist; When $B_1$, $B_2$, $B_3$, $B_4$ or $B_5$ is C, $R_3'$, $R_4'$, $R_5'$, $R_6'$ or $R_7'$ is independently selected from: —H, halogen, —CN, —OC$_{0-10}$ alkyl, C$_{0-10}$ linear/branched alkyl, —N(C$_{0-10}$ alkyl)(C$_{0-10}$ alkyl), C$_{3-10}$ cycloalkyl, —C≡C—R$_{10}$, —O heterocyclyl or —N heterocyclyl, or R$_5$ and R$_4$, R$_4$ and R$_3$, R$_3$ and R$_7$, or R$_7$ and R$_6$ together with the atom(s) to which they are attached form a $C_{3-8}$ cycloalkyl, $C_{3-8}$ heterocyclyl containing 0 or S, —N heteroaryl, —O heteroaryl, —S heteroaryl or phenyl, wherein the H on the C is optionally substituted with one or more of the following groups: —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, C$_{0-10}$ linear/branched alkyl, —N(C$_{0-10}$ alkyl)(C$_{0-10}$ alkyl), —OC$_{0-10}$ alkyl, C$_{3-10}$ cycloalkyl, —O heterocyclyl, —N heterocyclyl, —N heteroaryl, —O heteroaryl or —S heteroaryl.

Preferably, $R_3'$ is selected from: —H, halogen, —OC$_{0-10}$ alkyl, C$_{0-10}$ linear/branched alkyl, —N(C$_{0-10}$ alkyl)(C$_{0-10}$ alkyl), C$_{3-10}$ cycloalkyl.

Preferably, $R_3'$ is selected from: —H, halogen, —OC$_{0-10}$ alkyl or C$_{1-10}$ linear/branched alkyl.

In some preferred embodiments, $R_3'$ is —H, —F or —OCH$_3$.

$R_4'$ is selected from: —H, halogen, —OC$_{0-10}$ alkyl, —CN, $C_{3-10}$ cycloalkyl, —C≡C—R$_{10}$', $C_{1-10}$ linear/branched alkyl, —N(C$_{0-10}$ alkyl)(C$_{0-10}$ alkyl), —O heterocyclyl or —N heterocyclyl.

Preferably, $R_4'$ is selected from: —H, halogen, —OC$_{0-10}$ alkyl, —CN, $C_{3-10}$ cycloalkyl, —C≡C—R$_{10}$'.

In some preferred embodiments, $R_4'$ is selected from: —H, —F, —Cl, —OCH$_3$, —CN,

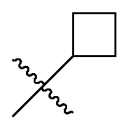 [SMILES: *C1CCC1]

or —C≡C—R$_{10}$'.

$R_5'$, $R_6'$, $R_7'$ are independently selected from: —H, halogen, —CN, —OC$_{0-10}$ alkyl, $C_1$-10 linear/branched alkyl, —N(C$_{0-10}$ alkyl)(C$_{0-10}$ alkyl), $C_{3-10}$ cycloalkyl, —C≡C—R$_{10}$', —O heterocyclyl or —N heterocyclyl, or R$_6'$ and R$_7'$ together with the atom(s) to which they are attached form a $C_{3-8}$ cycloalkyl, $C_{3-8}$ heterocyclyl containing O or S, wherein the H on the C is optionally substituted with F.

Preferably, $R_5'$, $R_6'$, $R_7'$ are independently selected from: —H, halogen, —OC$_{0-3}$ alkyl, $C_{1-3}$ linear/branched alkyl, $C_{1-3}$ linear/branched alkyl containing or N, or R$_6'$ and R$_7'$ together with the atom(s) to which they are attached form a $C_{3-8}$ cycloalkyl, $C_{3-8}$ heterocyclyl containing O or S, wherein the H on the C is optionally substituted with F.

In some preferred embodiments, $R_5'$, $R_6'$, $R_7'$ are independently selected from —H, —F, —Cl, —CH$_3$, —CH$_2$NH$_2$, —CN or —OCH$_3$, or R$_6$, and R$_7'$ together with the atom(s) to which they are attached form a five-membered cycloalkyl containing O.

$R_{10}'$ is selected from: H, $C_{1-5}$ linear/branched alkyl, $C_{3-10}$ cycloalkyl or

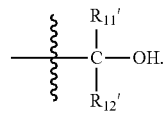

Preferably, $R_{11}'$, $R_{12}'$ are independently selected from: —H, —CF$_3$, —CHF$_2$H, —CH$_2$F, $C_{1-10}$ linear/branched alkyl, —CH=C(C$_{0-10}$ alkyl)(C$_{0-10}$ alkyl), $C_{3-10}$ cycloalkyl five-membered heteroaryl or six-membered heteroaryl, or $R_{11}'$ and $R_{12}'$ together with the atom(s) to which they are attached form a $C_{3-8}$ cycloalkyl, $C_{3-8}$ heterocyclyl containing O or S, $C_{4-9}$ fused cycloalkyl, $C_{5-10}$ spiro cycloalkyl, $C_{4-9}$ bridged cycloalkyl, $C_{3-7}$ lactam, $C_{3-7}$ lactone or $C_{3-7}$ cyclic ketone, wherein the H on the C is optionally substituted with a group selected from —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, C$_{0-10}$ linear/branched alkyl, —N(C$_{0-10}$ alkyl)(C$_{0-10}$ alkyl), —OC$_{0-10}$ alkyl, C$_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, —N(C$_{0-10}$ alkyl)(C$_{0-10}$ alkyl), —OC$_{0-10}$ alkyl, C$_{3-10}$ cycloalkyl, —O heterocyclyl, —N heteroaryl, —O heteroaryl or —S heteroaryl.

Preferably, R$_{11}$', R$_{12}$' are independently selected from: —H, —CF$_3$, —CHF$_2$H, —CH$_2$F, C$_{1-10}$ linear/branched alkyl, —CH=C(C$_{0-10}$ alkyl)(C$_{0-10}$ alkyl), C$_{3-10}$ cycloalkyl or six-membered heteroaryl, or R$_{11}$' and R$_{12}$' together with the atom(s) to which they are attached form a C$_{3-8}$ cycloalkyl, C$_{4-9}$ fused cycloalkyl, C$_5$-10 spiro cycloalkyl, C$_{4-9}$ bridged cycloalkyl, C$_{3-7}$ lactam, C$_{3-7}$ lactone or C$_{3-7}$ cyclic ketone, wherein the H on the C is optionally substituted with one group selected from —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, C$_{1-10}$ linear/branched alkyl, —N(C$_{0-10}$ alkyl)(C$_{0-10}$ alkyl), —OC$_{0-10}$ alkyl, C$_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, —N(C$_{0-10}$ alkyl)(C$_{0-10}$ alkyl), —OC$_{0-10}$ alkyl, C$_{3-10}$ cycloalkyl, —O heterocyclyl, —N heteroaryl, —O heteroaryl or —S heteroaryl.

Preferably, R$_{11}$', R$_{12}$' are independently selected from: —H, —CF$_3$, —CHF$_2$H, —CH$_2$F, C$_{1-5}$ linear/branched alkyl, —CH=CH(C$_{1-10}$ alkyl), C$_{3-10}$ cycloalkyl or six-membered heteroaryl, or R$_{11}$' and R$_{12}$' together with the atom(s) to which they are attached form a C$_{3-6}$ cycloalkyl, C$_{4-6}$ fused cycloalkyl, C$_{5-8}$ spiro cycloalkyl, C$_{4-8}$ bridged cycloalkyl, C$_{3-7}$ lactam, C$_{3-7}$ lactone or C$_{3-7}$ cyclic ketone, wherein the H on the C is optionally substituted with a group selected from —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, C$_{1-10}$ linear/branched alkyl, —N(C$_{0-10}$ alkyl)(C$_{0-10}$ alkyl), —OC$_{0-10}$ alkyl, C$_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, —N(C$_{0-10}$ alkyl)(C$_{0-10}$ alkyl), —OC$_{0-10}$ alkyl, C$_{3-10}$ cycloalkyl, —O heterocyclyl, —N heteroaryl, —O heteroaryl or —S heteroaryl.

In some preferred embodiments, R$_{11}$', R$_{12}$' are independently selected from:

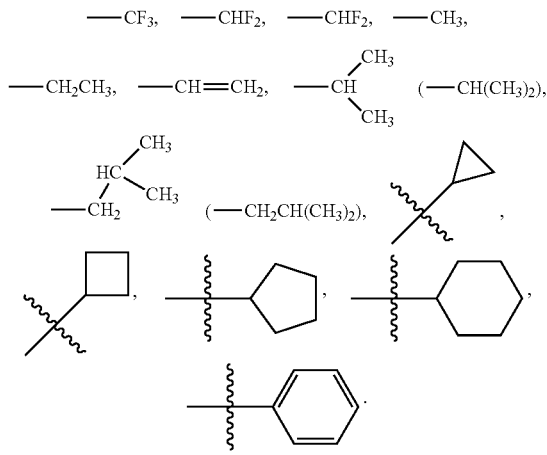

or R$_{11}$' and R$_{12}$' together with the atom(s) to which they are attached form:

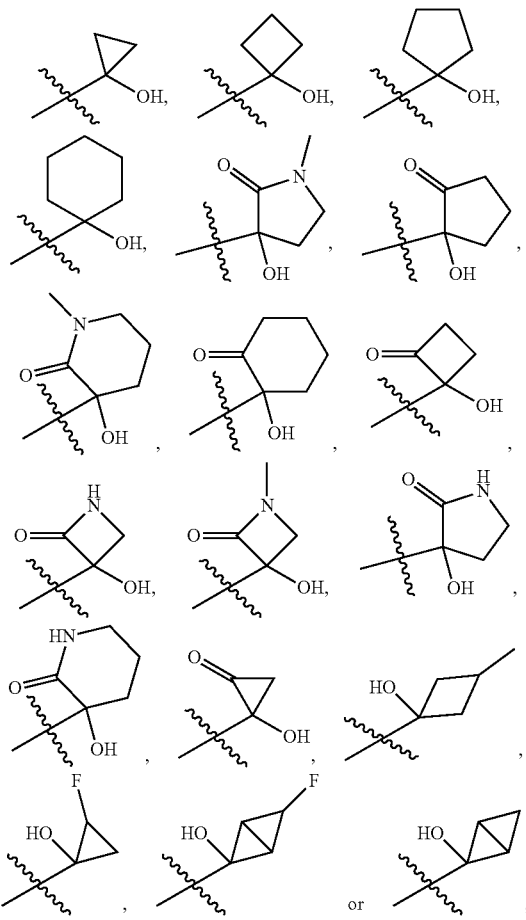

R$_8$', R$_9$' are independently selected from the followings: —H, halogen or C$_{1-10}$ linear/branched alkyl.

Preferred, R$_8$', R$_9$' are independently selected from the followings: —H or C$_{1-10}$ linear/branched alkyl.

In some preferred embodiments, R$_8$', R$_9$' are independently selected from the followings: —H or C$_{1-3}$ linear/branched alkyl.

In some preferred embodiments, $R_8'$, $R_9'$ are independently selected from —H or —CH$_3$.

In one embodiment, the present disclosure provides a compound selected from any one of the specifically drawn compounds in Embodiment 15 in the Exemplary Embodiments section.

The compounds of the present disclosure (e.g., Formulae I, II, V, X, Y or Z, or any of the compounds A1 to A85, or any one of the specifically drawn compounds in Embodiment 15 in the Exemplary Embodiments section) also include pharmaceutically acceptable salt, stereoisomer, ester, prodrug, solvate or deuterated compound thereof.

The pharmaceutically acceptable salts include acid addition salts and base addition salts.

Acid addition salt include inorganic acid salts and organic acid salts. The inorganic acid salts include, but are not limited to, salts of hydrochloric acid, nitric acid, phosphoric acid, sulfuric acid, hydrobromic acid, hydroiodic acid, and phosphonic acid. Organic acid salts include, but are not limited to, salts of aliphatic monocarboxylic acid, aliphatic dicarboxylic acid, phenyl alkanoic acid, hydroxyalkanoic acid, alkanedioic acid and sulfonic acid. More particularly, the acid addition salt include one or more of the following: sulfates, pyrosulfate, hydrogen sulfates, sulfites, bisulfites, nitrates, monohydrogen phosphate, dihydrogen phosphate, metaphosphate, pyrophosphate, hydrochloride, hydrobromide, iodate, acetate, propionate, octoate, isobutyrate, oxalate, malonate, succinate, suberate, sebacate, fumarate, maleate, amygdalate, benzoate, chlorobenzoate, benzoate, tosylate, phenylacetate, citrate, lactate, maleate, tartrate, methanesulfonate, and salt of arginine, glucose acid, galacturonic acid. The acid addition salt can be prepared by methods well known in the art.

The base addition salts include hydroxides of alkali metal and alkaline earth metal, or organic ammonium salts. Alkali metal and alkaline earth metal salts include, but are not limited to, sodium, potassium, magnesium or calcium salts. Examples of amine salts include, but are not limited to, N,N'-dibenzylethylenediamine, chloroprocaine, choline, diethanolamine, ethylenediamine (ethane-1,2-diamine), N-methyl glucosamine and procaine salts. The base addition salts can be prepared by methods well known in the art.

Stereoisomers herein includes enantiomers, diastereomers and geometric isomers. The present disclosure is meant to include all such possible isomers, including racemic mixtures, scalemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

"Solvate" refers to a physical association of the compound disclosed herein with one or more solvent molecules. The physical association includes electrostatic adsorption, covalent bonding and hydrogen bonding. In some cases, the solvate can be isolated, for example, when one or more solvent molecules are incorporated into the crystal lattice of the crystalline solid. "Solvate" includes solution phases and isolatable solvates, the representative solvates include ethanolates, methanolates etc. "Hydrate" is a solvate in which one or more solvent molecules are H$_2$O.

Prodrug refers to chemically-modified versions of a pharmacologically active compound that undergo in vivo chemical or enzymatic transformation to release the active compound described herein. More specifically, functional moieties amenable to chemical or enzymatic transformation are attached to pharmacologically active compounds to improve drug targeting.

Method of Synthesis

Compounds of the present disclosure can be prepared by those skilled in the art in view of this application. Representative synthetic procedures are described in the Examples section.

For example, in some embodiments, compounds of Formula X can be prepared by a method as shown in Scheme 1. In some embodiments, the method can comprise coupling a compound of S-1, wherein $G^1$ is a leaving group, such as a halo or an oxygen leaving group such as tosylate, mesylate, triflate, etc., with a compound of S-2, wherein $G^2$ is a metal ion (Zn, Mg, etc., i.e., Ar-$G^2$ is an organozinc or organomagnesium reagent, etc.), boronic acid or ester residue (e.g., —B(OH)$_2$, or

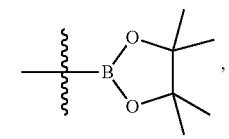 [SMILES: *B1OC(C)(C)C(C)(C)O1]

etc., i.e., Ar-$G^2$ is an organoboron reagent with the boron atom attached directly to the Ar), tin (such as —SnBu$_3$, i.e., Ar-$G^2$ is an organotin reagent), or other suitable coupling partners. The cross coupling is typically carried out with a palladium catalyst to yield a compound of S-3, which can be followed by reduction of the nitro group to provide a compound of Formula X. In some embodiments, the role of the coupling partners S-1 and S-2 can change. For example, in some embodiments, the compound of S-1 can have a $G^1$ as a metal ion (Zn, Mg, etc.), boronic acid or ester residue (e.g., —B(OH)$_2$, or

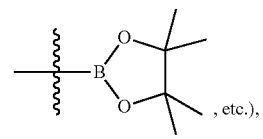

, etc.), tin (such as —SnBu$_3$), or other suitable coupling partners, whereas the compound of S-2 include a $G^2$, which is a leaving group, such as a halo or an oxygen leaving group such as tosylate, mesylate, triflate, etc. Representative conditions for the cross coupling reaction and the reduction are shown in the Examples section. The variables A, Ar, L, and Cy$^1$ in scheme 1 are as defined and preferred herein.

Scheme 1

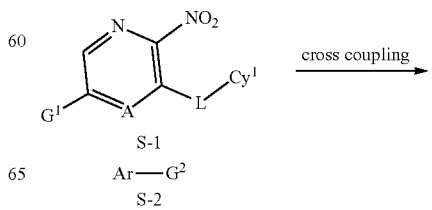

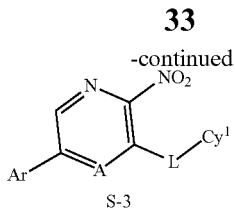

S-3 reduction →

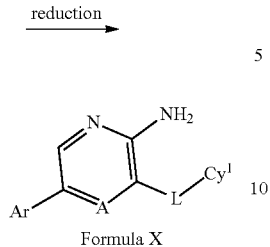

Formula X

In some embodiments, compounds of Formula X can also be prepared by following a method shown in Scheme 2. For example, in some embodiments, the method can include coupling a compound of S-4, wherein $G^{10}$ and $G^{11}$ are each independently hydrogen or a nitrogen protecting group, such as Boc, and $G^3$ is a metal ion (Zn, Mg, etc.), boronic acid or ester residue (e.g., —B(OH)$_2$, or

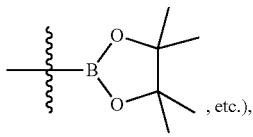 [SMILES: *B1OC(C)(C)C(C)(C)O1]
, etc.), tin (such as —SnBu$_3$), or other suitable coupling partners, with a compound of S-5, wherein $G^4$ is a leaving group, such as a halo or an oxygen leaving group such as tosylate, mesylate, triflate, etc. Similarly, the roles of the coupling partners S-4 and S-5 can change. For example, in some embodiments, $G^4$ in compound S-5 can be a metal ion (Zn, Mg, etc.), boronic acid or ester residue (e.g., —B(OH)$_2$, or

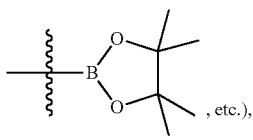 [SMILES: *B1OC(C)(C)C(C)(C)O1]
, etc.), tin (such as —SnBu$_3$), or other suitable coupling partners, whereas $G^3$ in compound S-4 is a leaving group. The cross coupling is typically carried out with a palladium catalyst to provide a compound of S-6, which can be followed by deprotection to provide a compound of Formula X. Representative conditions for the cross coupling and deprotection are shown in the Examples section. The variables A, Ar, L, and Cy$^1$ in scheme 2 are as defined and preferred herein.

Scheme 2

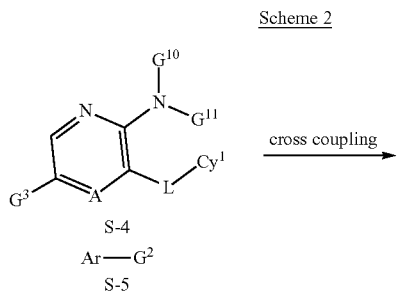

S-4

Ar—G$^2$

S-5 cross coupling →

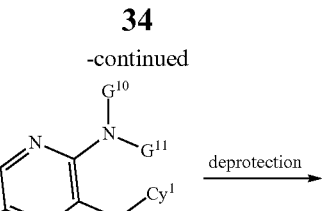

S-6 deprotection →

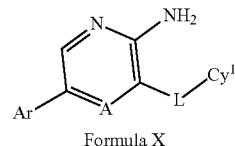

Formula X

Compounds of Formula Y can also be synthesized similarly. For example, as shown in Scheme 3, in some embodiments, a compound of Y-1, wherein $G^6$ is hydrogen or a oxygen protecting group such as tetrahydropyranyl (THP), $G^5$ is a leaving group, such as a halo or an oxygen leaving group such as tosylate, mesylate, triflate, etc., can be coupled with a compound of Y-2, wherein $G^7$ is a metal ion (Zn, Mg, etc.), boronic acid or ester residue (e.g., —B(OH)$_2$, or

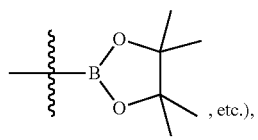
, etc.), tin (such as —SnBu$_3$), or other suitable coupling partners, with a palladium catalyst, to yield a compound of Y-3, which can be followed by reduction of the nitro group and optionally deprotection, e.g., when $G^6$ is an oxygen protecting group, to provide a compound of Formula Y. Similarly, the roles of the coupling partners Y-1 and Y-2 can change. For example, in some embodiments, $G^5$ of Y-1 can be a metal ion (Zn, Mg, etc.), boronic acid or ester residue (e.g., —B(OH)$_2$, or

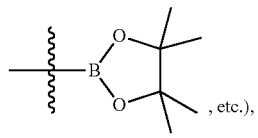
, etc.), tin (such as —SnBu$_3$), or other suitable coupling partners, and $G^7$ in Y-2 can be a leaving group, such as a halo or an oxygen leaving group such as tosylate, mesylate, triflate, etc. Representative conditions for the cross coupling reaction, the reduction and deprotection are shown in the Examples section. The variables A, Ar, L, ring B, $R^A$, $R^B$, $R^C$, and n in scheme 3 are as defined and preferred herein.

Scheme 3

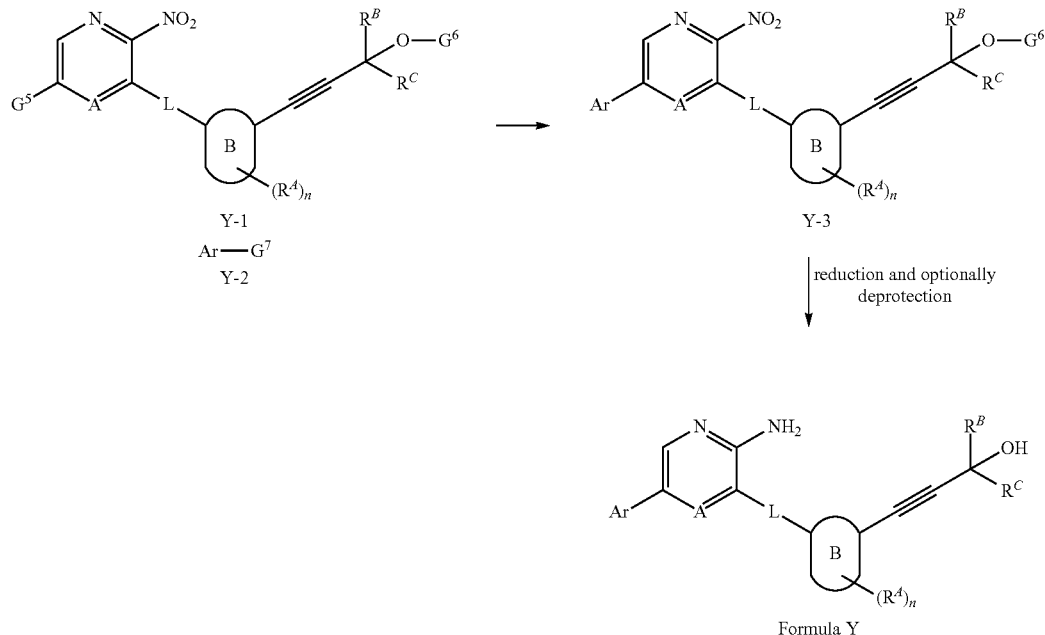

In some embodiments, compounds of Formula Y can also be prepared according to a method of Scheme 4. In some embodiments, a compound of Y-4, wherein $G^{12}$ and $G^{13}$ are each independently hydrogen or a nitrogen protecting group, such as Boc, $G^6$ is hydrogen or a oxygen protecting group such as tetrahydropyranyl (THP), and $G^8$ is a metal ion (Zn, Mg, etc.), boronic acid or ester residue (e.g., —B(OH)$_2$, or

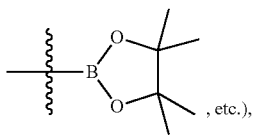 [SMILES: *B1OC(C)(C)C(C)(C)O1]

tin (such as —SnBu$_3$), or other suitable coupling partners, can be coupled with a compound of Y-5, wherein $G^9$ is a leaving group, such as a halo or an oxygen leaving group such as tosylate, mesylate, triflate, etc., with a palladium catalyst, to yield a compound of Y-6, which can be followed by deprotection to provide a compound of Formula Y. Similarly, in some embodiments, Y-5 can be a coupling partner with $G^9$ as a metal ion (Zn, Mg, etc.), boronic acid or ester residue (e.g., —B(OH)$_2$, or

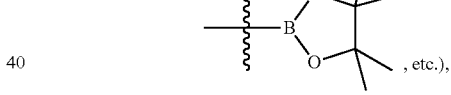

tin (such as —SnBu$_3$), or other suitable coupling partner, whereas Y-4 is a coupling partner with a leaving group as $G^8$. Representative conditions for the cross coupling reaction, and deprotection are shown in the Examples section. The variables A, Ar, L, ring B, $R^A$, $R^B$, $R^C$, and n in scheme 4 are as defined and preferred herein.

Scheme 4

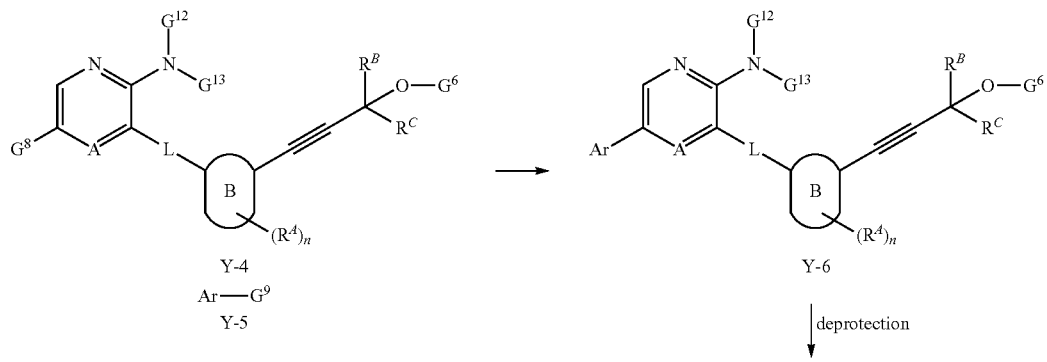

-continued

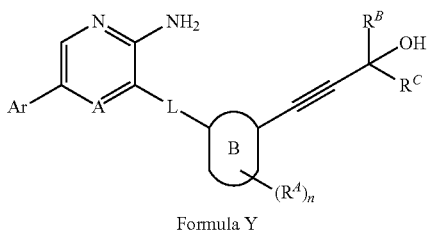

Formula Y

In some embodiments, the $Cy^1$ unit in Formula Y can be introduced at a later stage of a synthetic sequence. For example, as shown in Scheme 5, in some embodiments, a compound of Z-1, wherein $G^{20}$ is $NO_2$, $NH_2$ or protected $NH_2$, can react with a suitable $Cy^1$ molecule, which can form a compound of Formula X after optional reduction and/or deprotection. For example, in some embodiments, $L^{10}$ is OH, and a Mitsunobu reaction with $Cy^1$—OH can provide an intermediate, which can be converted into a compound of Formula X after optional reduction and/or deprotection. The variables A, Ar, L, and $Cy^1$ in scheme 5 are as defined and preferred herein.

Scheme 6, in some embodiments, a compound of Z-2, wherein $G^{20}$ is $NO_2$, $NH_2$ or protected $NH_2$, and $G^{21}$ is a leaving group, such as a halo or an oxygen leaving group such as tosylate, mesylate, triflate, etc., can couple with a molecule of Z-3 to provide a compound of Z-4. Typically, such coupling reaction can be mediated by palladium and/or copper catalysis. Exemplary conditions are shown in the examples section. Z-4 can then be deprotected or reduced and then deprotected to provide a compound of Formula Y. The variables A, $G^6$, Ar, L, ring B, $R^A$, $R^B$, $R^C$, and n in scheme 6 are as defined and preferred herein.

Scheme 6

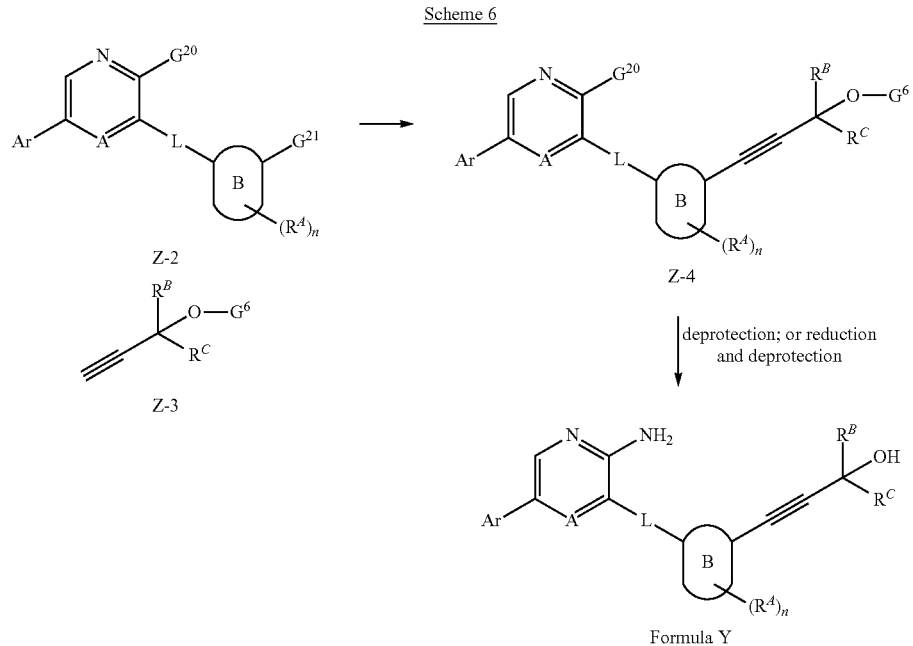

Scheme 5

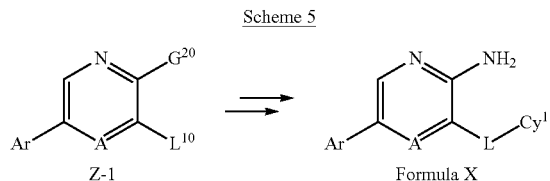

As will be apparent to those skilled in the art in view of this disclosure, in some embodiments, the substituents on Ar or $Cy^1$ can be introduced at a different stage as shown in the schemes herein. For example, the alkynyl unit in formula Y can be introduced at a later stage of synthesis. As shown in Compounds of Formula Z can be synthesized similarly to compounds of Formula Y. As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4$^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wis., USA), Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7$^{th}$ Edition), and Larock's Comprehensive Organic Transformations (Wiley-VCH, 1999).

In one aspect, the present disclosure provides a preparation method of a compound of formula (I), the steps of the method are as follows:

(1) reacting

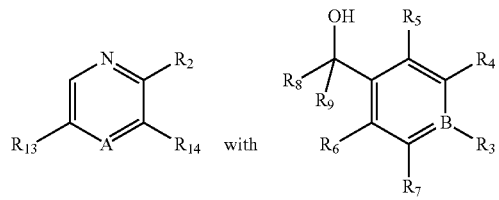

to form

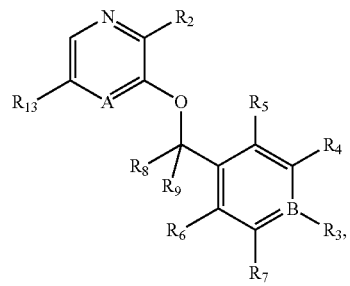

wherein $R_{13}$ is halogen or

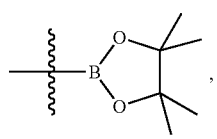 [SMILES: *B1OC(C)(C)C(C)(C)O1]

$R_{14}$ is —OH or —F.

(2) reacting

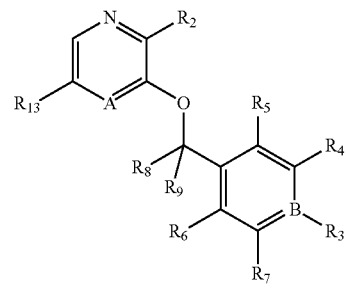

with Ar—$R_{15}$ to form

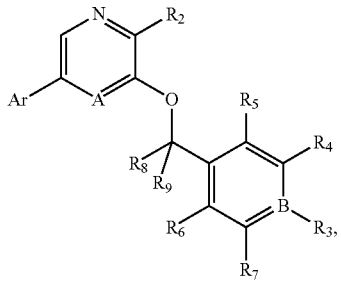

wherein $R_{15}$ is —Br or —SnBu$_3$.

Preferably, in the step (1), $R_{13}$ is —Br.

Preferably, in the step (2), $R_{13}$ is —Br or

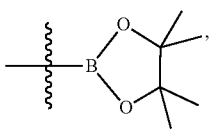 [SMILES: *B1OC(C)(C)C(C)(C)O1]

when $R_{13}$ is —Br, $R_{15}$ is —SnBu$_3$, and when $R_{13}$ is

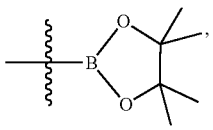

$R_{15}$ is —Br.

In one aspect, the present invention provides a compound of formula (III):

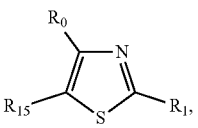

(III)

wherein $R_{15}$ is —Br or —SnBu$_3$, the definitions of $R_0$ and $R_1$ are as described above.

In one aspect, the present invention provides a compound of formula (IV):

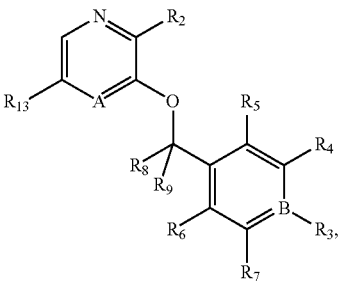

(IV)

wherein $R_{13}$ is halogen or

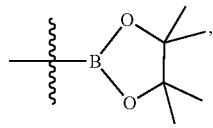 [SMILES: *B1OC(C)(C)C(C)(C)O1]

the definitions of $R_2$ to $R_9$ are as described above. Preferred, $R_{13}$ is —Br.

In one aspect, the present disclosure provides a preparation method of a compound of formula (V), the steps of the method are as follows:

(1) reacting

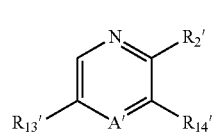 with 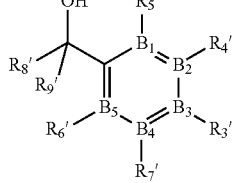

to form

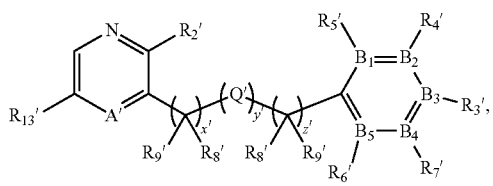

wherein $R_{13}'$ is halogen or

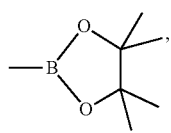

$R_{14}'$ is —OH or —F.

(2) reacting

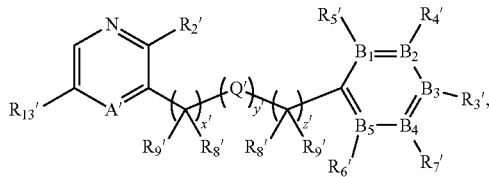

with Ar'—$R_{15}'$ to form

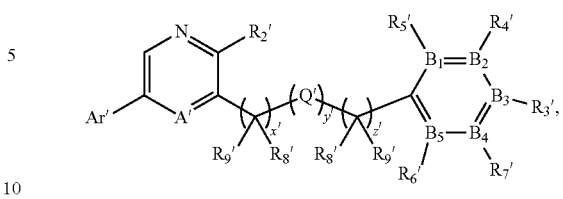

wherein $R_{15}'$ is —Br or —SnBu$_3$.

Preferably, in the step (1), $R_{13}'$ is —Br.
Preferably, in the step (2), $R_{13}'$ is —Br or

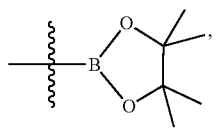 [SMILES: *B1OC(C)(C)C(C)(C)O1]

when $R_{13}'$ is —Br, $R_{15}'$ is —SnBu$_3$, and when $R_{13}'$ is

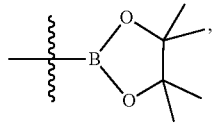 [SMILES: *B1OC(C)(C)C(C)(C)O1]

$R_{15}'$ is —Br.

In one aspect, the present invention also provides a compound of formula (VI):

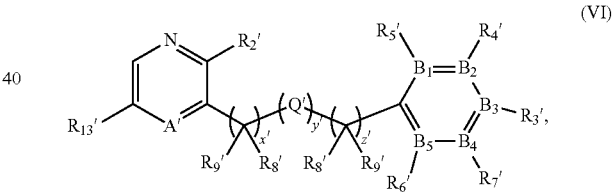

(VI)

wherein, A' is C or N; $B_1$, $B_2$, $B_3$, $B_4$ or $B_5$ are independently selected from C or N.

Q' is O or S; x' and z' are integers from 0-6; y' is 0 or 1.

$R_2'$ is selected from: —H, halogen, —NO$_2$, —CN, $C_{1-5}$ linear/branched alkyl, $C_{3-10}$ cycloalkyl, —N($C_{0-10}$ alkyl)($C_{0-10}$ alkyl), —CF$_3$, —OCF$_3$, —OCHF$_2$, —OCH$_2$F or —OC$_{0-10}$ alkyl.

When $B_1$, $B_2$, $B_3$, $B_4$ or $B_5$ is N, $R_3$, $R_4'$, $R_5'$, $R_6'$ or $R_7'$ does not exist; When $B_1$, $B_2$, $B_3$, $B_4$ or $B_5$ is C, $R_3'$ is selected from: —H, halogen, —OC$_{0-10}$ alkyl, $C_{1-10}$ linear/branched alkyl, —N($C_{0-10}$ alkyl)($C_{0-10}$ alkyl), $C_{3-10}$ cycloalkyl.

$R_4'$ is selected from: —H, halogen, —OC$_{0-10}$ alkyl, —CN, $C_{3-10}$ cycloalkyl, —C≡C—$R_{10}'$, $C_{1-10}$ linear/branched alkyl, —N($C_{0-10}$ alkyl)($C_{0-10}$ alkyl), —O heterocyclyl or —N heterocyclyl.

$R_5'$, $R_6'$, $R_7'$ are independently selected from: —H, halogen, —CN, —OC$_{0-10}$ alkyl, $C_{1-10}$ linear/branched alkyl, —N($C_{0-10}$ alkyl)($C_{0-10}$ alkyl), $C_{3-10}$ cycloalkyl, —C≡C—$R_{10}'$, —O heterocyclyl or —N heterocyclyl.

$R_8'$, $R_9'$ are independently selected from: —H, halogen or $C_{1-10}$ linear/branched alkyl.

$R_{13}'$ is halogen or

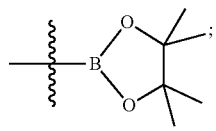

$R_{10}'$ is selected from: H, $C_{1-5}$ linear/branched alkyl, $C_{3-10}$ cycloalkyl or

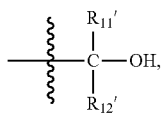

Preferred, $R_{11}'$, $R_{12}'$ are independently selected from: —H, —CF$_3$, $C_{1-10}$ linear/branched alkyl, —CH=C($C_{1-10}$ alkyl)($C_{0-10}$ alkyl), $C_{3-10}$ cycloalkyl five-membered heteroaryl or six-membered heteroaryl, or $R_{11}'$ and $R_{12}'$ together with the atom(s) to which they are attached form a $C_{3-8}$ cycloalkyl.

Pharmaceutical Compositions and Methods of Use

As shown in the Examples, representative compounds of the present disclosure are shown to inhibit HPK1 activity. The structure and activity relationship presented herein also shows that compounds having either a pyridine or pyrazine core, and having various Ar, Cy$^1$, and L are useful as HPK1 inhibitors. In one aspect, the present disclosure provides a pharmaceutical composition comprising a compound of the present disclosure (e.g., Formula I, Formula II, Formula V, Formula X, Formula Y, Formula Z, any subformulae thereof, or any of compounds A1 to A85, or pharmaceutically acceptable salt thereof), and a pharmaceutically acceptable excipient selected from: carrier, diluent, binder, lubricant and moisturizer agent. Preferably, the pharmaceutical composition comprises a therapeutically effective amount of a compound of the present disclosure (e.g., Formula I, Formula II, Formula V, Formula X, Formula Y, Formula Z, any subformulae thereof, or any of compounds A1 to A85, or pharmaceutically acceptable salt thereof). In some embodiments, these pharmaceutical compositions are useful for treating diseases associated with HPK1. The compound of the present disclosure (e.g., Formula I, Formula II, Formula V, Formula X, Formula Y, Formula Z, any subformulae thereof, or any of compounds A1 to A85, or pharmaceutically acceptable salt thereof) can be incorporated into pharmaceutical compositions which are useful for the cancer or disorder caused by HPK1.

The compound of the present disclosure (e.g., Formula I, Formula II, Formula V, Formula X, Formula Y, Formula Z, any subformulae thereof, or any of compounds A1 to A85, or pharmaceutically acceptable salt thereof) can be prepared into pharmaceutical compositions in the form of syrups, suspensions, powders, granules, tablets, capsules, aqueous solutions, creams, ointments, lotions, gels, emulsions, etc.

Preferably, the pharmaceutical composition is unit dosage form. The unit dosage form can be a packaged preparation containing a fixed amount of the compound of the present disclosure (e.g., Formula I, Formula II, Formula V, Formula X, Formula Y, Formula Z, any subformulae thereof, or any of compounds A1 to A85, or pharmaceutically acceptable salt thereof), which can be a capsule, a tablet, or a powder packaged in a vial or ampule. The amount of active ingredient in a unit dosage form can vary from 0.1 mg to 1000 mg, depending on the particular application and potency of the active ingredient. The composition may also contain other suitable therapeutic agents if desired.

The pharmaceutically acceptable carrier depends on the particular method of administration of the compound disclosed in the present. Therefore, the pharmaceutical compositions of the present are prepared in various dosage forms.

The compound of the present disclosure (e.g., Formula I, Formula II, Formula V, Formula X, Formula Y, Formula Z, any subformulae thereof, or any of compounds A1 to A85, or pharmaceutically acceptable salt thereof), or in combination with other suitable components, can be formulated as aerosols (i.e., they can be "atomized"), which are administered via inhalation. The aerosol can be placed in propellant selected from the group consisting of dichlorodifluorohexane, propane, nitrogen, etc.

Pharmaceutical composition suitable for parenteral administration such as intravenous, intramuscular, intradermal and subcutaneous routes include aqueous or non-aqueous isotonic sterile injections, which may contain antioxidants, buffers, bacteriostatic agents and isotonic solutes; as well as aqueous or nonaqueous sterile suspensions, which may contain suspending agents, solubilizers, thickening agents, stabilizers and preservatives. In some embodiments, the compound of the present disclosure (e.g., Formula I, Formula II, Formula V, Formula X, Formula Y, Formula Z, any subformulae thereof, or any of compounds A1 to A85, or pharmaceutically acceptable salt thereof) can be administered by intravenous infusion, orally, topically, intraperitoneally, intravesically, and intrathecally. The compositions can be presented in unit dose or multi-dose sealed containers such as ampoules or vials. The solutions and suspensions for injection can be prepared from sterile powders, granules and tablets as described above.

Effective amount refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated.

In one aspect, the present disclosure provides a use of a composition comprising a compound of the present disclosure (e.g., Formula I, Formula II, Formula V, Formula X, Formula Y, Formula Z, any subformulae thereof, or any of compounds A1 to A85, or pharmaceutically acceptable salt thereof, stereoisomer, ester, prodrug, solvate or deuterated compound thereof) for the prevention and/or treatment of cancer.

In one aspect, the present disclosure provides a use of a composition comprising a compound of the present disclosure (e.g., Formula I, Formula II, Formula V, Formula X, Formula Y, Formula Z, any subformulae thereof, or any of compounds A1 to A85, or pharmaceutically acceptable salt thereof, stereoisomer, ester, prodrug, solvate or deuterated compound thereof) for manufacturing a medicament for the prevention and/or treatment of cancer.

In one aspect, the present disclosure provides a use of a composition comprising a compound of the present disclosure (e.g., Formula I, Formula II, Formula V, Formula X, Formula Y, Formula Z, any subformulae thereof, or any of compounds A1 to A85, or pharmaceutically acceptable salt thereof, stereoisomer, ester, prodrug, solvate or deuterated compound thereof), in combination with PD-1, PD-L1, CTLA-4, TIM-3, TLR4, TLR7, TLR8, TLR9, TGF-β and its receptor, LAG3 antagonist or STING agonists, in a cancer immunotherapy.

The cancer of the present disclosure can be a carcinoma selected from: lymphoma, blastoma, medulloblastoma, retinoblastoma, sarcoma, liposarcoma, synovial cell sarcoma, neuroendocrine tumors, carcinoid tumors, gastrinoma, islet cell cancer, mesothelioma, schwannoma, acoustic neuroma, meningioma, adenocarcinoma, melanoma, leukemia or lymphoid malignancies, squamous cell cancer, epithelial squamous cell cancer, lung cancer, small-cell lung cancer (SCLC), non-small cell lung cancer (NSCLC), adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, metastatic breast cancer, colon cancer, rectal cancer, colorectal cancer, endometrial or uterine carcinoma, salivary gland carcinoma, kidney or renal cancer, prostate cancer, vulval cancer, thyroid cancer, anal carcinoma, penile carcinoma, Merkel cell cancer, esophageal cancer, tumors of the biliary tract, head and neck cancer, and hematological malignancies.

In one aspect, the present disclosure provides a use of a composition comprising a compound of the present disclosure (e.g., Formula I, Formula II, Formula V, Formula X, Formula Y, Formula Z, any subformulae thereof, or any of compounds A1 to A85, or pharmaceutically acceptable salt thereof, stereoisomer, ester, prodrug, solvate or deuterated compound thereof), in combination with CAR-T immunotherapy, in cancer immunotherapy.

The CAR-T immunotherapy refers to chimeric antigen receptor T cell immunotherapy, which is one of the treatment methods for malignant tumors at present, and the basic principle is to use the patient's own immune cells to remove cancer cells, belonging to a cell therapy. Unlike traditional medicines, CAR-T has potential to eradicate widespread cancer and provides long-term protection in the form of immunologic memory.

In some embodiments, the present disclosure provides a method of inhibiting HPK1 activity. In some embodiments, the method comprises administering to a subject in need thereof a compound of the present disclosure (e.g., Formula I, Formula II, Formula V, Formula X, Formula Y, Formula Z, any subformulae thereof, or any of compounds A1 to A85, or pharmaceutically acceptable salt thereof), or a pharmaceutical composition described herein. In some embodiments, the subject is characterized as having cancer. In some embodiments, the subject has a disease or disorder associated with aberrant HPK1 activity, such as cancer, metastasis, inflammation, and/or an autoimmune disease.

In some embodiments, the present disclosure provides a method of treating a disease or disorder associated with aberrant activity of HPK1. In some embodiments, the method comprises administering to a subject in need thereof a compound of the present disclosure (e.g., Formula I, Formula II, Formula V, Formula X, Formula Y, Formula Z, any subformulae thereof, or any of compounds A1 to A85, or pharmaceutically acceptable salt thereof), or a pharmaceutical composition described herein. In some embodiments, the disease or disorder is cancer, metastasis, inflammation, and an autoimmune disease.

In some specific embodiments, the present disclosure provides a method of treating cancer. In some embodiments, the method comprises administering to a subject in need thereof a compound of the present disclosure (e.g., Formula I, Formula II, Formula V, Formula X, Formula Y, Formula Z, any subformulae thereof, or any of compounds A1 to A85, or pharmaceutically acceptable salt thereof), or a pharmaceutical composition described herein. In some embodiments, the cancer is breast cancer, colorectal cancer, hematological malignancy, lung cancer (e.g., non-small cell lung cancer), melanoma, ovarian cancer, pancreatic cancer, and/or kidney cancer (e.g., renal cell carcinoma). In some embodiments, the method further comprises administering to the subject one or more additional anticancer therapy. In some embodiments, the one or more additional anticancer therapy is a CAR-T cell therapy. In some embodiments, the one or more additional anticancer therapy can be an immunocancer therapy, including PD-1, PD-L1, CTLA-4, TIM-3, TLR4, TLR7, TLR8, TLR9, TGF-β and its receptor, LAG3 antagonist or STING agonists, related cancer immunotherapy, which can be small molecule based, protein based (e.g., PD-1, PD-L1, or CTLA-4 antibody) or cell based.

In some embodiments, the present disclosure also provides a method of enhancing cytotoxicity, inhibiting exhaustion, and/or enhancing infiltration in spleen and/or tumors, of an immune cell (e.g., a T cell), the method comprising administering to a subject receiving the immune cell (e.g., a T cell such as a Car-T cell) an effective amount of a compound of the present disclosure (e.g., Formula I, Formula II, Formula V, Formula X, Formula Y, Formula Z, any subformulae thereof, or any of compounds A1 to A85, or pharmaceutically acceptable salt thereof), or a pharmaceutical composition described herein. In some embodiments, the immune cell is a T cell (e.g., a CD4+ or CD8+ T cell, CAR-T cell, NK T cell, alpha beta T cell or gamma delta T cell) or NK cell. In some embodiments, the subject suffers from cancer, wherein the cancer is lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and/or medulloblastoma.

In some embodiments, the present disclosure also provides a method of treating cancer in a subject in need thereof, the method comprising administering to the subject an effective amount of a compound of the present disclosure (e.g., Formula I, Formula II, Formula V, Formula X, Formula Y, Formula Z, any subformulae thereof, or any of compounds A1 to A85, or pharmaceutically acceptable salt thereof), or a pharmaceutical composition described herein, in combination with a CAR-T cell therapy. In some embodiments, the cancer is lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and/or medulloblastoma. In some embodiments, the compound of the present disclosure or the pharmaceutical composition is administered in an amount effective to enhance cytotoxicity, inhibit exhaustion, and/or enhance infiltration in spleen and/or tumors of the Car-T cell.

In some embodiments, the present disclosure also provides a method of identifying a candidate agent for use in combination with a CAR-T cell therapy. In some embodiments, the method comprises: a) Incubating a test agent and CAR-T cells with a tumor cell, wherein the tumor cell comprises an antigen that can bind to and induce cytotoxicity of the CAR-T cells; b) Measuring the cytotoxicity of the CAR-T cells in the presence of the test agent, and optionally; c) Identifying a candidate agent that enhances the cytotoxicity of the CAR-T cells compared to a control. Conditions for incubating the test agent, CAR-T cells, and tumor cells include any of those known in the art, with some conditions exemplified herein. The cytotoxicity can also be measured via any of the known methods in the art. The screening methods herein are also not limited to tumor cell types or any specific CAR-T cell populations. In some embodiments, the test agent is prescreened as an HPK-1 kinase inhibitor. In some embodiments, the test agent is not prescreened in an HPK-1 kinase inhibition assay. As shown in FIG. 1 and the relevant examples, the methods identified a few of the compounds of the present disclosure as effective in enhancing cytotoxicity of the tested Car-T cells.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable groups for the variables in compounds of Formula I, II, III, IV, V, VI, X, Y and Z or subformula thereof, as applicable, are independently selected. It should be noted that the Formula I, II, etc. can in some cases expressed as Formula (I), Formula (II), etc. The described embodiments of the present invention can be combined. Such combination is contemplated and within the scope of the present invention.

As used herein, the term "compound(s) of the present disclosure" or "compound(s) of the present invention" refers to any of the compounds described herein according to Formula I, Formula II, Formula V, Formula X, Formula Y, Formula Z, any subformulae thereof, or any of Compounds A1-A85, or any of the specific compounds shown in Embodiment 15 (see the Exemplary Embodiments section), isotopically labeled compound(s) thereof (such as a deuterated analog wherein one of the hydrogen atoms is substituted with a deuterium atom with an abundance above its natural abundance), possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt or base addition salt such as Na salt). Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

The term "subject" (alternatively referred to herein as "patient") as used herein, refers to an animal, preferably a mammal, most preferably a human, who has been the object of treatment, observation or experiment. In some embodiments, the subject can be a vertebrate such as a dog, a cat, a horse or a monkey.

Oxygen protecting groups and nitrogen protecting groups are well known in the art and include those described in detail in "*Protective Groups in Organic Synthesis*", 4*th* ed. P. G. M. Wuts; T. W. Greene, John Wiley, 2007, incorporated herein by reference. Exemplary oxygen protecting groups include, but are not limited to, alkyl ethers or substituted alkyl ethers such as methyl, allyl, benzyl, substituted benzyls, silyl ethers such as trymethylsilyl (TMS), triethylsilyl (TES), triisopropylsilyl (TIPS), t-butyldimethylsilyl (TBDMS), etc., acetals or ketals, such as tetrahydropyranyl (THP), esters such as formate, acetate, chloroacetate, dichloroacetate, trichloroacetate, trifluoroacetate, methoxyacetate, etc., carbonates, sulfonates such as methanesulfonate (mesylate), benzylsulfonate, and tosylate (Ts), etc. Exemplary nitrogen protecting groups include, but are not limited to, alkyls or substituted alkyls, such as methyl, allyl, benzyl, substituted benzyls, amides, such as actyl, carbamates, such as Boc, sulfonates such as methanesulfonate (mesylate), benzylsulfonate, and tosylate (Ts).

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkanesulfonyloxy, arenesulfonyloxy, etc.

An "optionally substituted" group, such as an optionally substituted alkyl, an optionally substituted alkenyl, an optionally substituted alkynyl, an optionally substituted cycloalkyl, an optionally substituted heterocyclyl, an optionally substituted aryl, and an optionally substituted heteroaryl groups, refers to the respective group that is unsubstituted or substituted. In general, the term "substituted", means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable. Two of the optional substituents can join to form an optionally substituted cycloalkyl, heterocylyl, aryl, or heteroaryl ring. Substitution can occur on any available carbon, oxygen, or nitrogen atom, and can form a spirocycle. When a bicyclic or polycyclic ring structure is designated as connected to two groups, each point of attachment can be independently selected from any available positions on any of the rings. Typically, substitution herein does not result in an O—O, O—N, S—S, S—N(except $SO_2$—N bond), heteroatom-halogen, heteroatom-CN bond, or —C(O)—S bond or three or more consecutive heteroatoms, with the exception of O—SO$_2$—O, O—SO$_2$—N, and N—SO$_2$—N, except that some of such bonds or connections may be allowed if in a stable aromatic system.

In any of the embodiments described herein, unless otherwise indicated, the "optionally substituted" non-aromatic group can be unsubstituted or substituted with 1, 2, or 3 substituents independently selected from F, Cl, —OH, oxo (as applicable), C$_{1-7}$ alkyl (e.g., C$_{1-4}$ alkyl), C$_{1-4}$ alkoxy, C$_{3-6}$ cycloalkyl, C$_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), C$_{1-7}$ alkyl (e.g., C$_{1-4}$ alkyl) and C$_{1-4}$ alkoxy. In any of the embodiments described herein, unless otherwise indicated, the "optionally substituted" aromatic group (including aryl and heteroaryl groups) can be unsubstituted or substituted with 1, 2, or 3 substituents independently selected from F, Cl, —OH, —CN, C$_{1-7}$ alkyl (e.g., C$_{1-4}$ alkyl), C$_{1-4}$ alkoxy, C$_{3-6}$ cycloalkyl, C$_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), C$_{1-7}$ alkyl (e.g., C$_{1-4}$ alkyl) and C$_{1-4}$ alkoxy.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

As used herein, in the term C$_{1-10}$ alkyl, C$_0$ alkyl means H, and therefore, C$_{1-10}$ alkyl includes H, C$_1$ alkyl, C$_2$ alkyl, C$_3$ alkyl, C$_4$ alkyl, C$_5$ alkyl, C$_6$ alkyl, C$_7$ alkyl, C$_8$ alkyl, C$_9$ alkyl, C$_{10}$ alkyl.

The C$_{1-10}$ linear/branched alkyl includes methyl, ethyl, C$_3$ linear/branched alkyl, C$_4$ linear/branched alkyl, C$_5$ linear/branched alkyl, C$_6$ linear/branched alkyl, C$_7$ linear/branched alkyl, C$_8$ linear/branched alkyl, C$_9$ linear/branched alkyl, C$_{10}$ linear/branched alkyl.

The C$_{3-10}$ branched alkyl includes isopropyl, isobutyl, tert-butyl, isopentyl.

The C$_{3-10}$ cycloalkyl includes C$_3$ cycloalkyl, C$_4$ cycloalkyl, C$_5$ cycloalkyl, C$_6$ cycloalkyl, C$_7$ cycloalkyl, C$_8$ cycloalkyl, C$_9$ cycloalkyl, C$_{10}$ cycloalkyl.

The C$_{3-8}$ cycloalkyl includes C$_3$ cycloalkyl, C$_4$ cycloalkyl, C$_5$ cycloalkyl, C$_6$ cycloalkyl, C$_7$ cycloalkyl, C$_8$ cycloalkyl.

The C$_{4-8}$ cycloalkyl includes C$_4$ cycloalkyl, C$_5$ cycloalkyl, C$_6$ cycloalkyl, C$_7$ cycloalkyl, C$_8$ cycloalkyl.

The C$_{4-6}$ cycloalkyl includes C$_4$ cycloalkyl, C$_5$ cycloalkyl, C$_6$ cycloalkyl.

Halogen includes fluorine, chlorine, bromine, and iodine.

The heterocycle refers to a non-aromatic saturated monocyclic or polycyclic ring system containing 3 to 10 ring atoms, preferably containing 5 to 10 ring atoms, wherein one or more ring atoms are nitrogen, oxygen or sulfur atom. Preferred, heterocycle contains 5 or 6 ring atoms.

The heteroalkyl refers to an alkyl in which one or more of the carbon atoms (and any associated hydrogen atoms) are each independently replaced with the same or different heteroatom or heteroatomin group. Heteroatoms include, but are not limited to N, O, S.

The heteroaryl refers to an aromatic monocyclic or polycyclic ring system containing 5 to 14 ring atoms, preferably containing 5 to 10 ring atoms, wherein one or more ring atoms are nitrogen, oxygen or sulfur atom. Preferred, heteroaryl contains 5 or 6 ring atoms. The heteroaryl includes, but is not limited to pyrazinyl, furyl, thienyl, pyridyl, pyrimidinyl, isoxazolyl, isothiazolyl, oxazolyl, thiazolyl, pyrazolyl, pyrrolyl, pyrazolyl, triazolyl, pyrazinyl, pyridazinyl, quinoxalinyl, 2,3-naphthyridinyl, imidazo[1,2-a]pyridine, imidazo[2,1-b]thiazolyl, fluorenyl, azaindole, benzimidazolyl, benzothienyl, quinolyl, imidazolyl, thienopyridinyl, quinazoline, thienopyrimidinyl, pyrrolopyridinyl, imidazopyridinyl, isoquinolinyl, 1,2,4-triazinyl, benzothiazolyl.

EXEMPLARY EMBODIMENTS

Embodiment 1. A compound of formula (I), pharmaceutically acceptable salt, stereoisomer, ester, prodrug, solvate and deuterated compound thereof,

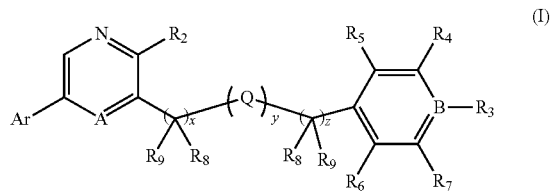

wherein,

A is C or N; B is C or N;

Ar is five-membered heteroaryl, six-membered heteroaryl or phenyl, wherein the five-membered heteroaryl is selected from furanyl, thienyl, pyrrolyl, pyrazolyl, imidazolyl, oxazolyl or thiazolyl; the six-membered heteroaryl comprises pyridyl, pyridazinyl, pyrimidinyl or pyrazinyl; wherein the H on the five-membered heteroaryl, six-membered heteroaryl or phenyl is optionally substituted with a group selected from —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, C$_{0-10}$ linear/branched alkyl, —N(C$_{0-10}$ alkyl)(C$_{0-10}$ alkyl), —OC$_{0-10}$ alkyl, C$_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —SO$_2$, —SO$_2$N(C$_{0-10}$ alkyl)(C$_{0-10}$ alkyl), —N(C$_{0-10}$ alkyl)SO$_2$(C$_{0-10}$ alkyl), —CON(C$_{0-10}$ alkyl)(C$_{0-10}$ alkyl), —N(C$_{0-10}$ alkyl)CO(C$_{0-10}$ alkyl), —N(C$_{0-10}$ alkyl)COO(C$_{0-10}$ alkyl), —OCON(C$_{0-10}$ alkyl)(C$_{0-10}$ alkyl), halogen, —CN, —OCH$_2$F, —OCHF$_2$, —OCF$_3$, —N(C$_{0-10}$ alkyl)(C$_{0-10}$ alkyl), —OC$_{0-10}$ alkyl, C$_{3-10}$ cycloalkyl, —O heterocyclyl, —N heterocyclyl, —O heteroaryl or —S heteroaryl;

R$_2$ is selected from: —H, halogen, —NO$_2$, —CN, C$_{1-5}$ linear/branched alkyl, C$_{3-10}$ cycloalkyl, —N(C$_{0-10}$ alkyl)(C$_{0-10}$ alkyl), —CF$_3$, —OCF$_3$, —OCHF$_2$, —OCH$_2$F or —OC$_{0-10}$ alkyl;

When B is N, $R_3$ does not exist; when B is C, $R_3$ is selected from: —H, halogen, —$OC_{0-10}$ alkyl, $C_{1-10}$ linear/branched alkyl, —N($C_{0-10}$ alkyl)($C_{0-10}$ alkyl) or $C_{3-10}$ cycloalkyl;

$R_4$ is selected from: —H, halogen, —$OC_{0-10}$ alkyl, —CN, $C_{3-10}$ cycloalkyl, —C≡C—$R_{10}$, $C_{1-10}$ linear/branched alkyl, —N($C_{0-10}$ alkyl)($C_{0-10}$ alkyl), —O heterocyclyl or —N heterocyclyl;

$R_5$, $R_6$, $R_7$ are independently selected from: —H, halogen, —CN, —$OC_{0-10}$ alkyl, $C_{0-10}$ linear/branched alkyl, —N($C_{0-10}$ alkyl)($C_{0-10}$ alkyl), $C_{3-10}$ cycloalkyl, —C≡C—$R_{10}$, —O heterocyclyl or —N heterocyclyl, or $R_6$ and $R_7$ together with the atom(s) to which they are attached form a $C_{3-8}$ cycloalkyl, $C_{3-8}$ heterocyclyl containing O or S, —N heteroaryl, —O heteroaryl, —S heteroaryl or phenyl, wherein the H on the C is optionally substituted with one or more of the following groups: —$SO_2$, —$SO_2N(C_{0-10}$ alkyl)($C_{0-10}$ alkyl), —N($C_{0-10}$ alkyl)$SO_2(C_{0-10}$ alkyl), —CON($C_{0-10}$ alkyl)($C_{0-10}$ alkyl), —N($C_{0-10}$ alkyl)CO($C_{0-10}$ alkyl), —N($C_{0-10}$ alkyl)COO($C_{0-10}$ alkyl), —OCON($C_{0-10}$ alkyl)($C_{0-10}$ alkyl), halogen, —CN, —$OCH_2F$, —$OCHF_2$, —$OCF_3$, $C_{1-10}$ linear/branched alkyl, —N($C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl;

$R_8$, $R_9$ are independently selected from the followings: —H, halogen or $C_{0-10}$ linear/branched alkyl;

$R_{10}$ is selected from: H, $C_{1-5}$ linear/branched alkyl, $C_{3-10}$ cycloalkyl or

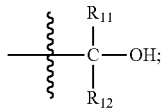

$R_{11}$, $R_{12}$ are independently selected from: —H, —$CF_3$, —$CHF_2H$, —$CH_2F$, $C_{1-10}$ linear/branched alkyl, —CH=C($C_{0-10}$ alkyl)($C_{0-10}$ alkyl), —C≡C($C_{0-10}$ alkyl), $C_{3-10}$ cycloalkyl, five-membered heteroaryl or six-membered heteroaryl, or $R_1$ and $R_{12}$ together with the atom(s) to which they are attached form a $C_{3-8}$ cycloalkyl, $C_{3-8}$ heterocyclyl containing O or S, $C_{4-9}$ fused cycloalkyl, $C_{3-7}$ lactam, $C_{3-7}$ lactone or $C_{3-7}$ cyclic ketone, wherein the H on the C is optionally substituted with alkyl or halogen;

Q is O or S; x and z are integers from 0-6; y is 0 or 1.

Embodiment 2. The compound of embodiment 1, pharmaceutically acceptable salt, stereoisomer, ester, prodrug, solvate and deuterated compound thereof, wherein the compound structure is formula (II),

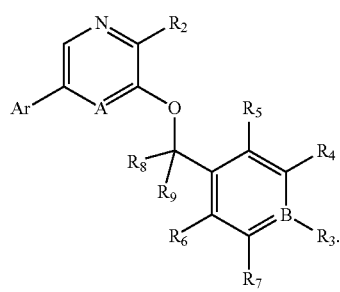

(II)

Embodiment 3. The compound of embodiment 2, pharmaceutically acceptable salt, stereoisomer, ester, prodrug, solvate and deuterated compound thereof, wherein Ar is thiazolyl, selenothiazolyl, imidazolyl, pyrazolyl or pyridyl, wherein at least one H on the thiazolyl, imidazolyl, pyrazolyl or pyridyl is substituted with one group selected from —$SO_2NH_2$, —$NHSO_2$, —$CONH(C_{0-10}$ alkyl), halogen, —CN, —$OCF_3$, —O heterocyclyl, —N heterocyclyl, $C_{1-10}$ linear/branched alkyl, —$OC_{0-10}$ alkyl, $C_{3-10}$ cycloalkyl, —N($C_{0-10}$ alkyl)($C_{0-10}$ alkyl), —N heteroaryl, —O heteroaryl or —S heteroaryl;

$R_2$ is selected from: —$NO_2$, —N($C_{0-10}$ alkyl)($C_{0-10}$ alkyl), —$OCF_3$, or —$OC_{0-10}$ alkyl;

When B is N, $R_3$ does not exist; when B is C, $R_3$ is selected from: —H, halogen, —$OC_{0-10}$ alkyl or $C_{0-10}$ linear/branched alkyl;

$R_4$ is selected from: —H, halogen, —$OC_{0-10}$ alkyl, —CN, $C_{3-10}$ cycloalkyl, —C≡C—$R_{10}$;

$R_5$, $R_6$, $R_7$ are independently selected from: —H, halogen, $C_{3-6}$ cycloalkyl, —$OC_{0-5}$ alkyl, $C_{1-5}$ linear/branched alkyl, $C_{1-5}$ linear/branched alkyl containing O or N, or $R_6$ and $R_7$ together with the atom(s) to which they are attached form a $C_{3-8}$ cycloalkyl, $C_{3-8}$ heterocyclyl containing O or S, wherein the H on the C is optionally substituted with F;

$R_8$, $R_9$ are independently selected from the followings: —H or $C_{0-10}$ linear/branched alkyl;

$R_{11}$, $R_{12}$ are independently selected from: —H, —$CF_3$, —$CHF_2H$, —$CH_2F$, $C_{0-10}$ linear/branched alkyl, —CH=C($C_{1-10}$ alkyl)($C_{0-10}$ alkyl), $C_{3-10}$ cycloalkyl or six-membered heteroaryl, or $R_{11}$ and $R_{12}$ together with the atom(s) to which they are attached form a $C_{3-8}$ cycloalkyl, $C_{4-7}$ fused cycloalkyl, $C_{3-7}$ lactam, $C_{3-7}$ lactone or $C_{3-7}$ cyclic ketone, wherein the H on the C is optionally substituted with alkyl or F.

Embodiment 4. The compound of any one of embodiments 1-3, pharmaceutically acceptable salt, stereoisomer, ester, prodrug, solvate and deuterated compound thereof, wherein at least one H on the Ar is optionally substituted with —O heterocyclyl or —N heterocyclyl.

Embodiment 5. The compound of embodiment 2, pharmaceutically acceptable salt, stereoisomer, ester, prodrug, solvate and deuterated compound thereof, wherein Ar is

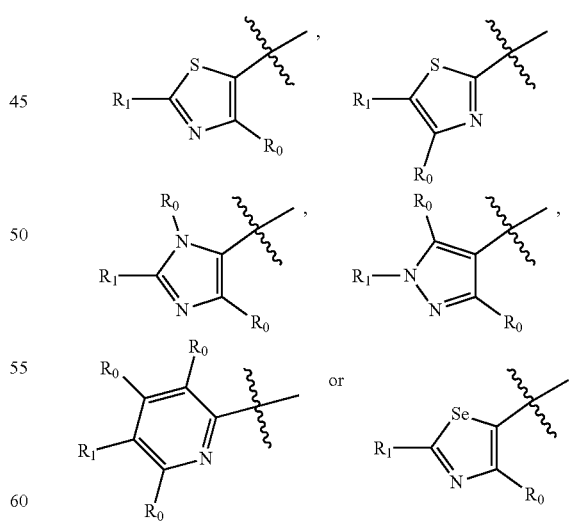

$R_0$ is selected from: —H, $C_{1-10}$ linear/branched alkyl, —N($C_{0-10}$ alkyl)($C_{0-10}$ alkyl), —$OC_{0-10}$ alkyl or $C_{3-10}$ cycloalkyl; $R_1$ is selected from: —H, —O heterocyclyl, —N heterocyclyl, $C_{0-10}$ linear/branched alkyl, $C_{3-10}$ cycloalkyl, —$OC_{0-10}$ alkyl, —N($C_{0-10}$ alkyl)($C_{0-10}$ alkyl), —$SO_2$ ($C_{0-10}$ alkyl), —O(C$_{0-10}$ alkyl), —O-phenyl, —S(C$_{0-10}$ alkyl), —N heteroaryl, —O heteroaryl or —S heteroaryl, wherein the H on the C or hetero atom is optionally substituted with a group selected from C$_{1-3}$ linear alkyl, —N(C$_{0-10}$ alkyl)(C$_{0-10}$ alkyl), —CF$_3$.

Embodiment 6. The compound of embodiment 5, pharmaceutically acceptable salt, stereoisomer, ester, prodrug, solvate and deuterated compound thereof, wherein R$_0$ is selected from: C$_{1-5}$ linear/branched alkyl or —N(C$_{0-10}$ alkyl)(C$_{0-10}$ alkyl);

R$_1$ is selected from: —O heterocyclyl, —N heterocyclyl, —SO$_2$ (C$_{0-3}$ alkyl), —O-phenyl, —S(C$_{0-4}$ alkyl), C$_{3-6}$ cycloalkyl, C$_{3-5}$ linear/branched alkyl, wherein the H on the C or hetero atom is optionally substituted with —NH$_2$ or —CF$_3$, —CF$_2$H, —O heterocyclyl, —N heterocyclyl, C$_{3-5}$ linear/branched alkyl, C$_{3-7}$ cycloalkyl;

R$_2$ is —NH$_2$ or —NO$_2$;

When B is N, R$_3$ does not exist; when B is C, R$_3$ is —H, —F or —OCH$_3$;

R$_4$ is selected from the followings: —H, —F, —Cl, —OCH$_3$, —CN,

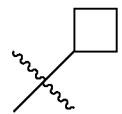 或 —C≡C—R$_{10}$;

R$_5$, R$_6$, R$_7$ are independently selected from: —H, halogen, —OC$_{0-3}$ alkyl, C$_{1-3}$ linear/branched alkyl, C$_{1-3}$ linear/branched alkyl containing N, or R$_6$ and R$_7$ together with the atom(s) to which they are attached form a C$_{3-8}$ cycloalkyl, C$_{3-8}$ heterocyclyl containing 0, wherein the H on the C is optionally substituted with F;

R$_8$, R$_9$ are independently selected from the followings: —H or C$_{1-3}$ linear/branched alkyl;

R$_{11}$, R$_{12}$ are independently selected from: —H, —CF$_3$, —CHF$_2$H, —CH$_2$F, C$_{1-5}$ linear/branched alkyl, —CH═CH(C$_{0-10}$ alkyl), C$_{3-10}$ cycloalkyl or six-membered heteroaryl, or R$_1$ and R$_{12}$ together with the atom(s) to which they are attached form a C$_{3-6}$ cycloalkyl, C$_{4-6}$ fused cycloalkyl, C$_{3-7}$ lactam, C$_{3-7}$ lactone or C$_{3-7}$ cyclic ketone, wherein the H on the C is optionally substituted with alkyl or F.

Embodiment 7. The compound of embodiment 6, pharmaceutically acceptable salt, stereoisomer, ester, prodrug, solvate and deuterated compound thereof, wherein R$_0$ is —CH$_3$, —CH$_2$CH$_3$ or —NH$_2$;

R$_1$ is selected from the followings:

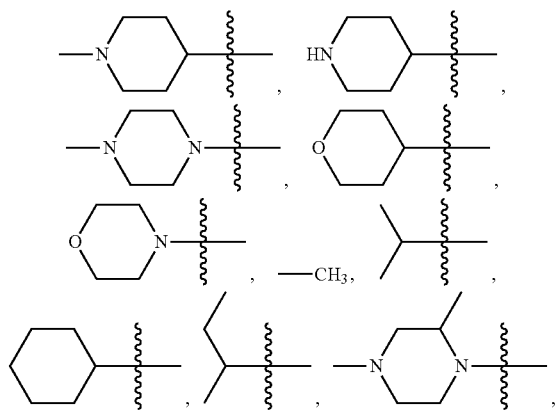

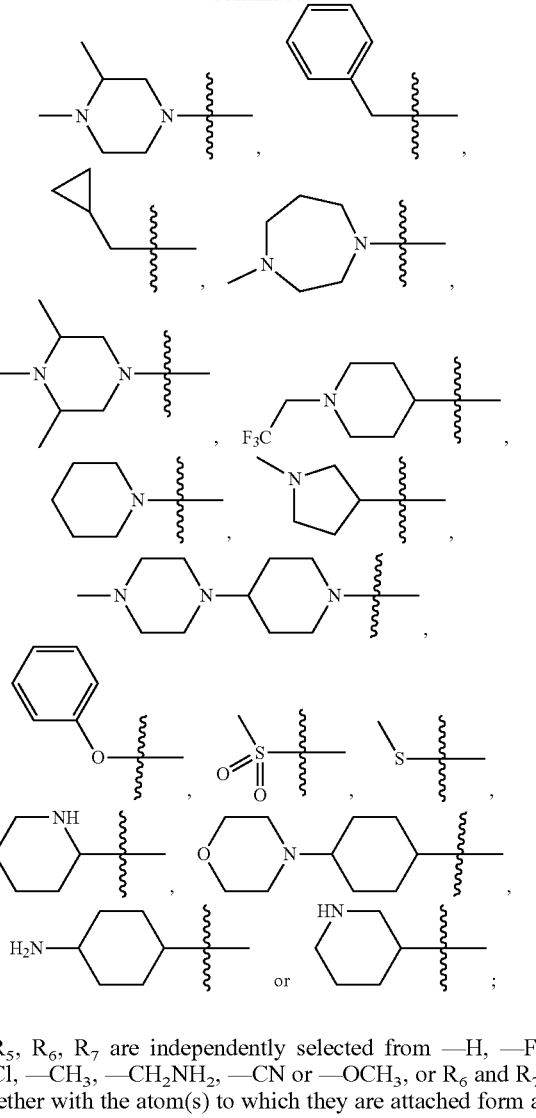

R$_5$, R$_6$, R$_7$ are independently selected from —H, —F, —Cl, —CH$_3$, —CH$_2$NH$_2$, —CN or —OCH$_3$, or R$_6$ and R$_7$ together with the atom(s) to which they are attached form a five-membered cycloalkyl containing O;

R$_8$, R$_9$ are independently selected from —H or —CH$_3$: R$_{11}$, R$_{12}$ are independently selected from:

—H, —CF$_3$, —CHF$_2$, —CH$_2$F, —CH$_3$,

—CH$_2$CH$_3$, —CH═CH$_2$, CH$_3$(—CH(CH$_3$)$_2$),

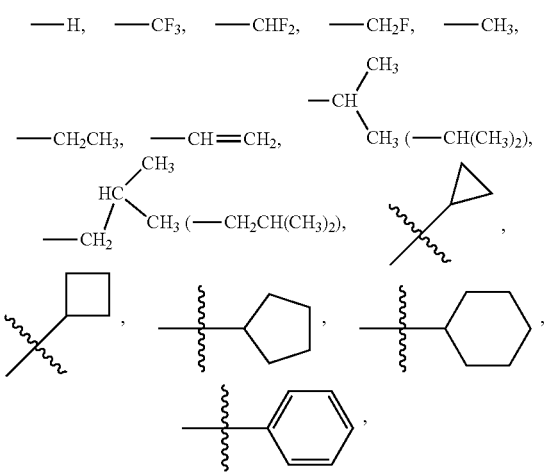

or $R_{11}$ and $R_{12}$ together with the atom(s) to which they are attached form

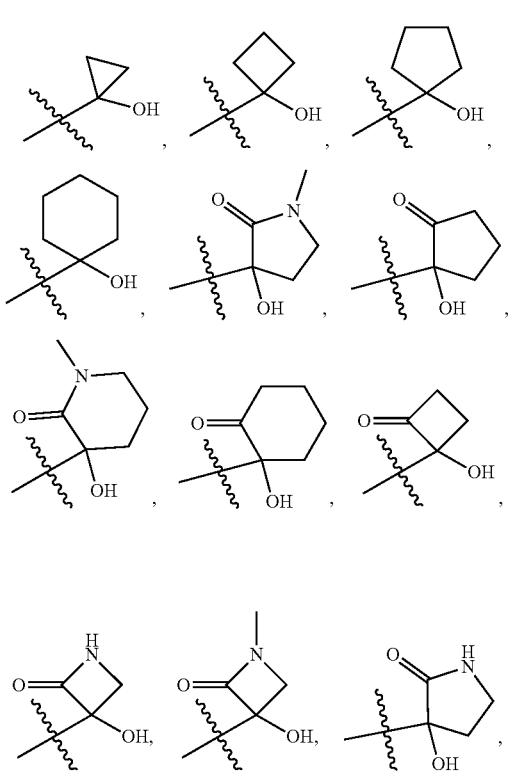

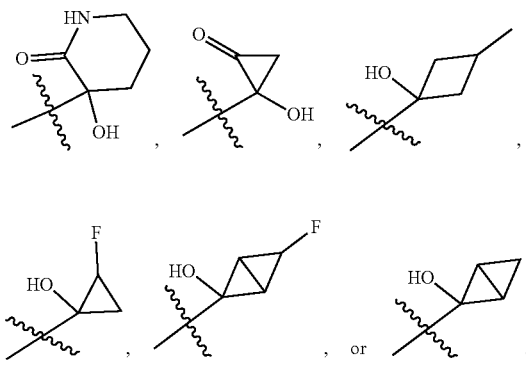

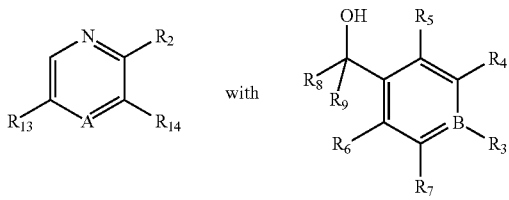

Embodiment 8. A method of preparing the compound of embodiment 2, the steps of the method are as follows:

(1) reacting

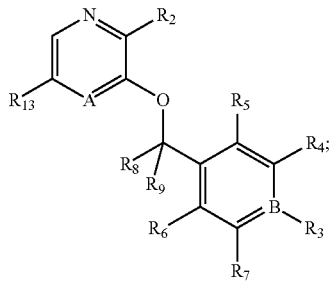

to form

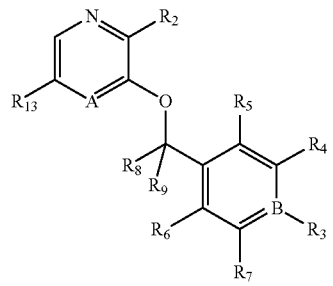

(2) reacting (image of intermediate compound)

reacts Ar—$R_{15}$ to form (image of product compound)

wherein, $R_{13}$ is halogen or

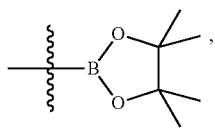 [SMILES: *B1OC(C)(C)C(C)(C)O1]

$R_{14}$ is —OH or —F, $R_{15}$ is —Br or —SnBu$_3$.

Embodiment 9. A compound of formula (V), pharmaceutically acceptable salt, stereoisomer, ester, prodrug, solvate and deuterated compound thereof,

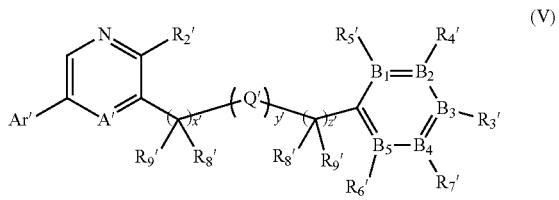 (V)

wherein,

A' is C or N; $B_1$, $B_2$, $B_3$, $B_4$ or $B_5$ are independently selected from C or N;

Ar' is five-membered heteroaryl, six-membered heteroaryl or phenyl, wherein the five-membered heteroaryl is selected from furanyl, thienyl, pyrrolyl, pyrazolyl, imidazolyl, oxazolyl or thiazolyl; the six-membered heteroaryl comprises pyridyl, pyridazinyl, pyrimidinyl or pyrazinyl; wherein the H on the five-membered heteroaryl, six-membered heteroaryl or phenyl is optionally substituted with a group selected from —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{0-10}$ linear/branched alkyl, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, —$N(C_{0-10}$ alkyl)($C_{0-10}$ alkyl), —$OC_{0-10}$ alkyl, $C_{3-10}$ cycloalkyl, —O heterocyclyl, —N heteroaryl, —O heteroaryl or —S heteroaryl;

$R_2'$ is selected from: —H, halogen, —$NO_2$, —CN, $C_{1-5}$ linear/branched alkyl, $C_{3-10}$ cycloalkyl, —$N(C_{0-10}$ alkyl)($C_{0-10}$ alkyl), —$CF_3$, —$OCF_3$, —$OCHF_2$, —$OCH_2F$ or —$OC_{0-10}$ alkyl;

When $B_1$, $B_2$, $B_3$, $B_4$ or $B_5$ is N, $R_3'$, $R_4'$, $R_5'$, $R_6'$ or $R_7'$ does not exist; When $B_1$, $B_2$, $B_3$, $B_4$ or $B_5$ is C, $R_3'$, $R_4'$, $R_5'$, $R_6'$ or $R_7'$ is independently selected from: —H, halogen, —CN, —$OC_{0-10}$ alkyl, $C_{1-10}$ linear/branched alkyl, —$N(C_{0-10}$ alkyl)($C_{0-10}$ alkyl), $C_{3-10}$ cycloalkyl, —C≡C—$R_{10}$, —O heterocyclyl or —N heterocyclyl, or $R_5$ and $R_4$, $R_4$ and $R_3$, $R_3$ and $R_7$, or $R_7$ and $R_6$ together with the atom(s) to which they are attached form a $C_{3-8}$ cycloalkyl, $C_{3-8}$ heterocyclyl containing O or S, —N heteroaryl, —O heteroaryl, —S heteroaryl or phenyl, wherein the H on the C is optionally substituted with one or more of the following groups: —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{0-10}$ linear/branched alkyl, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl;

$R_8'$, $R_9'$ are independently selected from the followings: —H, halogen or $C_{1-10}$ linear/branched alkyl;

$R_{10}'$ is selected from: H, $C_{1-5}$ linear/branched alkyl, $C_{3-10}$ cycloalkyl or

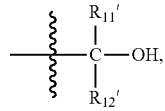

$R_{11}'$, $R_{12}'$ are independently selected from: —H, —$CF_3$, —$CHF_2H$, —$CH_2F$, $C_{1-10}$ linear/branched alkyl, —CH═C ($C_{0-10}$ alkyl)($C_{0-10}$ alkyl), $C_{3-10}$ cycloalkyl five-membered heteroaryl or six-membered heteroaryl, or $R_{11}'$ and $R_{12}'$ together with the atom(s) to which they are attached form a $C_{3-8}$ cycloalkyl, $C_{3-8}$ heterocyclyl containing O or S, $C_{4-9}$ fused cycloalkyl, $C_{5-10}$ spiro cycloalkyl, $C_{4-9}$ bridged cycloalkyl, $C_{3-7}$ lactam, $C_{3-7}$ lactone or $C_{3-7}$ cyclic ketone, wherein the H on the C is optionally substituted with a group selected from —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{0-10}$ linear/branched alkyl, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, —$N(C_{0-10}$ alkyl)($C_{0-10}$ alkyl), —$OC_{0-10}$ alkyl, $C_{3-10}$ cycloalkyl, —O heterocyclyl, —N heteroaryl, —O heteroaryl or —S heteroaryl;

Q' is O or S; x' and z' are integers from 0-6; y' is 0 or 1.

Embodiment 10. The compound of embodiment 9, pharmaceutically acceptable salt, stereoisomer, ester, prodrug, solvate and deuterated compound thereof, wherein $B_1$, $B_2$, $B_3$, $B_4$ or $B_5$ are C, or at least one of $B_1$, $B_2$, $B_3$, $B_4$ or $B_5$ is N; Ar' is thiazolyl, selenothiazolyl, imidazolyl, pyrazolyl or pyridyl, at least one H on the thiazolyl, selenothiazolyl, imidazolyl, pyrazolyl or pyridyl is optionally substituted with one group selected from —$SO_2NH_2$, —$NHSO_2$, —$CONH(C_{0-10}$ alkyl), —O heterocyclyl, —N heterocyclyl, $C_{1-10}$ linear/branched alkyl, —$OC_{0-10}$ alkyl, $C_{3-10}$ cycloalkyl, or —$N(C_{1-10}$ alkyl)($C_{0-10}$ alkyl), —N heteroaryl, —O heteroaryl or —S heteroaryl;

$R_2'$ is selected from: —$NO_2$, —$N(C_{1-10}$ alkyl)($C_{0-10}$ alkyl), —$OCF_3$, or —$OC_{0-10}$ alkyl;

$R_3'$ is selected from: —H, halogen, —$OC_{0-10}$ alkyl, $C_{1-10}$ linear/branched alkyl, —$N(C_{0-10}$ alkyl)($C_{0-10}$ alkyl), $C_{3-10}$ cycloalkyl;

$R_4'$ is selected from: —H, halogen, —$OC_{0-10}$ alkyl, —CN, $C_{3-10}$ cycloalkyl, —C≡C—$R_{10}'$, $C_{1-10}$ linear/branched alkyl, —$N(C_{0-10}$ alkyl)($C_{0-10}$ alkyl), —O heterocyclyl or —N heterocyclyl;

$R_5'$, $R_6'$, $R_7'$ are independently selected from: —H, halogen, —CN, —$OC_{0-10}$ alkyl, $C_{1-10}$ linear/branched alkyl, —$N(C_{0-10}$ alkyl)($C_{0-10}$ alkyl), $C_{3-10}$ cycloalkyl, —C≡C—$R_{10}'$, —O heterocyclyl or —N heterocyclyl, or $R_6'$ and $R_7'$ together with the atom(s) to which they are attached form a $C_{3-8}$ cycloalkyl, $C_{3-8}$ heterocyclyl containing O or S, wherein the H on the C is optionally substituted with F;

$R_8'$, $R_9'$ are independently selected from: —H or $C_{1-10}$ linear/branched alkyl;

$R_{11}'$, $R_{12}'$ are independently selected from: —H, —$CF_3$, —$CHF_2H$, —$CH_2F$, $C_{1-10}$ linear/branched alkyl, —CH═C ($C_{1-10}$ alkyl)($C_{0-10}$ alkyl), $C_3$-10 cycloalkyl or six-membered heteroaryl, or $R_{11}'$ and $R_{12}'$ together with the atom(s) to which they are attached form a $C_{3-8}$ cycloalkyl, $C_{4-9}$ fused cycloalkyl, $C_{5-10}$ spiro cycloalkyl, $C_{4-9}$ bridged cycloalkyl, $C_{3-7}$ lactam, $C_{3-7}$ lactone or $C_{3-7}$ cyclic ketone, wherein the H on the C is optionally substituted with one group selected from —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{1-10}$ linear/branched alkyl, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, —$N(C_{0-10}$ alkyl)($C_{0-10}$ alkyl), —$OC_{0-10}$ alkyl, $C_{3-10}$ cycloalkyl, —O heterocyclyl, —N heteroaryl, —O heteroaryl or —S heteroaryl;

x' and z' are integers from 0-2, such as 0, 1 or 2.

Embodiment 11. The compound of embodiment 9 or 10, pharmaceutically acceptable salt, stereoisomer, ester, prodrug, solvate and deuterated compound thereof, wherein at least one H on the Ar' is optionally substituted with one group selected from —O heterocyclyl or —N heterocyclyl; $R_3'$ is selected from: —H, halogen, —$OC_{0-10}$ alkyl, $C_{1-10}$ linear/branched alkyl; $R_4'$ is selected from: —H, halogen, —$OC_{0-10}$ alkyl, —CN, $C_{3-10}$ cycloalkyl, —C≡C—$R_{10}'$.

Embodiment 12. The compound of embodiment 9, pharmaceutically acceptable salt, stereoisomer, ester, prodrug, solvate and deuterated compound thereof, wherein Ar' is

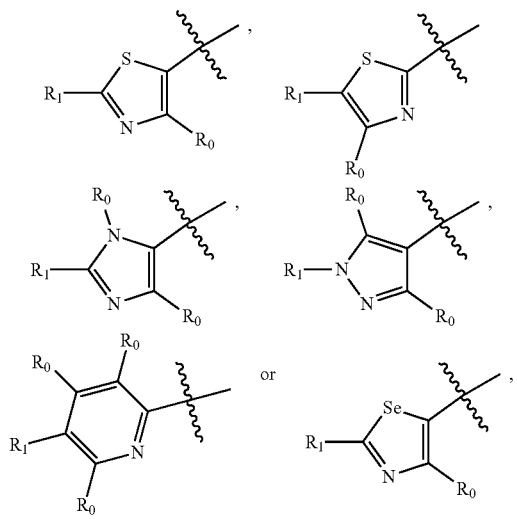

is selected from: —H, $C_{0-10}$ linear/branched alkyl, —$N(C_{0-10}$ alkyl)($C_{0-10}$ alkyl), —$OC_{0-10}$ alkyl or $C_{3-10}$ cycloalkyl; $R_1'$ is selected from: —H, —O heterocyclyl, —N heterocyclyl, $C_{1-10}$ linear/branched alkyl, $C_{3-10}$ cycloalkyl, —$OC_{0-10}$ alkyl, —$N(C_{0-10}$ alkyl)($C_{0-10}$ alkyl), —$SO_2$ ($C_{0-10}$ alkyl), —O($C_{0-10}$ alkyl), —O-phenyl, —S($C_{0-10}$ alkyl), —N heteroaryl, —O heteroaryl or —S heteroaryl, wherein the H on the C or hetero atom is optionally substituted with one group selected from $C_{1-3}$ linear alkyl, —$N(C_{0-10}$ alkyl)($C_{0-10}$ alkyl), —$CF_3$; When $R_0'$ is adjacent to $R_1'$, $R_0'$ and $R_1'$ together with the atom(s) to which they are attached form a $C_{3-8}$ cycloalkyl, $C_{3-8}$ heterocyclyl containing O or S, —N heteroaryl, —O heteroaryl, —S heteroaryl or phenyl.

Embodiment 13. The compound of any one of embodiments 9-12, pharmaceutically acceptable salt, stereoisomer, ester, prodrug, solvate and deuterated compound thereof, wherein $R_0'$ is selected from: $C_{1-5}$ linear/branched alkyl or —$N(C_{0-10}$ alkyl)($C_{0-10}$ alkyl);

$R_1'$ is selected from: —O heterocyclyl, —N heterocyclyl, —$SO_2$ ($C_{0-3}$ alkyl), —O-phenyl, —S($C_{0-4}$ alkyl), $C_{3-6}$ cycloalkyl, $C_{3-5}$ linear/branched alkyl, wherein the H on the C or hetero atom is optionally substituted with $C_{3-5}$ linear/branched alkyl, —$NH_2$, —$CF_2H$, —$CF_3$, $C_{3-7}$ cycloalkyl, —O heterocyclyl, —N heterocyclyl;

$R_2'$ is —$NH_2$ or —$NO_2$;

$R_3'$ is —H, —F or —$OCH_3$;

$R_4'$ is selected from the followings: —H, —F, —Cl, —$OCH_3$, —CN,

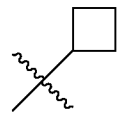

or —C≡C—$R_{10}'$;

$R_5'$, $R_6'$, $R_7'$ are independently selected from: —H, halogen, —$OC_{0-3}$ alkyl, $C_{1-3}$ linear/branched alkyl, $C_{1-3}$ linear/branched alkyl containing or N, or $R_6'$ and $R_7'$ together with the atom(s) to which they are attached form a $C_{3-8}$ cycloalkyl, $C_{3-8}$ heterocyclyl containing O or S, wherein the H on the C is optionally substituted with F;

$R_8'$, $R_9'$ are independently selected from: —H or $C_{1-3}$ linear/branched alkyl;

$R_{11}'$, $R_{12}'$ are independently selected from: —H, —$CF_3$, —$CHF_2H$, —$CH_2F$, $C_{1-5}$ linear/branched alkyl, —CH=CH ($C_{0-10}$ alkyl), $C_{3-10}$ cycloalkyl or six-membered heteroaryl, or $R_{11}'$ and $R_{12}'$ together with the atom(s) to which they are attached form a $C_{3-6}$ cycloalkyl, $C_{4-6}$ fused cycloalkyl, $C_{5-8}$ spiro cycloalkyl, $C_{4-8}$ bridged cycloalkyl, $C_{3-7}$ lactam, $C_{3-7}$ lactone or $C_{3-7}$ cyclic ketone, wherein the H on the C is optionally substituted with one group selected from —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, $C_{0-10}$ linear/branched alkyl, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl, wherein the alkyl moiety can be optionally substituted with one or more of the following groups: —$SO_2$, —$SO_2N(C_{0-10}$ alkyl)($C_{0-10}$ alkyl), —$N(C_{0-10}$ alkyl)$SO_2(C_{0-10}$ alkyl), —$CON(C_{0-10}$ alkyl)($C_{0-10}$ alkyl), —$N(C_{0-10}$ alkyl)$CO(C_{0-10}$ alkyl), —$N(C_{0-10}$ alkyl)$COO(C_{0-10}$ alkyl), —$OCON(C_{0-10}$ alkyl)($C_{0-10}$ alkyl), halogen, —CN, —$OCH_2F$, —$OCHF_2$, —$OCF_3$, —$N(C_{0-10}$ alkyl)($C_{0-10}$ alkyl), —$OC_{0-10}$ alkyl, $C_{3-10}$ cycloalkyl, —O heterocyclyl, —N heterocyclyl, —N heteroaryl, —O heteroaryl or —S heteroaryl.

Embodiment 14. The compound of embodiment 12, pharmaceutically acceptable salt, stereoisomer, ester, prodrug, solvate and deuterated compound thereof, wherein $R_0'$ is —$CH_3$, —$CH_2CH_3$ or —$NH_2$;

$R_1'$ is selected from the followings:

$R_{11}'$, $R_{12}'$ are independently selected from:

—H, —CF$_3$, —CHF$_2$, —CH$_2$F, —CH$_3$, —CH$_2$CH$_3$,

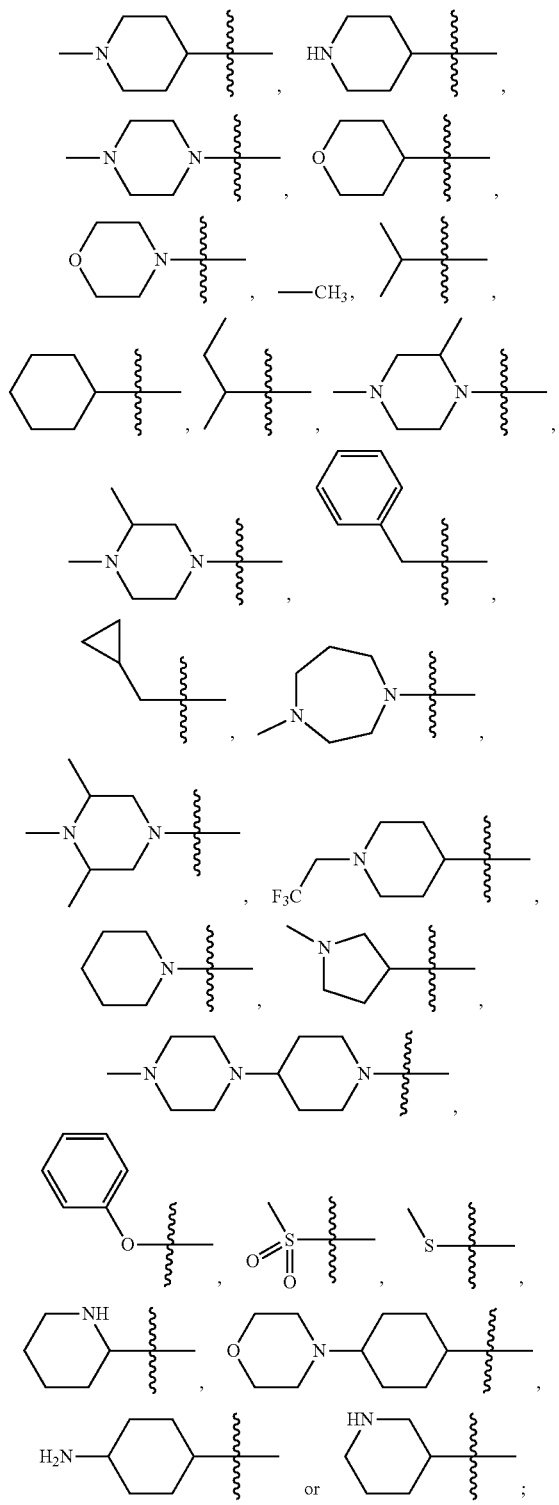

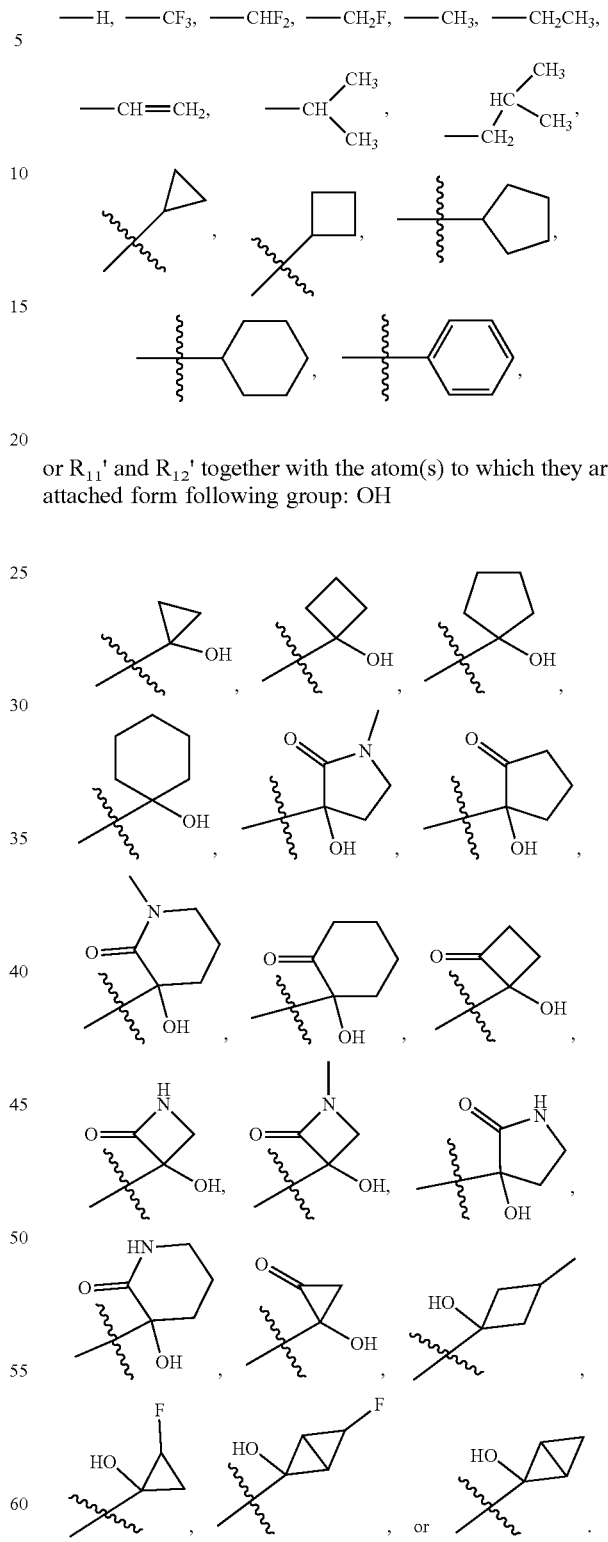

or $R_{11}'$ and $R_{12}'$ together with the atom(s) to which they are attached form following group: OH $R_5'$, $R_6'$, $R_7'$ are independently selected from —H, —F, —Cl, —CH$_3$, —CH$_2$NH$_2$, —CN or —OCH$_3$, or $R_6'$ and $R_7'$ together with the atom(s) to which they are attached form a five-membered cycloalkyl containing O;

$R_8'$, $R_9'$ are independently selected from —H or —CH$_3$;

Embodiment 15. The compound of embodiment 9, pharmaceutically acceptable salt, stereoisomer, ester, prodrug, solvate and deuterated compound thereof, wherein the compound is selected from:

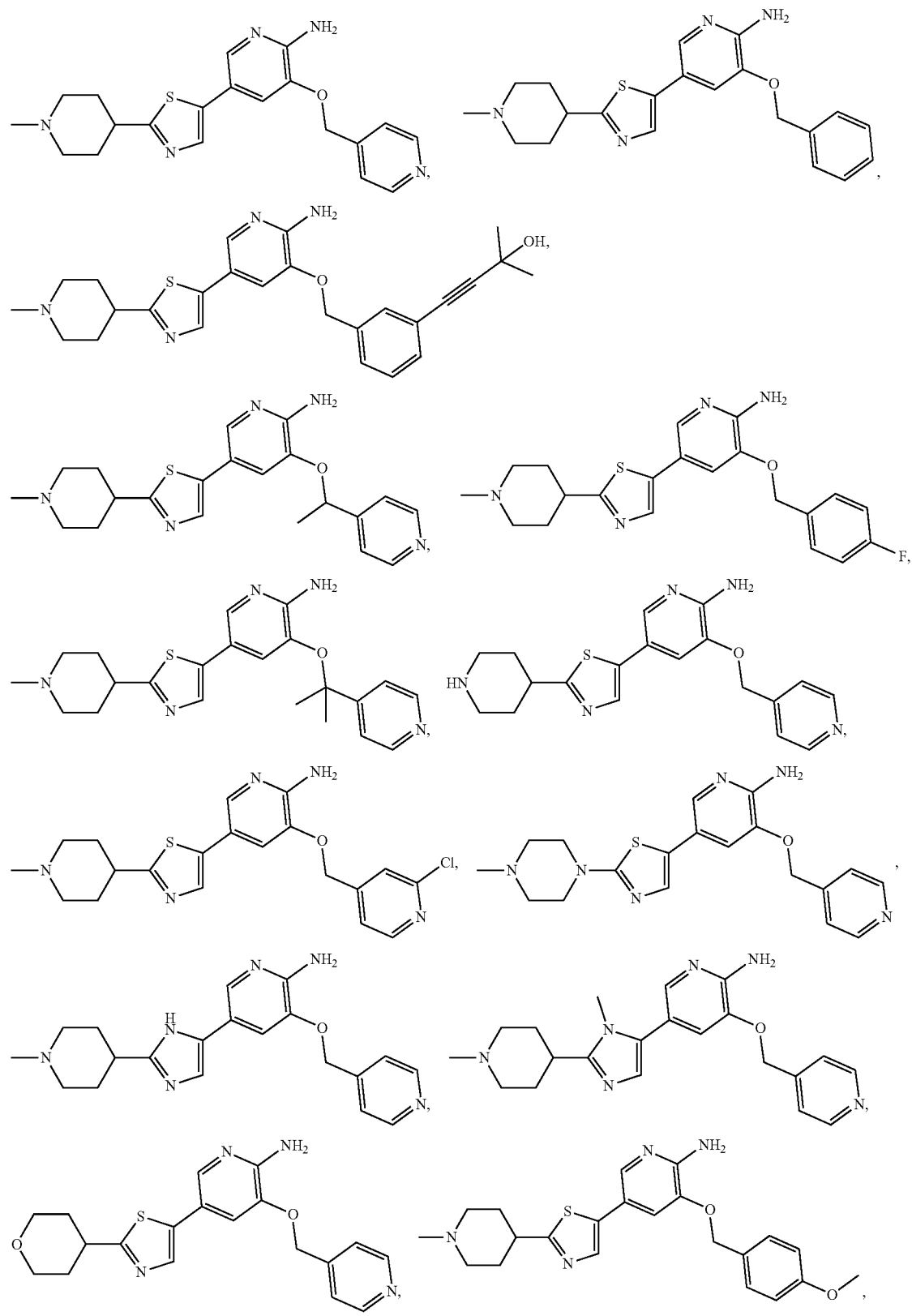

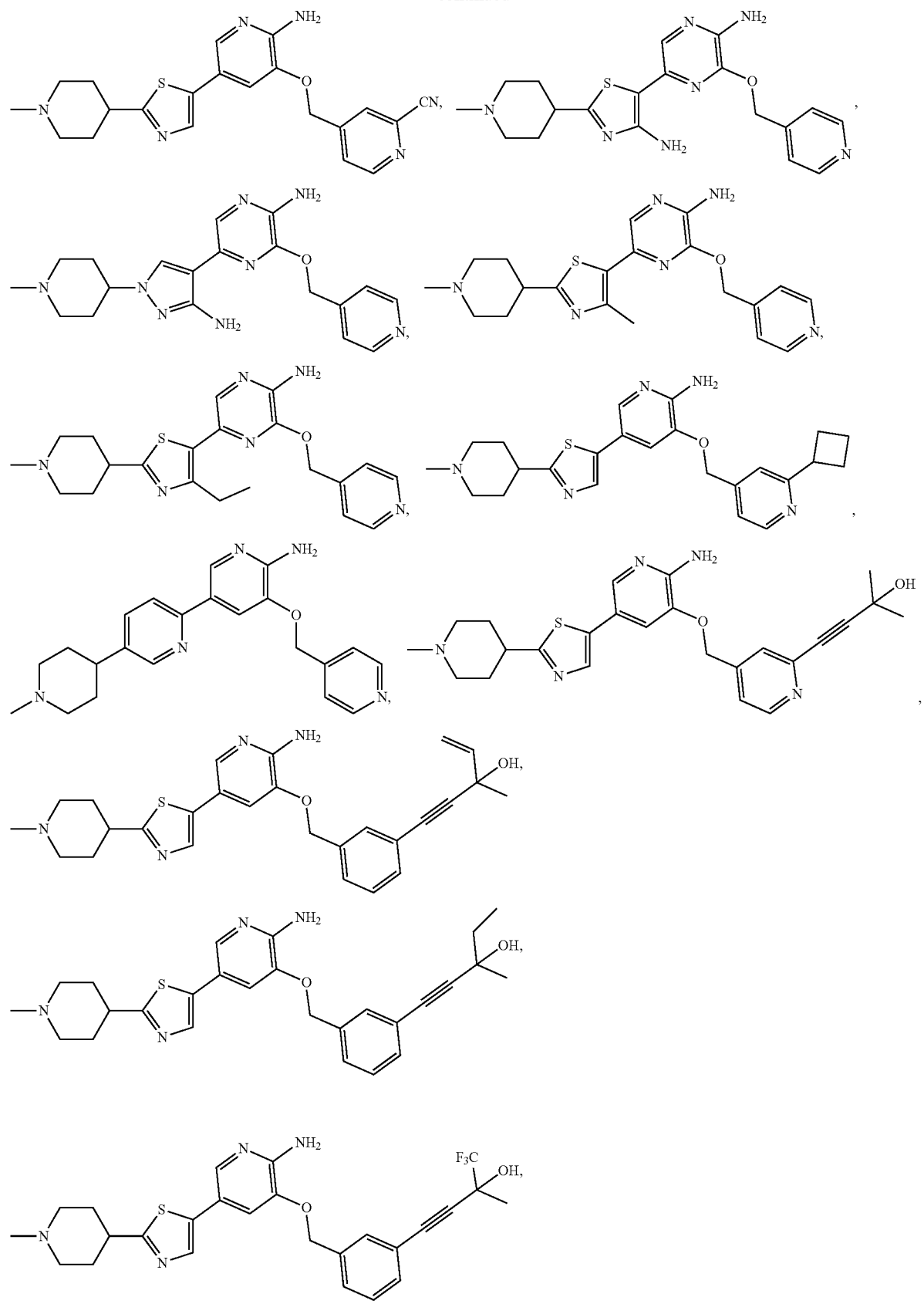

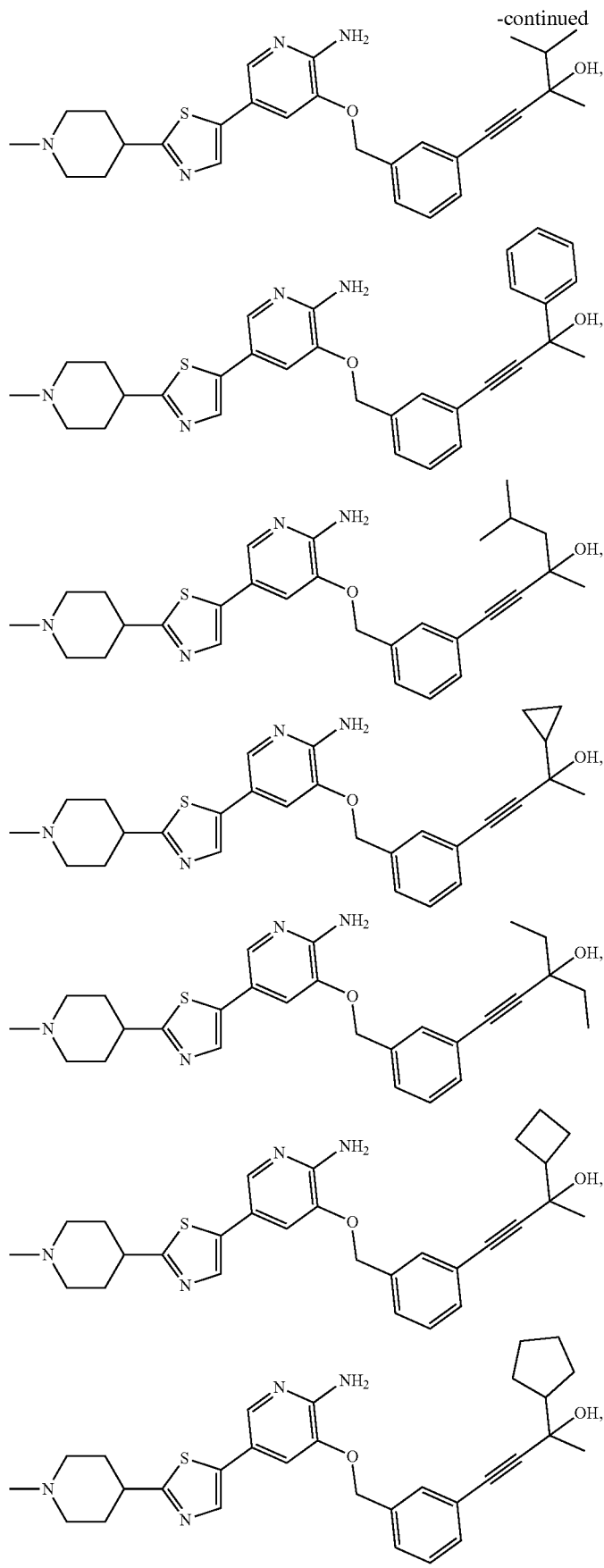

-continued
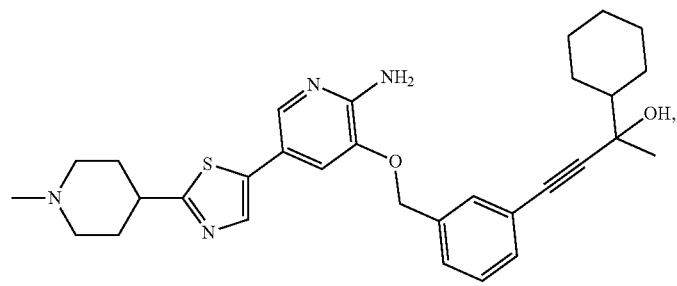
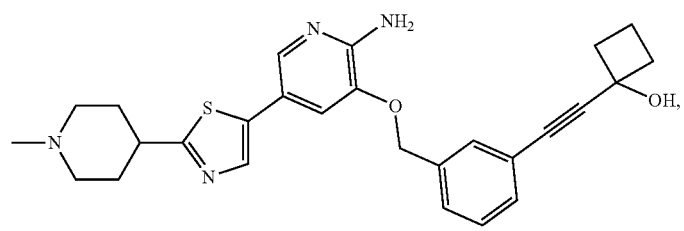
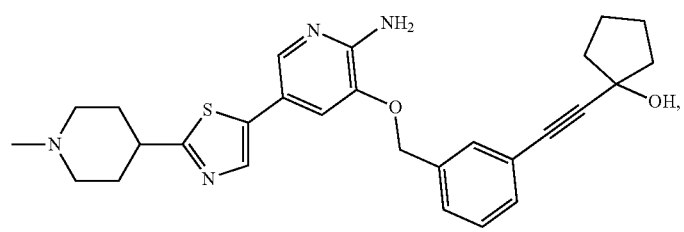
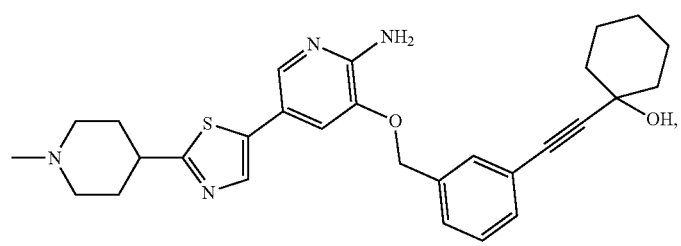
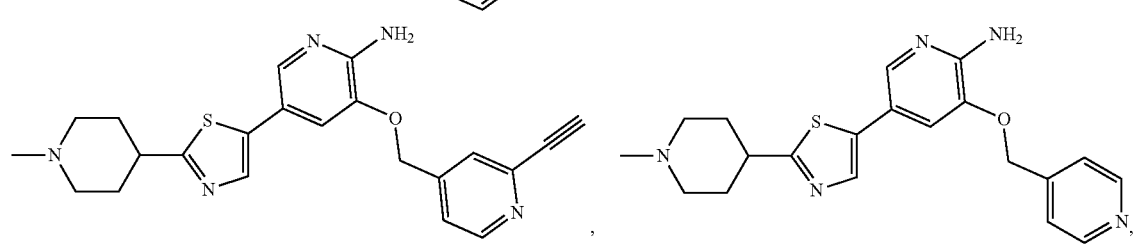
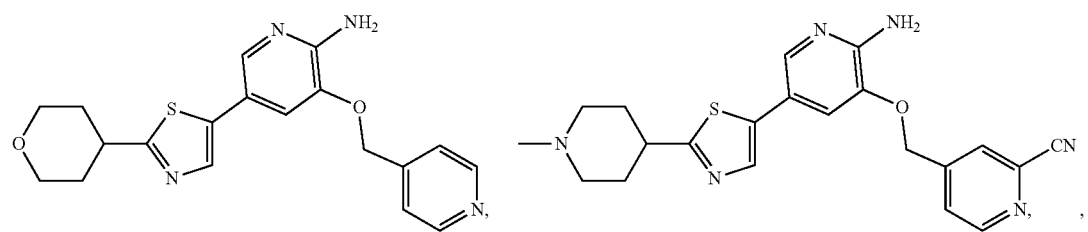
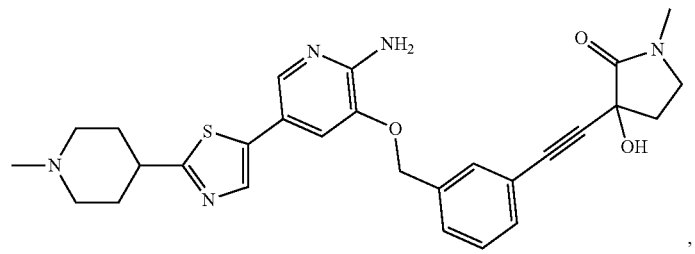

-continued
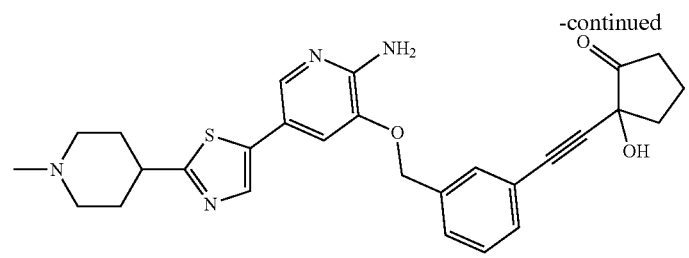
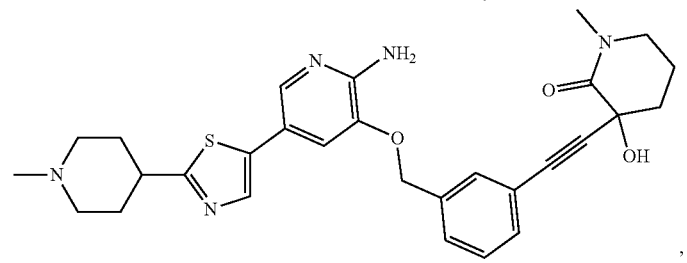
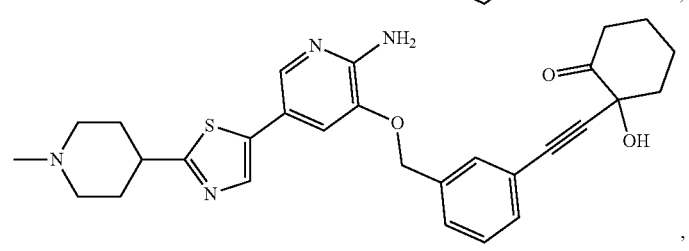
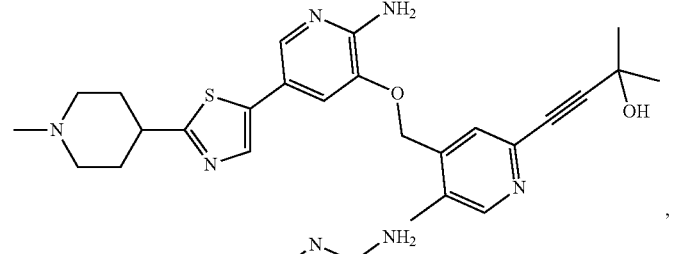

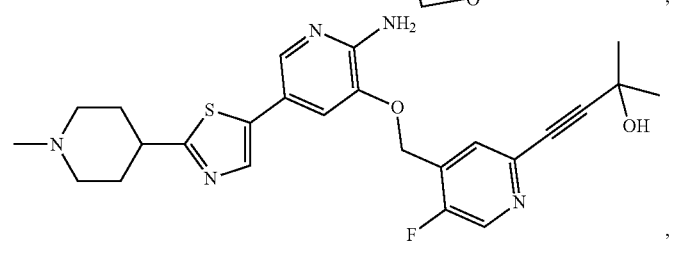
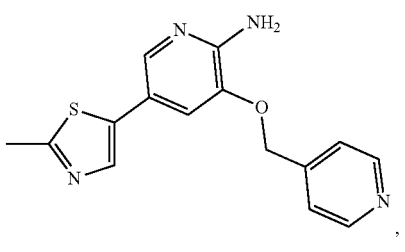

-continued
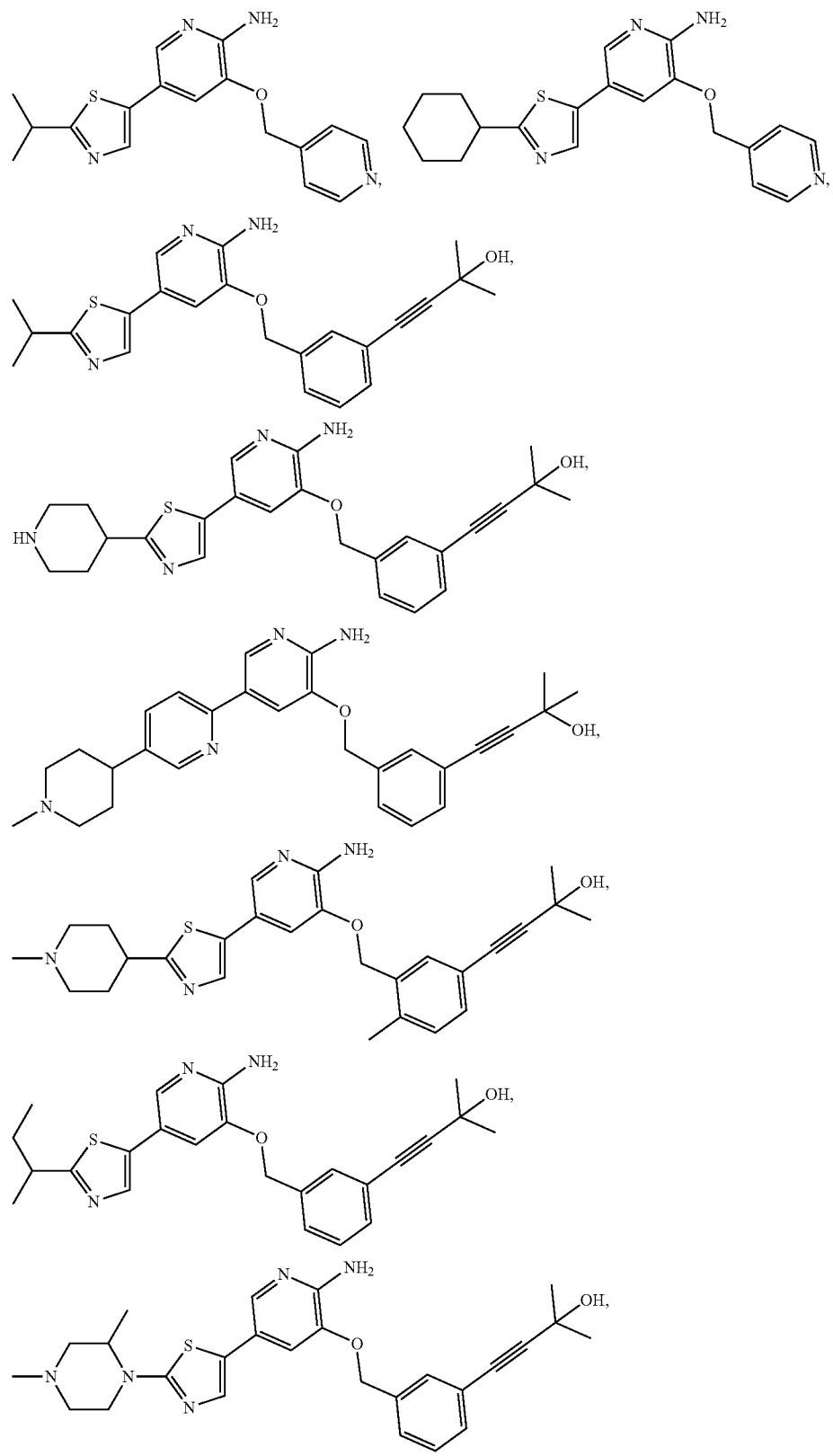

-continued
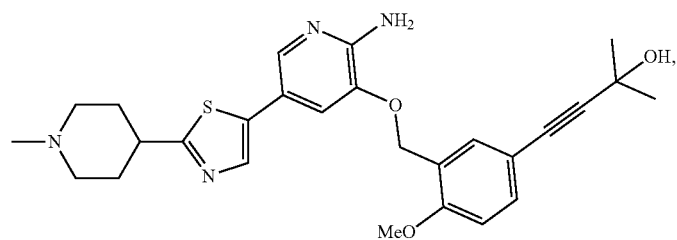
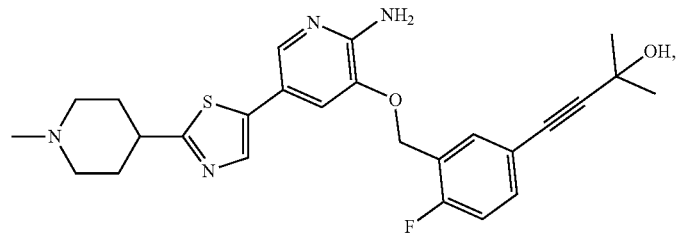
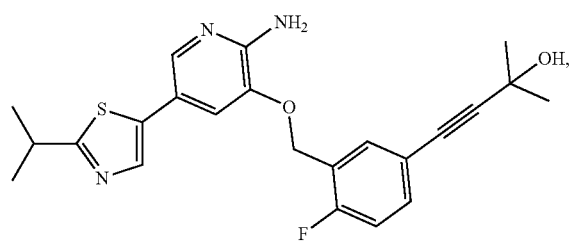
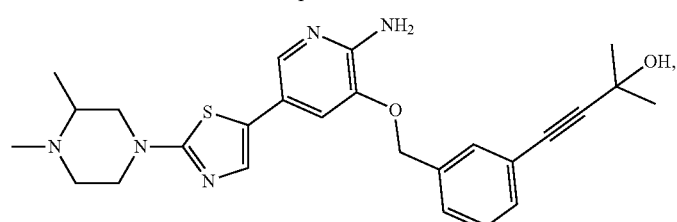
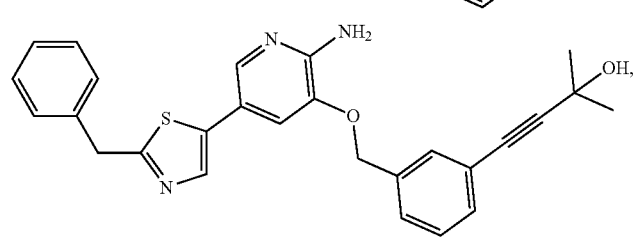
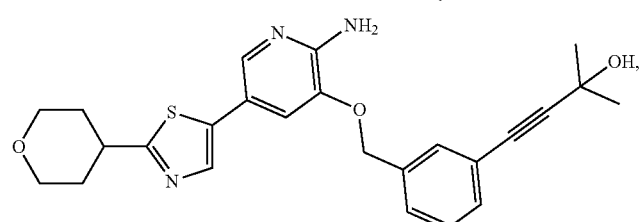
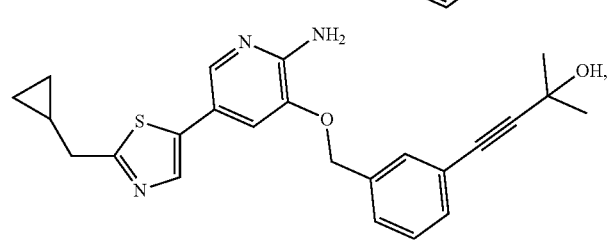

-continued
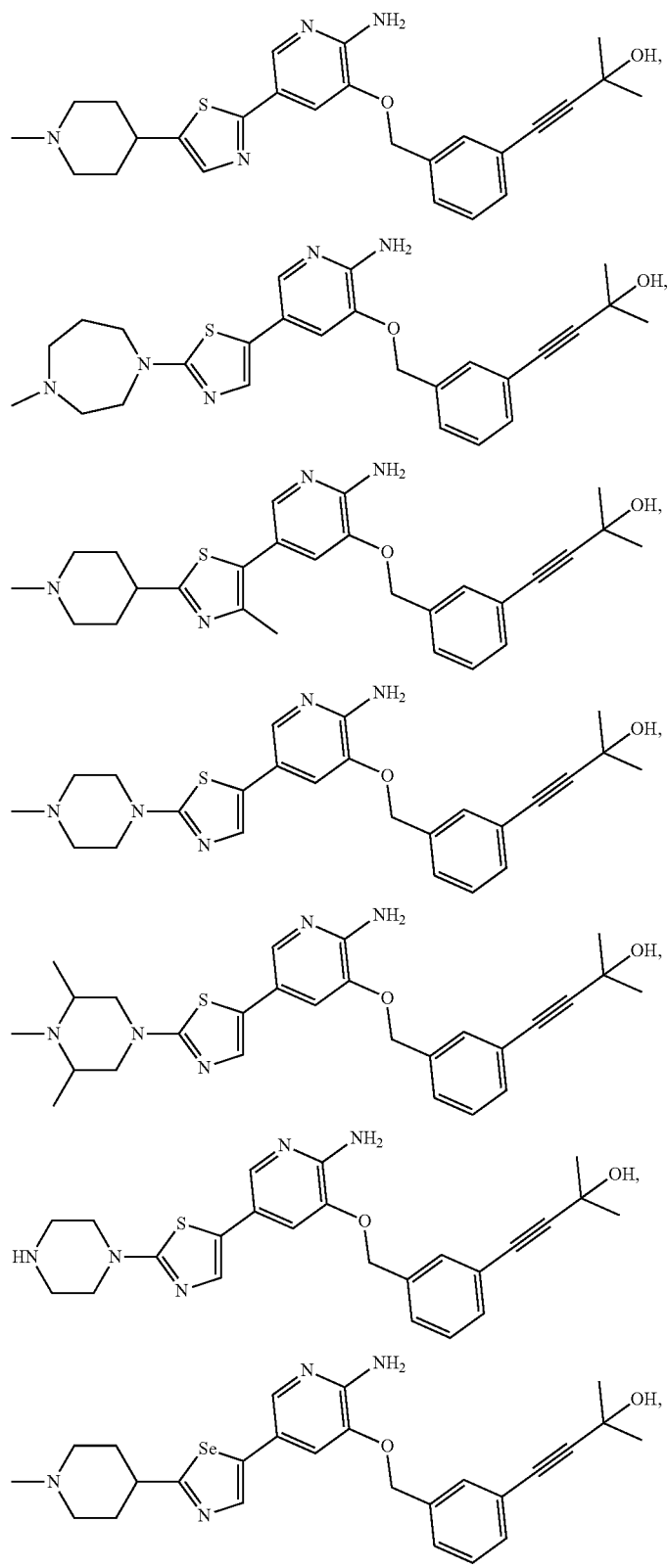

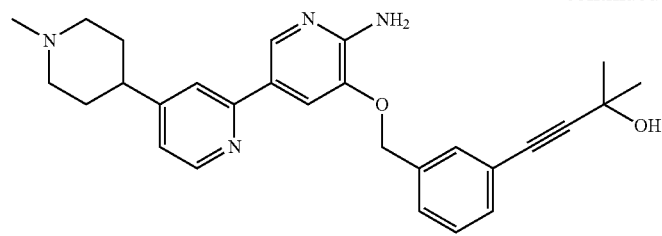
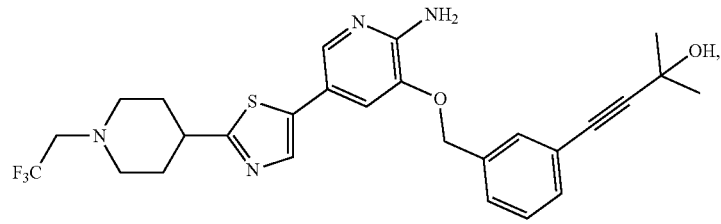
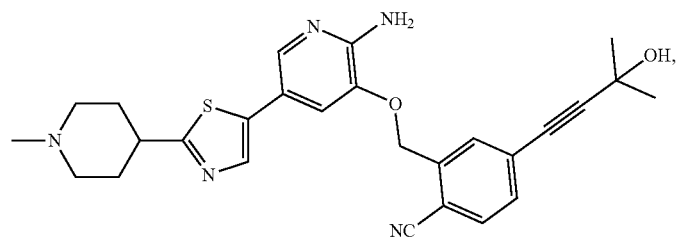
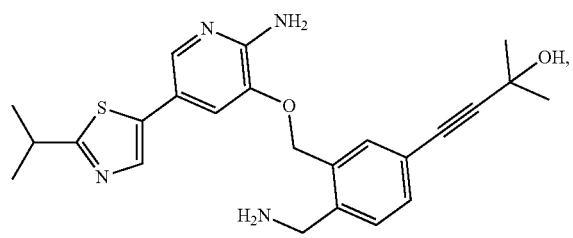
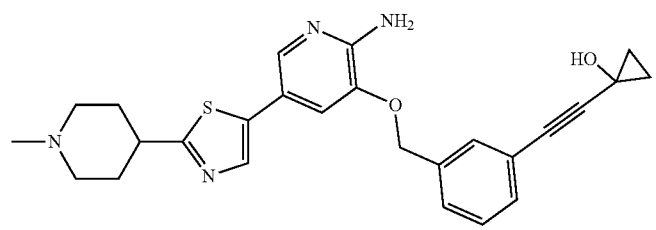
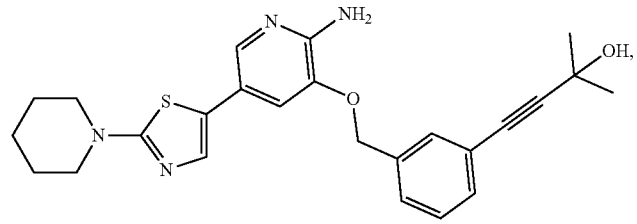
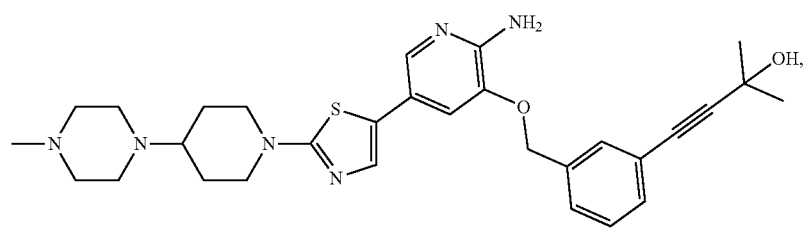

-continued
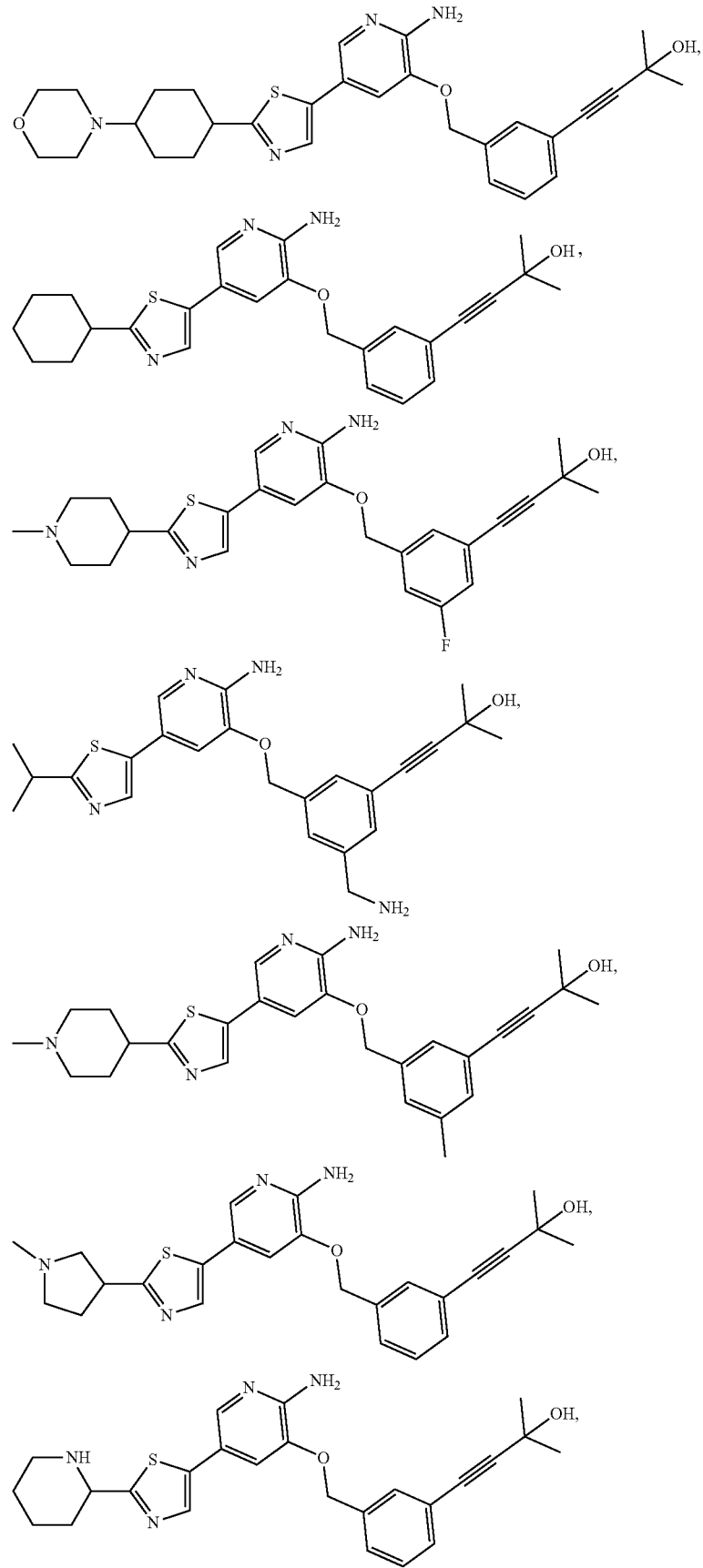

-continued
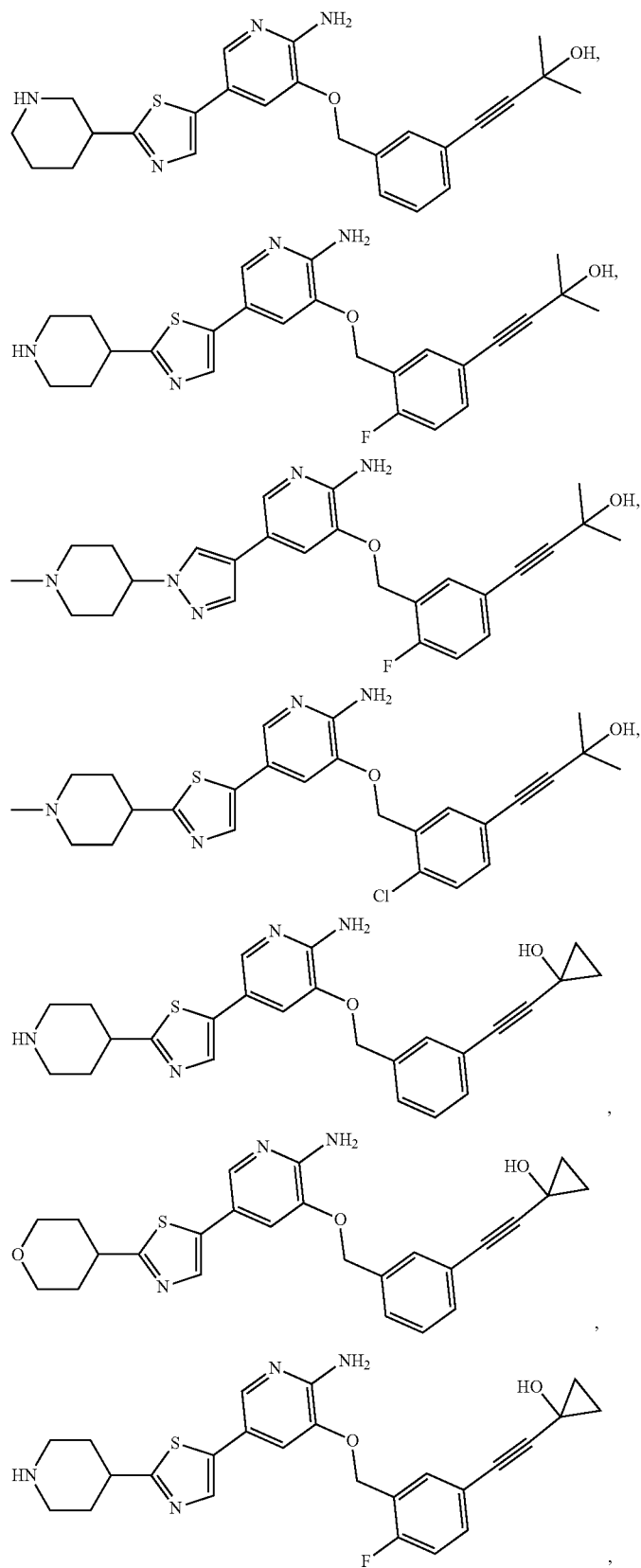

-continued
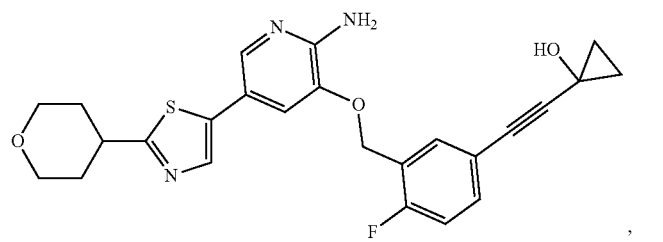,
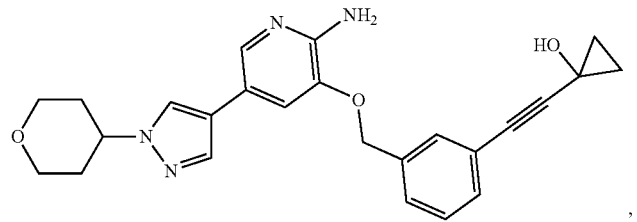,
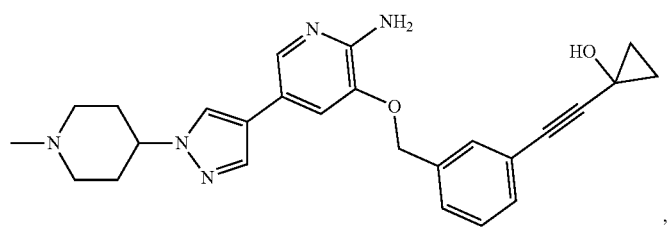,
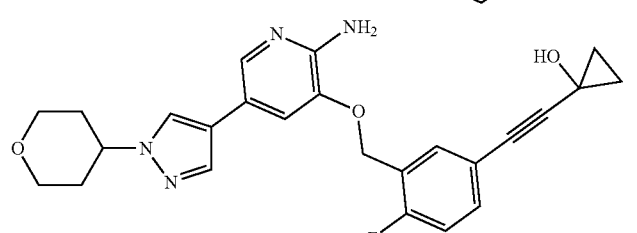,
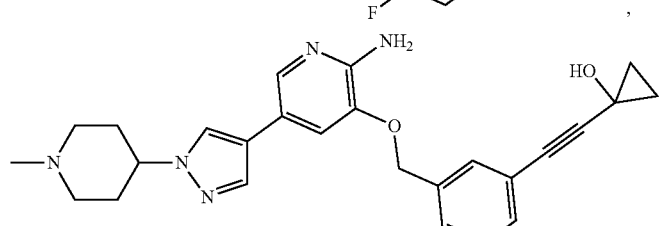,
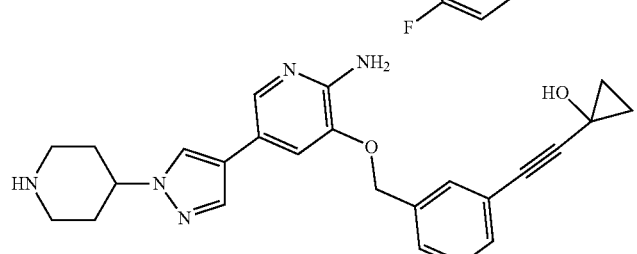,
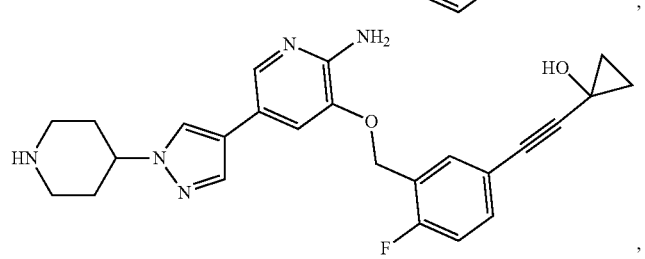,

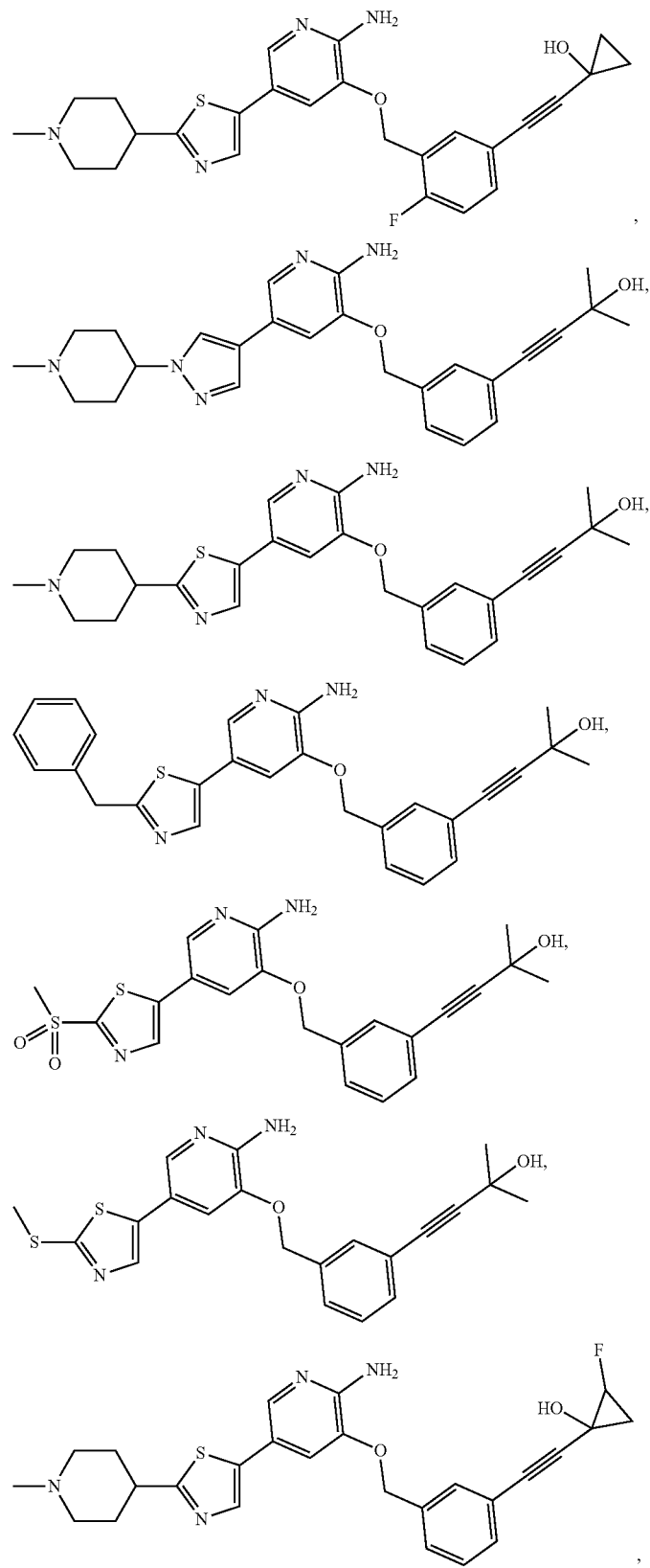

-continued
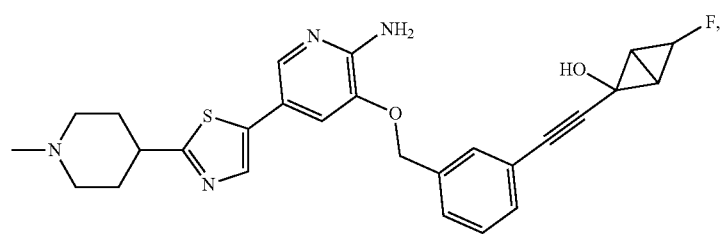
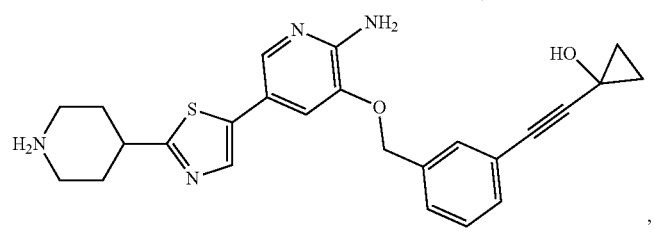
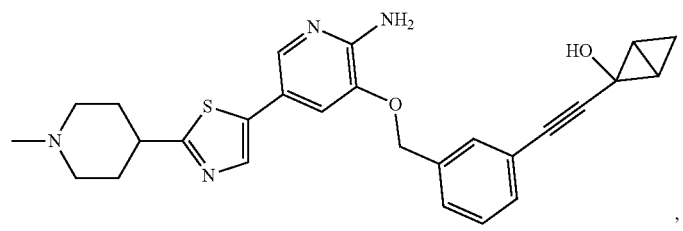
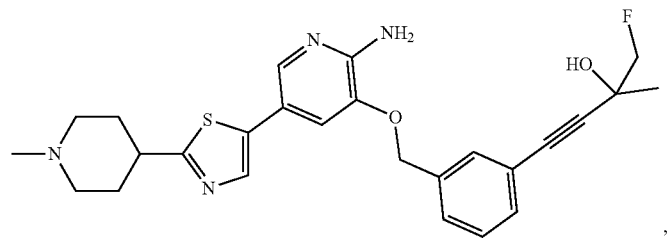
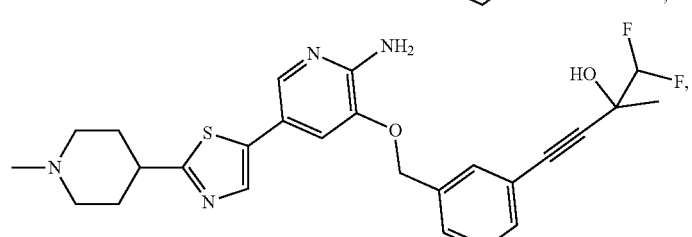
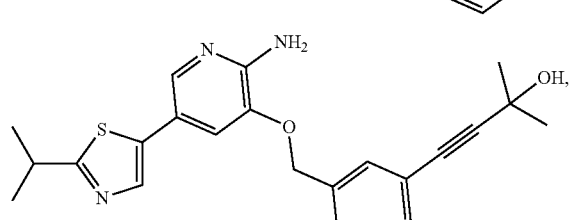
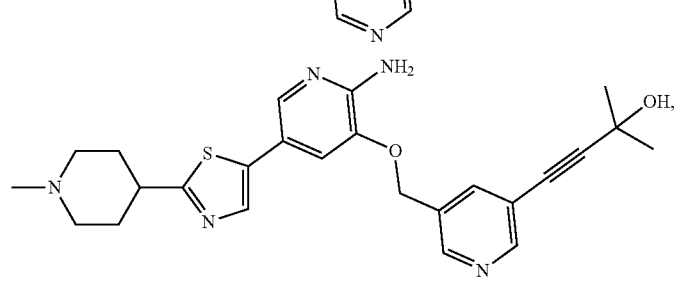

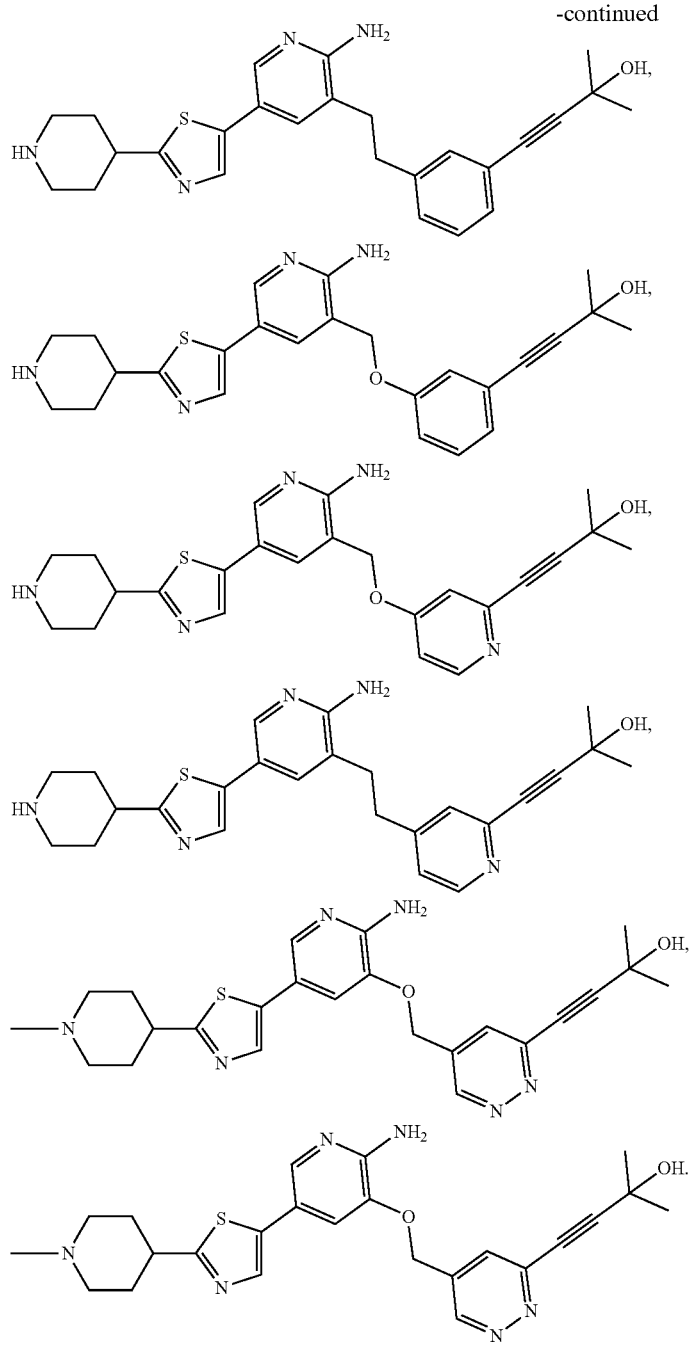
Embodiment 16. A method of preparing the compound of embodiment 9, the steps of the method are as follows:
(1) reacting
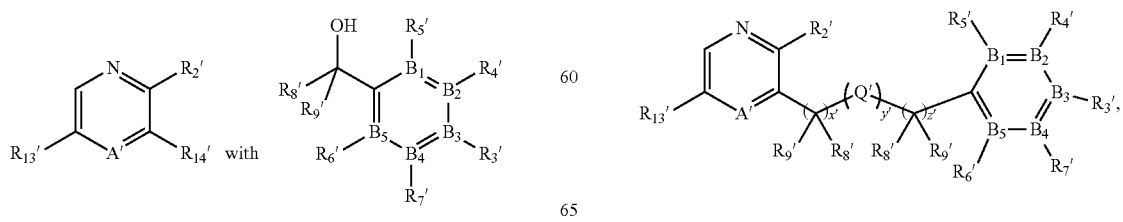
to form (2) reacting

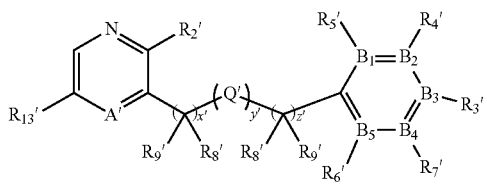

with Ar'—R$_{15}$' to form

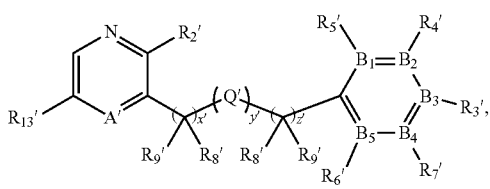

wherein R$_{13}$' is halogen or

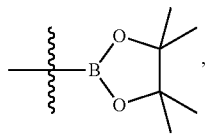 [SMILES: *B1OC(C)(C)C(C)(C)O1]

R$_{14}$' is —OH or halogen, R$_{15}$' is halogen or —SnBu$_3$.

Embodiment 17. A pharmaceutical composition, comprising compound of embodiment 1 or 9, pharmaceutically acceptable salt, stereoisomer, ester, prodrug, solvate and deuterated compound thereof, and further comprising a pharmaceutically acceptable excipient.

Embodiment 18. Use of the compound of embodiment 1 or 9, pharmaceutically acceptable salt, stereoisomer, ester, prodrug, solvate and deuterated compound thereof for the prevention and/or treatment of cancer.

Embodiment 19. Use of the compound of embodiment 1 or 9, pharmaceutically acceptable salt, stereoisomer, ester, prodrug, solvate and deuterated compound thereof in manufacturing a medicament for the prevention and/or treatment of cancer.

Embodiment 20. Use of the compound of embodiment 1 or 9, pharmaceutically acceptable salt, stereoisomer, ester, prodrug, solvate and deuterated compound thereof in combination with PD-1, PD-L1, CTLA-4, TIM-3, TLR4, TLR7, TLR8, TLR9, TGF-β and its receptor, LAG3 antagonist or STING agonists in cancer immunotherapy.

Embodiment 21. Use of the compound of embodiment 1 or 9, pharmaceutically acceptable salt, stereoisomer, ester, prodrug, solvate and deuterated compound thereof in combination with CAR-T immunotherapy in cancer immunotherapy.

Embodiment 22. The use of any one of embodiments 18-21, wherein the cancer is selected from the group comprising of a carcinoma: lymphoma, blastoma, medulloblastoma, retinoblastoma, sarcoma, liposarcoma, synovial cell sarcoma, neuroendocrine tumors, carcinoid tumors, gastrinoma, islet cell cancer, mesothelioma, schwannoma, acoustic neuroma, meningioma, adenocarcinoma, melanoma, leukemia or lymphoid malignancies, squamous cell cancer, epithelial squamous cell cancer, lung cancer, small-cell lung cancer (SCLC), non-small cell lung cancer (NSCLC), adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, metastatic breast cancer, colon cancer, rectal cancer, colorectal cancer, endometrial or uterine carcinoma, salivary gland carcinoma, kidney or renal cancer, prostate cancer, vulval cancer, thyroid cancer, anal carcinoma, penile carcinoma, Merkel cell cancer, esophageal cancer, tumors of the biliary tract, head and neck cancer, and hematological malignancies.

DETAILED DESCRIPTION

The technical solutions in the embodiments of the present invention will be clearly and completely described below. It is obvious that the described embodiments are only partial embodiments of the present invention, and not all. All other embodiments obtained by a person of ordinary skill in the art based on the embodiments of the present invention without creative efforts are within the scope of the present invention.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

A typical chromatography condition for LC MS is as follows:
Instrument: Agilent 1200-6100
Column: HALO C-18, 4.6*50 mm, 2.7 μm
Mobile phase: ACN (0.1% FA)-Water (0.1% FA)
Gradient: 5% ACN to 95% ACN in 1.0 min, hold 1.0 min, total 2.5 min
Flow rate: 1.8 mL/min.

A typical chromatography condition for HPLC is as follows:
Shimadzu LC-2010
Column: Gemini, 4.6*150 mm, 5 μm
Mobile phase: ACN (0.05% TFA)-Water (0.05% TFA)
Gradient: 0% ACN to 60% ACN in 7.5 min, 60% ACN to 100% ACN in 0.5 min, hold 2.0 min, total 10 min
Flow rate: 1.2 mL/min Example 1 Preparation of Compound 8 (A1)

The synthetic route of the compound is as follows:

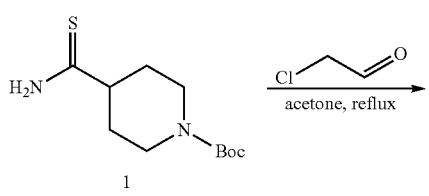

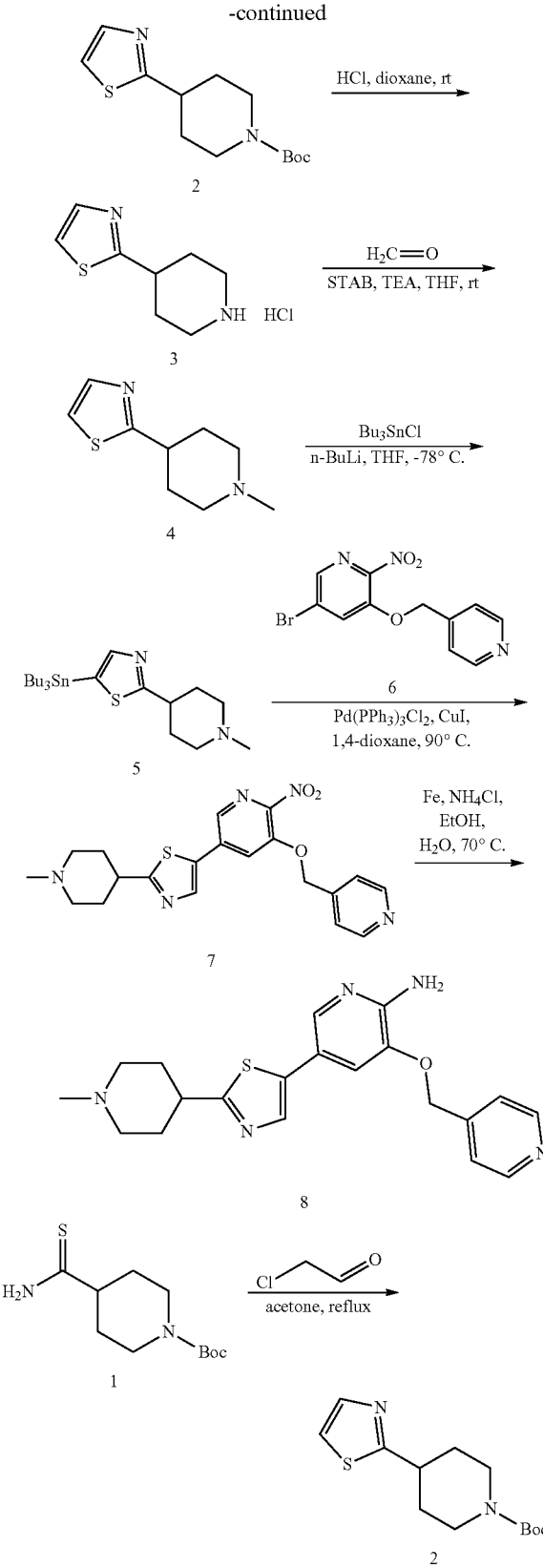

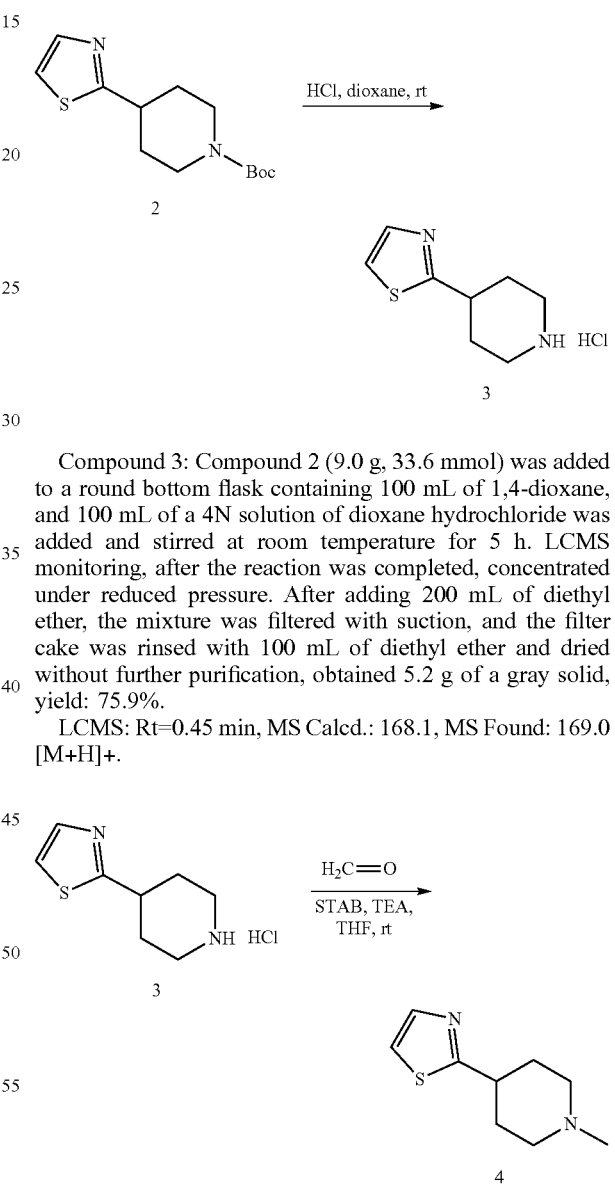

Compound 2: The compound 4-aminothiocarbonyltetrahydropyridine-1(2H)-carboxylic acid tert-butyl ester (25.0 g, 102.4 mmol) and chloroacetaldehyde (40% aqueous solution, 30.0 g, 153.6 mmol) were sequentially added to a round bottom flask containing 300 mL of acetone, stirred at 50° C. for 16 h. LCMS monitoring, after the reaction was completed, cooled to room temperature, concentrated, and then separated by column chromatography (eluent: petroleum ether/ethyl acetate, 5/1, v/v), obtained 9.0 g of a yellow oily liquid, yield: 32.9%. $^1$H NMR (400 MHz, CDCl$_3$) δ ppm 1.47 (s, 9H), 1.73 (ddd, J=25.0, 12.1, 4.3 Hz, 2H), 2.09 (dt, J=15.5, 4.7 Hz, 2H), 2.86 (dd, J=25.4, 13.1 Hz, 2H), 3.13-3.21 (m, 1H), 4.14 (dd, J=17.4, 10.1 Hz, 2H), 7.22 (d, J=3.3 Hz, 1H), 7.69 (d, J=3.3 Hz, 1H).

LCMS: Rt=0.45 min, MS Calcd.: 268.1, MS Found: 212.9 [M+H-56]+.

Compound 3: Compound 2 (9.0 g, 33.6 mmol) was added to a round bottom flask containing 100 mL of 1,4-dioxane, and 100 mL of a 4N solution of dioxane hydrochloride was added and stirred at room temperature for 5 h. LCMS monitoring, after the reaction was completed, concentrated under reduced pressure. After adding 200 mL of diethyl ether, the mixture was filtered with suction, and the filter cake was rinsed with 100 mL of diethyl ether and dried without further purification, obtained 5.2 g of a gray solid, yield: 75.9%.

LCMS: Rt=0.45 min, MS Calcd.: 168.1, MS Found: 169.0 [M+H]+.

Compound 4: In a 250 mL round bottom flask, compound 3 (5.2 g, 25.6 mmol) was dissolved in 80 mL of tetrahydrofuran, triethylamine (2.6 g, 25.6 mmol), 37% aqueous formaldehyde (3.1 g, 38.4 mmol), and sodium triacetoxyborohydride (8.1 g, 38.4 mmol) was added, stirred at room temperature for 16 h. LCMS monitoring, after the reaction was completed, concentrated under reduced pressure, diluted with 1N sodium hydroxide solution (50 mL), extracted with dichloromethane (100 mL×3), and the combined extracts were washed with saturated aqueous sodium chloride (100 mL), dried with anhydrous Na$_2$SO$_4$, concentrated under reduced pressure, and then separated by column chromatography (eluent: dichloromethane/methanol, 6/1, v/v), obtained 3.6 g of a yellow oily liquid, yield: 77.3%. $^1$H NMR (400 MHz, CD$_3$OD) δ ppm 1.81-1.90 (m, 2H), 2.21-2.67 (m, 4H), 2.34 (s, 3H), 2.98-3.08 (m, 3H), 7.71 (d, J=2.6 Hz, 1H), 7.48 (d, J=3.4 Hz, 1H).

LCMS: Rt=0.42 min, MS Calcd.: 182.1, MS Found: 183.0 [M+H]+.

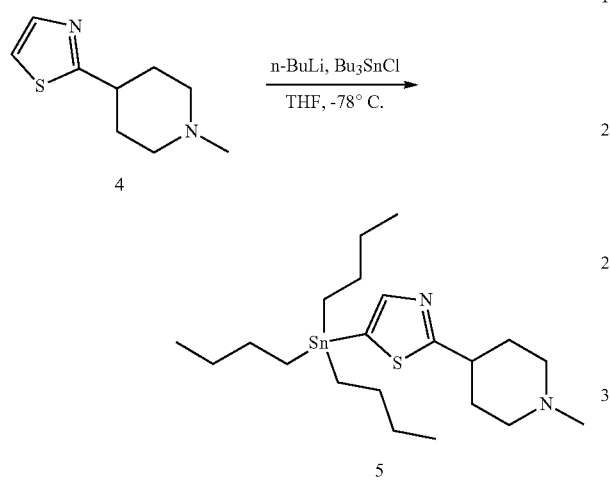

Compound 5: In a 250 mL three-necked flask, Compound 4 (3.6 g, 19.7 mmol) was dissolved in 60 mL of tetrahydrofuran, cooled to −78° C., and n-butyllithium (2.4 M in tetrahydrofuran, 8.2 mL, 19.7 mmol) was added under nitrogen, stirred at −78° C. for 1 h, then tributyltin chloride (6.4 g, 19.7 mmol) was added dropwise, stirred at −78° C. for 1 h. LCMS monitoring, after the reaction was completed, quenched with saturated ammonium chloride (50 mL), extracted with EtOAc (100 mL×3), and the combined extracts were washed with saturated aqueous sodium chloride (100 mL), dried with anhydrous Na$_2$SO$_4$, concentrated under reduced pressure without further purification, obtained 7.8 g of a yellow oily liquid.

LCMS: Rt=1.55 min, MS Calcd.: 472.2, MS Found: 473.0 [M+H]+.

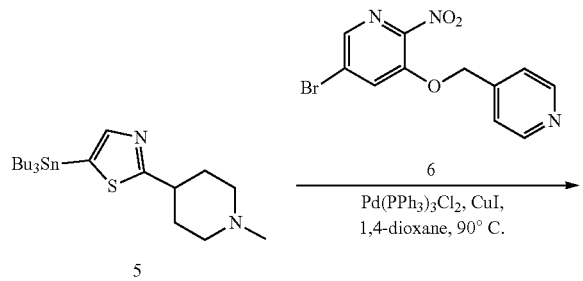

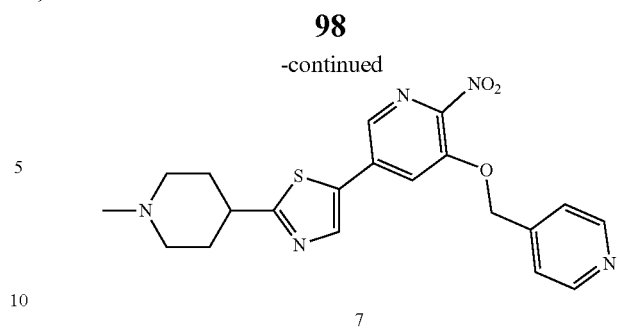

Compound 7: Compound 5 (764 mg, 1.62 mmol), 6 (500 mg, 1.62 mmol), bis(triphenylphosphine) palladium dichloride (112 mg, 0.16 mmol) and cuprous iodide (91 mg, 0.48 mmol) were sequentially added to a round bottom flask containing 15 mL of dioxane, protected with nitrogen, and stirred at 90° C. for 6 h. LCMS monitoring, after the reaction was completed, cooled to room temperature, concentrated, and separated by column chromatography (eluent: methylene chloride/methanol, 6/1, v/v), obtained 250 mg of a yellow solid, yield: 37.7%.

LCMS: Rt=1.04 min, MS Calcd.: 411.1, MS Found: 411.7 [M+H]+.

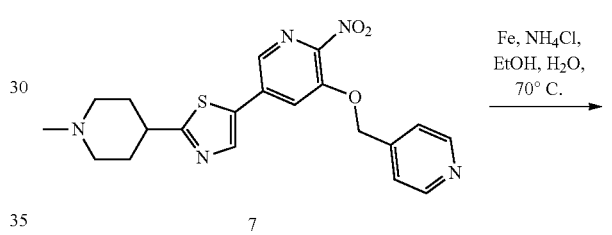

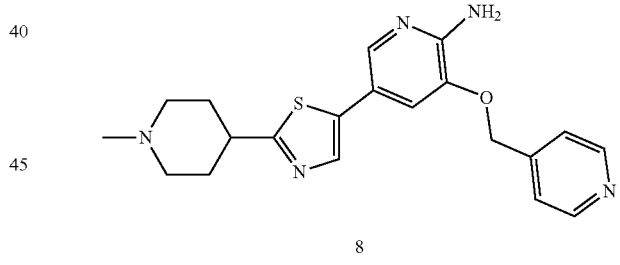

Compound 8: Compound 7 (250 mg, 0.61 mmol), reduced iron powder (170 mg, 3.04 mmol) and ammonium chloride (163 mg, 3.04 mmol) were sequentially added to a round bottom flask containing 10 mL of ethanol and 2 mL of water, Stirred at 70° C. for 3 h. LCMS monitoring, after the reaction was completed, cooled to room temperature, concentrated, and then separated by high performance liquid chromatography (column: Gemini-C18 150×21.2 mm, 5 μm, mobile phase: ACN-H2O (0.1% TFA), gradient: 0-20% ACN), lyophilized, obtained 115 mg of a white solid, yield: 37.7%. $^1$H NMR (400 MHz, D$_2$O) δ ppm 1.93-2.04 (m, 2H), 2.35 (d, J=14.7 Hz, 2H), 2.81 (s, 3H), 3.09-3.15 (m, 2H), 3.36-3.39 (m, 1H), 3.53-3.60 (m, 2H), 5.65 (s, 2H), 7.54 (d, J=2.5 Hz, 1H), 7.69 (d, J=2.5 Hz, 1H), 7.85 (s, 1H), 8.12 (d, J=6.5 Hz, 2H), 8.75 (d, J=6.7 Hz, 2H).

LCMS: Rt=0.34 min, MS Calcd.: 381.1, MS Found: 381.9 [M+H]+.

Example 2 Preparation of Compound 19 (A2)

The synthetic route of the compound is as follows:

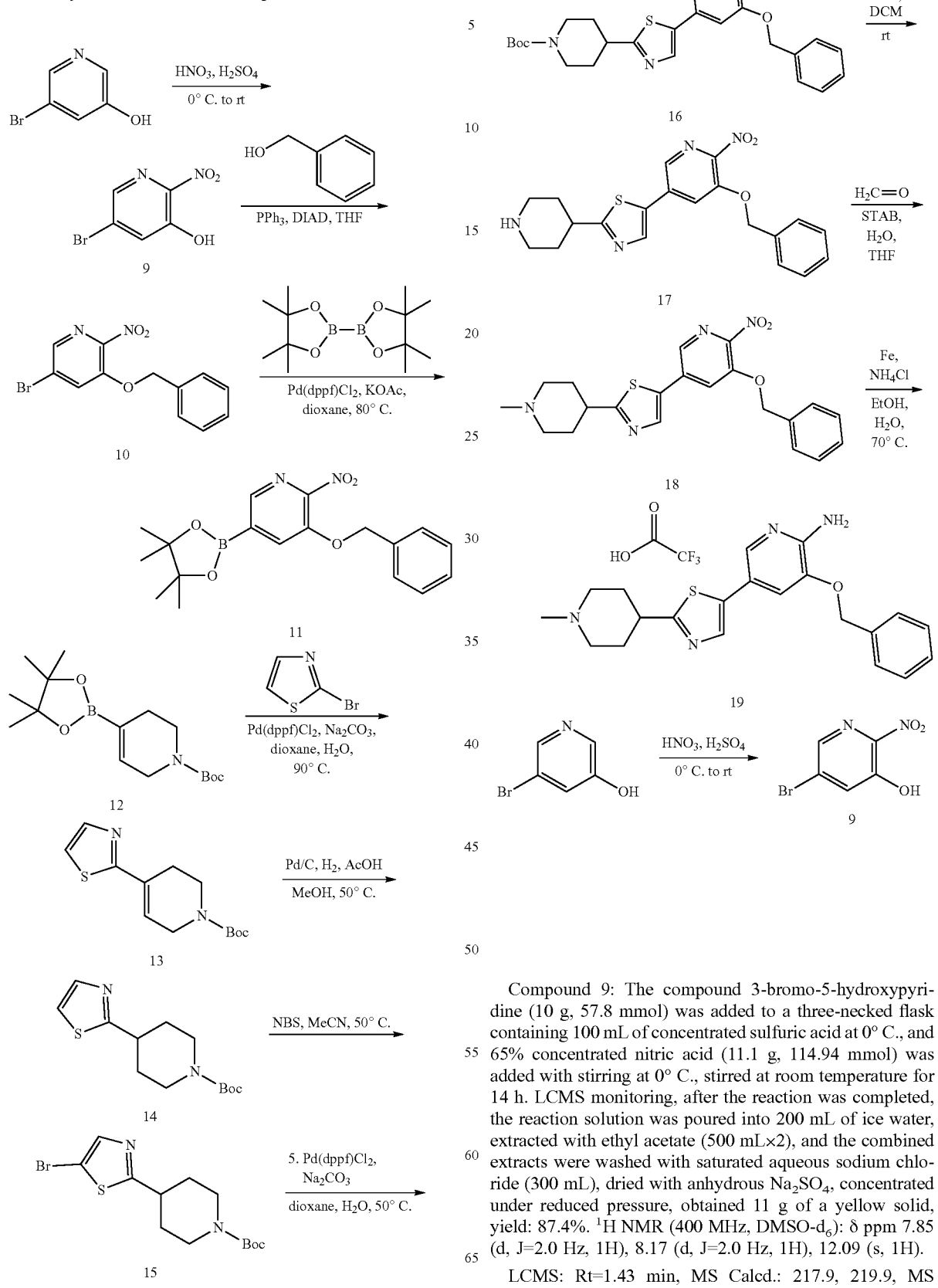

Compound 9: The compound 3-bromo-5-hydroxypyridine (10 g, 57.8 mmol) was added to a three-necked flask containing 100 mL of concentrated sulfuric acid at 0° C., and 65% concentrated nitric acid (11.1 g, 114.94 mmol) was added with stirring at 0° C., stirred at room temperature for 14 h. LCMS monitoring, after the reaction was completed, the reaction solution was poured into 200 mL of ice water, extracted with ethyl acetate (500 mL×2), and the combined extracts were washed with saturated aqueous sodium chloride (300 mL), dried with anhydrous $Na_2SO_4$, concentrated under reduced pressure, obtained 11 g of a yellow solid, yield: 87.4%. $^1$H NMR (400 MHz, DMSO-$d_6$): δ ppm 7.85 (d, J=2.0 Hz, 1H), 8.17 (d, J=2.0 Hz, 1H), 12.09 (s, 1H).

LCMS: Rt=1.43 min, MS Calcd.: 217.9, 219.9, MS Found: 218.7, 220.8 [M+H]$^+$.

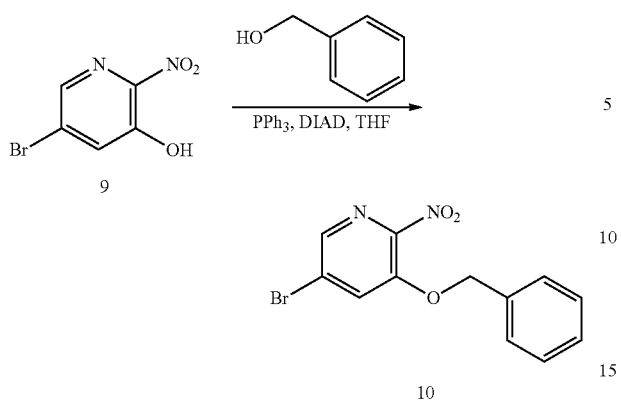

Compound 10: Compound 9 (4.4 g, 20 mmol), benzyl alcohol (2.6 g, 24 mmol), triphenylphosphine (6.4 g, 24 mmol) was sequentially added to a three-neck bottle containing 100 ml of anhydrous tetrahydrofuran, protected with nitrogen, diisopropyl azodicarboxylate (4.85 g, 24 mmol) was added at 0° C. and stirred at 0° C. for 4 h. LCMS monitoring, after the reaction was completed, concentrated under reduced pressure. Added 100 mL of water, extracted with ethyl acetate (100 mL×2), and the combined extracts were washed with saturated aqueous sodium chloride (100 mL), dried with anhydrous $Na_2SO_4$, concentrated under reduced pressure, and then purified by column chromatography (eluent: petroleum ether/ethyl acetate, 10/1, v/v), obtained 3.2 g of a white solid, yield: 49%. $^1$H NMR (400 MHz, DMSO-$d_6$): δ ppm 5.41 (s, 2H), 7.37-7.45 (m, 5H), 8.31 (d, J=2.0 Hz, 1H), 8.43 (d, J=1.6 Hz, 1H).

LCMS: Rt=1.73 min, MS Calcd.: 308.0, 310.0, MS Found: 308.8, 310.8 [M+H]$^+$.

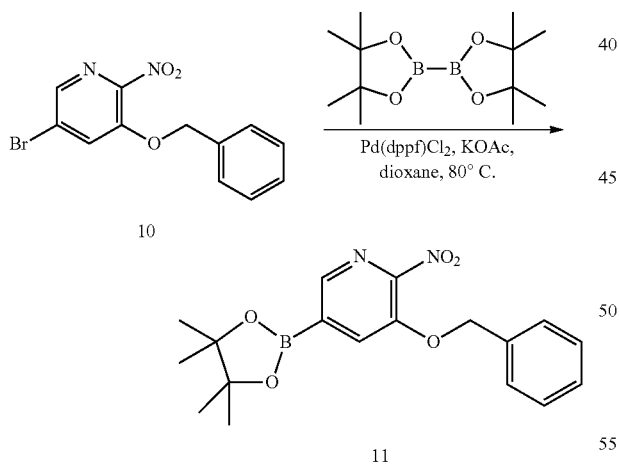

Compound 11: Compound 10 (3 g, 9.7 mmol), pinacol borate (4.9 g, 19.4 mmol), potassium acetate (2.9 g, 29.1 mmol), [1,1'-bis(diphenylphosphine) ferrocene] palladium dichloride dichloromethane complex (1.6 g, 1.94 mmol) was sequentially added to a 250 mL round bottom flask containing 100 mL of dioxane, protected with nitrogen, and stirred at 80° C. for 12 h. LCMS monitoring, after the reaction was completed, cooled to room temperature, concentrated under reduced pressure, and then purified by column chromatography (eluent: dichloromethane/methanol, 50/1-20/1, v/v), obtained 5 g of a red solid. $^1$H NMR (400 MHz, DMSO-$d_6$): δ ppm 1.35 (s, 12H), 5.42 (s, 2H), 7.36-7.43 (m, 5H), 8.09 (d, J=1.2 Hz, 1H), 8.28 (d, J=1.2 Hz, 1H).

LCMS: Rt=1.51 min, MS Calcd.: 356.2, MS Found: 274.8 [M+H-82]$^+$.

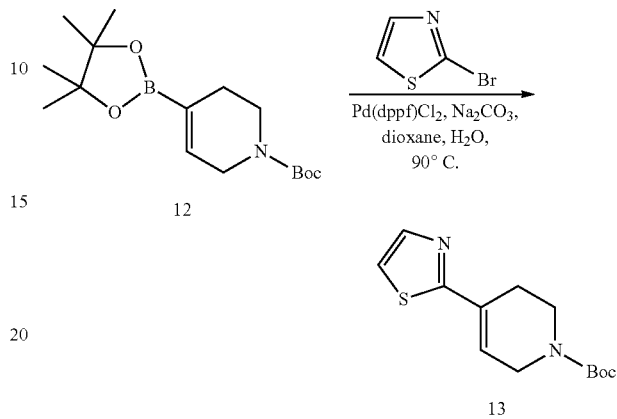

Compound 13: Compound 12 (10 g, 32.4 mmol), 2-bromothiazole (5.8 g, 35.6 mmol), sodium carbonate (10.2 g, 97.2 mmol), [1,1'-bis(diphenylphosphine) ferrocene] palladium dichloride dichloromethane complex (2.6 g, 3.2 mmol) was sequentially added to a 500 mL round bottom flask containing 200 mL of dioxane and 50 mL of water, protected with nitrogen, and stirred at 90° C. for 3 h. LCMS monitoring, after the reaction was completed, cooled to room temperature, concentrated under reduced pressure. Added 200 mL of water, extracted with ethyl acetate (300 mL×2), and the combined extracts were washed with saturated aqueous sodium chloride (200 mL), dried with anhydrous $Na_2SO_4$, concentrated under reduced pressure, and then purified by column chromatography (eluent: petroleum ether/ethyl acetate, 5/1, v/v), obtained 7.8 g of a yellow oily liquid, yield: 90.1%. $^1$H NMR (400 MHz, CDCl$_3$): δ ppm 1.50 (s, 9H), 2.70-2.73 (m, 2H), 3.66 (t, J=5.2 Hz, 2H), 4.13-4.14 (m, 2H), 6.59 (s, 1H), 7.24 (d, J=4.0 Hz, 1H), 7.77 (d, J=3.6 Hz, 1H).

LCMS: Rt=1.62 min, MS Calcd.: 266.1, MS Found: 266.9 [M+H]$^+$.

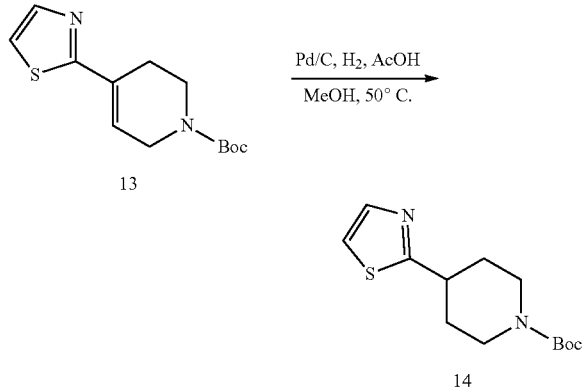

Compound 14: Compound 13 (7.8 g, 29.2 mmol), 10% palladium on carbon (10 g), acetic acid (10 ml) was sequentially added to a 1 L reactor containing 300 mL of methanol/

100 mL of tetrahydrofuran, stirred at 50° C. for 48 h in a 0.4 MPa hydrogen atmosphere. LCMS monitoring, after the reaction was completed, and filtered, the filtrate was concentrated under reduced pressure. Added 100 mL of water, extracted with ethyl acetate (200 mL×2), and the combined extracts were washed with saturated aqueous sodium chloride (100 mL), dried with anhydrous $Na_2SO_4$, concentrated under reduced pressure, and obtained 6.5 g of a yellow oily liquid, yield: 82.7%. $^1$H NMR (400 MHz, $CDCl_3$): δ ppm: 1.46 (s, 9H), 1.69-1.79 (m, 2H), 2.08-2.11 (m, 2H), 2.88 (t, J=12.2 Hz, 2H), 3.12-3.20 (m, 1H), 4.18 (br. s, 2H), 7.21 (d, J=3.6 Hz, 1H), 7.69 (d, J=3.2 Hz, 1H).

LCMS: Rt=1.58 min, MS Calcd.: 268.1, MS Found: 212.9 [M+H-56]$^+$.

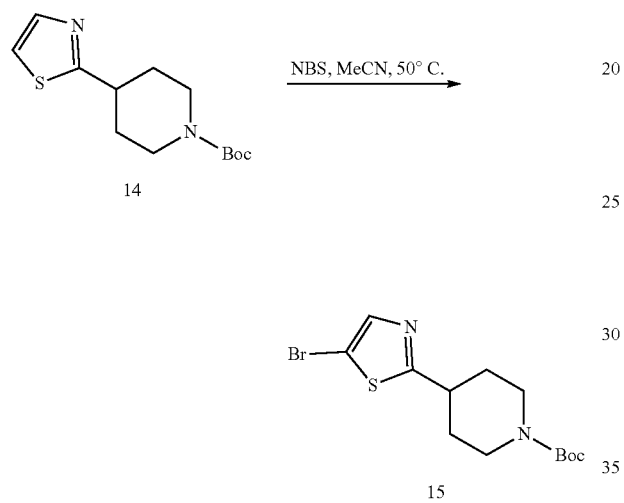

Compound 15: Compound 14 (4 g, 15 mmol), N-bromosuccinimide (5.3 g, 30 mmol) was sequentially added to a 250 mL round bottom flask containing 100 mL of acetonitrile and stirred at 50° C. for 4 h. LCMS monitoring, after the reaction was completed, quenched with saturated sodium thiosulfate solution (30 mL), extracted with EtOAc (100 mL×2), and the combined extracts were washed with saturated aqueous sodium chloride (100 mL), dried with anhydrous $Na_2SO_4$, concentrated under reduced pressure, and then purified by column chromatography (eluent: ethyl acetate/petroleum ether, 1:10, v/v), obtained 1.5 g of a yellow oily liquid, yield: 39.5%. $^1$H NMR (400 MHz, $CDCl_3$): δ ppm 1.47 (s, 9H), 1.65-1.75 (m, 2H), 2.04-2.08 (m, 2H), 2.87 (t, J=12.4 Hz, 2H), 3.06-3.14 (m, 1H), 4.19 (br. s, 2H), 7.57 (s, 1H).

LCMS: Rt=1.79 min, MS Calcd.: 346.0, 348.0, MS Found: 290.7, 292.7 [M+H-56]$^+$.

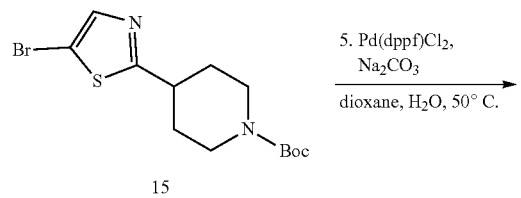

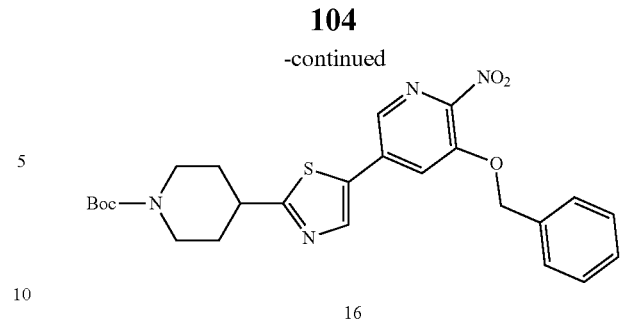

Compound 16: Compound 15 (1.5 g, 8.6 mmol), compound 5 (4 g (crude), 8.6 mmol), sodium carbonate (1.3 g, 12.9 mmol), [1,1'-bis(diphenylphosphine) ferrocene] palladium dichloride dichloromethane complex (708 mg, 0.86 mmol) was sequentially added to a 250 mL round bottom flask containing 100 mL of dioxane and 20 mL of water, protected with nitrogen, and stirred at 50° C. for 14 h. LCMS monitoring, after the reaction was completed, concentrated under reduced pressure. Added 100 mL of water, extracted with dichloromethane (200 mL×3), and the combined extracts were washed with saturated aqueous sodium chloride (100 mL), dried with anhydrous $Na_2SO_4$, concentrated under reduced pressure, and then purified by column chromatography (eluent: ethyl acetate/petroleum ether, 1/3, v/v), obtained 750 mg of a yellow solid, yield: 34.9%. $^1$H NMR (400 MHz, DMSO-$d_6$): δ ppm 1.42 (s, 9H), 1.55-1.61 (m, 2H), 2.07-2.10 (m, 2H), 2.94 (br. s, 2H), 4.01-4.06 (m, 3H), 5.47 (s, 2H), 7.36-7.49 (m, 5H), 8.26 (d, J=1.6 Hz, 1H), 8.42 (d, J=2.0 Hz, 1H), 8.45 (s, 1H).

LCMS: Rt=1.86 min, MS Calcd.: 496.2, MS Found: 440.7 [M+H-56]$^+$.

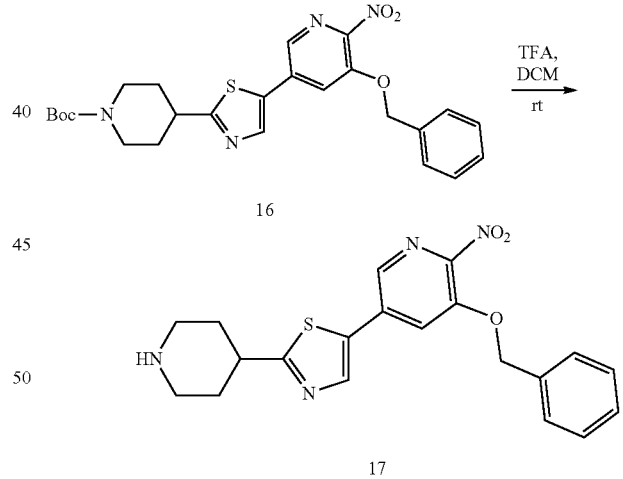

Compound 17: Compound 16 (750 mg, 1.5 mmol) was added to a 100 mL round bottom flask containing 10 mL dichloromethane, and 2 mL of trifluoroacetic acid was added, stirred at room temperature for 14 h. LCMS monitoring, after the reaction was completed, concentrated under reduced pressure. Added 20 mL of saturated sodium bicarbonate solution, pH>7, extracted with dichloromethane (100 mL×4), and the combined extracts were washed with saturated aqueous sodium chloride (50 mL), dried with anhydrous $Na_2SO_4$, concentrated under reduced pressure, and obtained 580 mg of a yellow solid, yield: 97.0%. $^1$H NMR (400 MHz, DMSO-$d_6$): δ ppm 1.70-7.76 (m, 2H), 2.05-2.08

(m, 2H), 2.68-2.77 (m, 3H), 3.10-3.13 (m, 2H), 5.48 (s, 1H), 7.38-7.49 (m, 5H), 8.28 (s, 1H), 8.43 (d, J=1.6 Hz, 1H), 8.46 (s, 1H).

LCMS: Rt=1.33 min, MS Calcd.: 396.1, MS Found: 396.8 [M+H]+.

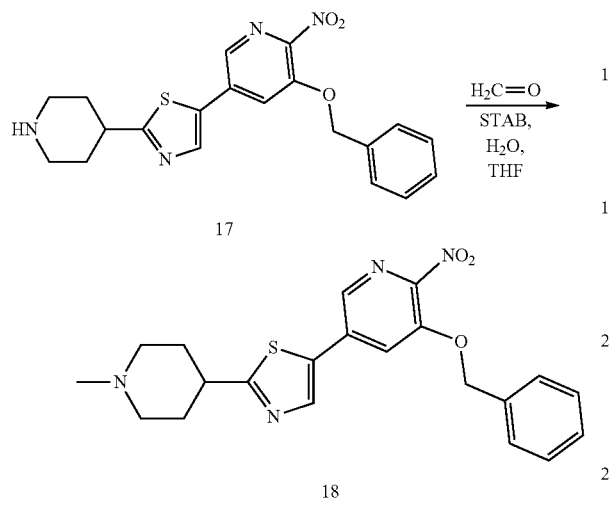

Compound 18: Compound 17 (580 mg, 1.46 mmol), 30% aqueous formaldehyde (732 mg, 7.3 mmol), sodium triacetoxyborohydride (465 mg, 2.2 mmol), acetic acid (4 mL) was sequentially added to a 100 mL round bottom flask containing 20 mL of tetrahydrofuran, stirred at room temperature for 14 h. LCMS monitoring, after the reaction was completed, concentrated under reduced pressure. Added 20 mL of water, extracted with dichloromethane (50 mL×3), and the combined extracts were washed with saturated aqueous sodium chloride, dried with anhydrous Na₂SO₄, concentrated under reduced pressure, and obtained 600 mg of a yellow solid, yield: 100%.

LCMS: Rt=1.33 min, MS Calcd.: 410.1, MS Found: 410.8 [M+H]+.

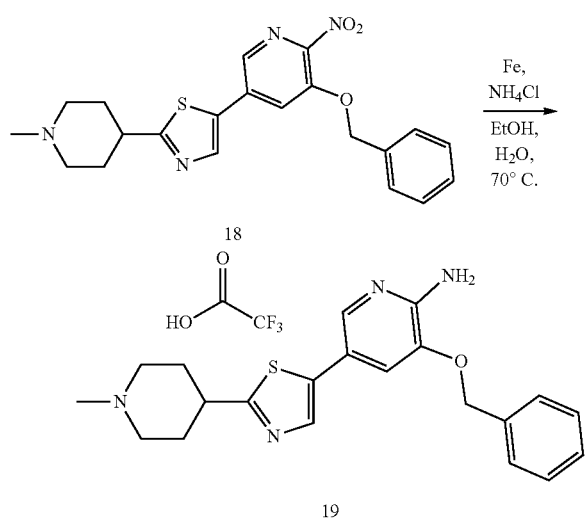

Compound 19: Compound 18 (600 mg, 1.46 mmol), iron powder (408 mg, 7.3 mmol) and ammonium chloride (390 mg, 7.3 mmol) were sequentially added to a 100 mL round bottom flask containing 20 mL of ethanol and 4 mL of water, stirred at 70° C. for 2 h. LCMS monitoring, after the reaction was completed, filtered, the filtrate was concentrated under reduced pressure. Added 20 mL of water, extracted with dichloromethane (50 mL×3), and the combined extracts were washed with saturated aqueous sodium chloride, dried with anhydrous Na₂SO₄, concentrated under reduced pressure, and then separated by high performance liquid chromatography (column: Gemini-C18 150×21.2 mm, 5 μm, mobile phase: ACN-H₂O (0.1% TFA), gradient: 10-40% ACN), lyophilized, obtained 186 mg of a yellow sticky substance, yield: 33.5%. ¹H NMR (400 MHz, CD₃OD): δ ppm 2.06-2.16 (m, 2H), 2.41-2.45 (m, 2H), 2.95 (s, 3H), 3.21 (td, J=13.0, 2.4 Hz, 2H), 3.39-3.46 (m, 1H), 3.66-3.69 (m, 2H), 5.42 (s, 2H), 7.40-7.47 (m, 3H), 7.55-7.57 (m, 2H), 7.72 (br. s, 2H), 8.04 (s, 1H). LCMS: Rt=1.14 min, MS Calcd.: 380.2, MS Found: 380.8 [M+H]+.

Example 3 Preparation of Compound 26 (A3)

The synthetic route of the compound is as follows:

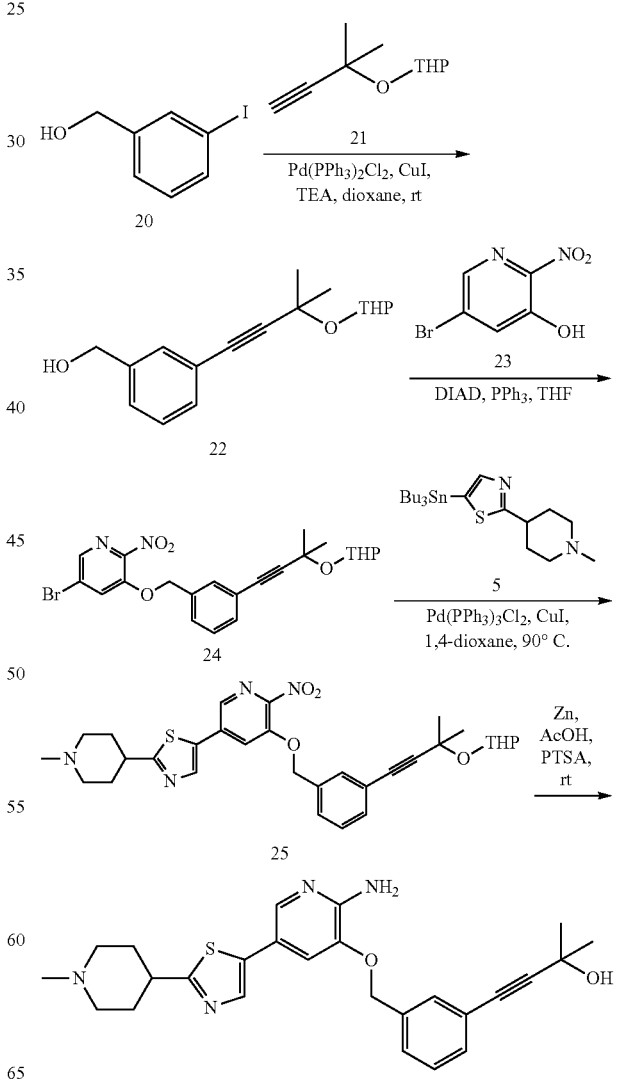

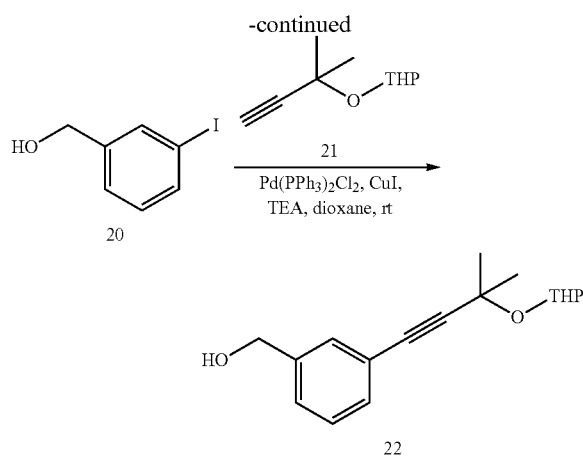

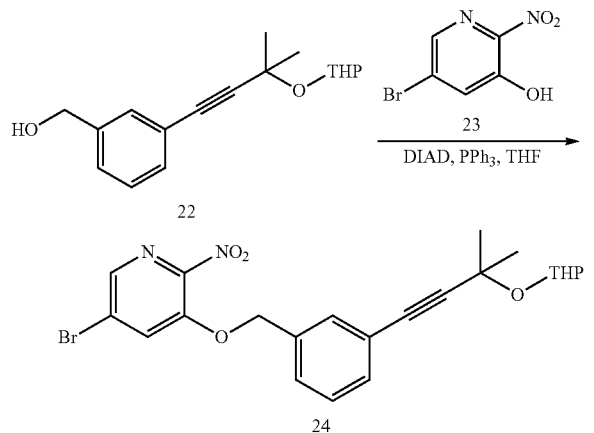

Compound 220 (1 g, 4.3 mmol), 21 (2.15 g, 12.8 mmol), bis(triphenylphosphine) palladium dichloride (302 mg, 0.43 mmol) and cuprous iodide (244 mg, 1.28 mmol) was sequentially added to a round bottom flask containing 10 mL of dioxane and 2 mL of triethylamine, and stirred at room temperature under nitrogen for 16 h. LCMS monitoring, after the reaction was completed, concentrated, and then purified by column chromatography (eluent: petroleum ether/ethyl acetate, 20/1, v/v), obtained 1 g of a yellow oily liquid, yield: 83.7%.

LCMS: Rt=1.67 min, MS Calcd.: 274.2 MS Found: 296.9 [M+Na]+.

Compound 24: Compound 22 (1.0 g, 3.65 mmol), 23 (795 mg, 3.65 mmol) and triphenylphosphine (1.24 g, 4.74 mmol) were sequentially added to a three-neck flask containing 30 mL of tetrahydrofuran, protected with nitrogen, diisopropyl azodicarboxylate (960 mg, 4.74 mmol) was added with stirring and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous Na$_2$SO$_4$, concentrated under reduced pressure, and then purified by column chromatography (eluent: petroleum ether/ethyl acetate, 10/1, v/v), obtained 1.5 g of a white solid, yield: 74.0%. $^1$H NMR (400 MHz, CDCl$_3$) δ ppm 1.47-1.69 (m, 11H), 1.71-1.84 (m, 1H), 3.52-3.58 (m, 1H), 3.98-4.02 (m, 1H), 5.15 (dd, J=5.4, 3.2 Hz, 1H), 5.22 (s, 2H), 7.33-7.51 (m, 4H), 7.68 (t, J=2.3 Hz, 1H), 8.17 (d, J=1.8 Hz, 1H).

LCMS: Rt=1.92 min, MS Calcd.: 474.1, 476.1 MS Found: 496.6, 498.6 [M+Na]+.

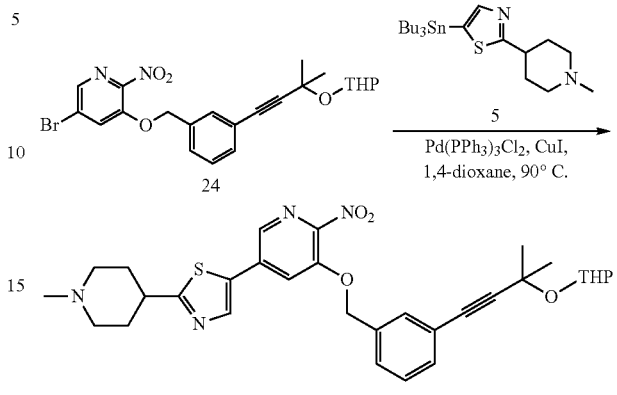

Compound 25: Compound 24 (1.3 g, 2.7 mmol), 5 (1.3 g, 2.7 mmol), bis(triphenylphosphine) palladium dichloride (190 mg, 0.27 mmol) and cuprous iodide (154 mg, 0.81 mmol)) were sequentially added to a round bottom flask containing 30 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 5/1, v/v), obtained 700 mg of a yellow sticky substance (crude).

LCMS: Rt=1.47 min, MS Calcd.: 576.2, MS Found: 576.8 [M+H]+.

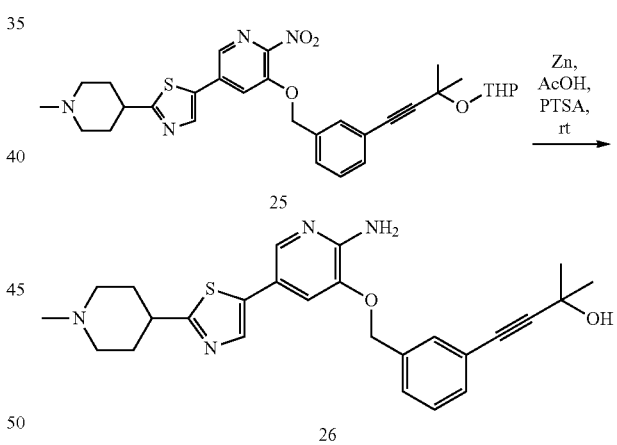

Compound 26: Compound 25 (600 mg, 1.04 mmol), zinc powder (677 mg, 10.4 mmol) and p-toluenesulfonic acid (30 mg) were sequentially added to a round bottom flask containing 10 mL of glacial acetic acid and stirred at room temperature for 24 h. LCMS monitoring, after the reaction was completed, filtered, the filtrate was concentrated, and then separated by high performance liquid chromatography (column: Gemini-C18 150×21.2 mm, 5 μm, mobile phase: ACN-H$_2$O (0.1% TFA), gradient: 15-30% ACN), lyophilized, obtained 79.4 mg of a white solid, yield: 16.3%. $^1$H NMR (400 MHz, DMSO-d$_6$) δ ppm 1.47 (s, 6H), 1.68-1.74 (m, 2H), 1.98-2.05 (m, 4H), 2.20 (s, 3H), 2.82-2.95 (m, 3H), 5.22 (s, 2H), 5.47 (s, 1H), 6.07 (s, 2H), 7.34-7.42 (m, 3H), 7.54 (dd, J=3.8, 1.9 Hz, 2H), 7.77 (d, J=1.9 Hz, 1H), 7.87 (s, 1H).

LCMS: Rt=1.13 min, MS Calcd.: 462.2, MS Found: 462.6 [M+H]+.

Example 4 Preparation of Compound 30 (A4)

The synthetic route of the compound is as follows:

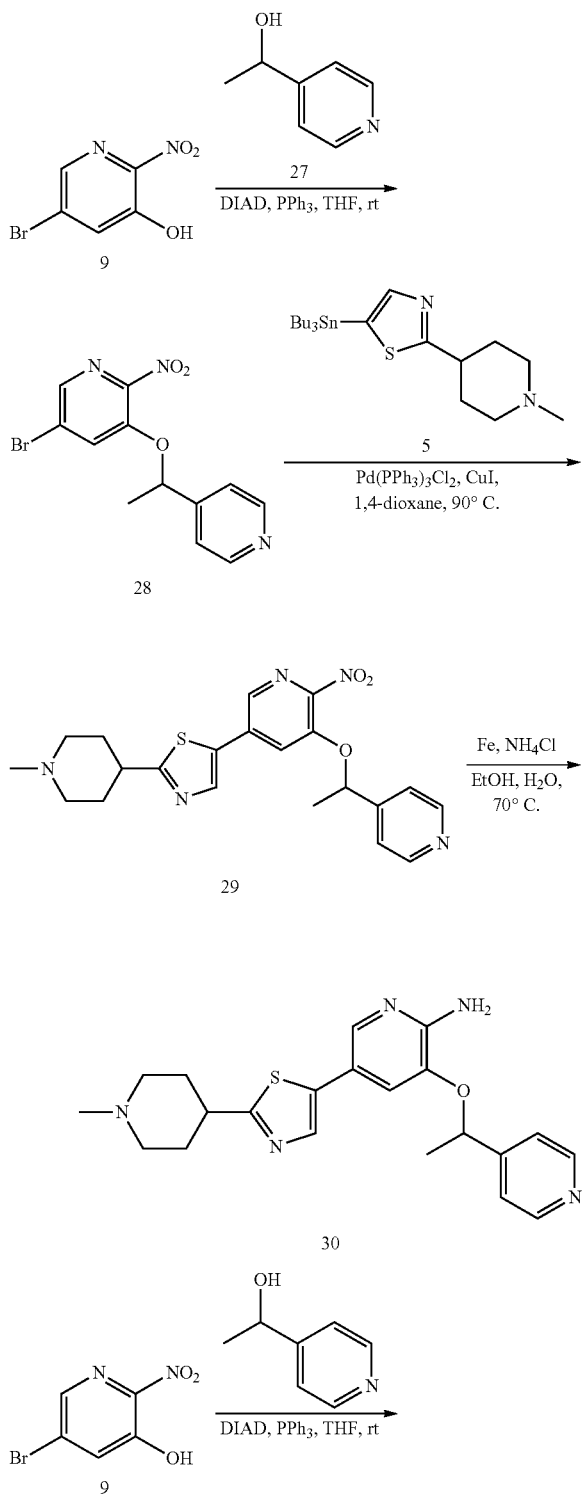

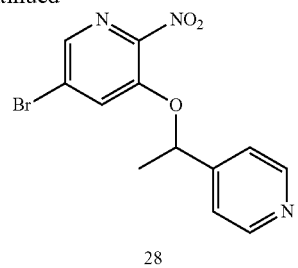

28

Compound 28: Compound 9 (1.0 g, 4.6 mmol), 27 (560 mg, 4.6 mmol) and triphenylphosphine (1.45 g, 5.5 mmol) were sequentially added to a three-neck flask containing 40 mL of tetrahydrofuran, protected with nitrogen, diisopropyl azodicarboxylate (1.12 g, 5.5 mmol) was added with stirring and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous $Na_2SO_4$, concentrated under reduced pressure, and then purified by column chromatography (eluent: petroleum ether/ethyl acetate, 1/2, v/v), obtained 1.4 g of a white solid (crude containing triphenylphosphine oxide).

LCMS: Rt=1.38 min, MS Calcd.: 323.1, 324.1 MS Found: 323.7, 325.7 [M+H]+.

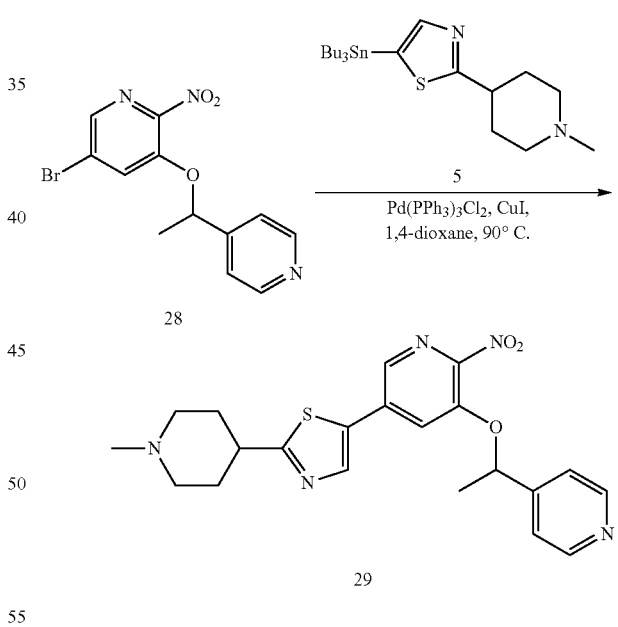

Compound 29: Compound 28 (500 mg, 1.55 mmol), 5 (730 mg, 1.55 mmol), bis(triphenylphosphine) palladium dichloride (109 mg, 0.16 mmol) and cuprous iodide (89 mg, 0.47 mmol) were sequentially added to a round bottom flask containing 10 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 3/1, v/v), obtained 320 mg of a light yellow solid, yield: 48.4%. LCMS: Rt=1.13 min, MS Calcd.: 425.1, MS Found: 425.7 [M+H]+.

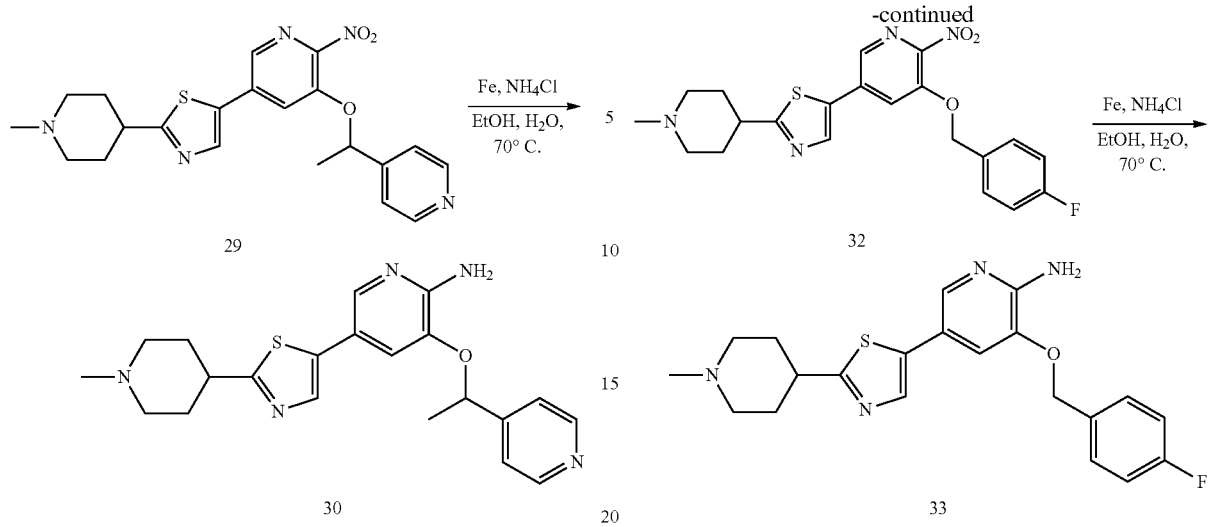

Compound 30: Compound 29 (320 mg, 0.75 mmol), reduced iron powder (211 mg, 3.76 mmol) and ammonium chloride (201 mg, 3.76 mmol) were sequentially added to a round bottom flask containing 10 mL of ethanol and 2 mL of water, and stirred at 70° C. for 3 h. LCMS monitoring, after the reaction was completed, cooled to room temperature, concentrated, and then separated by high performance liquid chromatography (column: Gemini-C18 150×21.2 mm, 5 μm, mobile phase: ACN-H$_2$O (0.1% TFA), gradient: 5-25% ACN), lyophilized, obtained 61 mg of a yellow solid, yield: 20.0%. $^1$H NMR (400 MHz, DMSO-d$_6$) δ ppm 1.67 (d, J=6.3 Hz, 3H), 1.86-1.95 (m, 2H), 2.26 (d, J=13.9 Hz, 2H), 2.78-2.82 (m, 3H), 3.06-3.14 (m, 2H), 3.25-3.31 (m, 1H), 3.54 (d, J=12.0 Hz, 2H), 6.09-6.11 (m, 1H), 7.62 (s, 1H), 7.84 (s, 1H), 7.90 (s, 2H), 8.04 (s, 1H), 8.80 (d, J=5.6 Hz, 2H), 9.72 (s, 1H). LCMS: Rt=0.92 min, MS Calcd.: 395.2, MS Found: 395.7 [M+H]+.

Example 5 Preparation of Compound 33 (A5)

The synthetic route of the compound is as follows:

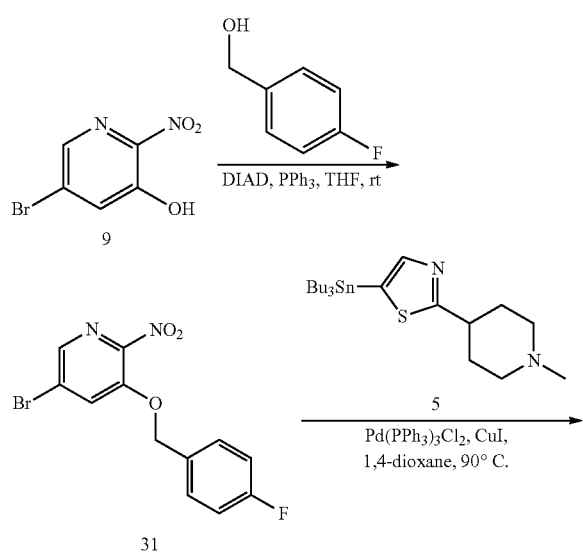

Compound 31: Compound 9 (1.0 g, 4.6 mmol), 61 (580 mg, 4.6 mmol) and triphenylphosphine (1.45 g, 5.5 mmol) were sequentially added to a three-neck flask containing 40 mL of tetrahydrofuran, protected with nitrogen, diisopropyl azodicarboxylate (1.12 g, 5.5 mmol) was added with stirring, and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous Na$_2$SO$_4$, concentrated under reduced pressure, and then purified by column chromatography (eluent: petroleum ether/ethyl acetate, 3/1, v/v), obtained 1.3 g of a yellow solid, yield: 86.7%. $^1$H NMR (400 MHz, CDCl$_3$) δ ppm 5.23 (s, 2H), 7.06-7.20 (m, 2H), 7.33-7.52 (m, 2H), 7.71 (d, J=1.7 Hz, 1H), 8.18 (d, J=1.8 Hz, 1H). LCMS: Rt=1.71 min, MS Calcd.: 326.1, 328.1; MS Found: 326.7, 328.7 [M+H]+.

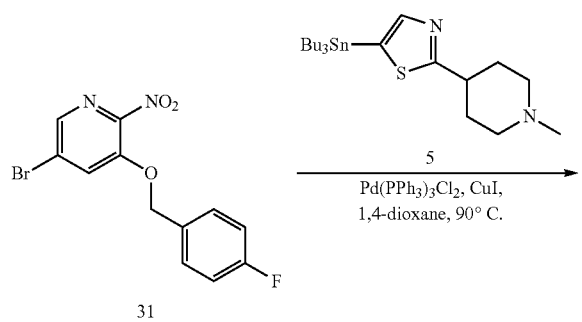

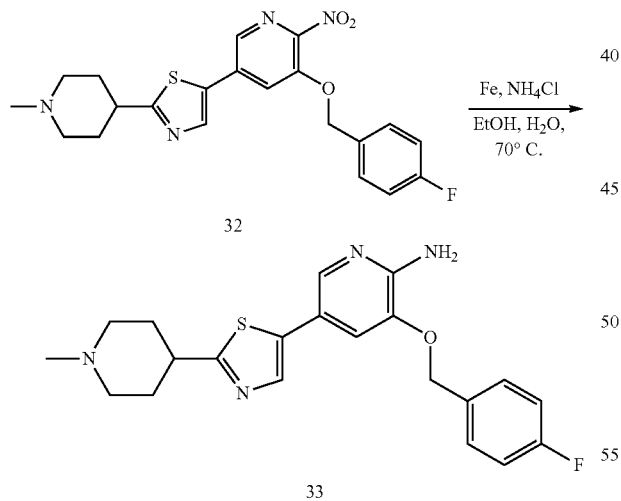

Compound 31: Compound 91 (0 g, 4.5 mmol), 61 (0 mg, 4.56 mmol), bis(triphenylphosphine) palladium dichloride (109 mg, 0.16 mmol) and cuprous iodide (89 mg, 0.47 mmol) were sequentially added to a round bottom flask containing 10 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 10/1, v/v), obtained 280 mg of a light yellow solid, yield: 41.9%. LCMS: Rt=1.31 min, MS Calcd.: 428.1, MS Found: 428.6 [M+H]+.

Compound 33: Compound 32 (280 mg, 0.65 mmol), reduced iron powder (183 mg, 3.27 mmol) and ammonium chloride (175 mg, 3.27 mmol) were sequentially added to a round bottom flask containing 10 mL of ethanol and 2 mL of water, stirred at 70° C. for 3 h. LCMS monitoring, after the reaction was completed, cooled to room temperature, concentrated, and then separated by high performance liquid chromatography (column: Gemini-C18 150×21.2 mm, 5 μm, mobile phase: ACN-H$_2$O (0.1% TFA), gradient: 9-20% ACN), lyophilized, obtained 108 mg of a light yellow solid, yield: 41.5%. $^1$H NMR (400 MHz, DMSO-d$_6$) δ ppm 1.89-1.97 (m, 2H), 2.29 (d, J=13.1 Hz, 2H), 2.80-2.83 (m, 3H), 3.07-3.16 (m, 2H), 3.28-3.34 (m, 1H), 3.56 (d, J=12.2 Hz, 2H), 5.35 (s, 2H), 7.27 (t, J=8.8 Hz, 2H), 7.62 (dd, J=8.3, 5.7 Hz, 2H), 7.73 (s, 1H), 7.84 (s, 1H), 8.15 (s, 1H), 9.67 (s, 1H). LCMS: Rt=1.17 min, MS Calcd.: 398.2, MS Found: 398.8 [M+H]+.

Example 6 Preparation of Compound 40 (A6)

The synthetic route of the compound is as follows:

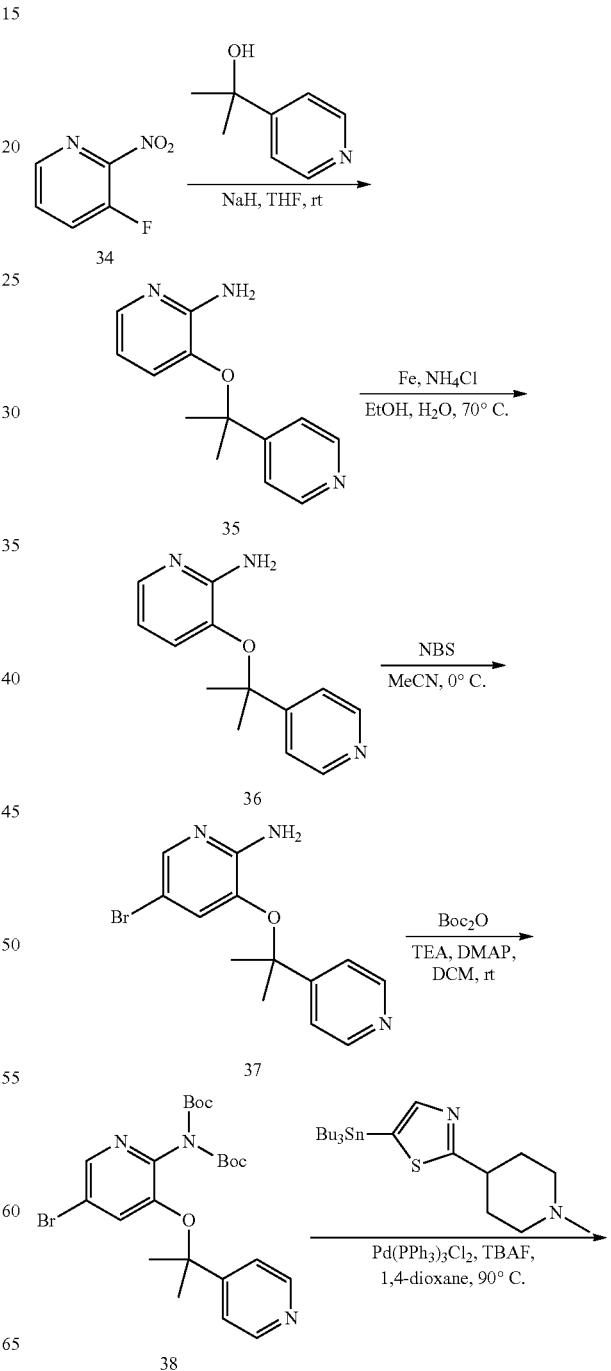

-continued

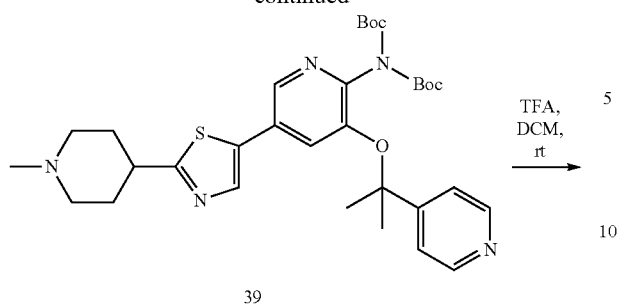

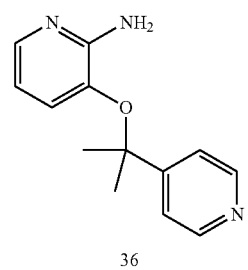

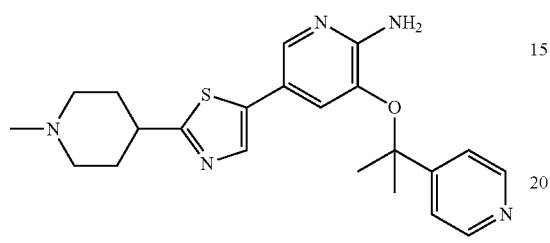

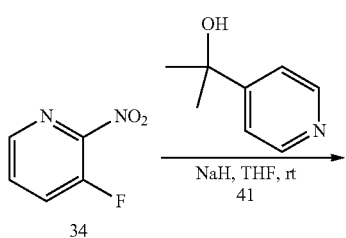

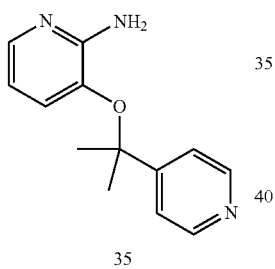

Compound 35: Compound 41 (3 g, 21.9 mmol) was added to a three-neck flask containing 60% sodium hydride (1 g, 26.3 mmol) and 100 mL of tetrahydrofuran, stirred under nitrogen for 30 min, and then added Compound 34 (3.1 g, 21.9 mmol), stirred at room temperature for 3 h. LCMS monitoring, after the reaction was completed, quenched with saturated ammonium chloride (50 mL), extracted with EtOAc (50 mL×3), and the combined extracts were washed with saturated aqueous sodium chloride (50 mL), dried with anhydrous Na$_2$SO$_4$, concentrated under reduced pressure, and then purified by column chromatography (eluent: petroleum ether/ethyl acetate, 1/1, v/v), obtained 2.4 g of a light yellow solid, yield: 42.5%. $^1$H NMR (400 MHz, CD$_3$OD) δ ppm 1.75 (s, 6H), 7.10 (dd, J=8.5, 1.1 Hz, 1H), 7.33 (dd, J=8.5, 4.6 Hz, 1H), 7.51 (dd, J=4.7, 1.7 Hz, 2H), 7.98 (dd, J=4.6, 1.1 Hz, 1H), 8.54 (dd, J=4.7, 1.6 Hz, 2H). LCMS: Rt=1.10 min, MS Calcd.: 259.1 MS Found: 260.1 [M+H]+.

Compound 36: Compound 35 (2.4 g, 9.3 mmol), reduced iron powder (2.6 g, 46.3 mmol) and ammonium chloride (2.5 g, 46.3 mmol) were sequentially added to a round bottom flask containing 50 mL of ethanol and 10 mL of water, stirred at 70° C. for 4 h. LCMS monitoring, after the reaction was completed, cooled to room temperature, filtered, the filtrate was diluted with water (50 mL), extracted with ethyl acetate (100 mL×3), and the combined extracts were washed with saturated aqueous sodium chloride (50 mL), dried with anhydrous Na$_2$SO$_4$, concentrated under reduced pressure, and obtained 1.3 g of a white solid, yield: 61.3%. $^1$H NMR (400 MHz, CDCl$_3$) δ ppm 1.75 (s, 3H), 4.79 (s, 2H), 6.28-6.43 (m, 2H), 7.38 (dd, J=4.5, 1.6 Hz, 2H), 7.66 (dd, J=4.1, 2.4 Hz, 1H), 8.64 (dd, J=4.5, 1.6 Hz, 2H). LCMS: Rt=0.39 min, MS Calcd.: 229.1 MS Found: 229.9 [M+H]+.

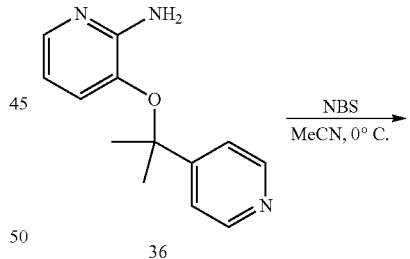

Compound 37: Compound 36 (1.2 g, 5.2 mmol) was added to a round bottom flask containing 20 mL of acetonitrile, then added NBS (980 mg, 5.5 mmol) at 0° C., stirred at room temperature for 2 h. LCMS monitoring, after the reaction was completed, filtered, the filtrate was diluted with EtOAc (150 mL), and was washed with saturated sodium bicarbonate solution (50 mL×3) and saturated aqueous sodium chloride (50 mL), dried with anhydrous Na$_2$SO$_4$, concentrated under reduced pressure, and then purified by column chromatography (eluent: petroleum ether/ethyl acetate, 1/2, v/v), obtained 1.1 g of a white solid, yield: 69.2%. $^1$H NMR (400 MHz, DMSO-d$_6$) δ ppm 1.68 (s, 6H), 6.04 (s, 2H), 6.35 (d, J=2.0 Hz, 1H), 7.46 (dd, J=4.5, 1.6 Hz, 2H), 7.59 (d, J=2.0 Hz, 1H), 8.61 (dd, J=4.5, 1.6 Hz, 2H). LCMS: Rt=1.15 min, MS Calcd.: 307.0, 309.0 MS Found: 307.9, 309.9 [M+H]+.

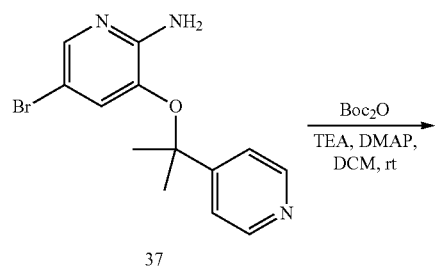

37

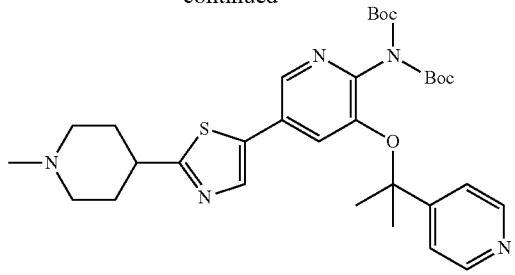

39

Compound 39: Compound 38 (610 mg, 1.2 mmol), 7 (625 mg, 1.32 mmol), bis(triphenylphosphine) palladium dichloride (84 mg, 0.12 mmol) and cuprous iodide (69 mg, 0.36 mmol) was sequentially added to a round bottom flask containing 15 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 5/1, v/v), obtained 330 mg of a yellow sticky substance, yield: 45%. LCMS: Rt=1.32 min, MS Calcd.: 609.3, MS Found: 609.6 [M+H]+.

38

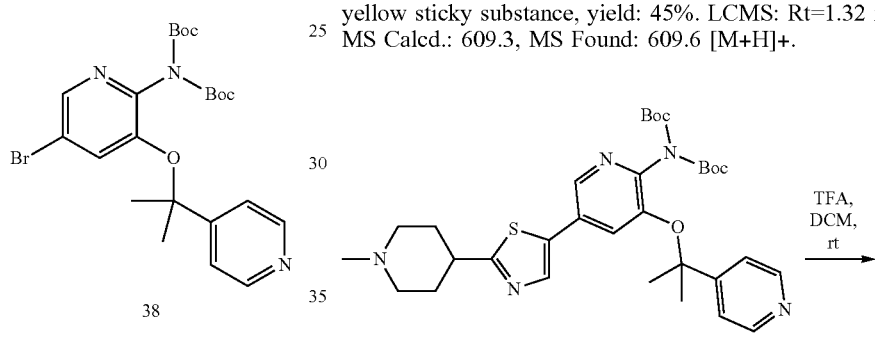

39

Compound 38: Compound 37 (0.5 g, 1.6 mmol), di-tert-butyldicarbonate (1.7 g, 4.9 mmol), triethylamine (823 mg, 8.2 mmol) and 4-dimethylaminopyridine (20 mg, 0.16 mmol) was sequentially added to a round bottom flask containing 20 mL of dichloromethane and stirred at room temperature for 24 h. LCMS monitoring, after the reaction was completed, concentrated under reduced pressure, and then purified by column chromatography (eluent: petroleum ether/ethyl acetate, 1/1, v/v), obtained 600 mg of a white solid, yield: 69.2%. $^1$H NMR (400 MHz, CD$_3$OD) δ ppm 1.47 (s, 18H), 1.81 (s, 6H), 6.96 (d, J=1.8 Hz, 1H), 7.53 (d, J=6.1 Hz, 2H), 8.14 (d, J=1.8 Hz, 1H), 8.62 (d, J=6.1 Hz, 2H). LCMS: Rt=1.15 min, MS Calcd.: 507.0, 509.0 MS Found: 507.7, 509.7 [M+H]+.

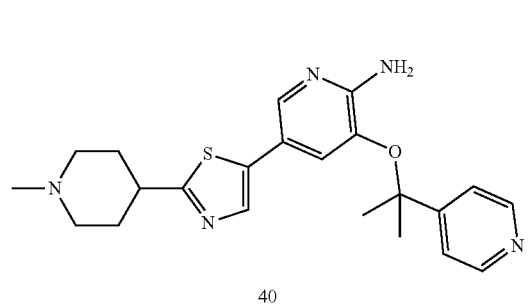

40

Compound 40: Compound 39 (400 mg, 0.66 mmol) and trifluoroacetic acid (3 mL) were sequentially added to a round bottom flask containing 15 mL of dichloromethane and stirred at room temperature for 5 h. LCMS monitoring, after the reaction was completed, concentrated, and then separated by high performance liquid chromatography (column: Gemini-C18 150×21.2 mm, 5 μm, mobile phase: ACN-H$_2$O (0.1% TFA), gradient: 0-20% ACN), lyophilized, obtained 160 mg of a white solid, yield: 54.5%. $^1$H NMR (400 MHz, CD$_3$OD) δ ppm 1.97 (s, 6H), 1.99-2.10 (m, 2H), 2.36 (d, J=13.1 Hz, 2H), 2.93 (s, 3H), 3.15-3.21 (m, 2H), 3.38-3.42 (m, 1H), 3.65 (d, J=12.6 Hz, 2H), 6.91 (s, 1H), 7.72 (s, 1H), 7.79 (s, 1H), 8.07 (d, J=5.5 Hz, 2H), 8.85 (s, 2H). LCMS: Rt=0.95 min, MS Calcd.: 409.2, MS Found: 409.9 [M+H]+.

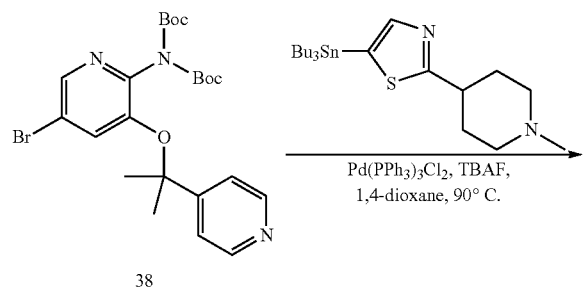

38

Example 7 Preparation of Compound 46 (A7)

The synthetic route of the compound is as follows:

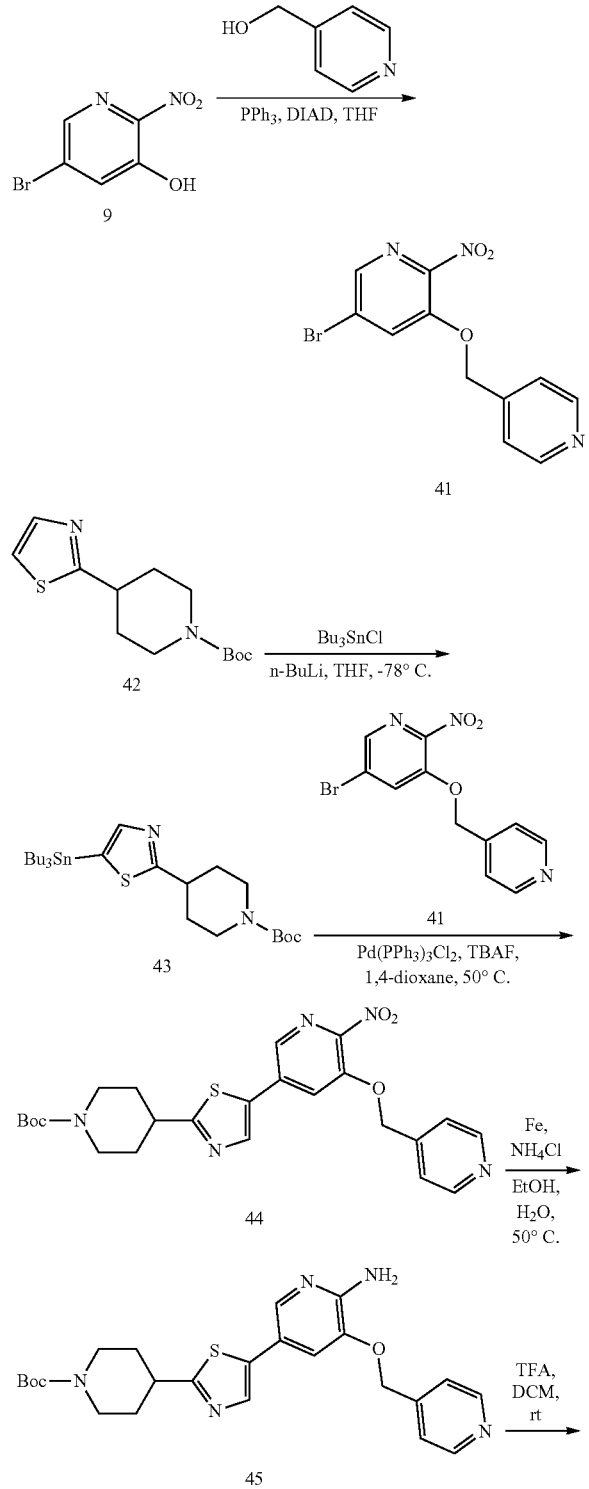

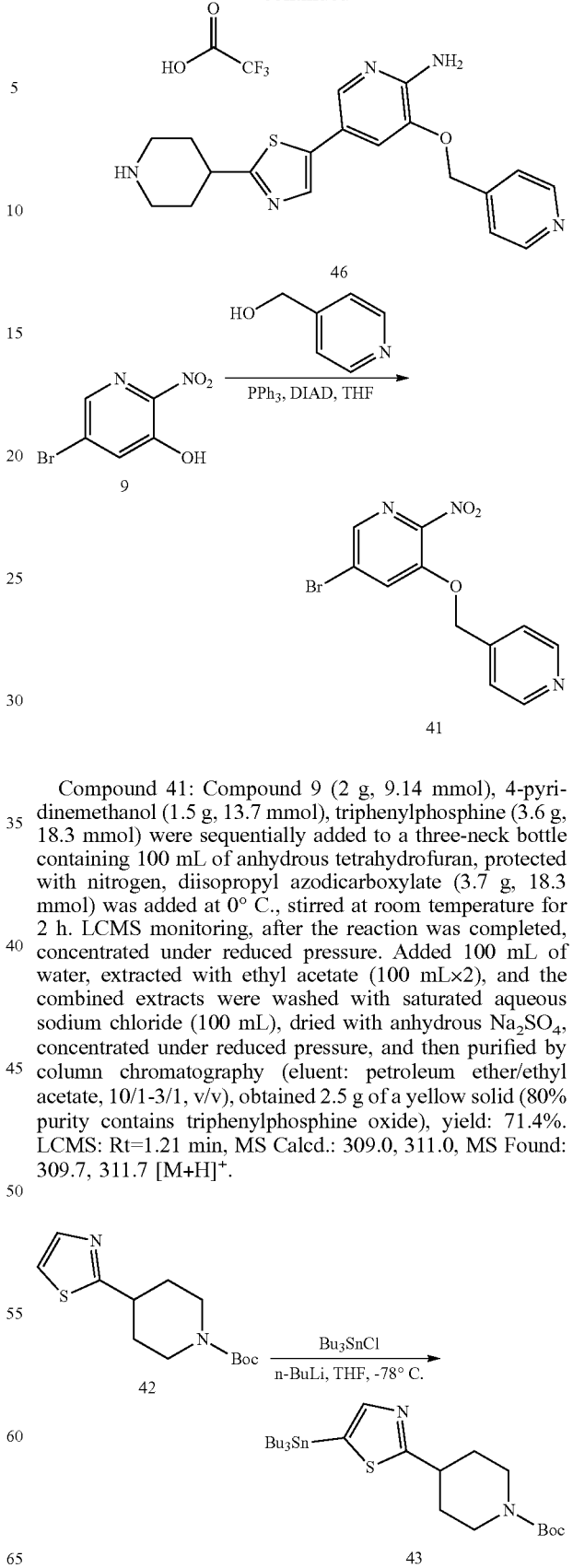

Compound 41: Compound 9 (2 g, 9.14 mmol), 4-pyridinemethanol (1.5 g, 13.7 mmol), triphenylphosphine (3.6 g, 18.3 mmol) were sequentially added to a three-neck bottle containing 100 mL of anhydrous tetrahydrofuran, protected with nitrogen, diisopropyl azodicarboxylate (3.7 g, 18.3 mmol) was added at 0° C., stirred at room temperature for 2 h. LCMS monitoring, after the reaction was completed, concentrated under reduced pressure. Added 100 mL of water, extracted with ethyl acetate (100 mL×2), and the combined extracts were washed with saturated aqueous sodium chloride (100 mL), dried with anhydrous $Na_2SO_4$, concentrated under reduced pressure, and then purified by column chromatography (eluent: petroleum ether/ethyl acetate, 10/1-3/1, v/v), obtained 2.5 g of a yellow solid (80% purity contains triphenylphosphine oxide), yield: 71.4%. LCMS: Rt=1.21 min, MS Calcd.: 309.0, 311.0, MS Found: 309.7, 311.7 $[M+H]^+$.

Compound 43: In a 250 mL three-necked flask. Compound 42 (1 g, 3.73 mmol) was dissolved in 30 mL of anhydrous tetrahydrofuran, cooled to −78° C., and n-butyllithium (2.4 M in tetrahydrofuran, 1.5 mL, 3.73 mmol) was added under nitrogen, stirred at −78° C. for 1 h, then tributyltin chloride (1.33 g, 4.1 mmol) was added dropwise, stirred at −78° C. for 1 h. LCMS monitoring, after the reaction was completed, quenched with saturated ammonium chloride (50 mL), extracted with EtOAc (100 mL×3), and the combined extracts were washed with saturated aqueous sodium chloride (100 mL), dried with anhydrous Na$_2$SO$_4$, concentrated under reduced pressure, and then purified by column chromatography (eluent: ethyl acetate/petroleum ether, 1/10, v/v), obtained 1.4 g of a yellow oily liquid, yield: 67.3%. $^1$H NMR (400 MHz, CDCl$_3$): δ ppm 0.91 (t, J=7.4 Hz, 9H), 1.11-1.15 (m, 5H), 1.26-1.38 (m, 8H), 1.49 (s, 9H), 1.51-1.61 (m, 5H), 1.78 (dq, J=12.4, 4.0 Hz, 2H), 2.12-2.15 (m, 2H), 2.91 (t, J=12.0 Hz, 2H), 3.19-3.27 (m, 1H), 4.11-4.20 (m, 2H), 7.64 (s, 1H).

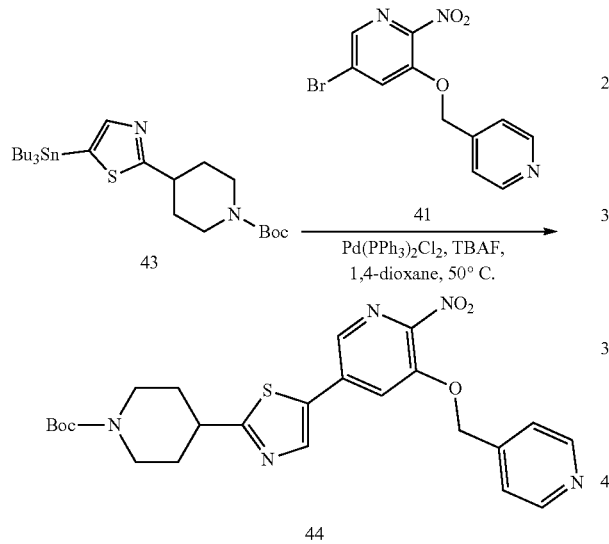

Compound 44: Compound 43 (1.1 g, 1.97 mmol), Compound 2 (600 mg, 1.97 mmol), bis(triphenylphosphine) palladium dichloride (278 mg, 0.39 mmol), tetrabutylammonium fluoride (150 mg, 0.59 mmol) was sequentially added to a 100 mL round bottom flask containing 50 mL of dioxane, protected with nitrogen, and stirred at 50° C. for 14 h. LCMS monitoring, after the reaction was completed, cooled to room temperature, concentrated under reduced pressure without further purification, and obtained 2.5 g of crude material. LCMS: Rt=1.35 min, MS Calcd.: 497.2, MS Found: 497.8 [M+H]$^+$.

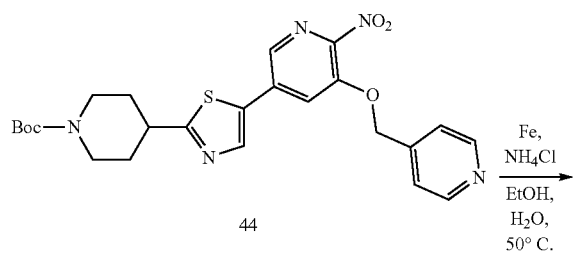

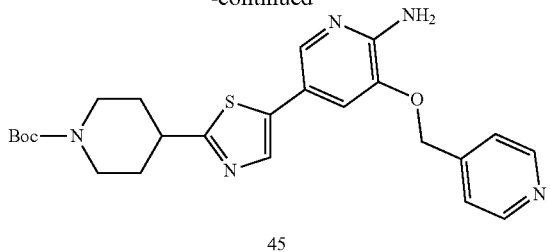

Compound 45: Compound 44 (2.5 g crude), iron powder (1.2 g, 20.1 mmol), ammonium chloride (1.1 g, 20.1 mmol) were sequentially added to a 100 mL round bottom flask containing 40 mL of ethanol/10 mL of water, and stirred at 50° C. for 2 h. LCMS monitoring, after the reaction was completed, filtered, the filtrate was concentrated under reduced pressure. Added 50 mL of water, extracted with ethyl acetate (100 mL×3), and the combined extracts were washed with saturated aqueous sodium chloride, dried with anhydrous Na$_2$SO$_4$, concentrated under reduced pressure, and then purified by column chromatography (eluent: petroleum ether/ethyl acetate, 3/1-methanol is 0%-10% in dichloromethane, v/v), obtained 340 mg of a yellow solid, two steps total yield: 37.0%. $^1$H NMR (400 MHz, DMSO-d$_6$): δ ppm 1.42 (s, 9H), 1.58-1.60 (m, 2H), 2.01-2.05 (m, 2H), 3.18-3.21 (m, 2H), 3.99-4.06 (m, 3H), 5.29 (s, 3H), 6.20 (s, 2H), 7.37 (s, 1H), 7.57 (d, J=5.2 Hz, 2H), 7.80 (s, 1H), 7.90 (s, 1H), 8.60 (d, J=4.8 Hz, 2H). LCMS: Rt=1.31 min, MS Calcd.: 467.2, MS Found: 467.8 [M+H]$^+$.

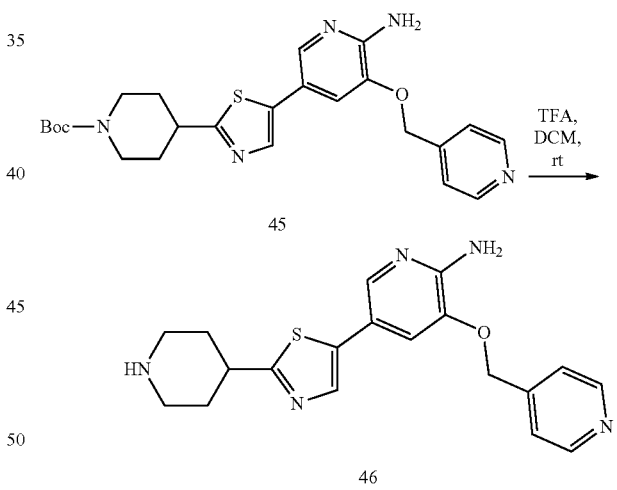

Compound 46: Compound 45 (340 mg, 0.73 mmol) was added to a 100 mL round bottom flask containing 10 mL of dichloromethane, and 2 mL of trifluoroacetic acid was added with stirring and stirred at room temperature for 14 h. LCMS monitoring, after the reaction was completed, concentrated under reduced pressure, and then separated by high performance liquid chromatography (column: Gemini-C18 150× 21.2 mm, 5 μm, mobile phase: ACN-H$_2$O (0.1% TFA), gradient: 0-20% ACN), lyophilized, obtained 13.4 mg of a yellow solid, yield: 5.0%. $^1$H NMR (400 MHz, CD$_3$OD): δ ppm 2.04-2.14 (m, 2H), 2.36-2.39 (m, 2H), 3.21 (t, J=11.6 Hz, 2H), 3.46-3.53 (m, 3H), 5.72 (s, 2H), 7.82 (s, 2H), 8.08 (s, 1H), 8.18 (br. s, 2H), 8.88 (s, 2H). LCMS: Rt=0.96 min, MS Calcd.: 367.1, MS Found: 367.8 [M+H]+.

Example 8 Preparation of Compound 49 (A8)

The synthetic route of the compound is as follows:

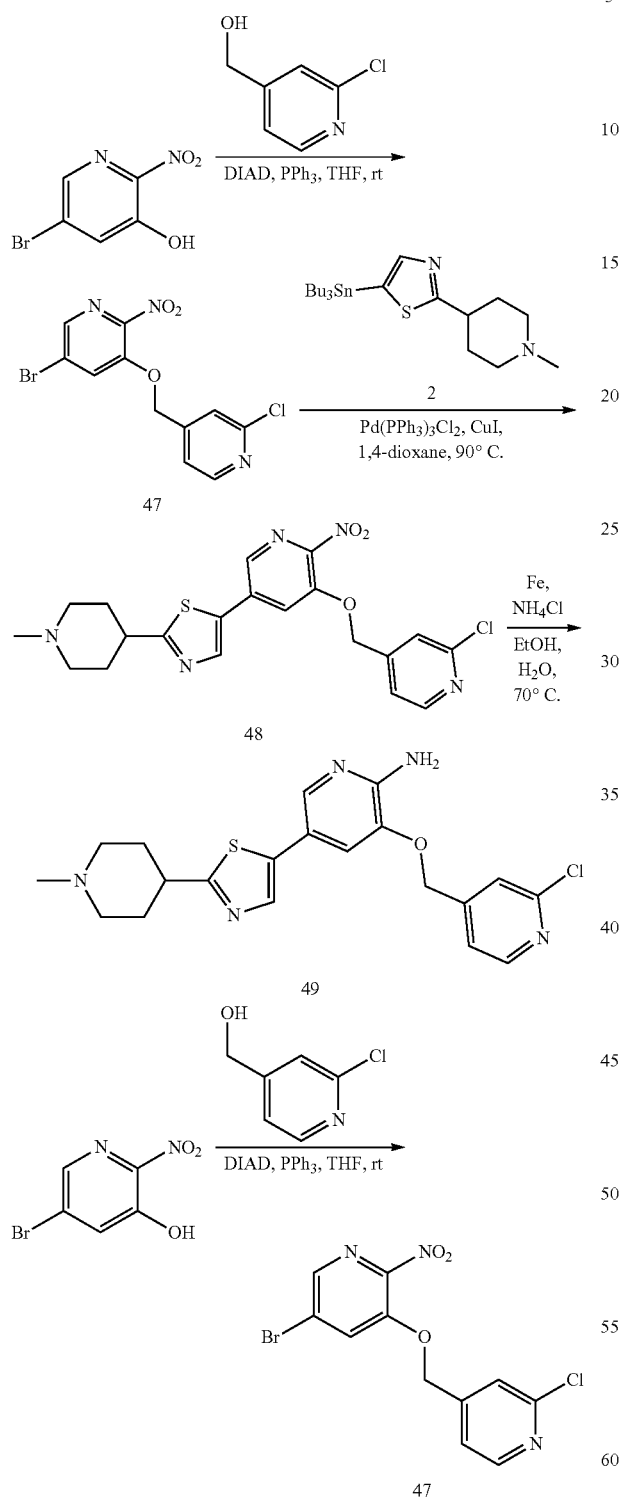

Compound 47: 5-Bromo-2-nitropyridin-3-ol (1.00 g, 4.59 mmol), (2-chloropyridin-4-yl) methanol (0.66 g, 4.59 mmol) and triphenylphosphine (1.45 g, 5.51 mmol) was sequentially added to a three-necked flask containing 40 mL of anhydrous tetrahydrofuran, stirred in an ice bath, and the nitrogen was pumped three times, diisopropyl azodicarboxylate (1.11 g, 5.51 mmol) was added dropwise to the mixed solution, after that, the mixture was stirred at room temperature for 2 h. LCMS monitoring, after the reaction was completed, concentrated under reduced pressure. Added 100 mL of water, extracted with ethyl acetate (100 mL×2), and the combined extracts were washed with saturated aqueous sodium chloride (100 mL), dried with anhydrous $Na_2SO_4$, concentrated under reduced pressure, and then purified by column chromatography (eluent: petroleum ether/ethyl acetate, 10/1, v/v), obtained 1.4 g of a white solid, yield: 89% LCMS: Rt=1.63 min, MS Calcd.: 342.9, 344.9, MS Found: 343.6, 345.6 [M+H]+.

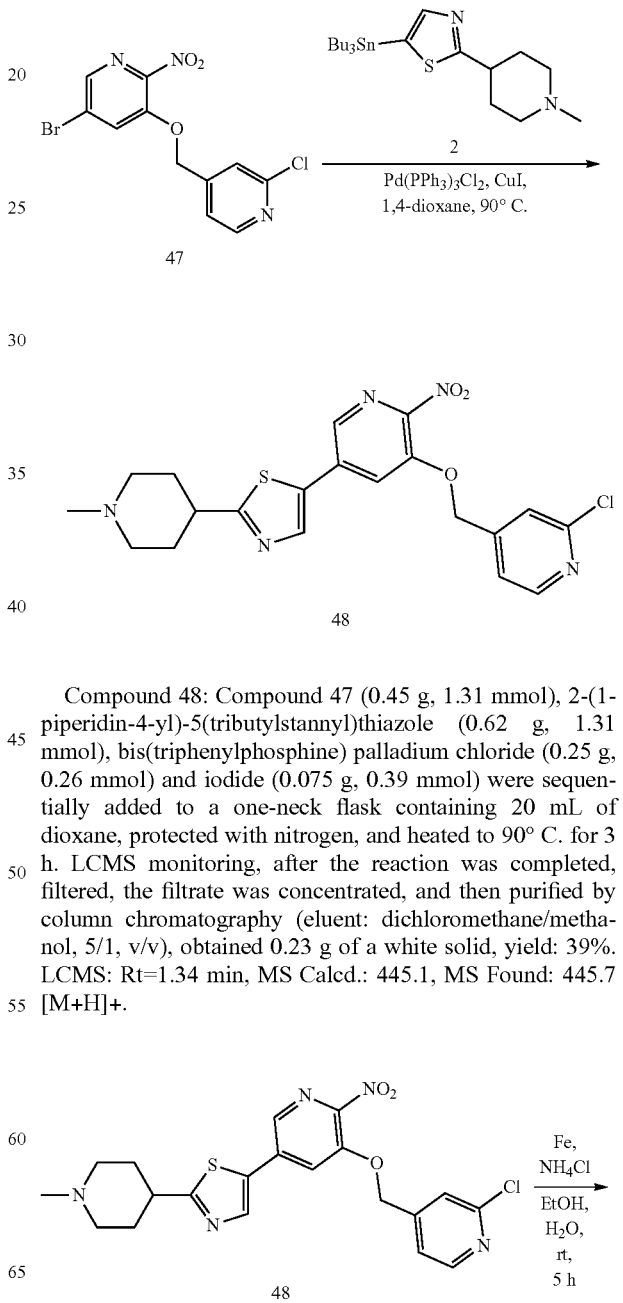

Compound 48: Compound 47 (0.45 g, 1.31 mmol), 2-(1-piperidin-4-yl)-5(tributylstannyl)thiazole (0.62 g, 1.31 mmol), bis(triphenylphosphine) palladium chloride (0.25 g, 0.26 mmol) and iodide (0.075 g, 0.39 mmol) were sequentially added to a one-neck flask containing 20 mL of dioxane, protected with nitrogen, and heated to 90° C. for 3 h. LCMS monitoring, after the reaction was completed, filtered, the filtrate was concentrated, and then purified by column chromatography (eluent: dichloromethane/methanol, 5/1, v/v), obtained 0.23 g of a white solid, yield: 39%. LCMS: Rt=1.34 min, MS Calcd.: 445.1, MS Found: 445.7 [M+H]+.

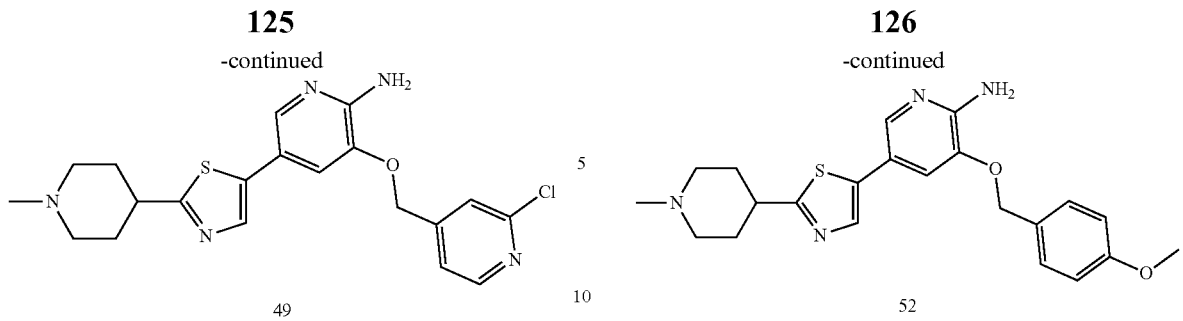

49

Compound 49: Compound 48 (150 mg, 0.34 mmol) was added to a mixed solvent of ethanol (5 mL) and water (1 mL), stirred at room temperature, added ammonium chloride (54 mg, 1.02 mol) and iron powder (57 mg, 1.02 mmol) sequentially. The reaction was carried out for 5 h at room temperature. LCMS monitoring, after the reaction was completed, concentrated, added 30 mL of methanol and stirred, filtered through diatomaceous earth and the filtrate was concentrated, then separated by high performance liquid chromatography (column: Gemini-C18 150×21.2 mm, 5 μm, mobile phase: ACN-H$_2$O (0.1% TFA), gradient: 5-20% ACN), lyophilized, obtained 15 mg of a yellow solid, yield: 11%. $^1$H NMR (400 MHz, DMSO-d$_6$): δ ppm 1.72-1.80 (m, 2H), 2.05 (d, J=12 Hz, 2H), 2.21 (t, J=11.6 Hz, 2H), 2.29 (s, 3H), 3.00-2.92 (m, 3H), 5.30 (s, 2H), 6.29 (s, 2H), 7.36 (s, 1H), 7.57 (d, J=4.8 Hz, 1H), 7.76 (s, 1H), 7.81 (s, 1H), 7.89 (s, 1H), 8.22 (s, 1H), 8.43 (d, J=5.2 Hz, 1H). LCMS: Rt=1.14 min, MS Calcd.: 415.1, MS Found: 415.7[M+H]+.

Example 9 Preparation of Compound 52 (A9)

The synthetic route of the compound is as follows:

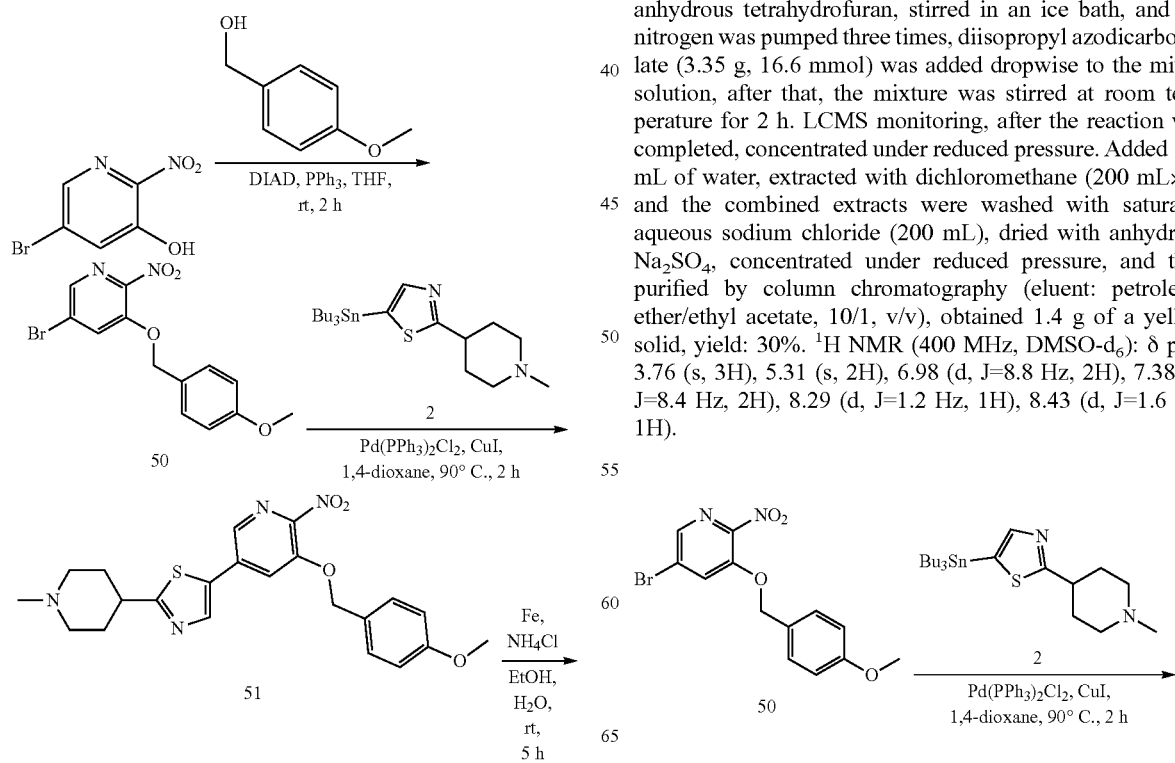

Compound 50: 5-Bromo-2-nitropyridin-3-ol (3.00 g, 13.8 mmol), (2-chloropyridin-4-yl) methanol (1.91 g, 13.8 mmol) and triphenylphosphine (4.35 g, 16.6 mmol) was sequentially added to a three-necked flask containing 100 mL of anhydrous tetrahydrofuran, stirred in an ice bath, and the nitrogen was pumped three times, diisopropyl azodicarboxylate (3.35 g, 16.6 mmol) was added dropwise to the mixed solution, after that, the mixture was stirred at room temperature for 2 h. LCMS monitoring, after the reaction was completed, concentrated under reduced pressure. Added 100 mL of water, extracted with dichloromethane (200 mL×2), and the combined extracts were washed with saturated aqueous sodium chloride (200 mL), dried with anhydrous Na$_2$SO$_4$, concentrated under reduced pressure, and then purified by column chromatography (eluent: petroleum ether/ethyl acetate, 10/1, v/v), obtained 1.4 g of a yellow solid, yield: 30%. $^1$H NMR (400 MHz, DMSO-d$_6$): δ ppm 3.76 (s, 3H), 5.31 (s, 2H), 6.98 (d, J=8.8 Hz, 2H), 7.38 (d, J=8.4 Hz, 2H), 8.29 (d, J=1.2 Hz, 1H), 8.43 (d, J=1.6 Hz, 1H).

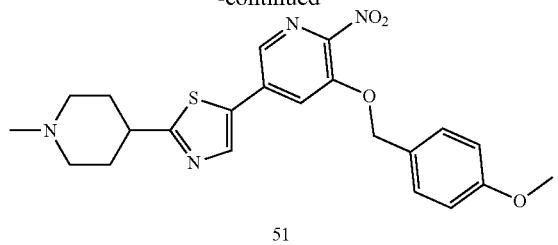

51

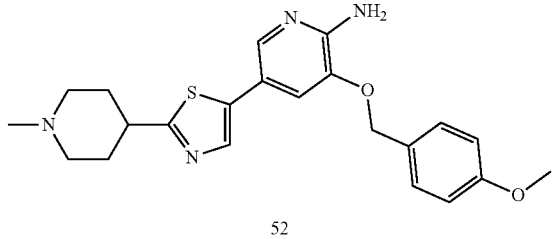

52

Compound 51: Compound 50 (1.40 g, 4.14 mmol), 2-(1-piperidin-4-yl)-5(tributylstannyl)thiazole (1.95 g, 4.14 mmol), bis(triphenylphosphine) palladium chloride (0.40 g, 0.41 mmol) and iodide (0.24 g, 1.24 mmol) were sequentially added to a one-neck flask containing 20 mL of dioxane, protected with nitrogen, and heated to 90° C. for 3 h. LCMS monitoring, after the reaction was completed, cooled to room temperature, filtered, and the filtrate was concentrated, and then purified by column chromatography (eluent: dichloromethane/methanol, 30/1, v/v), obtained 0.70 g of a white solid, yield: 38%. LCMS: Rt=1.37 min, MS Calcd.: 440.2, MS Found: 440.9 [M+H]+.

Compound 52: Compound 51 (200 mg, 0.45 mmol) was added to a mixed solvent of ethanol (5 mL) and water (1 mL), stirred at room temperature, added ammonium chloride (72 mg, 1.35 mol) and iron powder (76 mg, 1.35 mmol) sequentially. The reaction was carried out for 5 h at room temperature. LCMS monitoring, after the reaction was completed, concentrated, added 30 mL of methanol and stirred, filtered through diatomaceous earth and the filtrate was concentrated, then separated by high performance liquid chromatography (column: Gemini-C18 150×21.2 mm, 5 μm, mobile phase: ACN-$H_2O$ (0.1% TFA), gradient: 15-30% ACN), lyophilized, obtained 70 mg of a yellow solid, yield: 38%. $^1$H NMR (400 MHz, DMSO-$d_6$): δ ppm 1.70-1.80 (m, 2H), 2.04 (d, J=17.2 Hz, 2H), 2.27 (s, 2H), 2.90-2.98 (m, 3H), 3.76 (s, 3H), 5.13 (s, 2H), 5.98 (s, 2H), 6.95 (d, J=8.8 Hz, 2H), 7.37 (s, 1H), 7.46 (d, J=8.4 Hz, 2H), 7.74 (s, 1H), 7.90 (s, 1H), 8.19 (s, 1H). LCMS: Rt=1.20 min, MS Calcd.: 410.2, MS Found: 410.9 [M+H]+.

Example 10 Preparation of Compound 60 (A10)

The synthetic route of the compound is as follows:

-continued

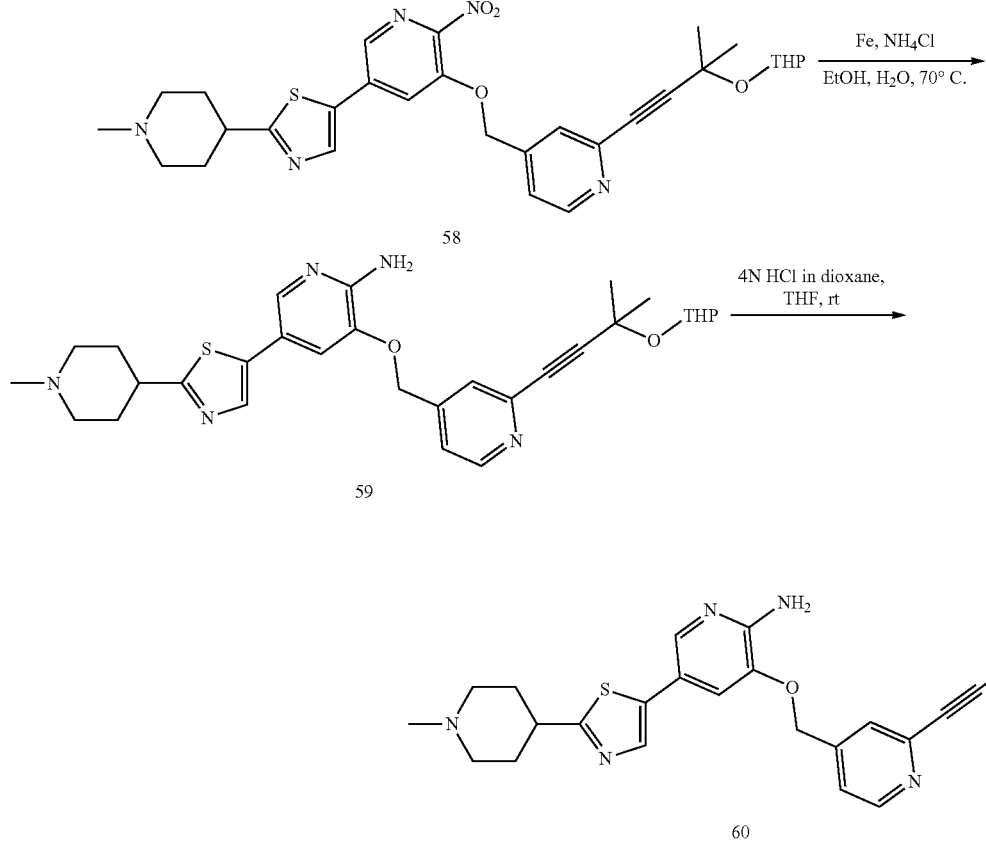

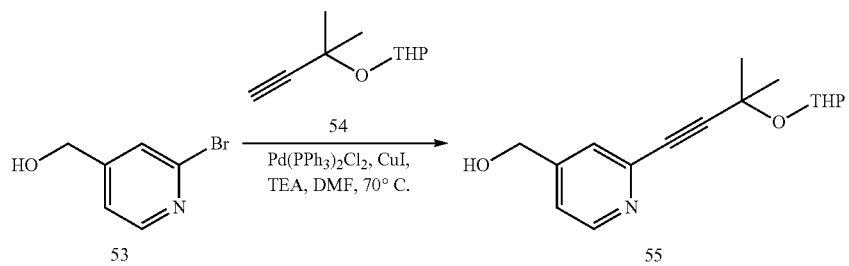

Compound 55: Compound 53 (2 g, 10.7 mmol), 54 (2.7 g, 16.0 mmol), bis(triphenylphosphine) palladium dichloride (751 mg, 1.07 mmol) and cuprous iodide (611 mg, 3.21 mmol)) were sequentially added to a round bottom flask containing 15 mL of DMF and 5 mL of triethylamine, protected with nitrogen, and stirred at 70° C. for 16 h. LCMS monitoring, after the reaction was completed, concentrated, and then purified by column chromatography (eluent: petroleum ether/ethyl acetate, 3/1, v/v), obtained 2.3 g of a yellow oily liquid, yield: 78.1%. $^1$H NMR (400 MHz, CDCl$_3$) δ ppm 1.53-1.65 (m, 10H), 1.71-1.96 (m, 2H), 3.22 (s, 1H), 3.51-3.56 (m, 1H), 3.95-4.01 (m, 1H), 4.74 (s, 2H), 5.15 (d, J=3.3 Hz, 1H), 7.24 (d, J=5.1 Hz, 1H), 7.43 (s, 1H), 8.47 (d, J=5.1 Hz, 1H). LCMS: Rt=1.67 min, MS Calcd.: 275.2, MS Found: 275.9 [M+H]+.

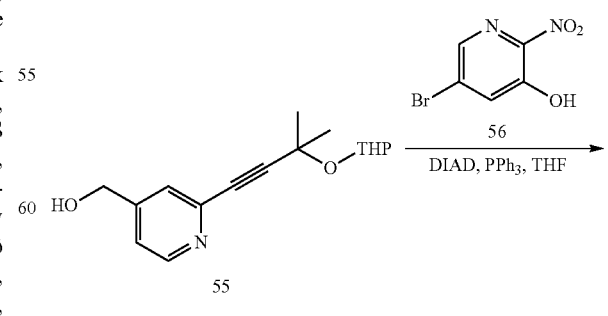

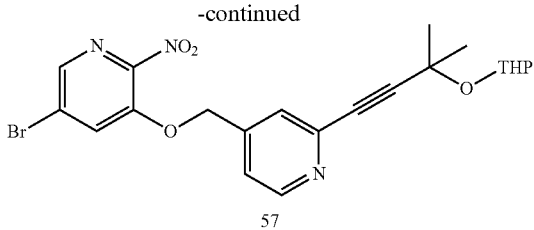

57

Compound 57: Compound 55 (1.3 g, 4.6 mmol), 56 (1 g, 4.6 mmol) and triphenylphosphine (1.45 g, 5.5 mmol) were sequentially added to a three-neck flask containing 30 mL of tetrahydrofuran, protected with nitrogen, diisopropyl azodicarboxylate (1.1 g, 5.5 mmol) was added with stirring, and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous $Na_2SO_4$, concentrated under reduced pressure, and then purified by column chromatography (eluent: petroleum ether/ethyl acetate, 1/1, v/v), obtained a 1.3 g dark brown sticky substance (crude containing triphenylphosphine oxide). LCMS: Rt=1.70 min, MS Calcd.: 475.1/477.1, MS Found: 475.5/477.5 [M+H]+.

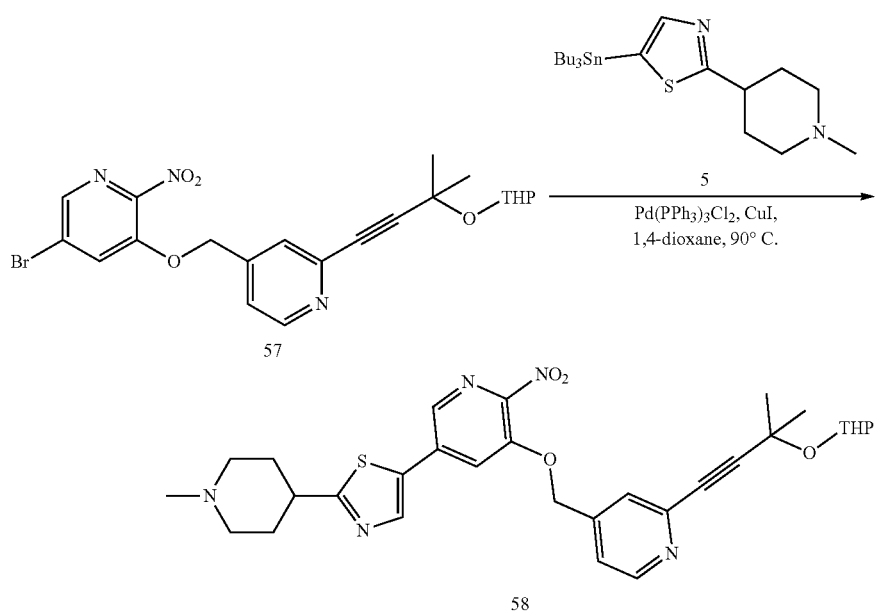

Compound 58: Compound 57 (1.3 g, crude), 5 (1.3 g, 2.7 mmol), bis(triphenylphosphine) palladium dichloride (190 mg, 0.27 mmol) and cuprous iodide (154 mg, 0.81 mmol) were sequentially added to a round bottom flask containing 30 mL of dioxane, protected with nitrogen, and stirred at 90° C. for 6 h. LCMS monitoring, after the reaction was completed, cooled to room temperature, concentrated, and separated by column chromatography (eluent: dichloromethane/methanol, 5/1, v/v), obtained 370 mg of a yellow sticky substance (crude). LCMS: Rt=1.41 min, MS Calcd.: 577.2, MS Found: 577.9 [M+H]+.

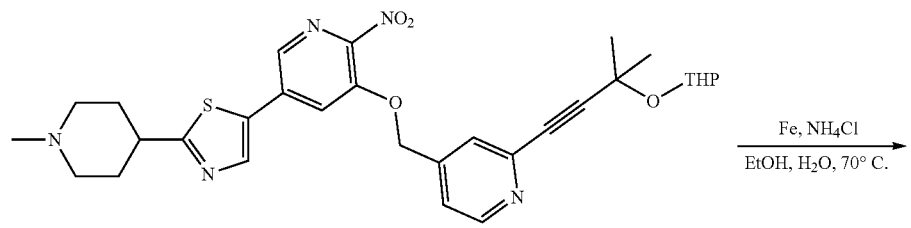

58

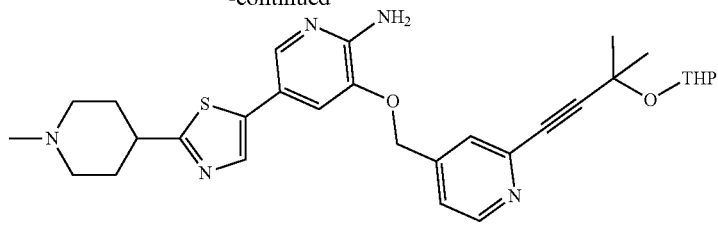

59

Compound 59: Compound 58 (370 mg, crude), iron powder (291 mg, 5.2 mmol) and ammonium chloride (281 mg, 5.2 mmol) were sequentially added to a round bottom flask containing 10 mL of ethanol and 2 mL of water, stirred at 70° C. for 4 h. LCMS monitoring, after the reaction was completed, filtered, the filtrate was diluted with water (10 mL), extracted with ethyl acetate (30 mL×3), and the combined extracts were washed with saturated aqueous sodium chloride (10 mL), dried with anhydrous $Na_2SO_4$, concentrated under reduced pressure, and obtained 200 mg of a brown solid. The crude was used directly in the next step without further purification. LCMS: Rt=1.25 min, MS Calcd.: 547.3, MS Found: 547.9 [M+H]+.

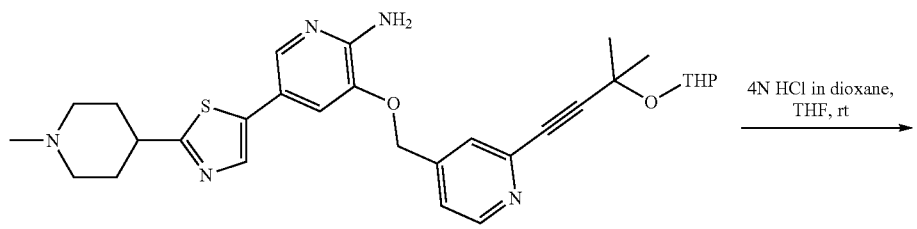

59

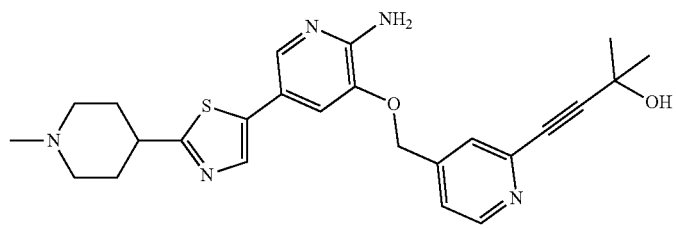

60

Compound 60: In a 50 mL round bottom flask, compound 59 (200 mg crude) was dissolved in 15 mL of tetrahydrofuran, and 4N hydrochloric acid dioxane solution (3 mL) was added and stirred at room temperature for 3 h. LCMS monitoring, after the reaction was completed, concentrated under reduced pressure, and then separated by high performance liquid chromatography (column: Gemini-C18 150× 21.2 mm, 5 μm, mobile phase: ACN—$H_2O$ (0.1% TFA), gradient: 0-40% ACN), lyophilized, obtained 25 mg of a white solid, four steps total yield: 1.2%. $^1$H NMR (400 MHz, DMSO-$d_6$) δ ppm 1.48 (s, 6H), 1.69-1.78 (m, 2H), 2.01-2.14 (m, 4H), 2.24 (s, 3H), 2.87-2.97 (m, 3H), 5.28 (s, 2H), 6.24 (s, 2H), 7.33 (s, 1H), 7.54 (d, J=4.9 Hz, 1H), 7.60 (s, 1H), 7.80 (s, 1H), 7.88 (s, 1H), 8.55 (d, J=5.0 Hz, 1H). LCMS: Rt=1.07 min, MS Calcd.: 463.2, MS Found: 463.6 [M+H]+.

Example 11 Preparation of Compound 66 (A12)

The synthetic route of the compound is as follows:

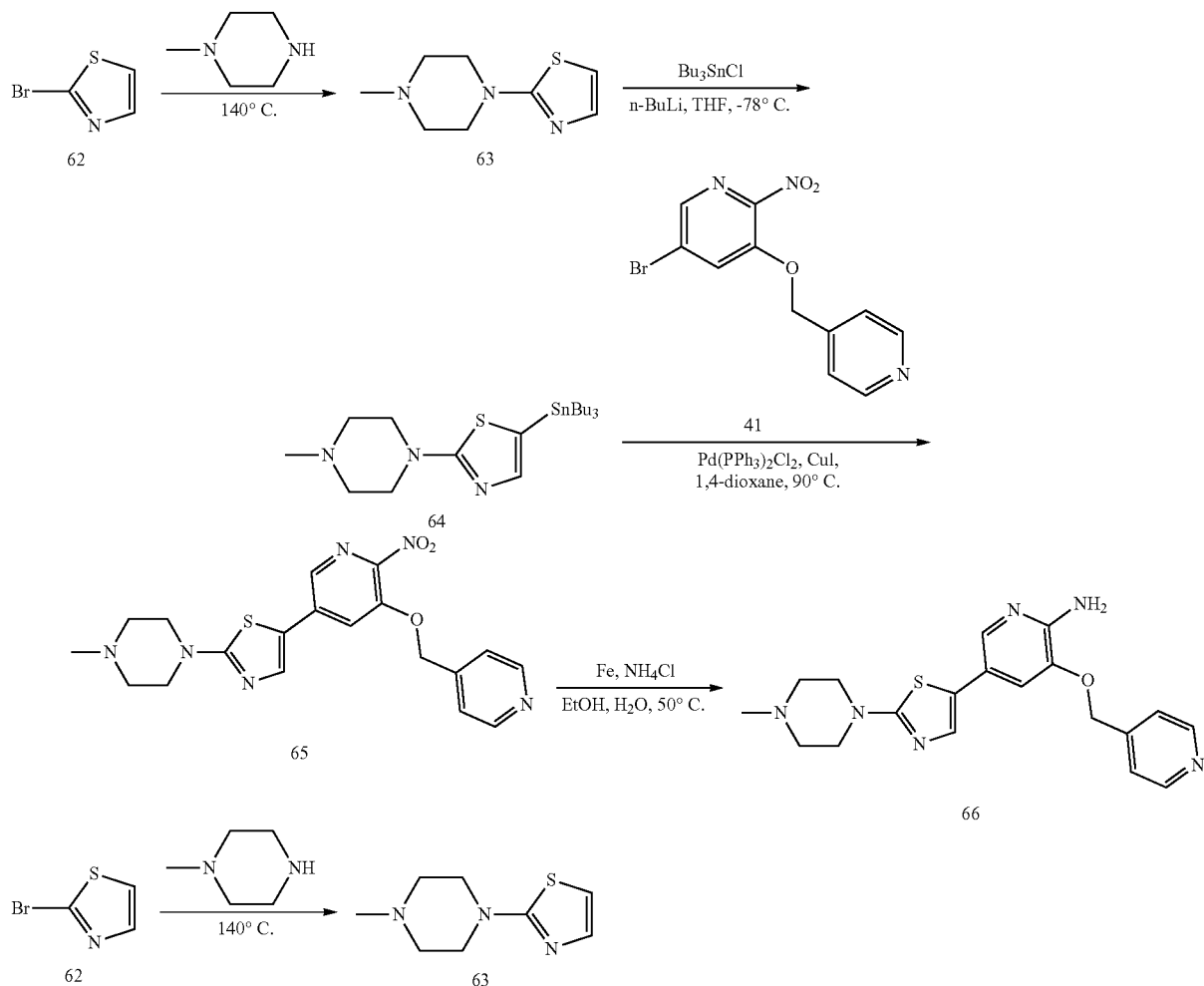

Compound 63: Compound 62 (2 g, 12.19 mmol), N-methylpiperazine (3.66 g, 36.58 mmol) was added to a 100 mL round bottom flask and stirred at 140° C. for 1 h. LCMS monitoring, after the reaction was completed, cooled to room temperature, diluted with water (50 mL), extracted with ethyl acetate (100 mL×2), and the combined extracts were washed with saturated aqueous sodium chloride (50 mL), dried with anhydrous Na$_2$SO$_4$, concentrated under reduced pressure, and then purified by column chromatography (eluent: methanol/dichloromethane, 1/10, v/v), obtained 1.8 g of a yellow oily liquid, yield: 81.8%. $^1$H NMR (400 MHz, DMSO-d$_6$). δ ppm 2.22 (s, 3H), 2.41 (t, J=5.2 Hz, 4H), 3.37-3.39 (m, 4H), 6.84 (d, J=3.6 Hz, 1H), 7.16 (d, J=3.6 Hz, 1H). LCMS: Rt=0.39 min, MS Calcd.: 183.1, MS Found: 183.9 [M+H]$^+$.

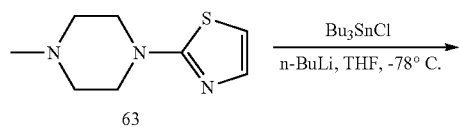

-continued

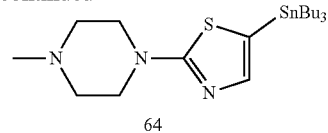

Compound 64: In a 250 mL three-necked flask, Compound 63 (900 mg, 4.91 mmol) was dissolved in 40 mL of anhydrous tetrahydrofuran, cooled to −78° C., and n-butyllithium (2.4 M in hexane solution, 2.1 mL, 4.91 mmol) was added under nitrogen, stirred at −78° C. for 1 h, then tributyltin chloride (6.4 g, 19.7 mmol) was added dropwise, stirred at −78° C. for 1 h. LCMS monitoring, after the reaction was completed, quenched with saturated ammonium chloride (50 mL), extracted with EtOAc (100 mL×3), and the combined extracts were washed with saturated aqueous sodium chloride (100 mL), dried with anhydrous Na$_2$SO$_4$, concentrated under reduced and then purified by column chromatography (eluent: methanol/dichloromethane, 1/10, v/v), obtained 950 mg of a yellow oily liquid, yield: 40.8%. $^1$H NMR (400 MHz, DMSO-d$_6$): δ ppm 0.86

(t, J=7.2 Hz, 9H), 1.04 (t, J=8.0 Hz, 5H), 1.25-1.34 (m, 7H), 1.48-1.59 (m, 6H), 2.22 (s, 3H), 2.39-2.42 (m, 4H), 3.37-3.40 (m, 4H), 7.06 (s, 1H). LCMS: Rt=1.59 min, MS Calcd.: 473.2, MS Found: 473.8 [M+H]+.

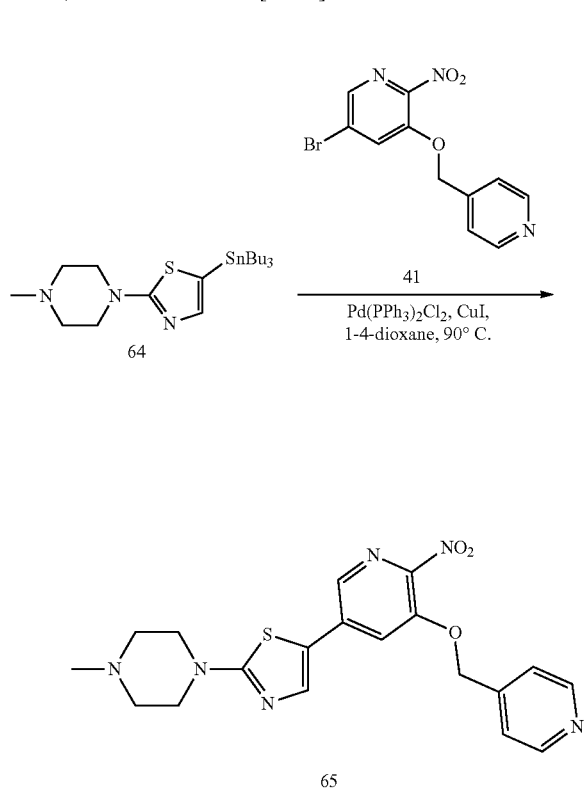

Compound 65: Compound 64 (900 mg, 1.90 mmol), Compound 41 (600 mg, 1.90 mmol), bis(triphenylphosphine) palladium dichloride (268 mg, 0.38 mmol), tetrabutylammonium fluoride (148 mg, 0.52 mmol) was sequentially added to a 100 mL round bottom flask containing 30 mL of dioxane, protected with nitrogen, and stirred at 90° C. for 4 h. LCMS monitoring, after the reaction was completed, cooled to room temperature, concentrated under reduced pressure. Added 100 mL of water, extracted with ethyl acetate (100 mL×3), and the combined extracts were washed with saturated aqueous sodium chloride (100 mL), dried with anhydrous Na$_2$SO$_4$, concentrated under reduced pressure, and then purified by column chromatography (eluent: methanol/dichloromethane, 1/5, v/v), obtained 250 mg of a yellow solid, yield: 31.9%. $^1$H NMR (400 MHz, DMSO-d$_6$): δ ppm 2.42-2.47 (m, 5H), 3.33 (s, 3H), 3.54 (t, J=4.8 Hz, 3H), 5.52 (s, 2H), 7.46 (d, J=5.2 Hz, 2H), 7.98 (s, 1H), 8.06 (s, 1H), 8.28 (s, 1H), 8.64 (d, J=5.2 Hz, 2H). LCMS: Rt=1.06 min, MS Calcd.: 412.1, MS Found: 412.8 [M+H]+.

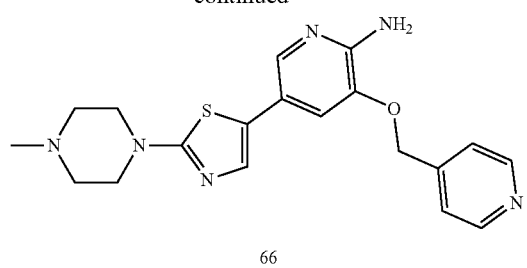

Compound 66: Compound 65 (250 mg, 0.61 mmol), iron powder (338 mg, 6.06 mmol), ammonium chloride (324 mg, 6.06 mmol) were sequentially added to a 100 mL round bottom flask containing ethanol/water (50 mL, 4/1, v/v), stirred at 50° C. for 2 hours. LCMS monitoring, after the reaction was completed, filtered, the filtrate was concentrated under reduced pressure, and then separated by high performance liquid chromatography (column: Gemini-C18 150×21.2 mm, 5 μm, mobile phase: ACN—H$_2$O (0.1% TFA), gradient: 0-20% ACN), lyophilized, obtained 39.5 mg of a white solid, yield: 17%. $^1$H NMR (400 MHz, CD$_3$OD): δ ppm 2.38 (s, 3H), 2.60 (t, J=4.8 Hz, 4H), 3.52 (t, J=4.8 Hz, 4H), 5.32 (s, 2H), 7.30 (d, J=7.2 Hz, 2H), 7.60-7.63 (m, 3H), 8.58 (d, J=4.8 Hz, 2H). LCMS: Rt=0.39 min, MS Calcd.: 382.2, MS Found: 382.9 [M+H]+.

Example 12 Preparation of Compound 72 (A13)

The synthetic route of the compound is as follows:

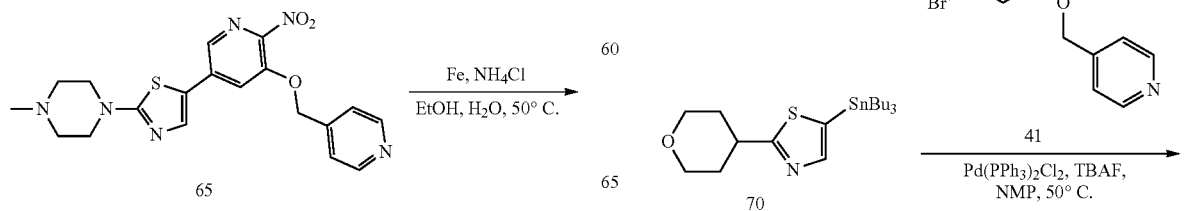

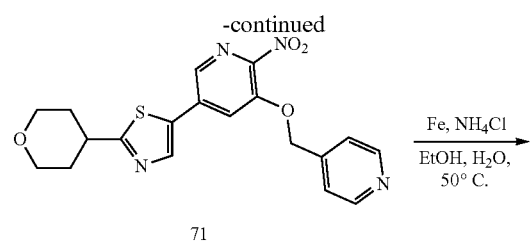

71

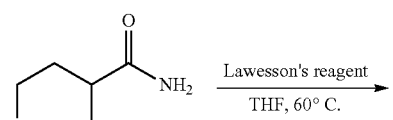

67

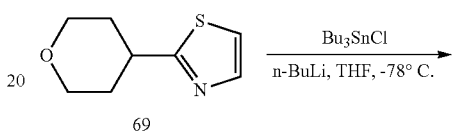

69

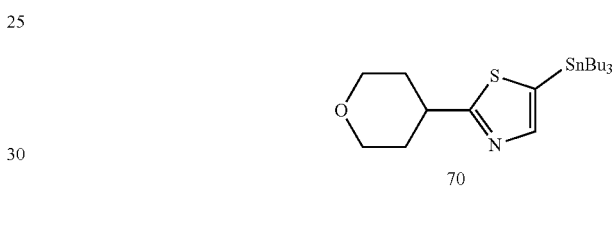

Compound 70: In a 250 mL three-necked flask, Compound 69 (700 mg, 4.14 mmol) was dissolved in 40 mL of anhydrous tetrahydrofuran, cooled to −78° C., and n-butyllithium (2.4 M in hexane solution, 21.8 mL, 1.14 mmol) was added under nitrogen, stirred at −78° C. for 1 h, then tributyltin chloride (1.62 g, 4.96 mmol) was added dropwise, stirred at −78° C. for 1 h. LCMS monitoring, after the reaction was completed, quenched with saturated ammonium chloride (50 mL), extracted with EtOAc (100 mL×3), and the combined extracts were washed with saturated aqueous sodium chloride (100 mL), dried with anhydrous Na$_2$SO$_4$, concentrated under reduced pressure, and then purified by column chromatography (eluent: methanol/dichloromethane, 1/10, v/v), obtained 600 mg of a yellow oily liquid, yield: 31.6%. LCMS: Rt=2.82 min, MS Calcd.: 459.2, MS Found: 459.6 [M+H]$^+$.

was added in a 100 mL round bottom flask containing 20 mL of acetone and stirred at 60° C. for 14 h. LCMS monitoring, after the reaction was completed, diluted with water (50 mL), extracted with ethyl acetate (100 mL×2), and the combined extracts were washed with saturated aqueous sodium chloride (50 mL), dried with anhydrous Na$_2$SO$_4$, concentrated under reduced pressure, and then purified by column chromatography (eluent: methanol/dichloromethane, 1/10, v/v), obtained 1.1 g of a brown oily liquid, yield: 68.8%. $^1$H NMR (400 MHz, DMSO-d$_6$): δ ppm 1.68-1.78 (m, 2H), 1.96-1.99 (m, 2H), 3.27-3.35 (m, 1H), 3.45-3.49 (m, 2H), 3.90-3.94 (m, 2H), 7.66 (d, J=3.2 Hz, 1H), 7.78 (d, J=3.2 Hz, 1H). LCMS: Rt=1.31 min, MS Calcd.: 169.2, MS Found: 169.9 [M+H]$^+$.

Compound 68: Compound 67 (3 g, 23.23 mmol), Lawson's reagent (4.7 g, 11.61 mmol) was added to a round bottom flask containing 50 mL of anhydrous tetrahydrofuran, protected with nitrogen, and stirred at 60° C. for 14 h. LCMS monitoring, after the reaction was completed, quenched with saturated sodium bicarbonate solution (100 mL), extracted with EtOAc (200 mL×2), and the combined extracts were washed with saturated aqueous sodium chloride (50 mL), dried with anhydrous Na$_2$SO$_4$, concentrated under reduced pressure, and then purified by column chromatography (eluent: dichloromethane/methanol, 10/1, v/v), obtained 2 g of a white solid, yield: 59.3%. $^1$HNMR (400 MHz, DMSO-d$_6$): δ ppm 1.55-1.59 (m, 2H), 1.70-1.81 (m, 2H), 2.68-2.76 (m, 1H), 3.30-3.34 (m, 2H), 3.86-3.90 (m, 2H), 9.10 (s, 1H), 9.40 (s, 1H). LCMS: Rt=1.01 min, MS Calcd.: 145.2, MS Found: 145.9 [M+H]$^+$.

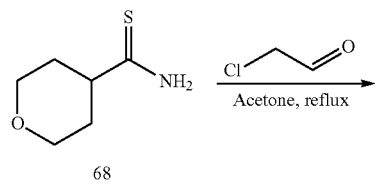

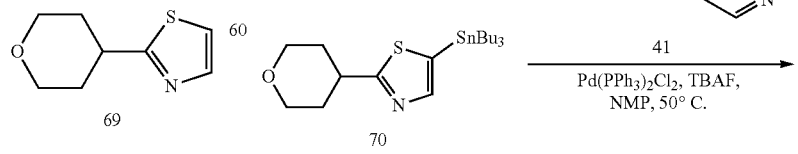

Compound 69: Compound 68 (1.4 g, 9.64 mmol), chloroacetaldehyde (40% aqueous solution, 3.8 g, 19.28 mmol)

141

-continued

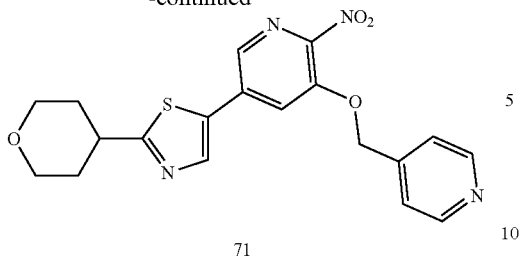

71

142

-continued

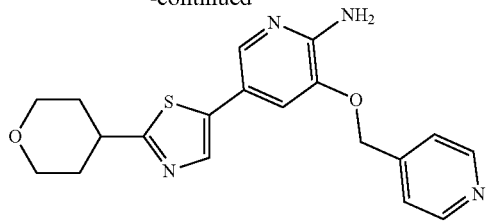

72

Compound 71: Compound 70 (350 mg, 0.76 mmol), Compound 41 (237 mg, 0.76 mmol), tetra(triphenylphosphine) palladium (177 mg, 0.15 mmol), tetrabutylammonium fluoride (60 mg, 0.23 mmol) was sequentially added to a 100 mL round bottom flask containing 30 mL of N-methylpyrrolidone, protected with nitrogen, and stirred at 50° C. for 4 h. LCMS monitoring, after the reaction was completed, cooled to room temperature, concentrated under reduced pressure. Added 100 mL of water, extracted with ethyl acetate (100 mL×3), and the combined extracts were washed with saturated aqueous sodium chloride (100 mL), dried with anhydrous $Na_2SO_4$, concentrated under reduced pressure, and then purified by column chromatography (eluent: methanol/dichloromethane, 1/5, v/v), obtained 900 mg of a yellow oily liquid (crude containing a large amount of N-methylpyrrolidone). LCMS: Rt=1.36 min, MS Calcd.: 398.1, MS Found: 398.9 [M+H]$^+$.

Compound 72: Compound 71 (900 mg, crude), iron powder (420 mg, 7.53 mmol), ammonium chloride (402 mg, 7.53 mmol) was added sequentially to a 100 mL round bottom flask containing ethanol/water (50 mL, 4/1, v/v), stirred at 50° C. for 2 h. LCMS monitoring, after the reaction was completed, filtered, the filtrate was concentrated under reduced pressure, and then separated by high performance liquid chromatography (column: Gemini-C18 150×21.2 mm, 5 μm, mobile phase: ACN—H$_2$O (0.1% TFA), gradient: 0-40% ACN), lyophilized, obtained 8 mg of a yellow solid, two steps total yield: 0.8%. $^1$H NMR (400 MHz, CDCl$_3$): δ ppm 1.93-2.00 (m, 2H), 2.07-2.10 (m, 2H), 3.23-3.29 (m, 1H), 3.58 (t, J=11.6 Hz, 2H), 4.09-4.12 (m, 2H), 5.09 (s, 2H), 5.20 (s, 2H), 7.07 (s, 1H), 7.38 (d, J=4.8 Hz, 2H), 7.67 (s, 1H), 7.91 (s, 1H), 8.70 (d, J=4.8 Hz, 2H). LCMS: Rt=0.96 min, MS Calcd.: 368.5, MS Found: 369.1 [M+H]$^+$.

Example 13 Preparation of Compound 75 (A11)

The synthetic route of the compound is as follows:

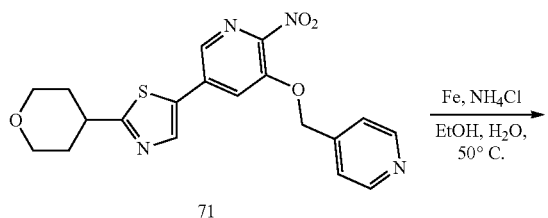

71

Fe, NH$_4$Cl
EtOH, H$_2$O,
50° C.

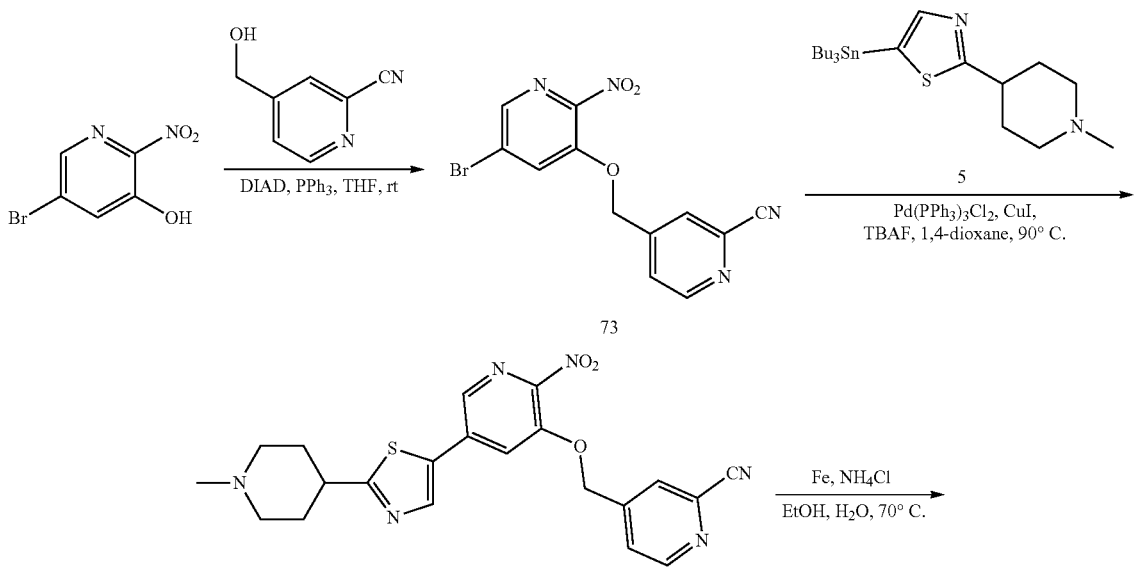

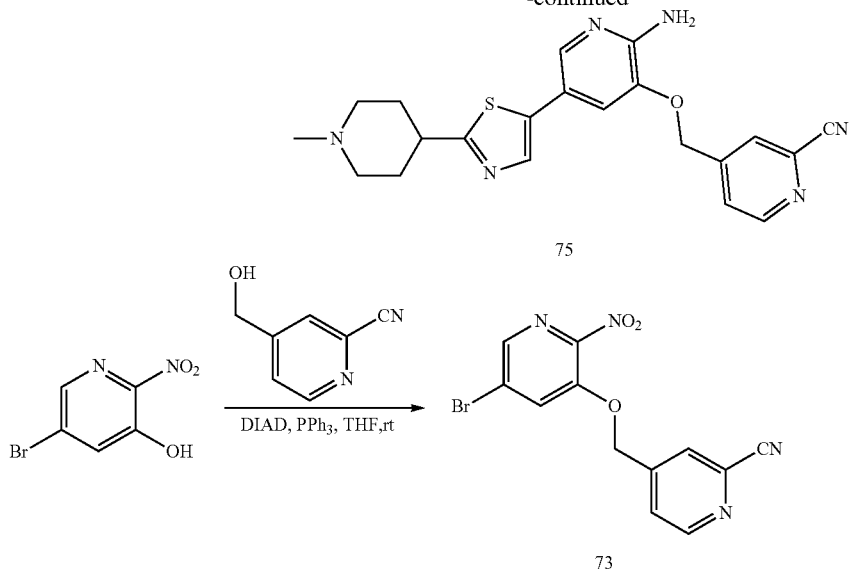

75

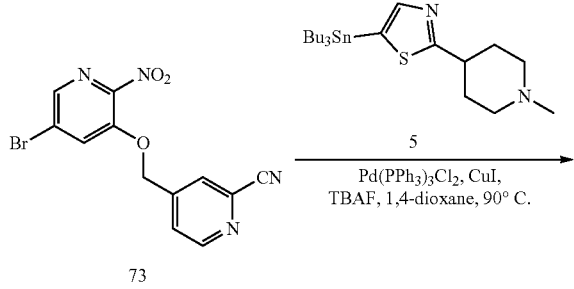

Compound 73: 5-Bromo-2-nitropyridin-3-ol (1.00 g, 4.59 mmol), (2-chloropyridin-4-yl) methanol (0.62 g, 4.59 mmol) and triphenylphosphine (1.45 g, 5.51 mmol) was sequentially added to a three-necked flask containing 40 mL of anhydrous tetrahydrofuran, stirred in an ice bath, and the nitrogen was pumped three times, diisopropyl azodicarboxylate (1.11 g, 5.51 mmol) was added dropwise to the mixed solution, after that, the mixture was stirred at room temperature for 2 h. LCMS monitoring, after the reaction was completed, concentrated under reduced pressure. Added 100 mL of water, extracted with dichloromethane (100 mL×2), and the combined extracts were washed with saturated aqueous sodium chloride (100 mL), dried with anhydrous Na$_2$SO$_4$, concentrated under reduced pressure, and then purified by column chromatography (eluent: petroleum ether/ethyl acetate, 5/1, v/v), obtained 0.55 g of a yellow solid, yield: 36%. LCMS: Rt=1.59 min, MS Calcd.: 334.0, 336.0, MS Found: 334.7, 336.7 [M+H]$^+$.

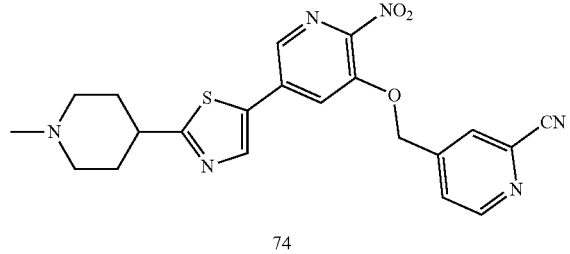

Compound 74: Compound 73 (0.55 g, 1.64 mmol), 2-(1-piperidin-4-yl)-5(tributylstannyl) thiazole (0.77 g, 1.64 mmol), bis(triphenylphosphine) palladium chloride (0.318 g, 0.33 mmol), iodide (0.063 g, 0.33 mmol) and tetrabutylammonium fluoride (0.64 g, 2.46 mmol) were sequentially added to a one-neck flask containing 10 mL of dioxane, protected with nitrogen, and heated to 90° C. for 3 h. LCMS monitoring, after the reaction was completed, cooled to room temperature, filtered, and the filtrate was concentrated, and then purified by column chromatography (eluent: dichloromethane/methanol, 10/1, v/v), obtained 0.5 g of a red oily liquid, yield: 70%. LCMS: Rt=1.32 min, MS Calcd.: 436.1, MS Found: 436.8 [M+H]+.

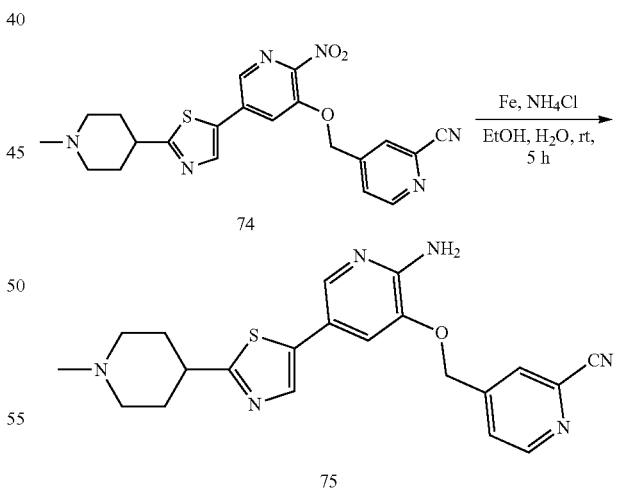

Compound 75: Compound 74 (300 mg, 0.69 mmol) was added to a mixed solvent of ethanol (5 mL) and water (1 mL), stirred at room temperature, added ammonium chloride (74 mg, 1.38 mol) and iron powder (77 mg, 1.38 mmol) sequentially. The reaction was carried out for 5 h at room temperature. LCMS monitoring, after the reaction was completed, concentrated, added 30 mL of methanol and stirred, filtered through diatomaceous earth and the filtrate was concentrated, then separated by preparative chromatography, and obtained 13 mg of a white solid, yield: 4.6%. ¹H NMR (400 MHz, DMSO-d₆): δ ppm 1.71-1.79 (m, 2H), 2.04 (d, J=15.2 Hz, 2H), 2.16 (t, J=10.8 Hz, 2H), 2.26 (s, 3H), 2.90-2.96 (m, 3H), 5.34 (s, 2H), 6.36 (s, 2H), 7.38 (s, 1H), 7.82 (s, 1H), 7.87 (d, J=4.0 Hz, 1H), 7.90 (s, 1H), 8.22 (s, 1H), 8.36 (s, 1H), 8.77 (d, J=4.8 Hz, 1H). LCMS: Rt=1.14 min, MS Calcd.: 406.2, MS Found: 406.9 [M+H]+.
Example 14 Preparation of Compound 85 (A40)
The synthetic route of the compound is as follows:
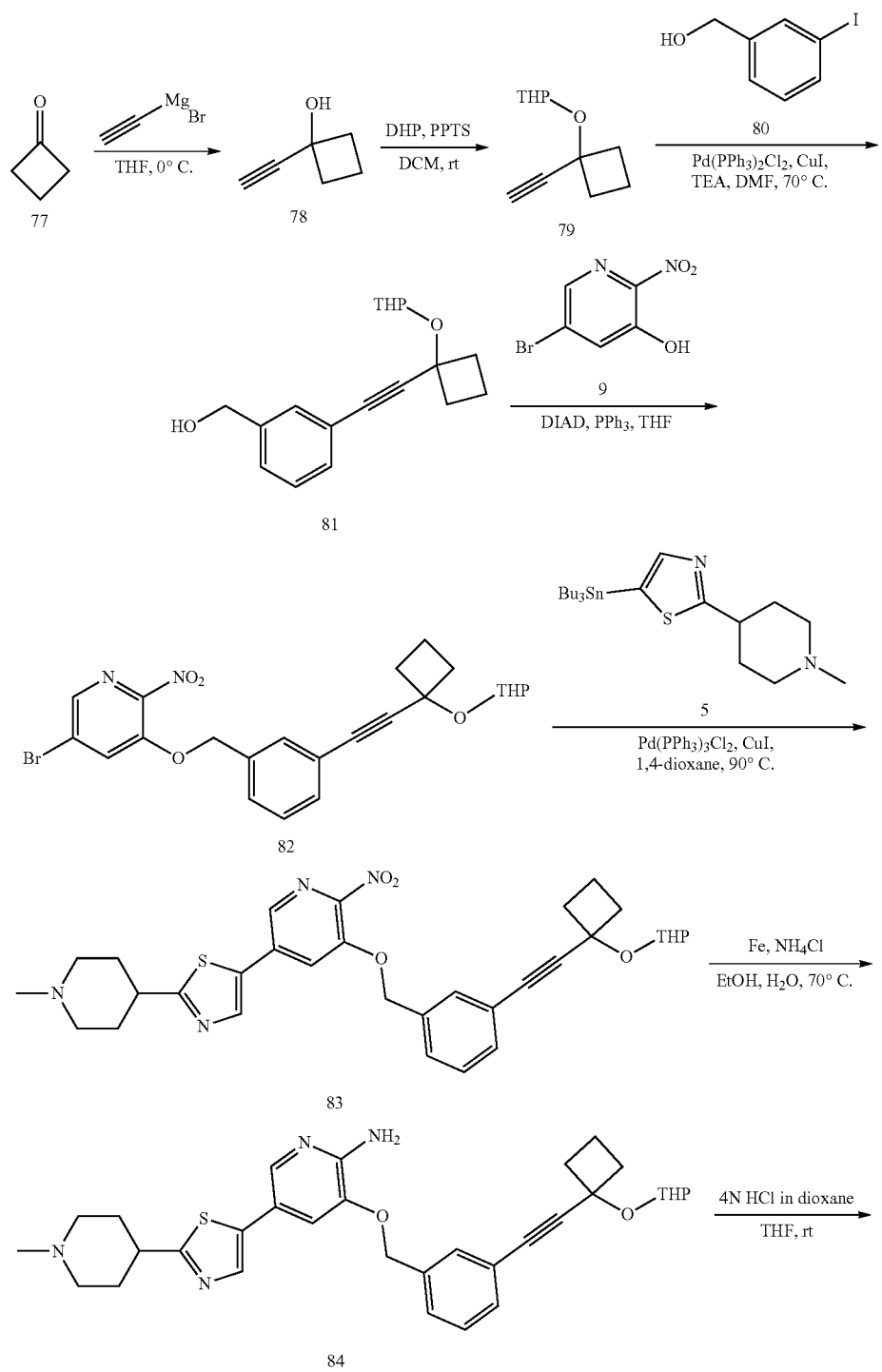

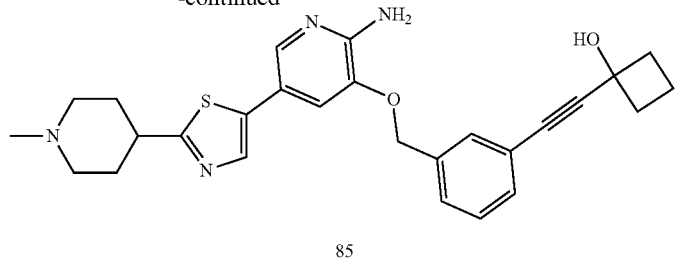

85

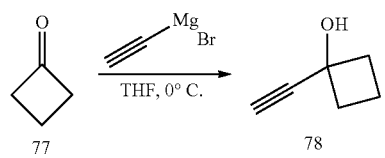

Compound 78: Compound 77 (5 g, 71.4 mmol) was added to a round bottom flask containing 100 mL of tetrahydrofuran, ethynylmagnesium bromide (285 mL, 142.8 mmol, 0.5 M in tetrahydrofuran) was added dropwise at 0° C., protected with nitrogen, stirred at 0° C. for 16 h. TLC monitoring, after the reaction was completed, quenched with water (200 mL), extracted with ether (100 mL×3), and the combined extracts were washed with saturated aqueous sodium chloride (100 mL), dried with anhydrous Na₂SO₄, concentrated under reduced pressure, and obtained 4.8 g of a yellow oily liquid, the crude was used directly in the next step.

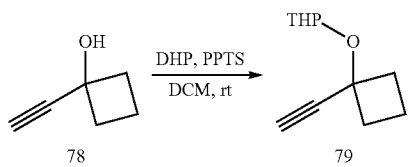

Compound 79: Compound 78 (4.8 g, 50.0 mmol), 4-methylbenzenesulfonic acid pyridinium salt (50 mg) was added in a round bottom flask containing 50 mL of tetrahydrofuran, followed by the addition of 3,4-dihydropyran (4.2 g, 50.0 mmol), protected with nitrogen, stirred at room temperature for 16 h. TLC monitoring, after the reaction was completed, concentrated, and then purified by column chromatography (eluent: petroleum ether/ethyl acetate, 50/1, v/v), obtained 2.9 g of a yellow oily liquid, the crude was used directly in the next step.

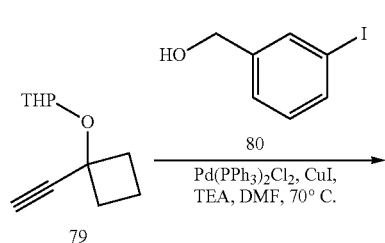

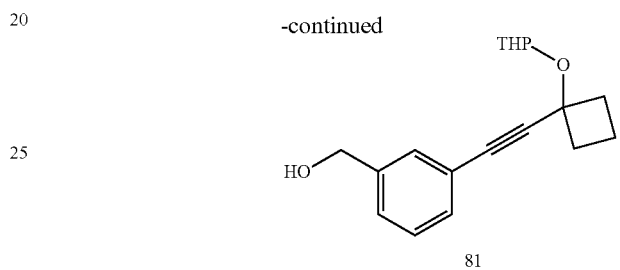

81

Compound 81: Compound 79 (1 g, 5.55 mmol), 80 (1.1 g, 4.63 mmol), bis(triphenylphosphine) palladium dichloride (323 mg, 0.46 mmol) and cuprous iodide (263 mg, 1.38 mmol) were sequentially added to a round bottom flask containing 10 mL of dioxane and 2 mL of triethylamine, protected with nitrogen, and stirred at room temperature for 6 h. LCMS monitoring, after the reaction was completed, concentrated, and separated by column chromatography (eluent: petroleum ether/ethyl acetate, 10/1, v/v), obtained 1.1 g of a yellow oily liquid, yield: 82.1%. LCMS: Rt=1.67 min, MS Calcd.: 286.2, MS Found: 308.9 [M+Na]+.

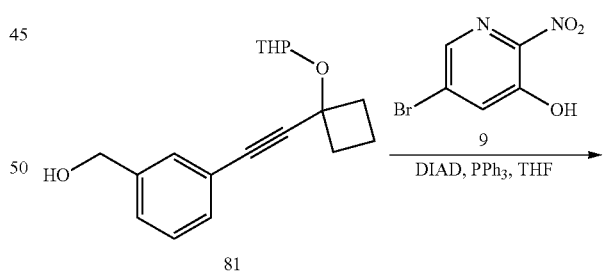

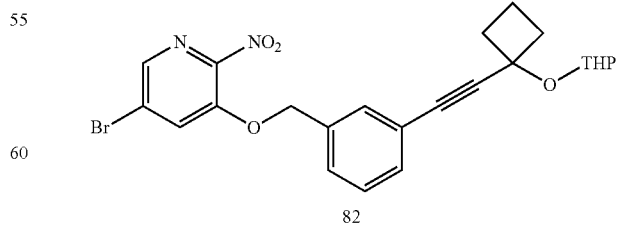

82

Compound 82: Compound 81 (1.0 g, 3.5 mmol), 9 (762 mg, 3.5 mmol) and triphenylphosphine (1.1 g, 4.2 mmol) were sequentially added to a three-neck flask containing 20 mL of tetrahydrofuran, protected with nitrogen, diisopropyl azodicarboxylate (849 mg, 4.2 mmol) was added with stirring, and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous $Na_2SO_4$, concentrated under reduced pressure, and then purified by column chromatography (eluent: petroleum ether/ethyl acetate, 10/1, v/v), obtained 1.0 g of a yellow sticky substance, yield: 58.6%. LCMS: Rt=1.90 min, MS Calcd.: 486.1, 488.1, MS Found: 508.7, 510.8 [M+Na]+.

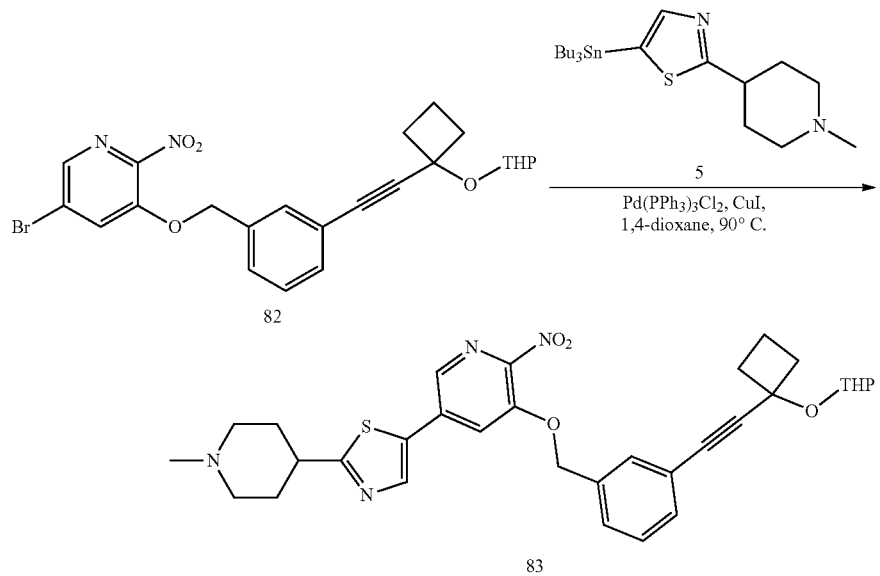

Compound 83: Compound 82 (950 mg, 1.95 mmol), 5 (923 mg, 1.95 mmol), bis(triphenylphosphine) palladium dichloride (137 mg, 0.195 mmol) and cuprous iodide (111 mg, 0.585 mmol) were sequentially added to a round bottom flask containing 15 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 8/1, v/v), obtained 260 mg of a yellow solid. The crude was used directly in the next step. LCMS: Rt=1.58 min, MS Calcd.: 588.2, MS Found: 588.9 [M+H]+.

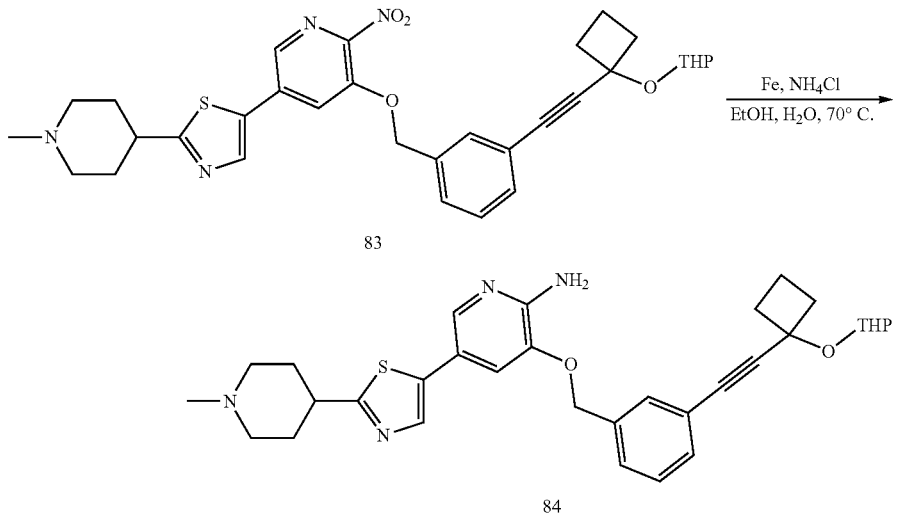

Compound 84: Compound 83 (260 mg, crude), reduced iron powder (124 mg, 2.2 mmol) and ammonium chloride (119 mg, 2.2 mmol) were sequentially added to a round bottom flask containing 5 mL of ethanol and 1 mL of water, stirred at 70° C. for 3 h. LCMS monitoring, after the reaction was completed, filtered, the filtrate was concentrated, and then obtained 230 mg of a yellow solid. The crude was used directly in the next step. LCMS: Rt=1.37 min, MS Calcd.: 558.3, MS Found: 558.9 [M+H]+.

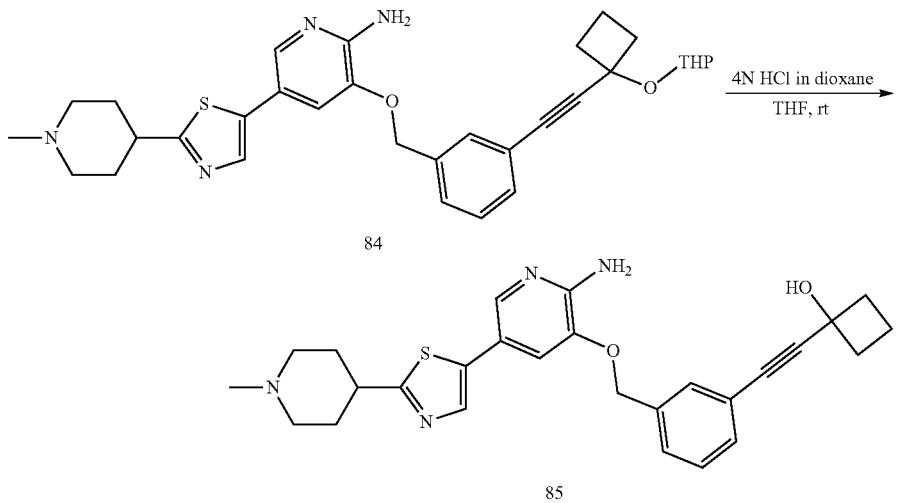

Compound 85: Compound 84 (230 mg, crude) was added to a round bottom flask containing 5 mL of tetrahydrofuran, protected with nitrogen, added 4N hydrochloric acid dioxane solution (1 mL), and stirred at room temperature for 3 h. LCMS monitoring, after the reaction was completed, concentrated, and separated by high performance liquid chromatography (column: Gemini-C18 150×21.2 mm, 5 μm, mobile phase: ACN—H$_2$O (0.05% NH$_3$), gradient: 40-90% ACN), lyophilized, obtained 79.2 mg of a yellow solid, three steps total yield: 8.6%. $^1$H NMR (400 MHz, DMSO-d6): δ ppm 1.67-1.82 (m, 4H), 1.99-2.04 (m, 4H), 2.19-2.25 (m, 5H), 2.33-2.41 (m, 2H), 2.81-2.94 (m, 3H), 5.23 (s, 2H), 5.89 (s, 1H), 6.08 (s, 2H), 7.36-7.43 (m, 3H), 7.54-7.58 (m, 2H), 7.77 (s, 1H), 7.88 (s, 1H). LCMS: Rt=1.22 min, MS Calcd.: 474.2, MS Found: 474.9 [M+H]+.

Example 15 Preparation of Compound 90 (A41)

The synthetic route of the compound is as follows:

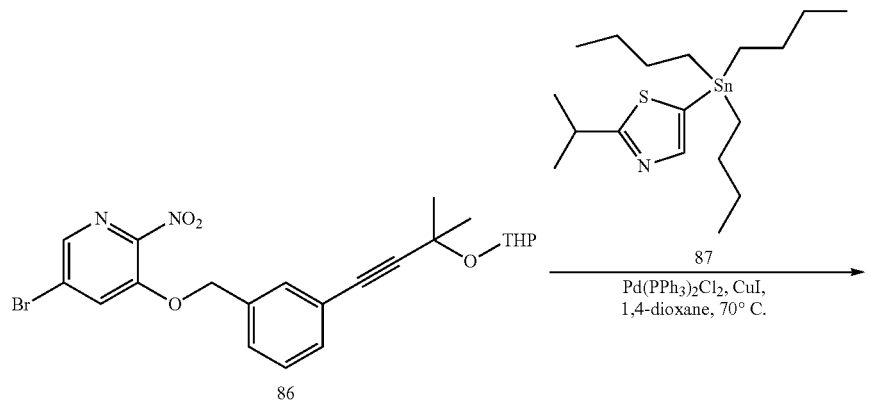

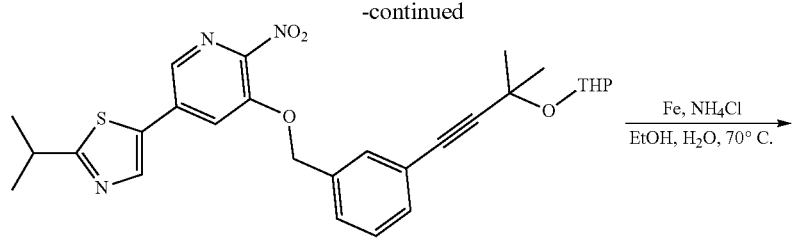

88

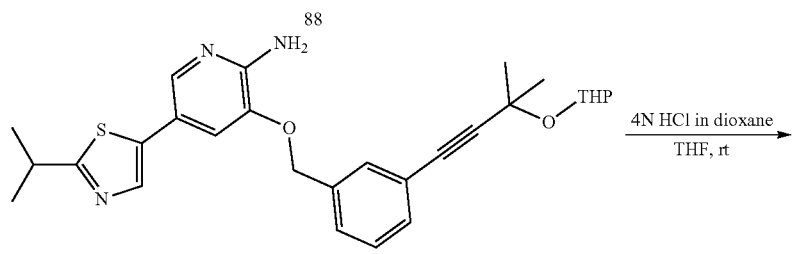

89

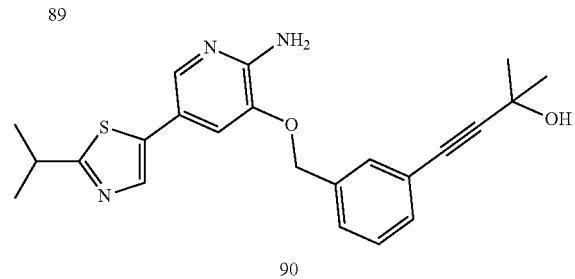

90

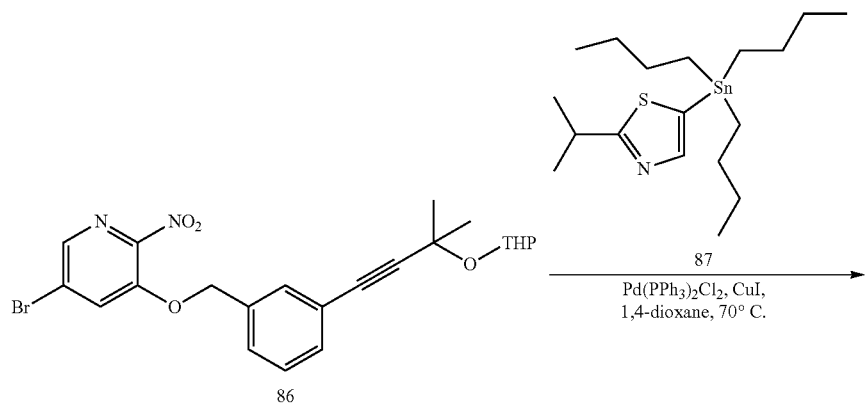

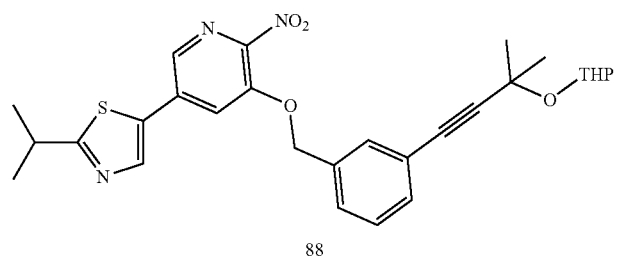

88

Compound 88: Compound 86 (500 mg, 1.05 mmol), 87 (528 mg, 1.26 mmol), bis(triphenylphosphine) palladium dichloride (74 mg, 0.105 mmol) and cuprous iodide (60 mg, 0.315 mmol) were sequentially added to a round bottom flask containing 10 mL of dioxane, protected with nitrogen, and stirred at 90° C. for 6 h. LCMS monitoring, after the reaction was completed, cooled to room temperature, concentrated, and separated by column chromatography (eluent: petroleum ether/ethyl acetate, 3/1, v/v), obtained 320 mg of a white solid, yield: 58.1%.

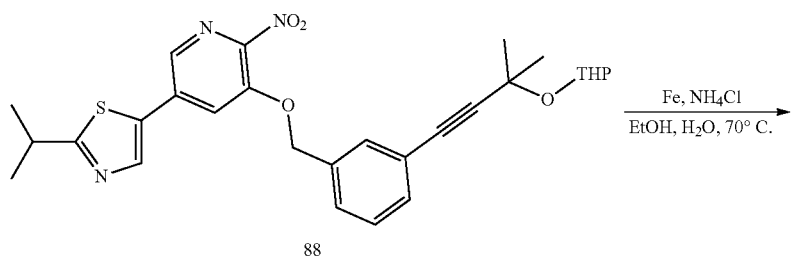

88

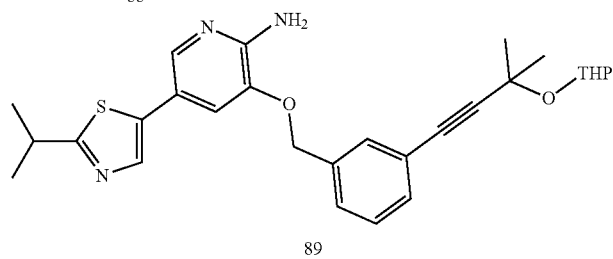

89

Compound 89: Compound 88 (320 mg, 0.61 mmol), reduced iron powder (172 mg, 3.1 mmol) and ammonium chloride (167 mg, 3.1 mmol) were sequentially added to a round bottom flask containing 5 mL of ethanol and 1 mL of water, stirred at 70° C. for 3 h. LCMS monitoring, after the reaction was completed, and then purified by column chromatography (eluent: petroleum ether/ethyl acetate, 1/2, v/v), obtained 240 mg of a yellow solid, yield: 80.3%.

LCMS: Rt=1.71 min, MS Calcd.: 491.2, MS Found: 491.9 [M+H]$^+$.

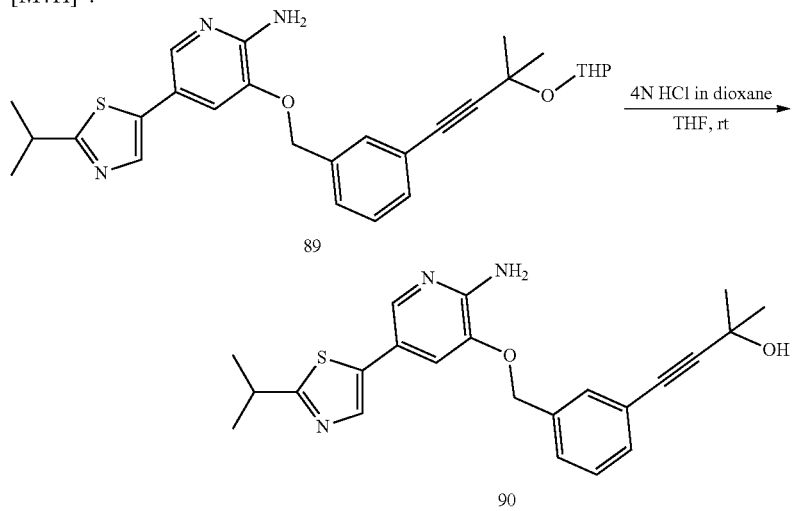

89

90

Compound 90: Compound 89 (240 mg, 0.49 mmol) was added to a round bottom flask containing 4 mL of tetrahydrofuran, protected with nitrogen, added 4N hydrochloric acid dioxane solution (1 mL), and stirred at room temperature for 3 h. LCMS monitoring, after the reaction was completed, concentrated, and then separated by high performance liquid chromatography (column: Gemini-C18 150×21.2 mm, 5 μm, mobile phase: ACN—H$_2$O (0.05% NH3), gradient: 40-70% ACN), lyophilized, obtained 56.8 mg of a white solid, yield: 28.4%. $^1$H NMR (400 MHz, DMSO-d$_6$): δ ppm 1.34 (d, J=6.8 Hz, 6H), 1.47 (s, 6H), 3.22-3.33 (m, 1H), 5.22 (s, 2H), 5.47 (s, 1H), 6.08 (s, 2H), 7.34-7.42 (m, 3H), 7.54 (s, 2H), 7.77 (s, 1H), 7.86 (s, 1H). LCMS: Rt=1.43 min, MS Calcd.: 407.2, MS Found: 407.9 [M+H]$^+$.

Example 16 Preparation of Compound 94 (A38)

The synthetic route of the compound is as follows:

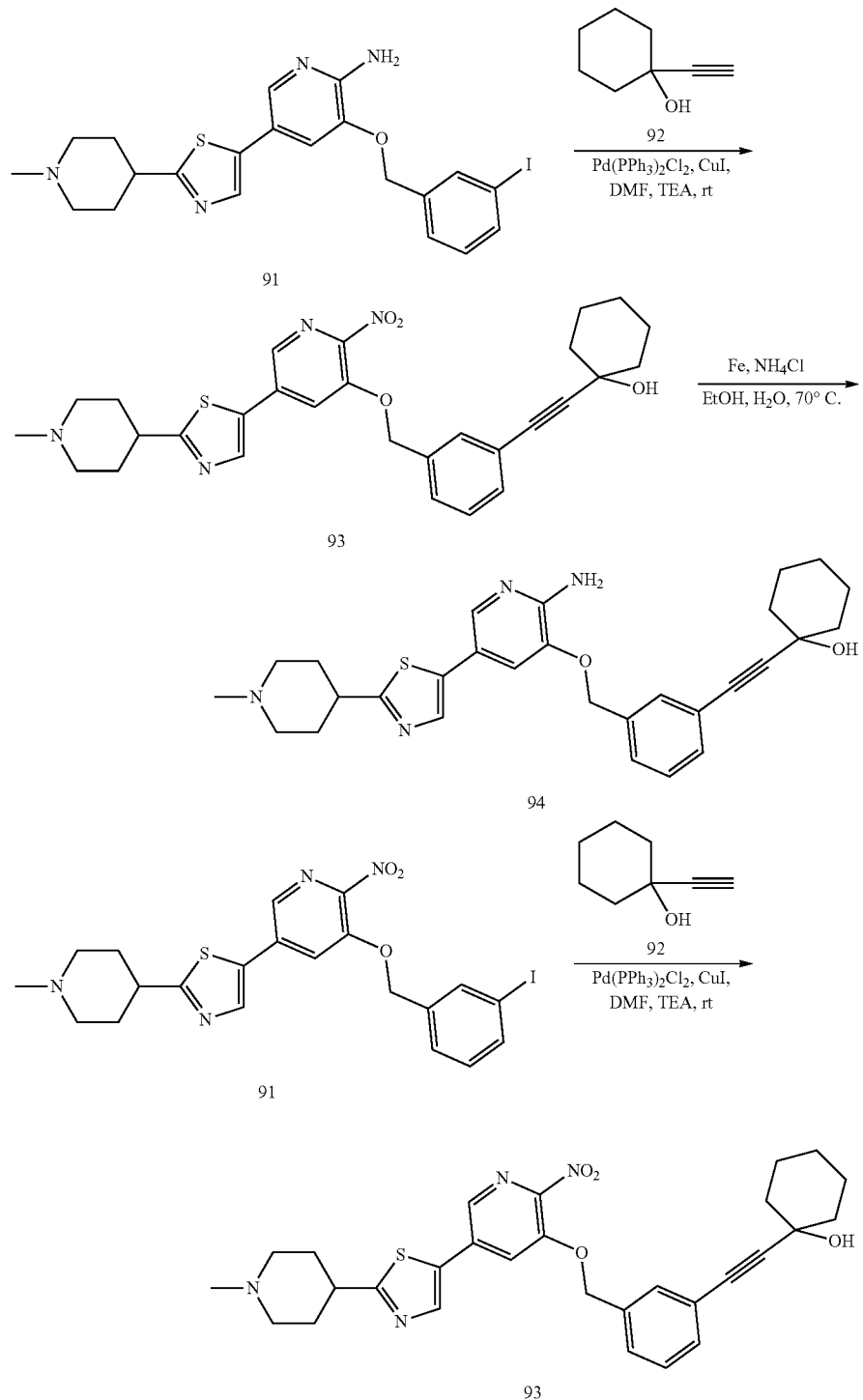

Compound 93: Compound 91 (300 mg, 0.56 mmol), 92 (139 mg, 1.12 mmol), bis(triphenylphosphine) palladium dichloride (39 mg, 0.056 mmol) and cuprous iodide (32 mg, 0.17 mmol) were sequentially added to a round bottom flask containing 5 mL of DMF and 1 mL of triethylamine, protected with nitrogen, and stirred at room temperature for 6 h. LCMS monitoring, after the reaction was completed, concentrated, and then purified by column chromatography (eluent: dichloromethane/methanol, 8/1, v/v), obtained 110 mg of a yellow sticky substance, yield: 70%. LCMS: Rt=1.32 min, MS Calcd.: 532.2, MS Found: 532.8 [M+H]+.

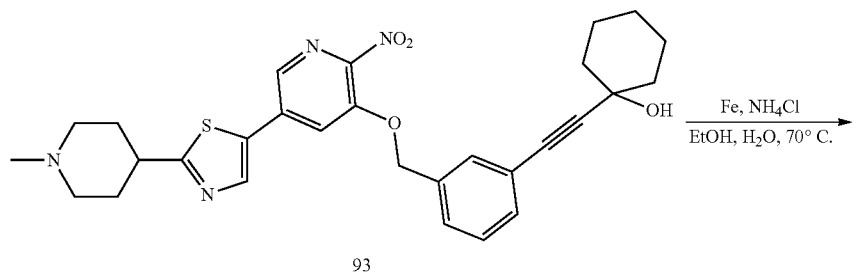

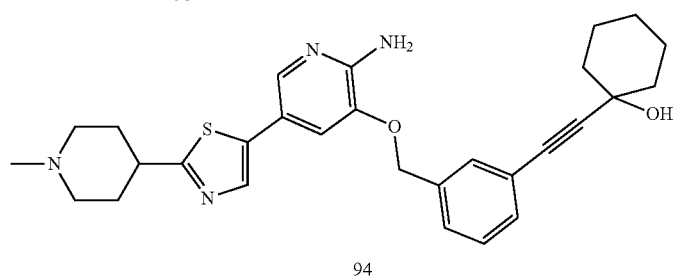

Compound 94: Compound 93 (110 mg, crude), reduced iron powder (58 mg, 1.03 mmol) and ammonium chloride (55 mg, 1.03 mmol) were sequentially added to a round bottom flask containing 5 mL of ethanol and 1 mL of water, stirred at 70° C. for 3 h. LCMS monitoring, after the reaction was completed, cooled to room temperature, and then separated by high performance liquid chromatography (column: Gemini-C18 150×21.2 mm, 5 μm, mobile phase: ACN—H₂O (0.1% TFA), gradient: 5-30% ACN), lyophilized, obtained 16 mg of a white solid, two steps total yield: 5.7%.

$^1$H NMR (400 MHz, DMSO-$d_6$): δ ppm 1.23-1.30 (m, 1H), 1.49-1.68 (m, 8H), 1.85-1.88 (m, 2H), 2.09-2.32 (m, 4H), 3.04 (s, 3H), 3.24-3.30 (m, 1H), 3.44-3.61 (m, 4H), 4.63 (s, 2H), 5.82 (s, 2H), 7.10 (s, 1H), 7.52-7.61 (m, 3H), 7.64 (s, 1H), 7.69 (s, 1H), 7.82 (s, 1H), 8.37 (s, 2H). LCMS: Rt=1.02 min, MS Calcd.: 502.2, MS Found: 503.1 [M+H]⁺.

Example 17 Preparation of Compound 104 (A39)

The synthetic route of the compound is as follows:

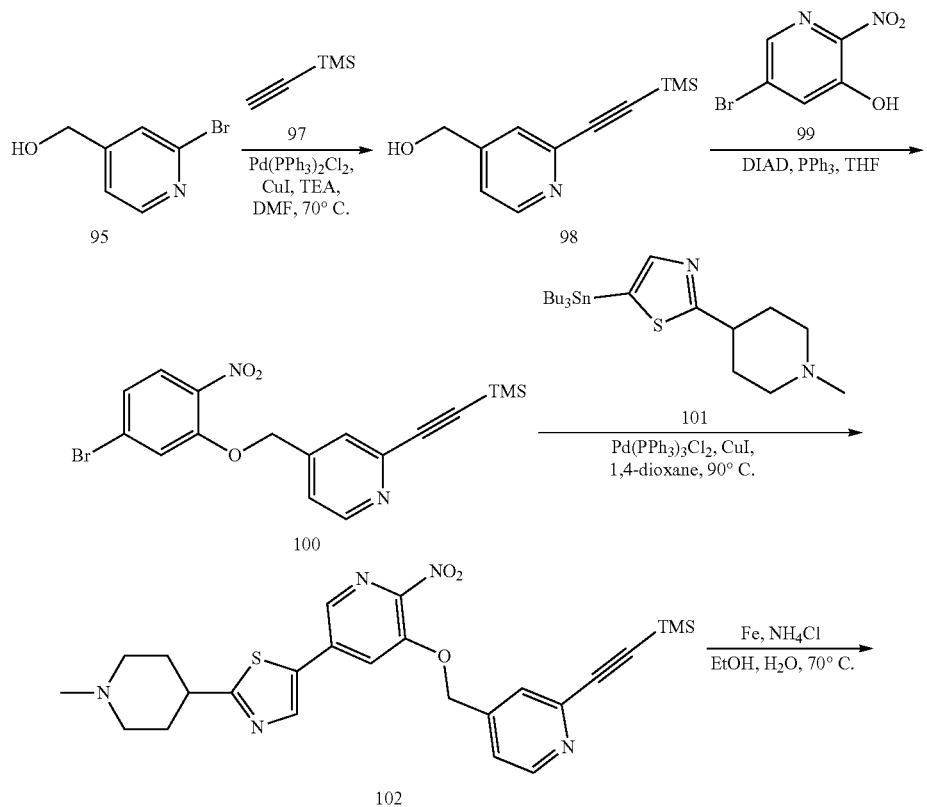

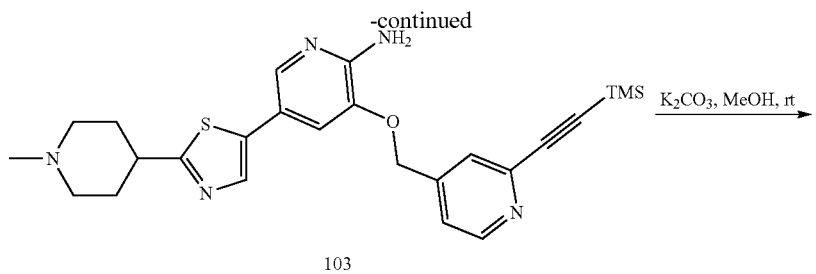

103

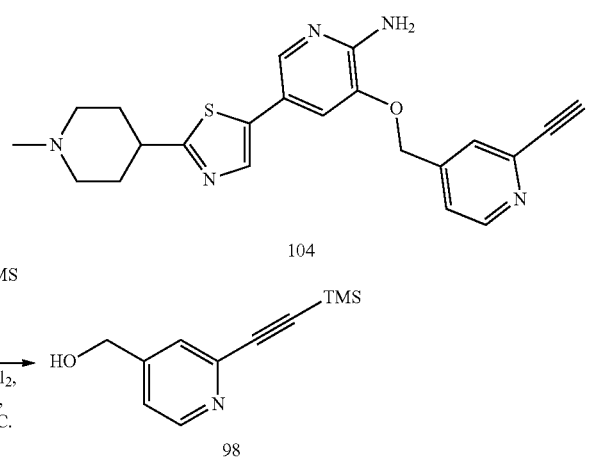

104

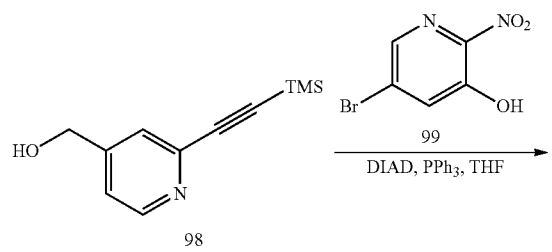

Compound 98: Compound 96 (1.5 g, 8.0 mmol), 97 (1.2 g, 12.0 mmol), bis(triphenylphosphine) palladium dichloride (562 mg, 0.8 mmol) and cuprous iodide (457 mg, 2.4 mmol) were sequentially added to a round bottom flask containing 20 mL of dioxane and 4 mL of triethylamine, protected with nitrogen, and stirred at 50° C. for 6 h. LCMS monitoring, after the reaction was completed, concentrated, and separated by column chromatography (eluent: petroleum ether/ethyl acetate, 1/1, v/v), obtained 1.5 g of a brown oily liquid, yield: 91.2%. $^1$H NMR (400 MHz, CDCl$_3$): δ ppm 0.27 (s, 9H), 4.75 (s, 2H), 7.25 (d, J=5.0 Hz, 1H), 7.49 (s, 1H), 8.48 (d, J=5.1 Hz, 1H). LCMS: Rt=1.51 min, MS Calcd.: 205.1, MS Found: 206.0 [M+H]$^+$.

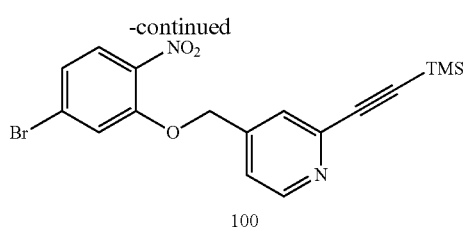

100

Compound 100: Compound 98 (1.5 g, 7.3 mmol), 99 (1.4 g, 6.6 mmol) and triphenylphosphine (2.0 g, 7.9 mmol) were sequentially added to a three-neck flask containing 30 mL of tetrahydrofuran, protected with nitrogen, diisopropyl azodicarboxylate (1.6 g, 7.9 mmol) was added with stirring, and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous Na$_2$SO$_4$, concentrated under reduced pressure, and then purified by column chromatography (eluent: petroleum ether/ethyl acetate, 2/1, v/v), obtained 1.2 g of a gray solid, yield: 45.5%. $^1$H NMR (400 MHz, CDCl$_3$): δ ppm 0.30 (s, 9H), 5.25 (s, 2H), 7.34 (d, J=4.9 Hz, 1H), 7.51 (s, 1H), 7.67 (s, 1H), 8.24 (s, 1H), 8.65 (d, J=5.0 Hz, 1H). LCMS: Rt=1.70 min, MS Calcd.: 405.0, 407.0, MS Found: 405.7, 407.7 [M+H]$^+$.

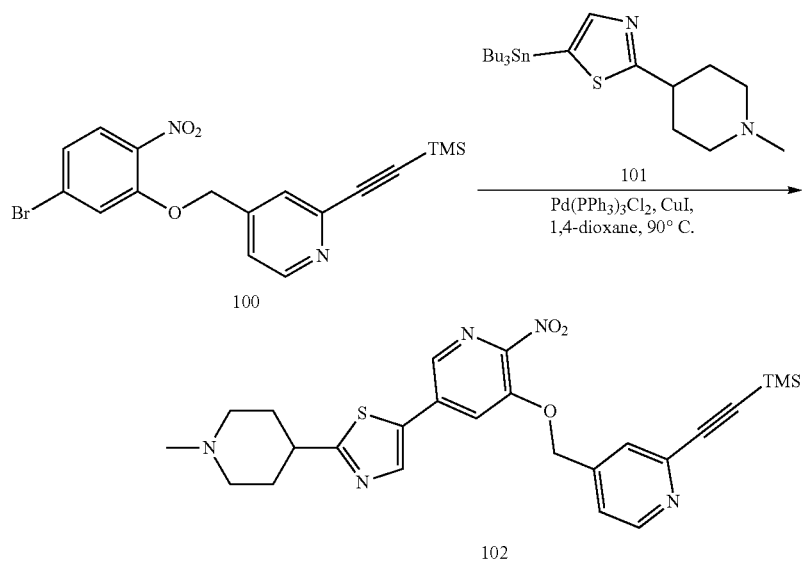

Compound 102: Compound 100 (0.8 g, 2.0 mmol), 101 (932 mg, 2.0 mmol), bis(triphenylphosphine) palladium dichloride (140 mg, 0.2 mmol) and cuprous iodide (114 mg, 0.6 mmol) were sequentially added to a round bottom flask containing 15 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 5/1, v/v), obtained 160 mg of a yellow sticky substance (crude). LCMS: Rt=1.46 min, MS Calcd.: 507.2, MS Found: 507.9 [M+H]$^+$.

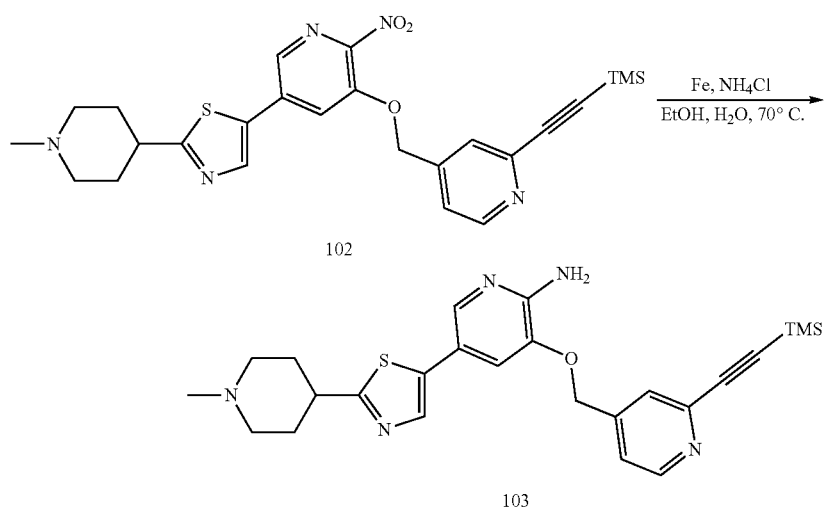

Compound 103: Compound 102 (160 mg, crude), reduced iron powder (88 mg, 1.6 mmol) and ammonium chloride (85 mg, 1.6 mmol) were sequentially added to a round bottom flask containing 5 mL of ethanol and 1 mL of water, stirred at 70° C. for 3 h. LCMS monitoring, after the reaction was completed, filtered, the filtrate was concentrated, and then obtained 140 mg of a yellow solid. The crude was used directly in the next step. LCMS: Rt=1.29 min, MS Calcd.: 477.2, MS Found: 477.9 [M+H]$^+$.

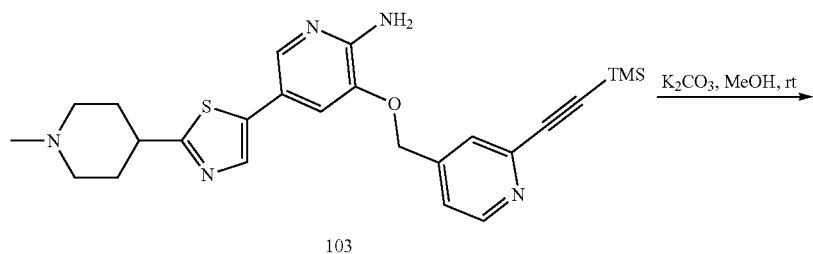

103

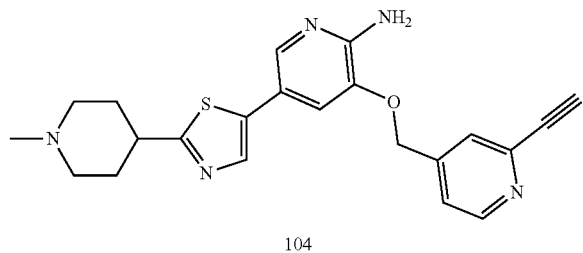

104

Compound 104: Compound 103 (140 mg, crude) and potassium carbonate (122 mg, 0.88 mmol) were sequentially added to a round bottom flask containing 300 mL of methanol, protected with nitrogen, stirred at room temperature overnight. LCMS monitoring, after the reaction was completed, concentrated, and then separated by high performance liquid chromatography (column: Gemini-C18 150× 21.2 mm, 5 μm, mobile phase: ACN—H$_2$O (0.1% TFA), gradient: 0-30% ACN), lyophilized, obtained 12 mg of a gray solid, two steps total yield: 1.5%. $^1$H NMR (400 MHz, CD$_3$OD): δ ppm 2.05-2.16 (m, 2H), 2.37 (d, J=13.2 Hz, 2H), 2.86 (s, 3H), 3.11 (t, J=11.7 Hz, 2H), 3.36 (s, 1H), 3.54 (d, J=12.3 Hz, 2H), 3.84 (s, 1H), 5.34 (s, 2H), 7.37 (s, 1H), 7.61 (d, J=5.0 Hz, 1H), 7.76 (s, 1H), 7.80 (s, 1H), 7.87 (s, 1H), 8.47 (s, 1H), 8.55 (d, J=5.1 Hz, 1H). LCMS: Rt=1.13 min, MS Calcd.: 405.2, MS Found: 405.9 [M+H]$^+$.

Example 18 Preparation of Compound 113 (A34)

The synthetic route of the compound is as follows:

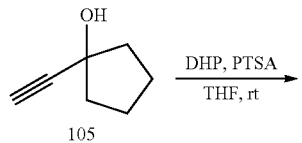

105

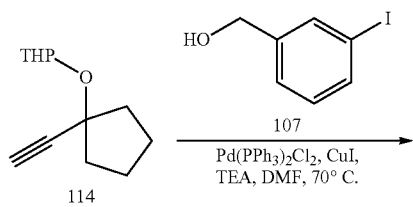

114

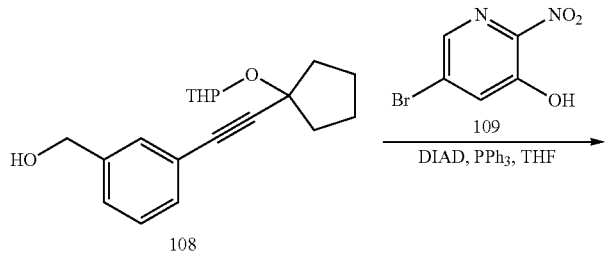

108

-continued

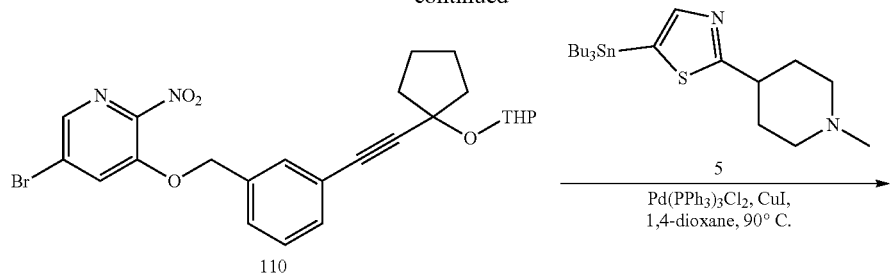
110

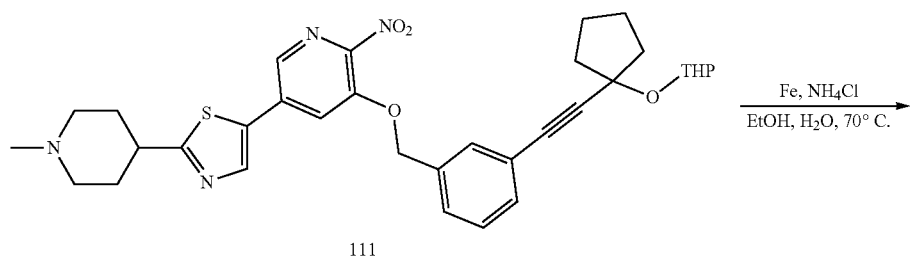
111

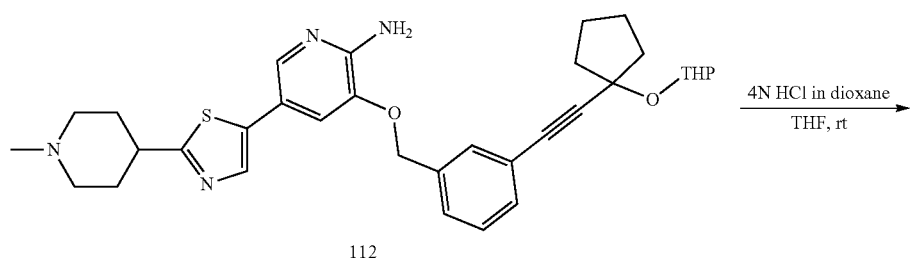
112

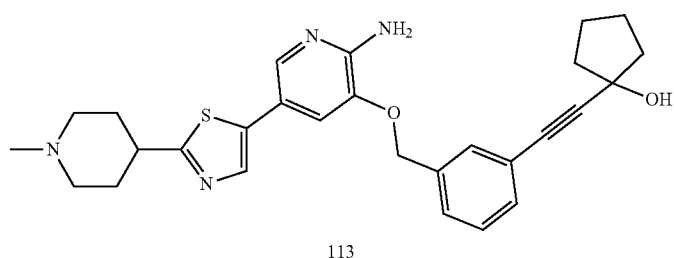
113

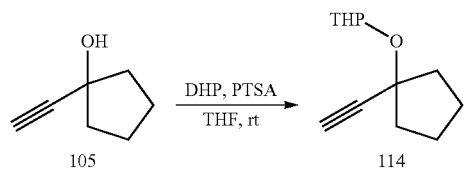

Compound 114: Compound 106 (3 g, 27.2 mmol), p-toluenesulfonic acid (50 mg) was added in a round bottom flask containing 50 mL of tetrahydrofuran, followed by the addition of 3,4-dihydropyran (3 g, 27.2 mmol), protected with nitrogen, stirred at room temperature for 16 h. TLC monitoring, after the reaction was completed, concentrated, and then purified by column chromatography (eluent: petroleum ether/ethyl acetate, 50/1, v/v), obtained 1.5 g of a yellow oily liquid, the crude was used directly in the next step.

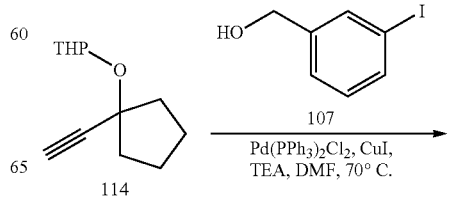

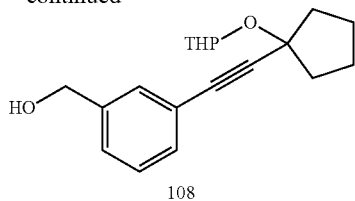

108

Compound 108: Compound 114 (1.3 g, 6.7 mmol), 107 (1.5 g, 6.7 mmol), bis(triphenylphosphine) palladium dichloride (470 mg, 0.67 mmol) and cuprous iodide (383 mg, 2.01 mmol) were sequentially added to a round bottom flask containing 20 mL of dioxane and 4 mL of triethylamine, protected with nitrogen, and stirred at room temperature for 16 h. LCMS monitoring, after the reaction was completed, concentrated, and separated by column chromatography (eluent: petroleum ether/ethyl acetate, 10/1, v/v), obtained 1.3 g of a yellow oily liquid, yield: 64.2%. LCMS: Rt=1.83 min, MS Calcd.: 300.2, MS Found: 323.1 [M+Na]+.

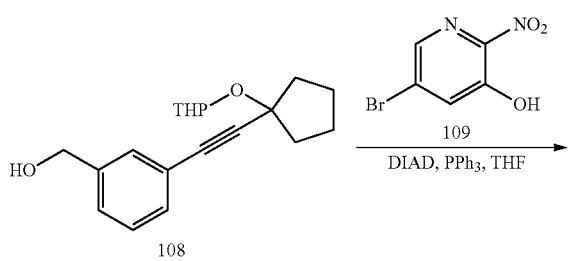

108     109    DIAD, PPh₃, THF

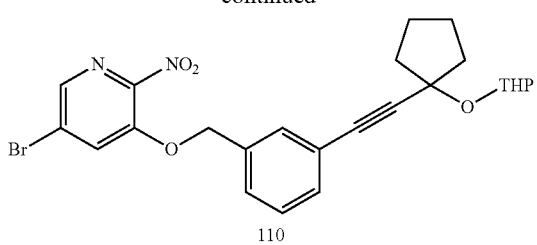

110

Compound 110: Compound 108 (1.3 g, 4.3 mmol), 109 (940 mg, 4.3 mmol) and triphenylphosphine (1.35 g, 5.16 mmol) were sequentially added to a three-neck flask containing 30 mL of tetrahydrofuran, protected with nitrogen, diisopropyl azodicarboxylate (1.04 g, 5.16 mmol) was added with stirring, and stirred at room temperature for 3 h. LCMS monitoring, after the reaction was completed, quenched with water (50 mL), extracted with EtOAc (50 mL×3), and the combined extracts were washed with saturated aqueous sodium chloride (50 mL), dried with anhydrous Na₂SO₄, concentrated under reduced pressure, and then purified by column chromatography (eluent: petroleum ether/ethyl acetate, 10/1, v/v), obtained 900 mg of a yellow sticky substance, yield: 41.9%. LCMS: Rt=1.99 min, MS Calcd.: 500.1, 502.1, MS Found: 522.8, 524.8 [M+Na]+.

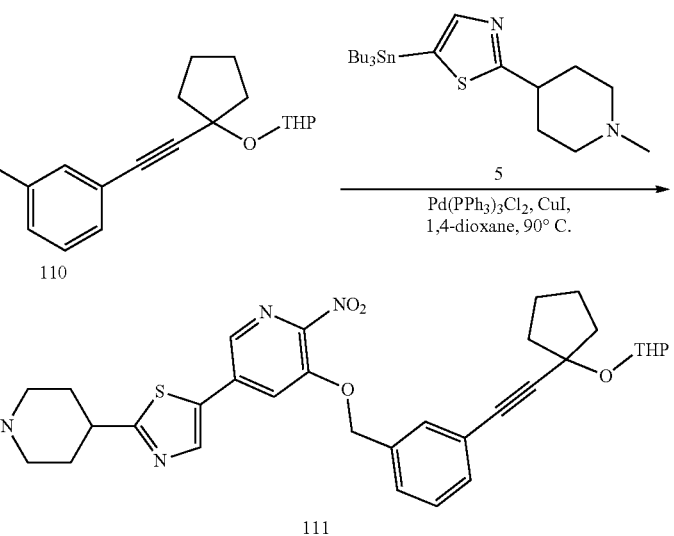

111

Compound 111: Compound 110 (0.5 g, 1.0 mmol), 5 (472 mg, 1.0 mmol), bis(triphenylphosphine) palladium dichloride (70 mg, 0.1 mmol) and cuprous iodide (57 mg, 0.3 mmol) were sequentially added to a round bottom flask containing 15 mL of dioxane, protected with nitrogen, and stirred at 90° C. for 6 h. LCMS monitoring, after the reaction was completed, cooled to room temperature, concentrated, and then purified by column chromatography (eluent: dichloromethane/methanol, 5/1, v/v), obtained 320 mg of a yellow solid (crude). LCMS: Rt=1.55 min, MS Calcd.: 602.3, MS Found: 602.9 [M+H]+.

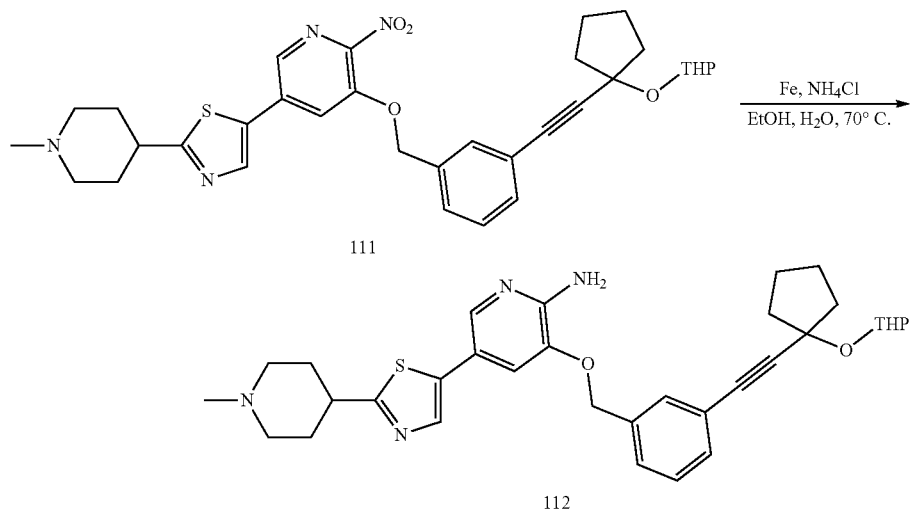

111

112

Compound 112: Compound 111 (320 mg, crude), reduced iron powder (149 mg, 2.65 mmol) and ammonium chloride (140 mg, 2.65 mmol) were sequentially added to a round bottom flask containing 5 mL of ethanol and 1 mL of water, stirred at 70° C. for 3 h. LCMS monitoring, after the reaction was completed, filtered, the filtrate was concentrated, and then obtained 260 mg of a yellow solid. The crude was used directly in the next step. LCMS: Rt=1.37 min, MS Calcd.: 572.3, MS Found: 572.9 [M+H]+.

50.1 mg of a white solid, three steps total yield: 10.2%. $^1$H NMR (400 MHz, DMSO-$d_6$): δ ppm 1.68-1.76 (m, 6H), 1.84-1.91 (m, 4H), 1.98-2.04 (m, 4H), 2.19 (s, 3H), 2.81-2.93 (m, 3H), 5.22 (s, 2H), 5.34 (s, 1H), 6.09 (s, 2H), 7.35-7.42 (m, 3H), 7.52-7.54 (m, 2H), 7.77 (s, 1H), 7.87 (s, 1H). LCMS: Rt=1.15 min, MS Calcd.: 488.2, MS Found: 488.6 [M+H]+.

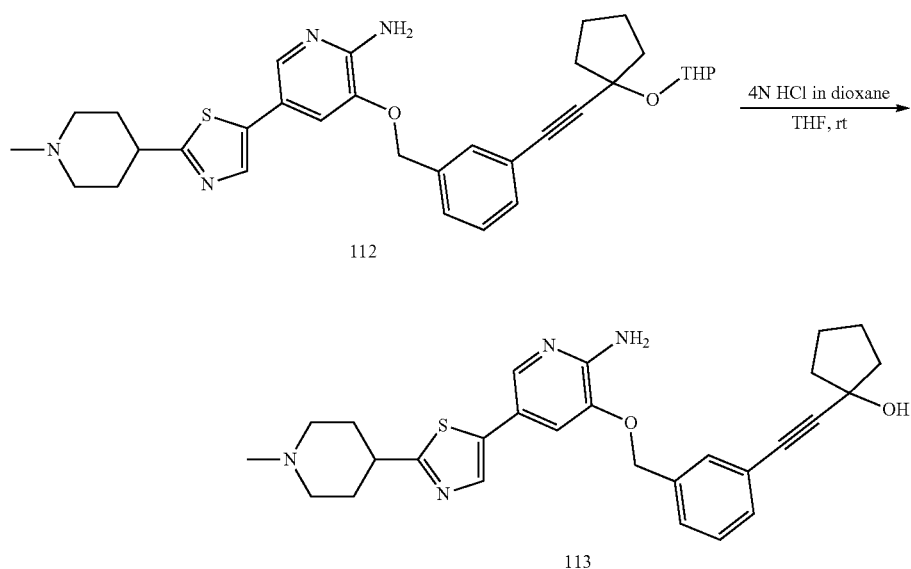

112

113

Compound 113: Compound 112 (260 mg, crude) was added to a round bottom flask containing 5 mL of tetrahydrofuran, protected with nitrogen, added 4N hydrochloric acid dioxane solution (1 mL), and stirred at room temperature for 3 h. LCMS monitoring, after the reaction was completed, concentrated, and then separated by high performance liquid chromatography (column: Gemini-C18 150×21.2 mm, 5 μm, mobile phase: ACN—H$_2$O (0.05% NH$_{40}$H), gradient: 30-90% ACN), lyophilized, obtained Example 19 Preparation of Compound 118 (A35)

The synthetic route of the compound is as follows:

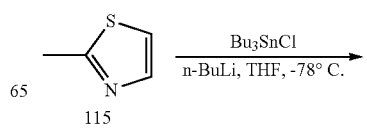

115

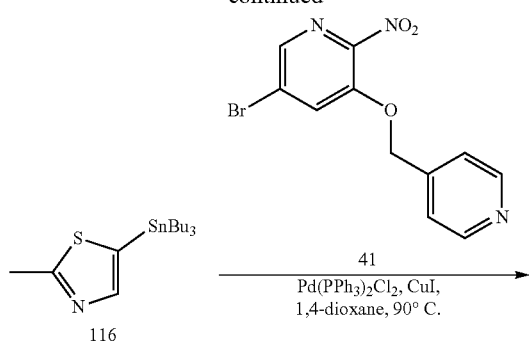

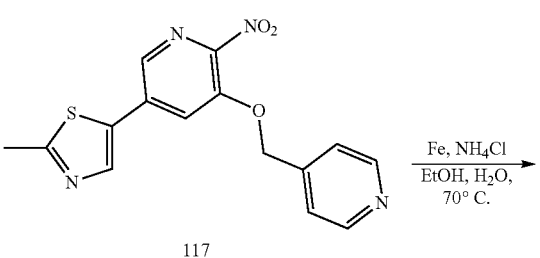

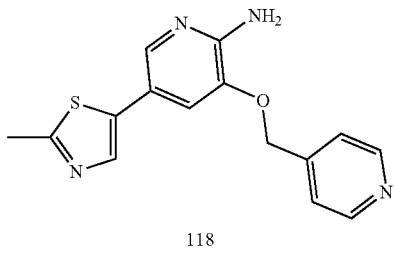

Compound 116: Compound 115 (2 g, 20.17 mmol) was added to a three-necked flask containing 50 mL of anhydrous tetrahydrofuran, cooled to −78° C., and n-butyllithium (2.4 M in hexane solution, 8.4 mL, 20.17 mmol) was added under nitrogen-protected, stirred at −78° C. for 1 h, then tributyltin chloride (7.2 g, 22.19 mmol) was added dropwise, stirred at −78° C. for 1 h. TLC monitoring, after the reaction was completed, quenched with saturated ammonium chloride (50 mL), extracted with EtOAc (100 mL×3), and the combined extracts were washed with saturated aqueous sodium chloride (100 mL), dried with anhydrous Na$_2$SO$_4$, concentrated under reduced pressure without further purification, obtained 7.8 g of a yellow oily liquid, yield: 99.2%. $^1$H NMR (400 MHz, CDCl$_3$): δ ppm 0.90 (t, J=7.4 Hz, 9H), 1.09-1.13 (m, 5H), 1.29-1.36 (m, 8H), 1.52-1.58 (m, 5H), 2.77 (s, 3H), 7.57 (s, 1H).

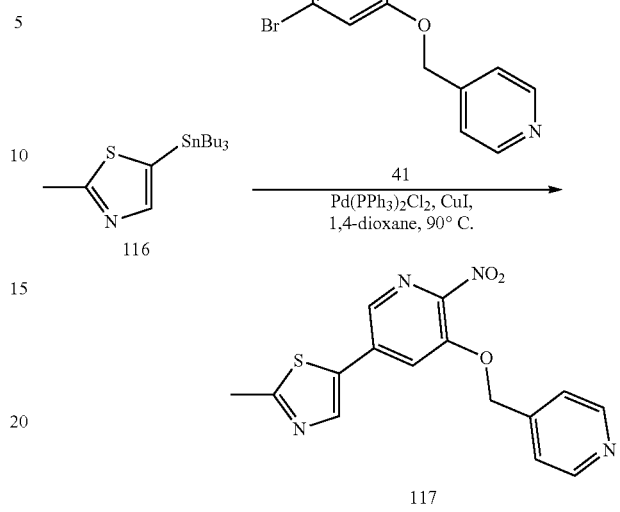

Compound 117: Compound 116 (1.5 g, 3.87 mmol), compound 41 (1 g, 3.22 mmol), bis(triphenylphosphine) palladium dichloride (450 mg, 0.65 mmol), cuprous iodide (180 mg, 0.97) Methyl) were sequentially added to a 100 mL round bottom flask containing 50 mL of dioxane, protected with nitrogen, and stirred at 90° C. for 3 h. LCMS monitoring, after the reaction was completed, cooled to room temperature, filtered, the filtrate was concentrated under reduced pressure. Added 100 mL of water, extracted with dichloromethane (100 mL×3), and the combined extracts were washed with saturated aqueous sodium chloride (100 mL), dried with anhydrous Na$_2$SO$_4$, concentrated under reduced pressure, and then separated by medium pressure rapid preparative chromatography (eluent: methanol/dichloromethane, 1/10, v/v), obtained 830 mg of a yellow solid, yield: 78.2%. LCMS: Rt=1.31 min, MS Calcd.: 328.1, MS Found: 328.8 [M+H]$^+$.

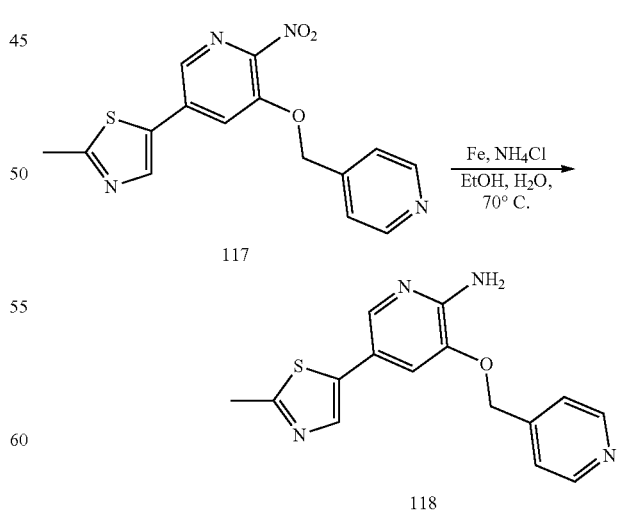

Compound 118: Compound 117 (730 mg, 2.22 mmol), iron powder (1.24 g, 22.23 mmol), ammonium chloride (1.19 mg, 22.23 mmol) were added sequentially to a 100 mL round bottom flask containing ethanol/water (50 mL, 4/1, v/v), stirred at 70° C. for 2 h. LCMS monitoring, after the reaction was completed, filtered, the filtrate was concentrated under reduced pressure, and then separated by medium pressure rapid preparative chromatography (eluent: methanol/dichloromethane, 1/10, v/v), lyophilized, obtained 125 mg of a yellow solid, yield: 18.8%. $^1$H NMR (400 MHz, DMSO-d$_6$): δ ppm 2.64 (s, 3H), 5.29 (s, 2H), 6.20 (s, 2H), 7.37 (s, 1H), 7.57 (d, J=4.8 Hz, 2H), 7.76 (s, 1H), 7.85 (s, 1H), 8.60 (d, J=4.0 Hz, 2H). LCMS: Rt=0.78 min, MS Calcd.: 298.1, MS Found: 299.0 [M+H]+.

Example 20 Preparation of Compound 124 (A36)

The synthetic route of the compound is as follows:

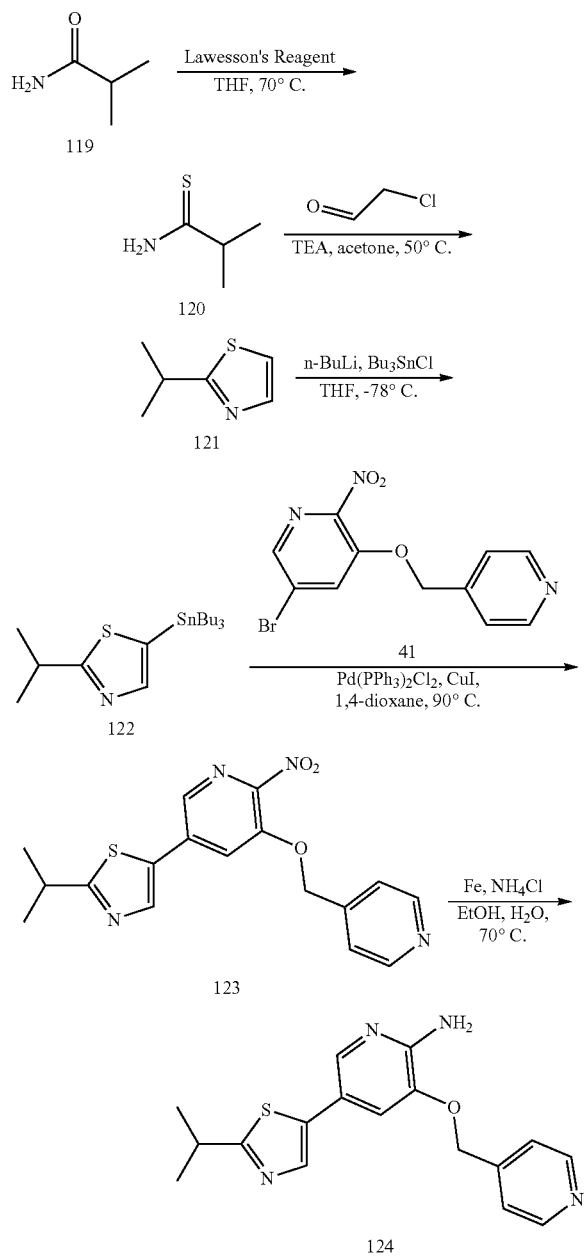

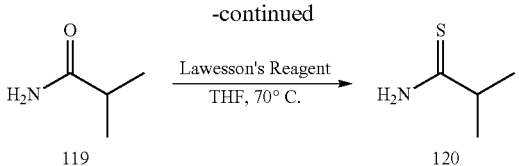

Compound 120: Compound 119 (10 g, 0.11 mol), Lawson's reagent (24 g, 0.06 mol) was added to a round bottom flask containing 150 mL of anhydrous tetrahydrofuran, protected with nitrogen, and stirred at 70° C. for 16 h. LCMS monitoring, after the reaction was completed, quenched with saturated sodium bicarbonate solution, extracted with EtOAc (400 mL×2), and the combined extracts were washed with saturated aqueous sodium chloride (100 mL), dried with anhydrous Na$_2$SO$_4$, concentrated under reduced pressure, and then purified by column chromatography (eluent: ethyl acetate/petroleum ether, 1/3, v/v), obtained 5 g of a yellow solid, yield: 42.4%. $^1$H NMR (400 MHz, CDCl$_3$): δ ppm 1.29 (d, J=6.8 Hz, 6H), 2.84-2.97 (m, 1H), 6.95 (s, 1H), 7.73 (s, 1H). LCMS: Rt=0.82 min, MS Calcd.: 103.0, MS Found: 104.2 [M+H]$^+$.

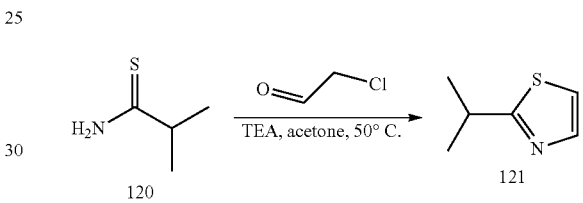

Compound 121: Compound 120 (2.5 g, 24 mmol), chloroacetaldehyde (5.7 g, 72 mmol) were added in a 100 mL round bottom flask containing 45 mL of acetone and stirred at 60° C. for 16 h. LCMS monitoring, after the reaction was completed, concentrated under reduced pressure, and then purified by column chromatography (eluent: ethyl acetate/petroleum ether, 1/2, v/v), obtained 0.6 g of a yellow solid, yield: 19.5%. $^1$H NMR (400 MHz, CDCl$_3$): δ ppm 1.44 (d, J=7.2 Hz, 6H), 3.30-3.44 (m, 1H), 7.21 (d, J=3.2 Hz, 1H), 7.70 (d, J=3.2 Hz, 1H). LCMS: Rt=1.19 min, MS Calcd.: 127.0, MS Found: 128.2 [M+H]$^+$.

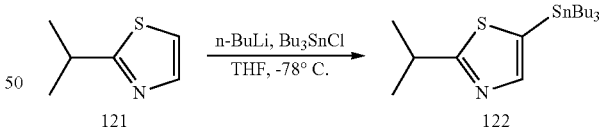

Compound 122: In a 100 mL three-necked flask, Compound 121 (600 mg, 4.72 mmol) was dissolved in 25 mL of anhydrous tetrahydrofuran, cooled to −78° C., and n-butyllithium (2.4 M in hexane solution, 2.2 mL, 5.2 mmol) was added under nitrogen-protected, stirred at −78° C. for 1 h, then tributyltin chloride (1.61 g, 5.00 mmol) was added dropwise, stirred at −78° C. for 1 h. LCMS monitoring, after the reaction was completed, quenched with saturated ammonium chloride (20 mL), extracted with EtOAc (100 mL×2), and the combined extracts were washed with saturated aqueous sodium chloride (50 mL), dried with anhydrous Na$_2$SO$_4$, concentrated under reduced pressure, obtained 1.5 g of a yellow solid, yield: 76.1%. LCMS: Rt=1.94 min, MS Calcd.: 417.2, MS Found: 418.0 [M+H]$^+$.

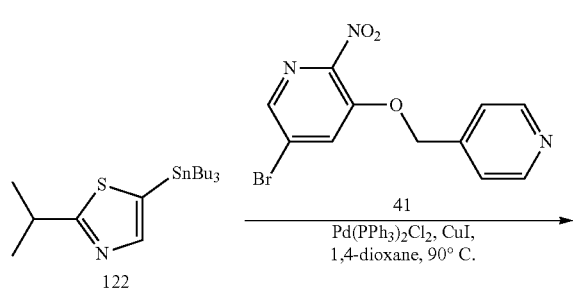

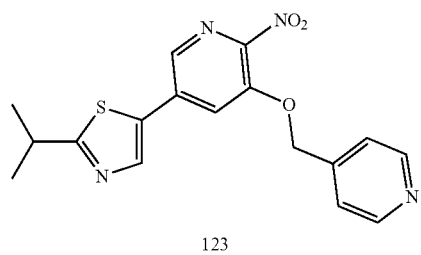

Compound 123: Compound 122 (800 mg, 1.93 mmol), 41 (400 mg, 1.29 mmol), bis(triphenylphosphine) palladium dichloride (180 mg, 0.26 mmol) and cuprous iodide (73 mg, 0.39 mmol) were sequentially added to a round bottom flask containing 25 mL of dioxane, protected with nitrogen, and stirred at 90° C. for 6 h. LCMS monitoring, after the reaction was completed, cooled to room temperature, concentrated, and separated by medium pressure rapid preparative chromatography (eluent: methanol/dichloromethane, 1/20, v/v), obtained 160 mg of a gray solid, yield: 34.8%. $^1$H NMR (400 MHz, DMSO-$d_6$): δ ppm 1.39 (d, J=6.8 Hz, 6H), 3.34-3.41 (m, 1H), 5.55 (s, 2H), 7.44-7.57 (m, 2H), 8.23 (s, 1H), 8.43 (s, 1H), 8.47 (s, 1H), 8.55-8.97 (m, 2H). LCMS: Rt=1.45 min, MS Calcd.: 356.1, MS Found: 356.8 [M+H]$^+$.

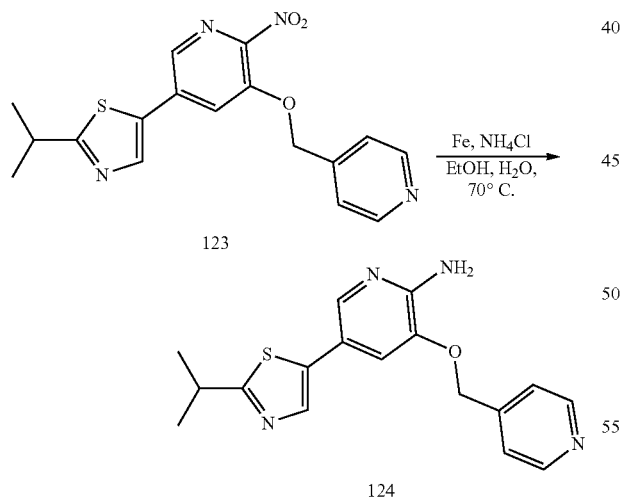

Compound 124: Compound 123 (160 mg, 0.45 mmol), iron powder (126 mg, 2.25 mmol), ammonium chloride (120 mg, 2.25 mmol) were added sequentially to a 100 mL round bottom flask containing ethanol/water (25 mL, 4/1, v/v), stirred at 70° C. for 2 h. LCMS monitoring, after the reaction was completed, filtered, the filtrate was concentrated under reduced pressure, and then separated by medium pressure rapid preparative chromatography (eluent: methanol/dichloromethane, 1/20, v/v), obtained 60 mg of a yellow solid, yield: 41.9%. $^1$H NMR (400 MHz, DMSO-$d_6$): δ ppm 1.34 (d, J=6.8 Hz, 6H), 3.21-3.30 (m, 1H), 5.29 (s, 2H), 6.20 (s, 2H), 7.37 (s, 1H), 7.57 (d, J=4.8 Hz, 2H), 7.80 (s, 1H), 7.87 (s, 1H), 8.60 (d, J=3.6 Hz, 2H). LCMS: Rt=0.99 min, MS Calcd.: 326.1, MS Found: 327.1 [M+H]$^+$.

Example 21 Preparation of Compound 130 (A37)

The synthetic route of the compound is as follows:

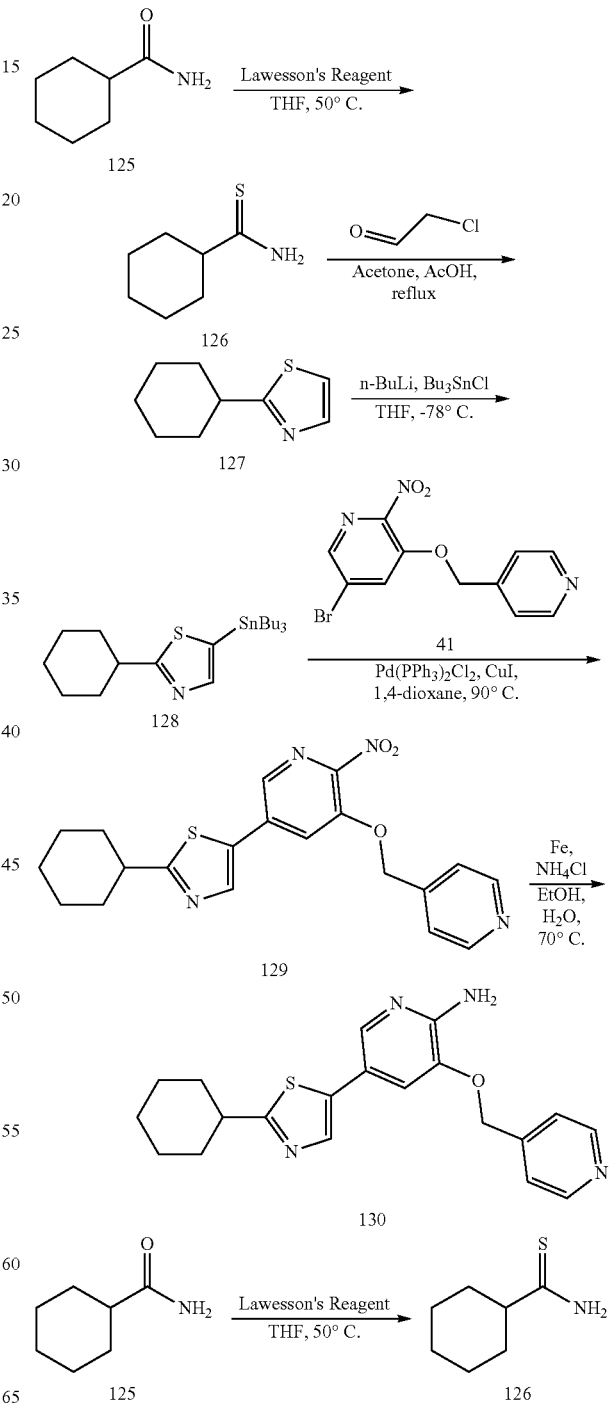

Compound 126: Compound 125 (6.5 g, 51.4 mmol), Lawson's reagent (10.3 g, 25.6 mmol) was added to a round bottom flask containing 150 mL of anhydrous tetrahydrofuran, protected with nitrogen, and stirred at 50° C. for 14 h. LCMS monitoring, after the reaction was completed, quenched with saturated sodium bicarbonate solution, extracted with EtOAc (200 mL×2), and the combined extracts were washed with saturated aqueous sodium chloride (100 mL), dried with anhydrous $Na_2SO_4$, concentrated under reduced pressure, and then purified by column chromatography (eluent: petroleum ether/ethyl acetate, 10:1-5:1, v/v), obtained 2.9 g of a white solid, yield: 39.7%. $^1$H NMR (400 MHz, DMSO-$d_6$): δ ppm 1.11-1.28 (m, 4H), 1.44-1.50 (m, 2H), 1.62-1.74 (m, 5H), 9.01 (s, 1H), 9.27 (s, 1H). LCMS: Rt=1.44 min, MS Calcd.: 143.1, MS Found: 144.0 $[M+H]^+$.

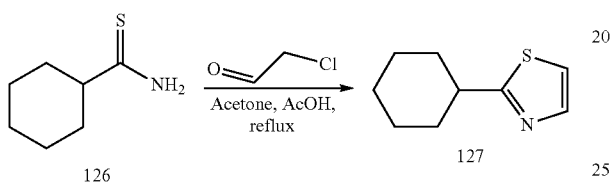

Compound 127: Compound 126 (2.9 g, 20.24 mmol), chloroacetaldehyde (3.2 g, 40.49 mmol), acetic acid (4 mL) was added in a 250 mL round bottom flask containing 50 mL of acetone and stirred at 50° C. for 14 h. LCMS monitoring, after the reaction was completed, concentrated under reduced pressure, diluted with water (50 mL), extracted with ethyl acetate (100 mL×2), and the combined extracts were washed with saturated aqueous sodium chloride (50 mL), dried with anhydrous $Na_2SO_4$, concentrated under reduced pressure, and then purified by column chromatography (eluent: ethyl acetate/petroleum ether, 1/3, v/v), obtained 2.4 g of a yellow oily liquid, yield: 75%. $^1$HNMR (400 MHz, CDCl$_3$): δ ppm 1.25-1.61 (m, 6H), 1.85-1.88 (m, 2H), 2.15-2.18 (m, 2H), 3.00-3.07 (m, 1H), 7.20 (d, J=3.6 Hz, 1H), 7.70 (d, J=3.2 Hz, 1H). LCMS: Rt=1.67 min, MS Calcd.: 167.1, MS Found: 168.0$[M+H]^+$.

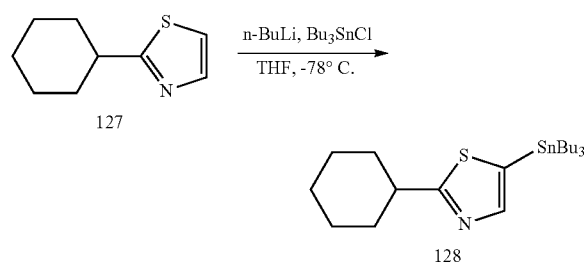

Compound 128: In a 250 mL three-necked flask, Compound 127 (2.3 g, 13.75 mmol) was dissolved in 100 mL of anhydrous tetrahydrofuran, cooled to −78° C., and n-butyllithium (2.4 M in hexane solution, 5.7 mL, 13.75 mmol) was added under nitrogen-protected, stirred at −78° C. for 1 h, then tributyltin chloride (4.9 g, 15.13 mmol) was added dropwise, stirred at −78° C. for 1 h. LCMS monitoring, after the reaction was completed, quenched with saturated ammonium chloride (50 mL), extracted with EtOAc (100 mL×3), and the combined extracts were washed with saturated aqueous sodium chloride (100 mL), dried with anhydrous $Na_2SO_4$, concentrated under reduced pressure, obtained 6.2 g of a yellow oily liquid, yield: 98.4%. $^1$H NMR (400 MHz, CDCl$_3$): δ ppm 0.89-0.93 (m, 9H), 1.10-1.14 (m, 4H), 1.27-1.38 (m, 12H), 1.53-1.59 (m, 8H), 1.85-1.88 (m, 2H), 2.16-2.19 (m, 2H), 3.03-3.11 (m, 1H), 7.61 (s, 1H).

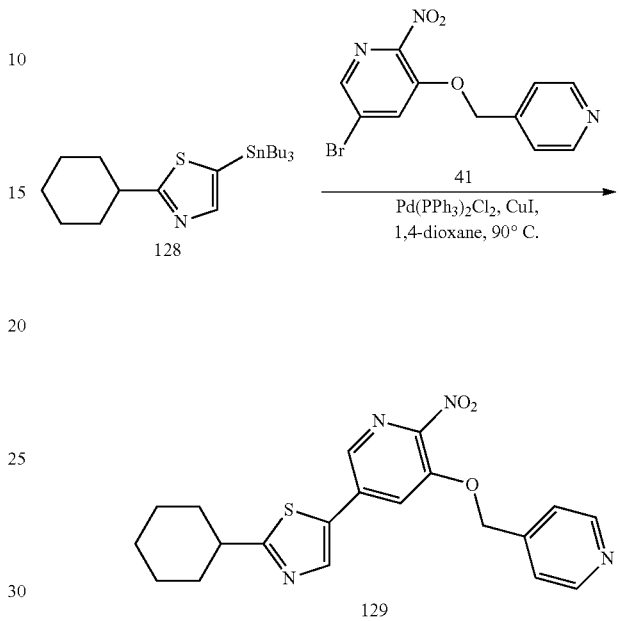

Compound 129: Compound 128 (1.7 g, 3.87 mmol), Compound 41 (1 g, 3.22), [1,1'-bis(diphenylphosphine) ferrocene] palladium dichloride dichloromethane complex (450 mg, 0.64 mmol), cuprous iodide (184 mg, 0.97 mmol) were sequentially added to a 100 mL round bottom flask containing 50 mL of dioxane, protected with nitrogen, and stirred at 90° C. for 4 h.

LCMS monitoring, after the reaction was completed, cooled to room temperature, concentrated under reduced pressure. Added 100 mL of water, extracted with ethyl acetate (100 mL×3), and the combined extracts were washed with saturated aqueous sodium chloride (100 mL), dried with anhydrous $Na_2SO_4$, concentrated under reduced pressure, and then separated by medium pressure rapid preparative chromatography (eluent: methanol/dichloromethane, 1/50-1/10, v/v), obtained 580 mg of a yellow solid, yield: 56.6%. $^1$H NMR (400 MHz, DMSO-$d_6$): δ ppm 1.25-1.28 (m, 2H), 1.38-1.54 (m, 4H), 1.79-1.82 (m, 2H), 2.09-2.12 (m, 2H), 3.05-3.10 (m, 1H), 5.55 (s, 2H), 7.47 (s, 2H), 8.22 (s, 1H), 8.43 (s, 1H), 8.47 (s, 1H), 8.66 (br. s, 2H). LCMS: Rt=1.62 min, MS Calcd.: 396.1, MS Found: 396.9 $[M+H]^+$.

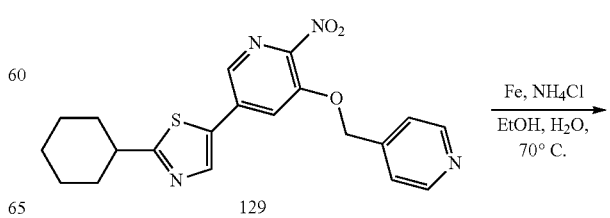

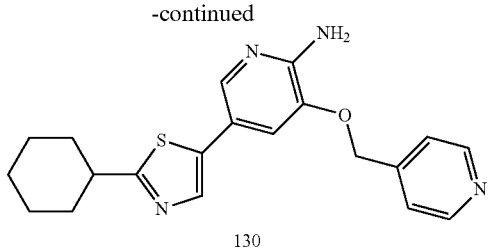

130

Compound 130: Compound 129 (530 mg, 1.34 mmol), iron powder (746 mg, 13.37 mmol), ammonium chloride (715 mg, 13.37 mmol) were added sequentially to a 100 mL round bottom flask containing ethanol/water (50 mL, 4/1, v/v), stirred at 70° C. for 2 h. LCMS monitoring, after the reaction was completed, filtered, the filtrate was concentrated under reduced pressure, and then separated by medium pressure rapid preparative chromatography (eluent: methanol/dichloromethane, 1/10, v/v), lyophilized, obtained 290 mg of a yellow solid, yield: 17%. $^1$H NMR (400 MHz, CD$_3$OD): δ ppm 1.32-1.39 (m, 2H), 1.44-1.62 (m, 2H), 1.88-1.91 (m, 2H), 2.12-2.15 (m, 2H), 2.98-3.03 (m, 1H), 5.35 (s, 2H), 7.37 (s, 1H), 7.62 (d, J=4.8 Hz, 2H), 7.78 (s, 2H), 8.59 (br. s, 2H). LCMS: Rt=1.35 min, MS Calcd.: 366.2, MS Found: 366.9 [M+H]+.

Example 22 Preparation of Compound 138 (A43)

The synthetic route of the compound is as follows:

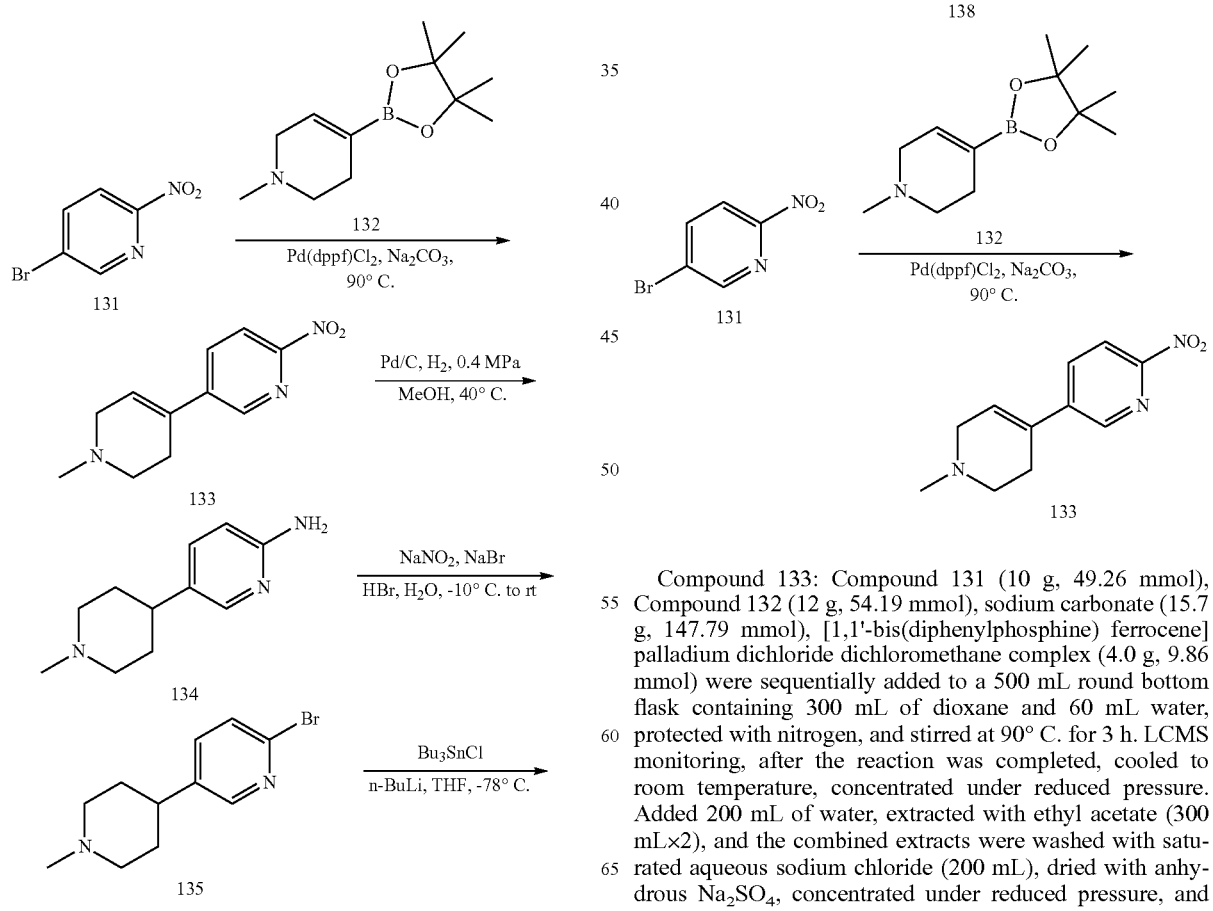

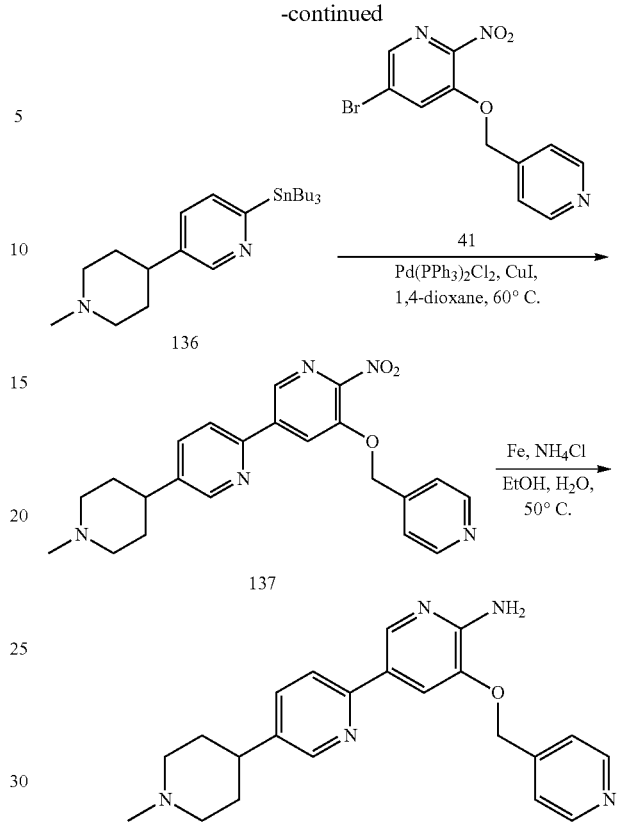

Compound 133: Compound 131 (10 g, 49.26 mmol), Compound 132 (12 g, 54.19 mmol), sodium carbonate (15.7 g, 147.79 mmol), [1,1'-bis(diphenylphosphine) ferrocene] palladium dichloride dichloromethane complex (4.0 g, 9.86 mmol) were sequentially added to a 500 mL round bottom flask containing 300 mL of dioxane and 60 mL water, protected with nitrogen, and stirred at 90° C. for 3 h. LCMS monitoring, after the reaction was completed, cooled to room temperature, concentrated under reduced pressure. Added 200 mL of water, extracted with ethyl acetate (300 mL×2), and the combined extracts were washed with saturated aqueous sodium chloride (200 mL), dried with anhydrous Na$_2$SO$_4$, concentrated under reduced pressure, and then separated by column chromatography (eluent: methanol/dichloromethane, 1/100, v/v), obtained 7.8 g of a brown solid, yield: 72.2%. ¹H NMR (400 MHz, DMSO-d₆): δ ppm 2.30 (s, 3H), 2.57-2.60 (m, 4H), 3.09 (br. s, 2H), 6.59 (s, 1H), 8.21-8.29 (m, 2H), 8.77 (s, 3H). LCMS: Rt=0.54 min, MS Calcd.: 219.1, MS Found: 220.0 [M+H]⁺.

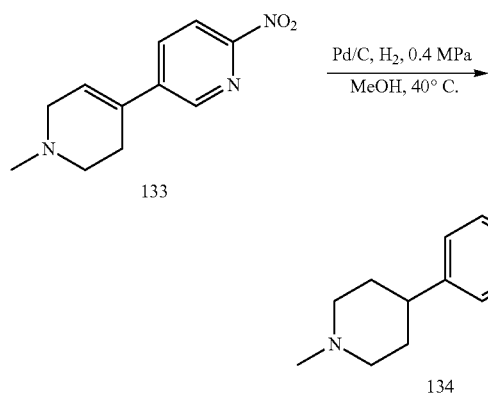

Compound 134: Compound 133 (7.8 g, 35.6 mmol), 10% palladium on carbon (7 g), acetic acid (4 ml) was sequentially added to a 1 L reactor containing 300 mL of methanol and 100 mL of tetrahydrofuran, stirred at 40° C. for 16 h in a 0.4 MPa hydrogen atmosphere. LCMS monitoring, after the reaction was completed, filtered, the filtrate was concentrated under reduced pressure. Added 100 mL of water, extracted with ethyl acetate (200 mL×2), and the combined extracts were washed with saturated aqueous sodium chloride (100 mL), dried with anhydrous Na₂SO₄, concentrated under reduced pressure, and obtained 7 g of a yellow oily liquid, yield: 97.1%. LCMS: Rt=0.30 min, MS Calcd.: 191.1, MS Found: 192.0 [M+H]⁺.

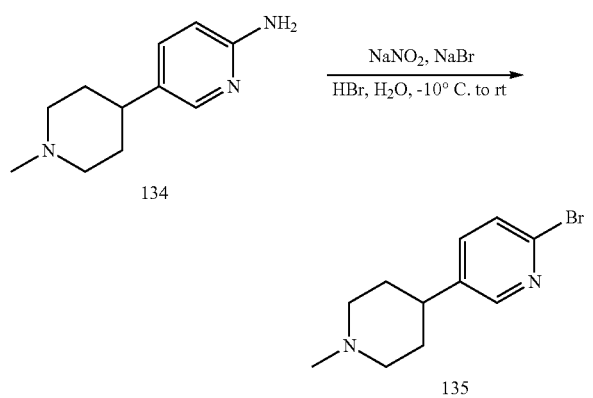

Compound 135: In a 500 mL three-necked flask, Compound 134 (7 g, 36.60 mmol) was dissolved in 80 mL of hydrobromic acid solution, cooled to −10° C., and sodium nitrite (3.8 g, 54.89 mmol) solution was added under nitrogen, stirred at −10° C. for 1 h, then sodium bromide solution (5.7 g, 54.89 mmol) was added dropwise, stirred at room temperature for 16 h. LCMS monitoring, after the reaction was completed, the mixture was adjusted to pH>7 with sodium carbonate, extracted with dichloromethane (200 mL×2), and the combined extracts were washed with saturated aqueous sodium chloride (100 mL), dried with anhydrous Na₂SO₄, concentrated under reduced pressure, and separated by medium pressure rapid preparative chromatography (eluent: methanol/dichloromethane, 1/10-1/5, v/v), obtained 700 mg of a yellow solid, yield: 7.4%. ¹H NMR (400 MHz, DMSO-d₆): δ ppm 1.83-1.91 (m, 2H), 2.00-2.03 (m, 2H), 2.79 (s, 3H), 2.87-2.92 (m, 1H), 3.01-3.07 (m, 2H), 3.46-3.48 (m, 2H), 7.65 (s, 2H), 8.33 (s, 1H). LCMS: Rt=1.10 min, MS Calcd.: 254.0, 256.0, MS Found: 254.9, 256.8 [M+H]⁺.

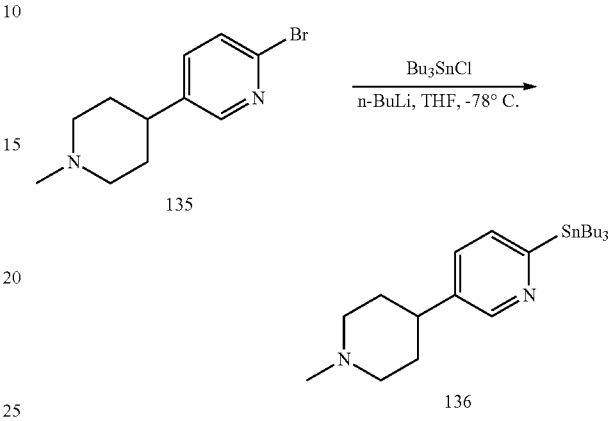

Compound 136: In a 250 mL three-necked flask, Compound 135 (440 mg, 1.7 mmol) was dissolved in 100 mL of anhydrous tetrahydrofuran, cooled to −78° C., and n-butyllithium (2.4 M in hexane solution, 0.86 mL) was added under nitrogen, stirred at −78° C. for 1 h, then tributyltin chloride (673 mg, 2.1 mmol) was added dropwise, stirred at −78° C. for 1 h. TLC monitoring, after the reaction was completed, quenched with saturated ammonium chloride (50 mL), extracted with EtOAc (100 mL×3), and the combined extracts were washed with saturated aqueous sodium chloride (100 mL), dried with anhydrous Na₂SO₄, concentrated under reduced pressure, obtained 800 mg of a yellow oily liquid, yield: 98.2%. LCMS: Rt=1.18 min, MS Calcd.: 466.2, MS Found: 467.2 [M+H]⁺.

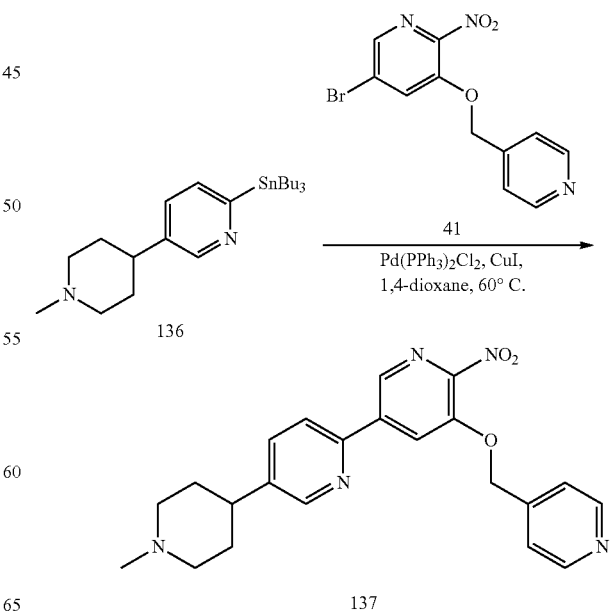

Compound 137: Compound 136 (800 mg, 1.72 mmol), 41 (300 mg, 0.97 mmol), bis(triphenylphosphine) palladium dichloride (136 mg, 0.19 mmol) and cuprous iodide (56 mg, 0.29 mmol) were sequentially added to a 100 mL round bottom flask containing 50 mL of dioxane, protected with nitrogen, and stirred at 60° C. for 6 h. LCMS monitoring, after the reaction was completed, cooled to room temperature, concentrated under reduced pressure.

Added 100 mL of water, extracted with dichloromethane (100 mL×3), and the combined extracts were washed with saturated aqueous sodium chloride (20 mL), dried with anhydrous Na$_2$SO$_4$, concentrated under reduced pressure, and separated by medium pressure rapid preparative chromatography (eluent: methanol/dichloromethane, 1/10-1/1, v/v), obtained 120 mg of a yellow solid, yield: 30.5%. LCMS: Rt=1.15 min, MS Calcd.: 405.2, MS Found: 405.9 [M+H]$^+$.

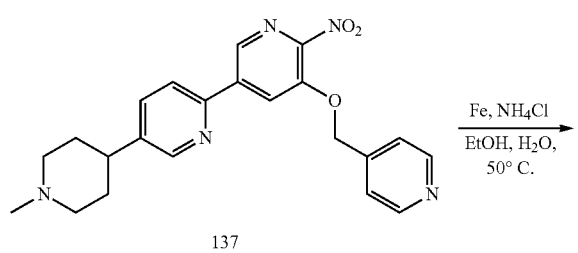

137

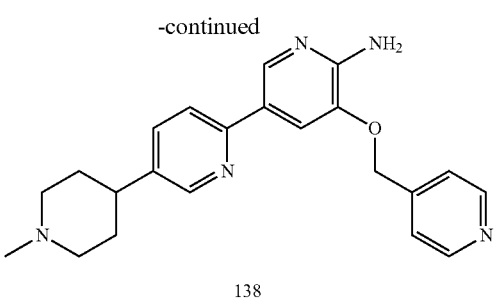

138

Compound 138: Compound 137 (120 mg, 0.30 mmol), iron powder (165 mg, 2.96 mmol), ammonium chloride (158 mg, 2.96 mmol) were sequentially added to a 100 mL round bottom flask containing 40 mL of ethanol and 10 mL of water, and stirred at 50° C. for 2 h. LCMS monitoring, after the reaction was completed, filtered, the filtrate was concentrated under reduced pressure, and then separated by high performance liquid chromatography (column: Gemini-C18 150×21.2 mm, 5 μm, mobile phase: ACN—H$_2$O (0.1% TFA), gradient: 0-20% ACN), lyophilized, obtained 30 mg of a yellow oily liquid, yield: 27%. $^1$H NMR (400 MHz, CD$_3$OD): δ ppm 1.98-2.08 (m, 2H), 2.16-2.19 (m, 2H), 2.94 (s, 3H), 2.97-3.03 (m, 1H), 3.16-3.22 (m, 2H), 3.62-3.65 (m, 2H), 5.39 (s, 2H), 7.63 (d, J=4.4 Hz, 2H), 7.75 (s, 1H), 7.78 (s, 2H), 8.19 (s, 1H), 8.50 (s, 1H), 8.59 (s, 2H). LCMS: Rt=0.40 min, MS Calcd.: 375.2, MS Found: 375.9 [M+H]$^+$.

Example 23 Preparation of Compound 143 (A42)

The synthetic route of the compound is as follows:

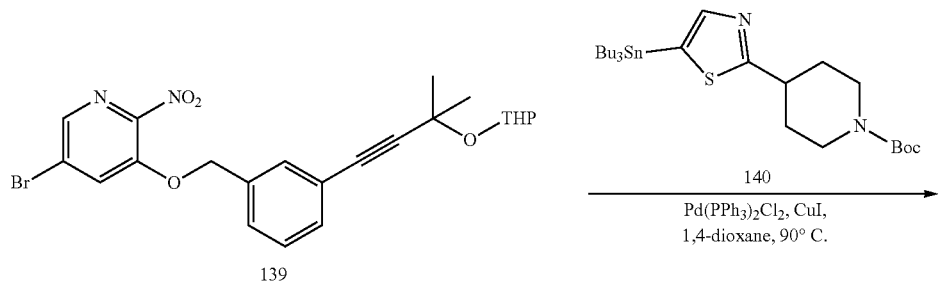

139

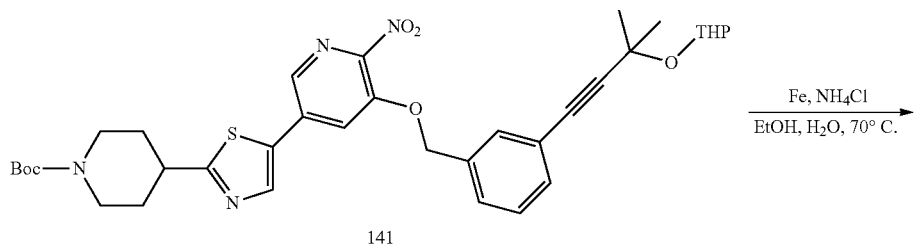

141

-continued

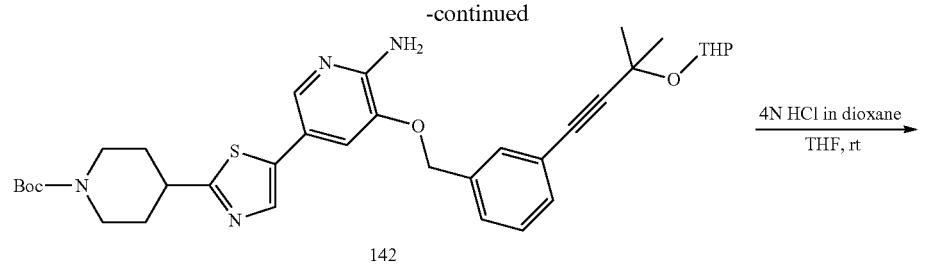

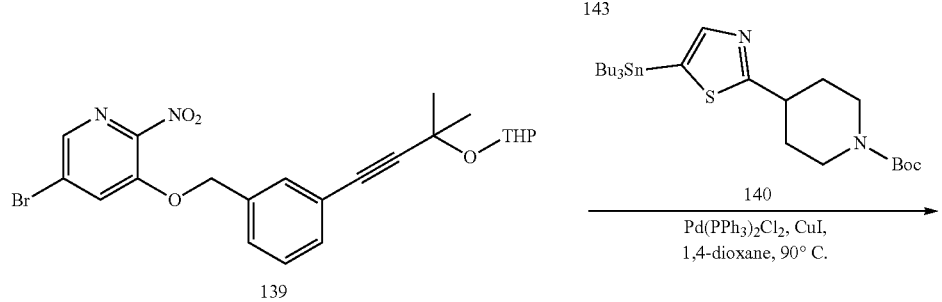

Compound 141: Compound 139 (2.0 g, 4.2 mmol), 140 (2.81 g, 5.04 mmol), bis(triphenylphosphine) palladium dichloride (295 mg, 0.42 mmol) and cuprous iodide (240 mg, 1.26 mmol) were sequentially added to a round bottom flask containing 40 mL of dioxane, protected with nitrogen, and stirred at 90° C. for 6 h. LCMS monitoring, after the reaction was completed, cooled to room temperature, concentrated, and separated by column chromatography (eluent: petroleum ether/ethyl acetate, 1/1, v/v), obtained 2.6 g of a light brown solid, yield: 92.8%. LCMS: Rt=2.06 min, MS Calcd.: 662.3, MS Found: 685.1 [M+Na]⁺.

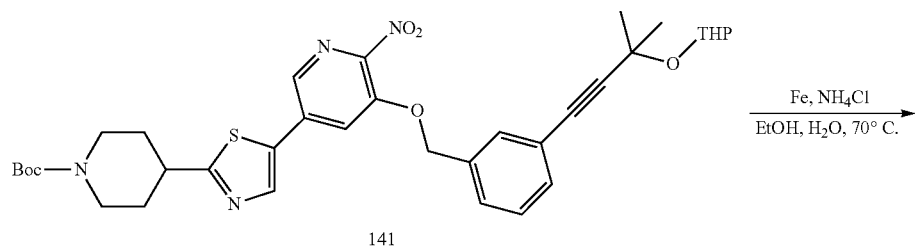

-continued

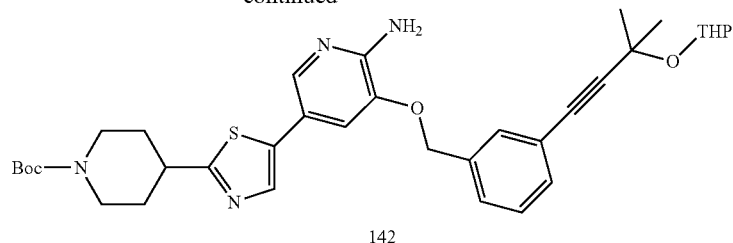

142

Compound 142: Compound 141 (2.5 g, 3.77 mmol), reduced iron powder (1.05 g, 18.9 mmol) and ammonium chloride (1.02 g, 18.9 mmol) were sequentially added to a round bottom flask containing 40 mL of ethanol and 10 mL of water, stirred at 70° C. for 3 h. LCMS monitoring, after the reaction was completed, and purified by column chromatography (eluent: petroleum ether/ethyl acetate, 1/2, v/v), obtained 1.7 g of a white solid, yield: 71.6%. LCMS: Rt=1.82 min, MS Calcd.: 632.3, MS Found: 632.8 [M+H]$^+$.

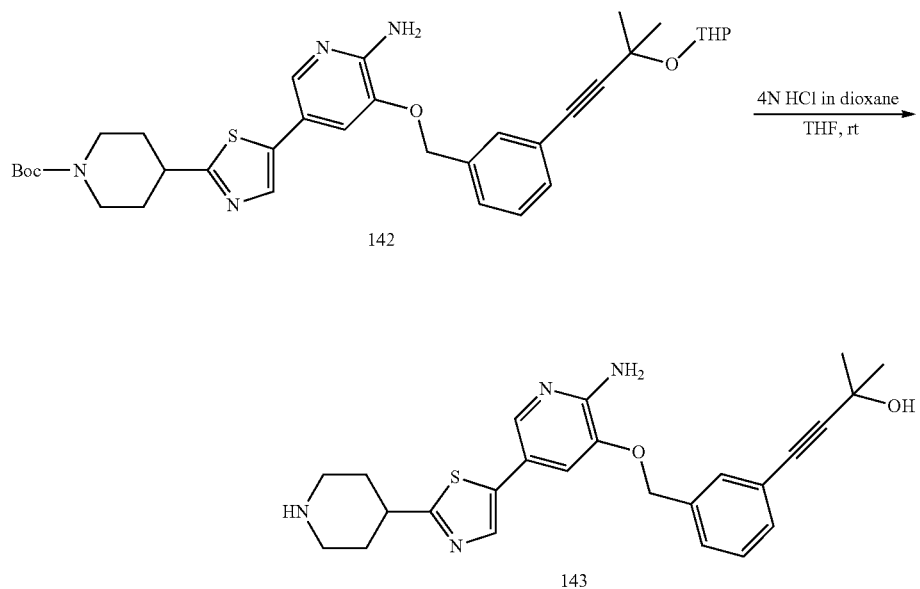

Compound 143: Compound 142 (1.0 g, 1.58 mmol) was added to a round bottom flask containing 30 mL of tetrahydrofuran, and 4N hydrochloric acid dioxane solution (10 mL) was added under nitrogen-protected, stirred at room temperature for 3 h. LCMS monitoring, after the reaction was completed, diluted with water (50 mL), extracted with ethyl acetate (30 mL×3), the aqueous phase was adjusted to pH 10 with a 2N aqueous sodium hydroxide solution, and a large amount of precipitate was precipitated, filtered, the filter cake was washed with water and dried in vacuo, obtained 530 mg of white solid, yield: 75.9%. $^1$H NMR (400 MHz, CD$_3$OD): δ ppm 1.58 (s, 6H), 1.71-1.80 (m, 2H), 2.11 (d, J=12.3 Hz, 2H), 2.75 (t, J=12.3 Hz, 2H), 3.15 (d, J=12.0 Hz, 3H), 5.22 (s, 2H), 7.34 (s, 1H), 7.38-7.41 (m, 2H), 7.48-7.51 (m, 1H), 7.56 (s, 1H), 7.76 (s, 1H), 7.79 (s, 1H). LCMS: Rt=1.20 min, MS Calcd.: 448.2, MS Found: 448.9 [M+H]$^+$.

Example 24 Preparation of Compound A14

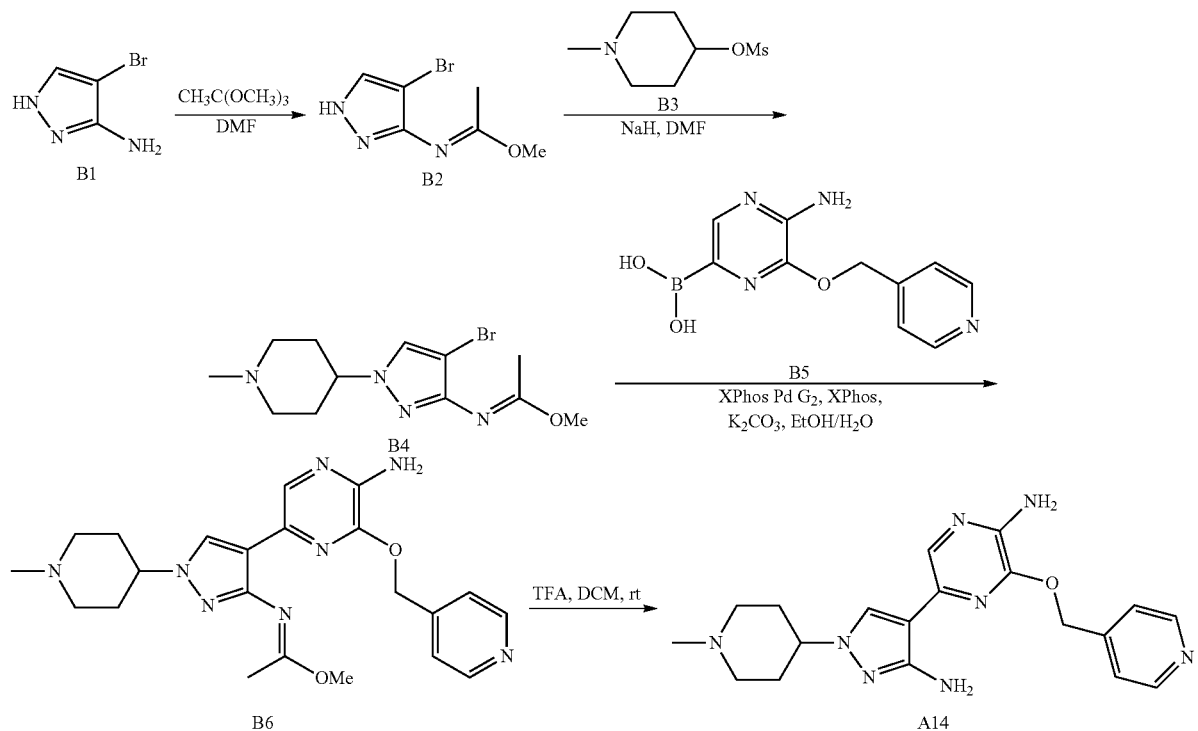

Step 1: Compound B2: To a solution of compound B1 (6.0 g, 37.04 mmol) in DMF (200 mL) was added trimethyl orthoacetate (14.2 g, 118.53 mmol), stirred for 16 hours at 110° C. The reaction mixture was cooled to room temperature and added into water (150 mL), extracted with EtOAc (100 mL×3). The organic layers were washed with brine (50 mL), dried over anhydrous $Na_2SO_4$ and concentrated under vacuum to afford crude product, which was purified by silica gel chromatography (elution gradient: petroleum ether/ethyl acetate, 3/1, v/v), pure fractions were evaporated to dryness to afford compound B2 (4.3 g) as a yellow oil, yield: 53.7%.

$^1$H NMR (400 MHz, DMSO-$d_6$): δ ppm 1.93 (s, 3H), 3.74 (s, 3H), 7.87 (s, 1H), 12.68 (s, 1H).

LCMS: Rt=1.29 min, MS Calcd.: 217.0, 219.0, MS Found: 217.9, 219.9 [M+H]$^+$.

Step 2: Compound B4: To a mixture of sodium hydride (550 mg, 13.76 mmol) in DMF (70 mL) was added compound B2 (2.5 g, 11.47 mmol), stirred for 1 h at 0° C., then added compound B3 (3.3 g, 17.2 mmol), stirred for 16 hours at 80° C. The mixture was quenched with water (200 mL), extracted with EtOAc (200 mL×3), the organic layers were washed with brine (100 mL), dried over anhydrous $Na_2SO_4$ and concentrated under vacuum to afford crude product, which was purified by silica gel chromatography (elution gradient: DCM/MeOH, 10/1, v/v), pure fractions were evaporated to dryness to afford compound B4 (1.24 g) as a brown oil, yield: 34.3%.

LCMS: Rt=1.15 min, MS Calcd.: 314.1, 316.1, MS Found: 314.9, 316.9[M+H]$^+$.

Step 3: Compound B6: Added compound B4 (400 mg, 1.27 mmol), compound 5 (312 mg, 1.27 mmol), Chloro(2-dicyclohexylphosphino-2',4',6'-triisopropyl-1,1'-biphenyl) [2-(2'-amino-1,1'-biphenyl)]-palladium(II) (102 mg, 0.13 mml), 2-Dicyclohexylphosphino-2',4',6'-triisopropylbiphenyl (119 mg, 0.25 mmol), potassium carbonate (351 mg, 2.54 mmol) into a mixture of ethanol (25 mL) and water (5 mL), stirred for 0.5 h at 135° C. under nitrogen atmosphere with MW. The mixture was concentrated under reduce pressure, the residue was purified by silica gel chromatography (elution gradient: DCM/MeOH, 4/1, v/v), pure fractions were evaporated to dryness to afford compound B6 (180 mg) as a yellow solid, yield: 32.5%.

LCMS: Rt=1.07 min, MS Calcd.: 436.2, MS Found: 437.0 [M+H]$^+$.

Step 4: Compound A14: To a solution of compound B6 (260 mg, 0.6 mmol) in dichloromethane (5 mL) was added trifluoroacetic acid (1 mL, 9.0 mmol), stirred for 16 hours at rt. The mixture was concentrated under reduce pressure, adjusted pH=8 with saturated sodium bicarbonate solution, then concentrated under vacuum to afford crude product, which was purified by preparative HPLC (Gemini-C18 column, 5p silica, 21 mm diameter, 150 mm length), using decreasingly polar mixtures of water (containing 0.1% FA) and ACN as eluents (0-15%), fractions containing the desired compound were evaporated to dryness to afford compound A14 (26.1 mg) as a yellow gum, yield: 8.8%.

$^1$H NMR (400 MHz, CD$_3$OD): δ ppm 2.17-2.20 (m, 2H), 2.28-2.39 (m, 2H), 2.96 (s, 3H), 3.21 (t, J=12.4 Hz, 2H), 3.70 (d, J=6.4 Hz, 2H), 4.43-4.49 (m, 1H), 5.96 (s, 1H), 7.73 (s, 1H), 8.26 (d, J=3.2 Hz, 2H), 8.90 (d, J=3.2 Hz, 2H).

LCMS: Rt=0.55 min, MS Calcd.: 380.2, MS Found: 381.0[M+H]$^+$.

Example 25 Preparation of Compound A16
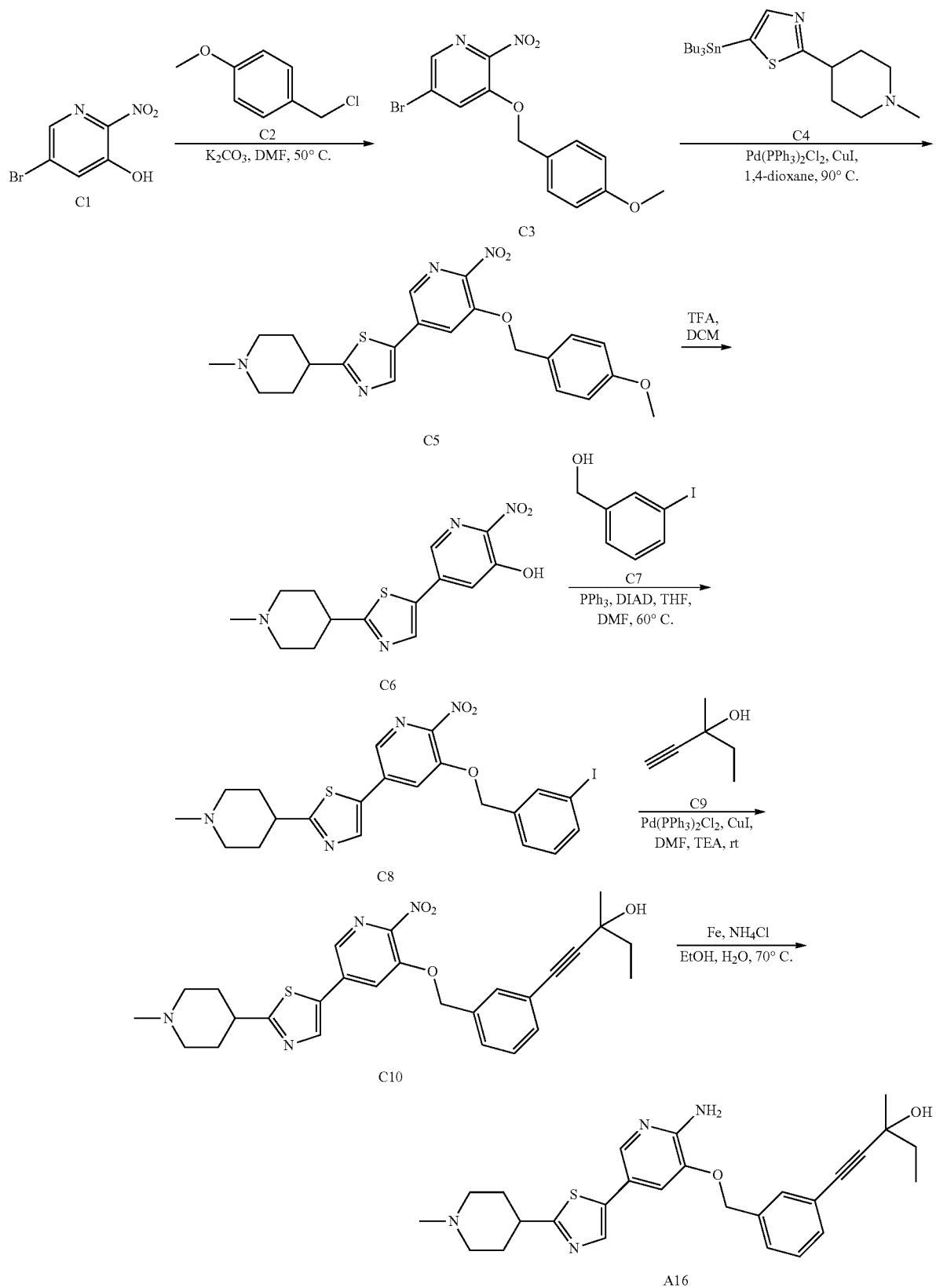

Step 1: Compound C3: To a solution of compound C1 (20 g, 91.33 mmol) and compound C2 (17 g, 109.59 mmol) in DMF (300 mL) was added K$_2$CO$_3$ (30 g, 91.33 mmol). The mixture was stirred at 50° C. for 14 hours. The mixture was cooled to room temperature and concentrated under reduced pressure. The residue was diluted with water (200 mL), extracted with EtOAc (300 mL×3). The organic layers were washed with brine (100 mL), dried over anhydrous Na$_2$SO$_4$ and concentrated under vacuum to afford crude product, which was purified by silica gel chromatography (elution gradient: Hexane/EtOAc 50/1-10/1, v/v). Pure fractions were evaporated to dryness to afford compound C3 (29 g) as a yellow solid, yield: 93.5%. $^1$H NMR (400 MHz, DMSO-d$_6$): δ ppm 3.77 (s, 3H), 5.32 (s, 2H), 6.98 (d, J=8.4 Hz, 2H), 7.38 (d, J=8.4 Hz, 2H), 8.29 (s, 1H), 8.43 (s, 1H).

LCMS: Rt=1.71 min, MS Calcd.: 338.0, 340.0, MS Found: 360.9, 362.7 [M+Na]$^+$.

Step 2: Compound C5: To a solution of compound C3 (3.9 g, 11.6 mmol), compound 4 (5.5 g, 11.6 mmol) and cuprous iodide (663 mg, 3.48 mmol) in 1,4-dioxane (50 mL) was added bis(triphenylphosphine)palladium(II) chloride (814 mg, 1.16 mmol). The mixture was stirred at 90° C. under N$_2$ for 6 hours. The mixture was cooled to room temperature and concentrated under reduced pressure to afford crude product, which was purified by silica gel chromatography (elution gradient: DCM/MeOH, 10/1, v/v). Pure fractions were evaporated to dryness to afford compound C5 (2.1 g) as a pale yellow solid, yield: 41.4%. $^1$H NMR (400 MHz, CDCl$_3$): δ ppm 1.28-1.40 (m, 2H), 1.96-2.07 (m, 2H), 2.22 (d, J=13.6 Hz, 2H), 2.41 (s, 3H), 3.05-3.17 (m, 3H), 3.79 (s, 3H), 5.23 (s, 2H), 6.91 (d, J=8.4 Hz, 2H), 7.35 (d, J=8.4 Hz, 2H), 7.55 (s, 1H), 7.89 (s, 1H), 8.19 (s, 1H).

LCMS: Rt=1.18 min, MS Calcd.: 440.2, MS Found: 441.1 [M+H]$^+$.

Step 3: Compound C6: To a solution of compound C5 (2.1 g, 4.8 mmol) in DCM (50 mL) was added trifluoroacetic acid (10 mL). The mixture was stirred at room temperature for 6 hours. The mixture was concentrated under vacuum. The residue was triturated with ether and the precipitate was collected by filtration, washed with ether, then air dried to afford compound C6 (1.4 g) as a yellow solid, yield: 66.7%. $^1$H NMR (400 MHz, DMSO-d$_6$): δ ppm 1.95 (dd, J=24.5, 11.7 Hz, 2H), 2.31 (d, J=13.3 Hz, 2H), 2.83 (s, 3H), 3.12 (t, J=12.3 Hz, 2H), 3.37 (t, J=10.5 Hz, 1H), 3.56 (d, J=12.0 Hz, 2H), 7.82 (s, 1H), 8.38 (s, 2H), 9.61 (s, 1H).

LCMS: Rt=1.09 min, MS Calcd.: 320.1, MS Found: 320.8 [M+H]$^+$.

Step 4: Compound C8: To a solution of compound C6 (1 g, 3.1 mmol), compound C7 (877 mg, 3.75 mmol) and triphenylphosphine (983 mg, 3.75 mmol) in THF (30 mL) and DMF (15 mL) was added diisopropyl azodicarboxylate (758 mg, 3.75 mmol) at 0° C. The mixture was stirred at 60° C. under N$_2$ for 16 hours. The mixture was quenched with water (50 mL), extracted with EtOAc (100 mL×3). The organic layers were washed with brine (100 mL), dried over anhydrous Na$_2$SO$_4$ and concentrated under vacuum to afford crude product, which was purified by silica gel chromatography (elution gradient: DCM/MeOH, 10/1-6/1, v/v). Pure fractions were evaporated to dryness to afford compound C8 (370 mg, crude) as a yellow solid.

LCMS: Rt=1.28 min, MS Calcd.: 536.0, MS Found: 537.0[M+H]$^+$.

Step 5: Compound C10: To a solution of compound C8 (370 mg, 0.69 mmol), compound C9 (203 mg, 2.1 mmol), bis(triphenylphosphine)palladium(II) chloride (48 mg, 0.069 mmol) and cuprous iodide (40 mg, 0.21 mmol) in DMF (5 mL) was added TEA (1 mL). The mixture was stirred at room temperature under N$_2$ for 16 hours. The mixture was concentrated under reduced pressure to afford a crude product, which was purified by silica gel chromatography (elution gradient: DCM/MeOH, 8/1, v/v). Pure fractions were evaporated to dryness to afford compound C10 (140 mg, crude) as a yellow gum.

LCMS: Rt=1.39 min, MS Calcd.: 506.2, MS Found: 506.9 [M+H]$^+$.

Step 6: Compound A16: To a solution of compound C10 (140 mg, 0.28 mmol) and ammonium chloride (75 mg, 1.4 mmol) in EtOH (5 mL) and water (1 mL) was iron powder (77 mg, 1.4 mmol). The mixture was stirred at 70° C. for 3 hours. The mixture was cooled to room temperature and concentrated under reduced pressure to afford crude product, which was purified by preparative HPLC (Gemini-C18 column, 5p silica, 21 mm diameter, 150 mm length), using decreasingly polar mixtures of water (containing 0.1% FA) and MeCN as eluents (10-40%). Fractions containing the desired compound were evaporated to dryness to afford compound A16 (50 mg, FA salt form) as an off-white solid. The overall yield of 3 steps: 3.2%. $^1$H NMR (400 MHz, DMSO-d$_6$): δ ppm 1.01 (t, J=7.4 Hz, 3H), 1.42 (s, 3H), 1.58-1.79 (m, 4H), 2.03 (d, J=11.5 Hz, 2H), 2.12 (t, J=11.4 Hz, 2H), 2.25 (s, 3H), 2.87-2.98 (m, 3H), 5.22 (s, 2H), 6.08 (s, 2H), 7.34-7.42 (m, 3H), 7.54-7.55 (m, 2H), 7.77 (s, 1H), 7.88 (s, 1H). LCMS: Rt=1.16 min, MS Calcd.: 476.2, MS Found: 476.8 [M+H]$^+$.

Example 26 Preparation of Compound A65

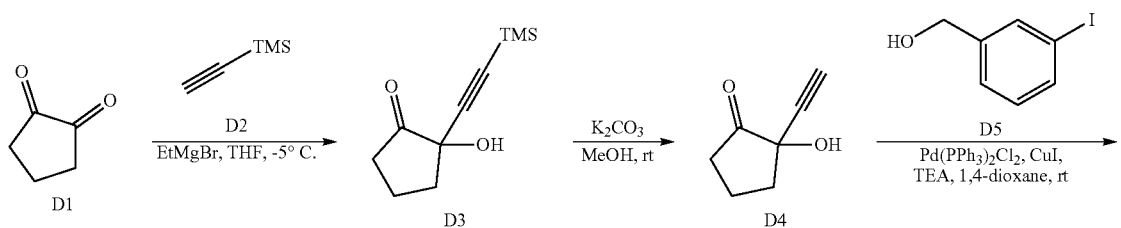

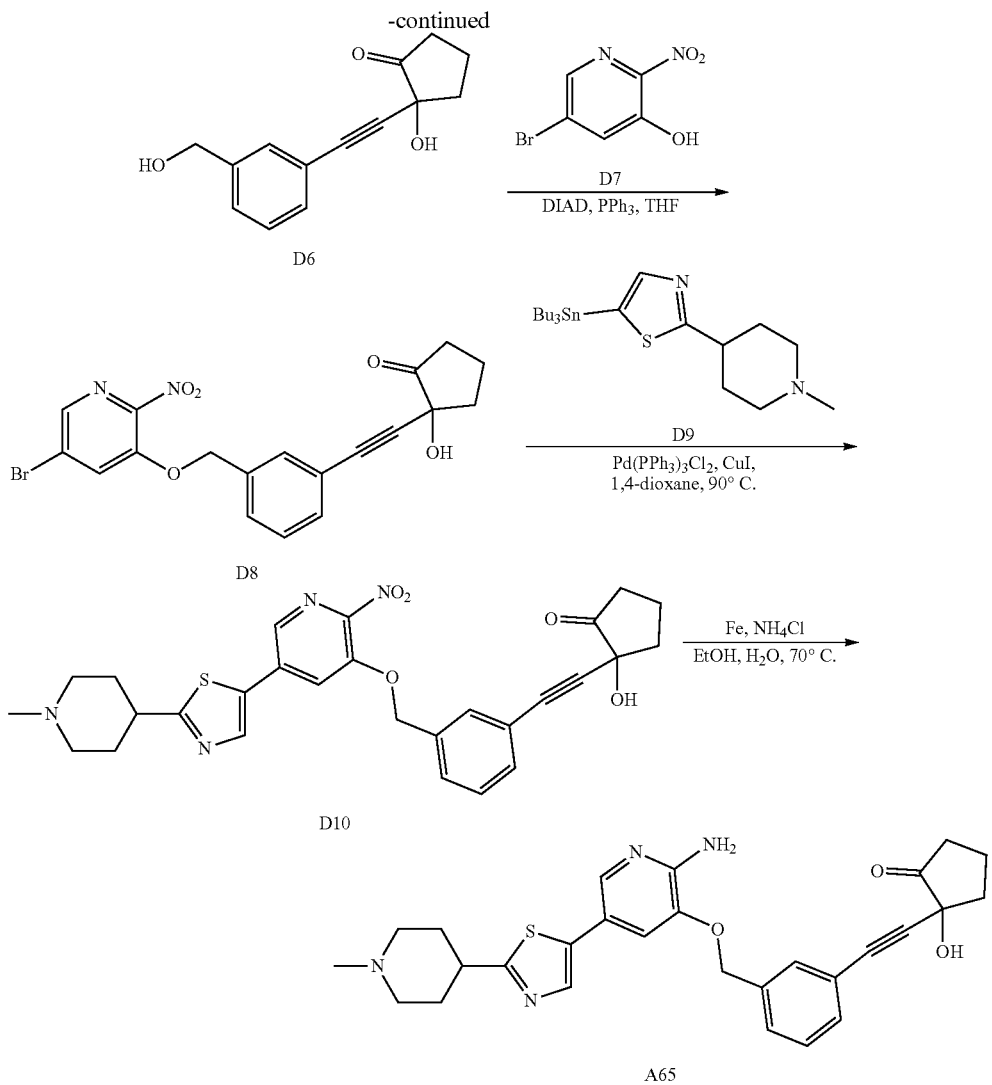

Step 1: Compound D3: To a solution of compound D2 (7.6 g, 77 mmol) in THF (40 mL) was added ethylmagnesium bromide (30.8 mL, 92 mmol, 3.0 M in THF). The mixture was stirred at −5° C. under $N_2$ for 0.5 hour. Then a solution of compound D1 (5 g, 51 mmol) in THF (15 mL) was added slowly. The reaction was stirred at −5° C. under $N_2$ for 2 hours. The mixture was quenched with water (50 mL), extracted with EtOAc (100 mL×2). The organic layers were washed with brine (50 mL), dried over anhydrous $Na_2SO_4$ and concentrated under vacuum to afford compound D3 (5.5 g) as a brown oil, yield: 55.0%. LCMS: Rt=1.36 min, MS Calcd.: 196.1, MS Found: 197.0 [M+H]$^+$.

Step 2: Compound D4: A solution of compound D3 (5.5 g, 28 mmol), potassium carbonate (3.87 g, 28 mmol) in methanol (100 mL) was stirred at room temperature for 3 hours. The mixture was concentrated and diluted with water (50 mL), then extracted with EtOAc (100 mL×2). The organic layers were washed with brine (50 mL), dried over anhydrous $Na_2SO_4$ and concentrated under vacuum to afford crude product, which was purified by silica gel chromatography (elution gradient: petroleum ether/EtOAc, 3/1, v/v). Pure fractions were evaporated to dryness to afford compound D4 (2 g) as a colorless oil, yield: 57.4%. LCMS: Rt=0.50 min, MS Calcd.: 124.1, MS Found: 125.1 [M+H]$^+$.

Step 3: Compound D6: To a solution of compound D4 (2 g, 16 mmol), compound D5 (3.7 g, 16 mmol) and cuprous iodide (0.92 g, 4.8 mmol) in 1,4-dioxane (15 mL) and TEA (5 mL) was added bis(triphenylphosphine)palladium(II) chloride (1.12 g, 1.6 mmol). The mixture was stirred at 25° C. under $N_2$ for 3 hours. The mixture was concentrated under reduced pressure and diluted with water (100 mL) and extracted with EA (100 mL×3). The organic phase was washed with brine (100 mL), dried, concentrated and purified by silica gel chromatography (elution gradient: EA/PE, 1/5, v/v). Pure fractions were evaporated to dryness to afford compound D6 (2.8 g) as a yellow solid, yield: 75.6%. $^1$H NMR (400 MHz, CDCl$_3$): δ 2.04-2.10 (m, 3H), 2.30-2.40 (m, 1H), 2.49-2.64 (m, 2H), 4.67 (s, 2H), 7.28-7.36 (m, 3H), 7.43 (s, 1H). LCMS: Rt=1.29 min, MS Calcd.: 230.1, MS Found: 252.9 [M+Na]$^+$.

Following procedures similar to those described in Example 3, compound D6 was converted into compound A65 as a white solid. $^1$H NMR (400 MHz, DMSO-d$_6$): δ ppm 1.65-1.78 (m, 2H), 1.85-2.09 (m, 7H), 2.18 (s, 3H), 2.21-2.47 (m, 3H), 2.76-2.83 (m, 2H), 2.86-2.97 (m, 1H), 5.22 (s, 2H), 6.08 (s, 2H), 6.42 (s, 1H), 7.31-7.47 (m, 3H), 7.72-7.80 (m, 2H), 7.76 (d, J=2.0 Hz, 1H), 7.87 (s, 1H). LCMS: Rt=1.03 min, MS Calcd.: 502.2, MS Found: 502.8 [M+H]$^+$.

Example 27 Preparation of Compound A32
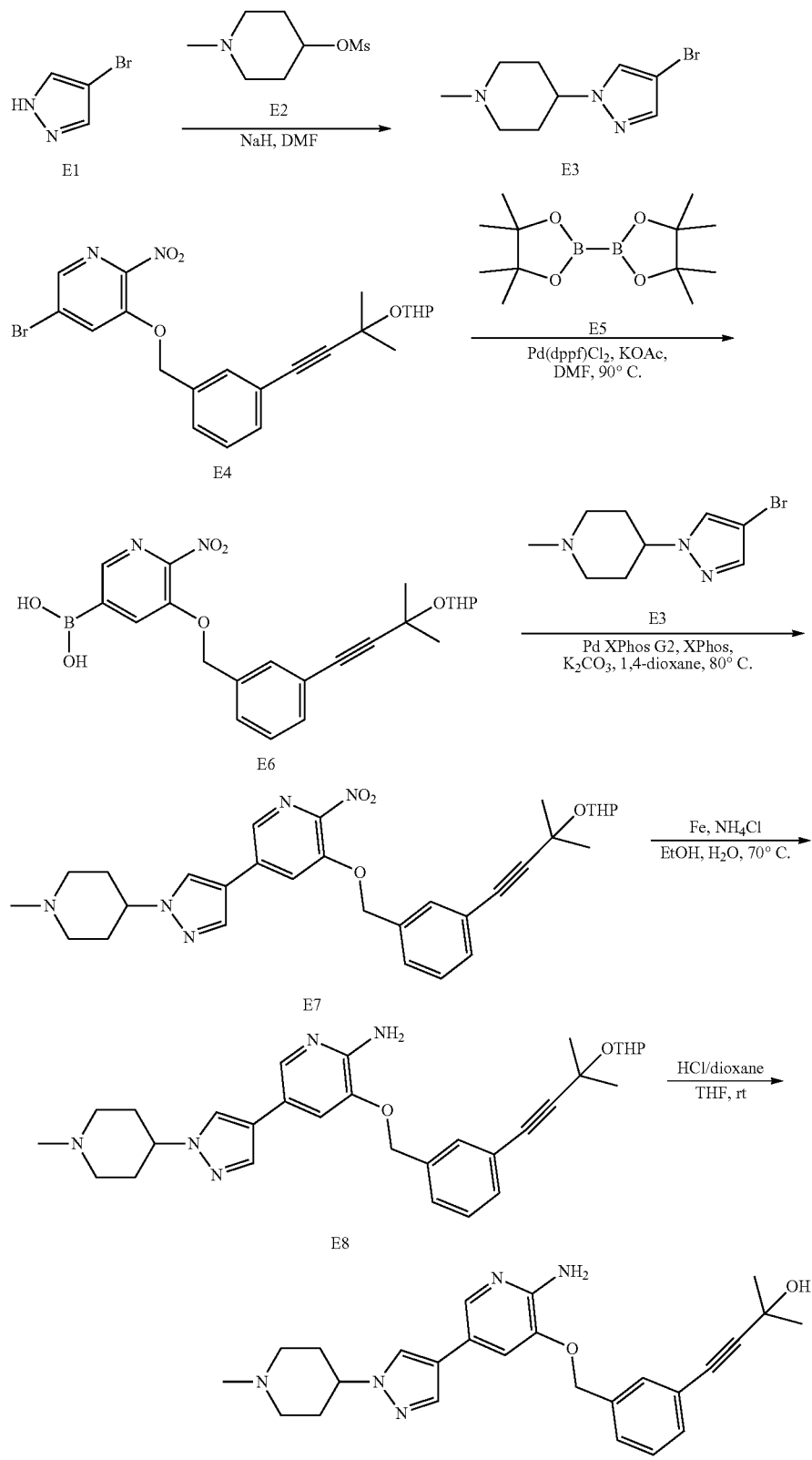

Step 1: Compound E3: To a solution of compound E1 (3 g, 20.5 mmol) in DMF (70 mL) was added NaH (1.23 g, 30.75 mmol), stirred for 0.5 h at room temperature, then added compound E2 (4.36 g, 22.6 mmol), stirred for 16 hours at 50° C. The mixture was quenched with water (100 mL), extracted with EtOAc (100 mL×3), the organic layers were washed with brine (300 mL), dried over anhydrous $Na_2SO_4$ and concentrated under vacuum to afford crude product, which was purified by silica gel chromatography (elution gradient: DCM/MeOH, 10/1, v/v), pure fractions were evaporated to dryness to afford compound E3 (0.9 g) as a yellow oil, yield: 44.1%.

LCMS: Rt=1.09 min, MS Calcd.: 243.0, 245.0, MS Found: 243.9, 245.9 $[M+H]^+$.

Step 2: Compound E6: Added compound E4 (1 g, 2.1 mmol), compound 5 (587 mg, 2.31 mmol), bis(triphenylphosphine)palladium(II) chloride (140 mg, 0.2 mmol), potassium acetate (314 mg, 3.2 mmol) into DMF (20 mL), stirred for 4 hours at 90° C. under nitrogen atmosphere. The mixture was concentrated under reduce pressure, the residue was added into water (50 mL), extracted with EtOAc (50 mL×3). The organic layers were washed with brine (100 mL), dried over anhydrous $Na_2SO_4$ and concentrated under vacuum to afford crude product, which was purified by silica gel chromatography (elution gradient: DCM/MeOH, 3/1, v/v), pure fractions were evaporated to dryness to afford compound E6 (490 mg) as a yellow oil, yield: 53.0%. LCMS: Rt=1.69 min, MS Calcd.: 440.18, MS Found: 462.9 $[M+Na]^+$.

Compound E7: Added compound E3 (220 mg, 0.9 mmol), compound E6 (400 mg, 0.9 mmol), XPhos Pd G2 (70 mg, 0.09 mmol), XPhos (43 mg, 0.09 mmol), potassium carbonate (230 mg, 1.8 mmol) into a mixture of 1,4-dioxane (20 mL) and water (5 mL), stirred for 6 hours at 80° C. under nitrogen atmosphere. The mixture was concentrated under reduce pressure, the residue was added into water (30 mL), extracted with EtOAc (30 mL×3), dried over anhydrous $Na_2SO_4$ and concentrated under vacuum to afford crude product, which was purified by silica gel chromatography (elution gradient: DCM/MeOH, 10/1, v/v), pure fractions were evaporated to dryness to afford compound E7 (280 mg) as a yellow solid, yield: 55.5%. LCMS: Rt=1.50 min, MS Calcd.: 559.3, MS Found: 560.2 $[M+H]^+$.

Compound E7 was then converted into compound A32 following a reduction and deprotection procedure similar to those described herein. $^1$H NMR (400 MHz, DMSO-$d_6$): δ ppm 1.46 (s, 6H), 1.90-2.07 (m, 6H), 2.20 (s, 3H), 2.85 (d, J=5.8 Hz, 2H), 4.04-4.10 (m, 1H), 5.18 (s, 2H), 5.47 (s, 1H), 5.65 (s, 2H), 7.33-7.42 (m, 3H), 7.52 (s, 2H), 7.75 (s, 1H), 7.79 (s, 1H), 8.10 (s, 1H). LCMS: Rt=1.19 min, MS Calcd.: 445.2, MS Found: 445.9 $[M+H]^+$.

Example 28 Preparation of Compound A66

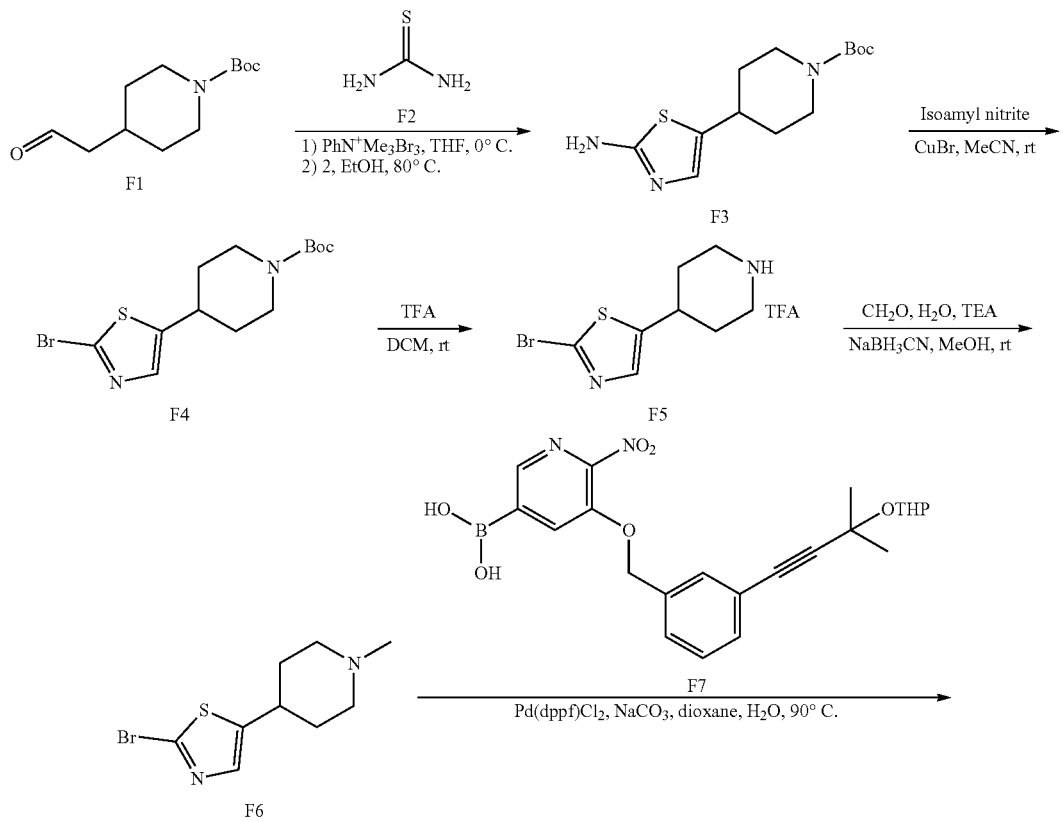

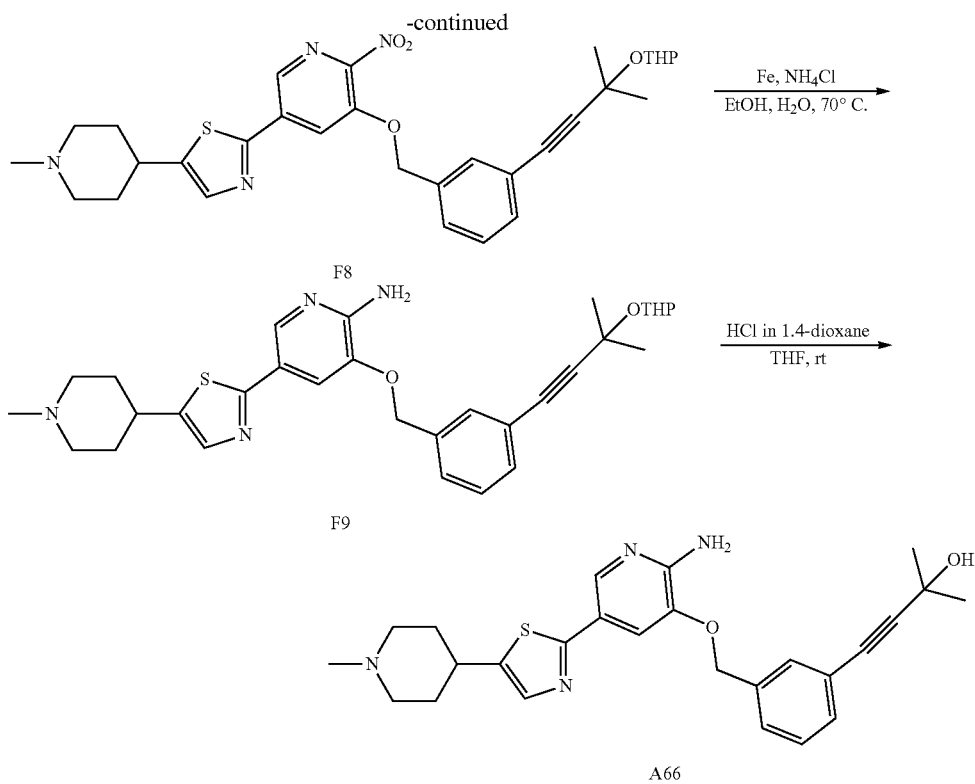

Compound F3: To a solution of compound F1 (15 g, 66 mmol) in THF (50 mL) was added phenyltrimethylammonium tribromide (37.2 g, 99 mmol) at 0° C. The mixture was stirred at 0° C. under $N_2$ for 1 hours. The mixture was quenched with water (50 mL) and extracted with EtOAc (200 mL×2). The organic phase was washed with brine (100 mL), dried over anhydrous $Na_2SO_4$, concentrated to give the residue (7.5 g). The residue was dissolved in ethanol (200 mL) was added compound F2 (7.5 g, 99 mmol). The mixture was stirred at 80° C. for 3 h. The mixture was cooled to room temperature and concentrated under reduced pressure to afford the crude product, which was purified by silica gel chromatography (elution gradient: EA/PE, 1/1, v/v). Pure fractions were evaporated to dryness to afford compound F3 (10 g) as a pale-yellow solid, yield: 53.5%. $^1$H NMR (400 MHz, $CDCl_3$): δ ppm 1.48 (s, 9H), 1.53-1.60 (m, 2H), 1.90-1.96 (m, 2H), 2.77-2.85 (m, 3H), 4.17 (s, 2H), 6.78 (s, 1H). LCMS: Rt=1.20 min, MS Calcd.: 283.1, MS Found: 283.9 $[M+H]^+$.

Compound F4: A solution of compound F3 (10 g, 35 mmol), isoamyl nitrite (8.2 g, 7 mmol) and cuprous bromide (7.6 g, 53 mmol) in acetonitrile (200 mL) was stirred at room temperature under $N_2$ for 16 h. The mixture was concentrated under reduced pressure to afford the residue. The residue was diluted with water (50 mL) and extracted with EtOAc (100 mL×2), The organic phase was washed with brine (50 mL), dried over anhydrous $Na_2SO_4$ and concentrated under vacuum to afford crude product, which was purified by silica gel chromatography (elution gradient: EA/PE, 1/5, v/v). Pure fractions were evaporated to dryness to afford compound F4 (4.5 g) as a white solid, yield: 36.8%. LCMS: Rt=1.55 min, MS Calcd.: 346.0, 348.0, MS Found: 368.7, 370.7 $[M+Na]^+$.

Compound F5: A solution of compound F4 (4.5 g, 13 mmol) in TFA (20 mL) and DCM (100 mL) was stirred at room temperature for 16 hours. The mixture was concentrated under vacuum to afford residue, which was triturated with diethyl ether (200 mL), the resulting solid was filtered and dried under vacuum to afford compound F5 (3.2 g) as a gray solid, yield: 68.3%. LCMS: Rt=0.64 min, MS Calcd.: 246.0, 248.0, MS Found: 246.8, 248.8 $[M+H]^+$.

Compound F6: A solution of compound F5 (3 g, 8.3 mmol), triethylamine (2.5 g, 25 mmol) and 30% formaldehyde aqueous solution (8.3 g, 83 mmol) in methanol (100 mL) was stirred at room temperature under $N_2$ for 1 h. To this sodium cyanoborohydride (1 g, 16.6 mmol) was added. The reaction mixture was stirred at room temperature for 16 h. The mixture was concentrated under reduced pressure to afford the residue. The residue was diluted with water (50 mL) and extracted with EtOAc (100 mL×2), The organic phase was washed with brine (50 mL), dried over anhydrous $Na_2SO_4$ and concentrated under vacuum to afford crude product, which was purified by silica gel chromatography (elution gradient: EA/PE, 1/1, v/v). Pure fractions were evaporated to dryness to afford compound F6 (1.6 g) as a white solid, yield: 74.1%. $^1$H NMR (400 MHz, $CDCl_3$): δ ppm 1.71-1.82 (m, 2H), 1.95-2.10 (m, 4H), 2.32 (s, 3H), 2.76-2.84 (m, 1H), 2.91-2.97 (m, 2H), 7.30 (d, J=0.8 Hz, 1H). LCMS: Rt=0.97 min, MS Calcd.: 260.0, 262.0, MS Found: 260.8, 262.8 $[M+H]^+$.

Compound F8: To a solution of compound F6 (890 mg, 3.41 mmol), compound 7 (1.8 g, 4.09 mmol) and potassium carbonate (722 mg, 6.82 mmol) in 1,4-dioxane (25 mL) and water (5 mL) was added bis(triphenylphosphine)palladium (II) chloride (477 mg, 0.68 mmol). The mixture was stirred at 90° C. under $N_2$ for 2 hours. The mixture was cooled to room temperature and concentrated under reduced pressure to afford the residue. The residue was diluted with water (100 mL) and extracted with EtOAc (100 mL×3), The organic phase was washed with brine (100 mL), dried over anhydrous Na₂SO₄ and concentrated under vacuum to afford crude product, which was purified by silica gel chromatography (elution gradient: EA/PE, 1/2, v/v). Pure fractions were evaporated to dryness to afford compound F8 (500 mg) as a gray solid, yield: 25.5%. ¹H NMR (400 MHz, CDCl₃): δ ppm 1.52-1.60 (m, 4H), 1.61 (s, 3H), 1.65 (s, 3H), 1.94-2.06 (m, 6H), 2.18-2.26 (m, 2H), 2.42 (s, 3H), 2.93-3.01 (m, 1H), 3.02-3.10 (m, 2H), 3.50-3.60 (m, 1H), 3.96-4.06 (m, 1H), 5.12-5.17 (m, 1H), 5.31 (s, 2H), 7.36-7.40 (m, 1H), 7.42-7.45 (m, 2H), 7.52 (s, 1H), 7.71 (d, J=0.8 Hz, 1H), 8.14 (d, J=1.6 Hz, 1H), 8.52 (d, J=1.6 Hz, 1H). LCMS: Rt=1.34 min, MS Calcd.: 576.2, MS Found: 576.8 [M+H]⁺.

Compound F8 was then converted into compound A66 following reduction and deprotection similar to the procedures described herein. ¹H NMR (400 MHz, DMSO-d₆): δ ppm 1.47 (s, 6H), 1.61-1.73 (m, 2H), 1.92-1.99 (m, 2H), 2.07-2.15 (m, 2H), 2.25 (s, 3H), 2.82-2.93 (m, 3H), 5.24 (s, 2H), 5.45 (s, 1H), 6.34 (s, 2H), 7.34 (d, J=7.7 Hz, 1H), 7.40 (t, J=7.9 Hz, 1H), 7.47 (d, J=2.0 Hz, 1H), 7.51-7.56 (m, 3H), 8.06 (d, J=1.6 Hz, 1H). LCMS: Rt=1.02 min, MS Calcd.: 462.2, MS Found: 462.8 [M+H]⁺.

Example 29 Preparation of Compound A62

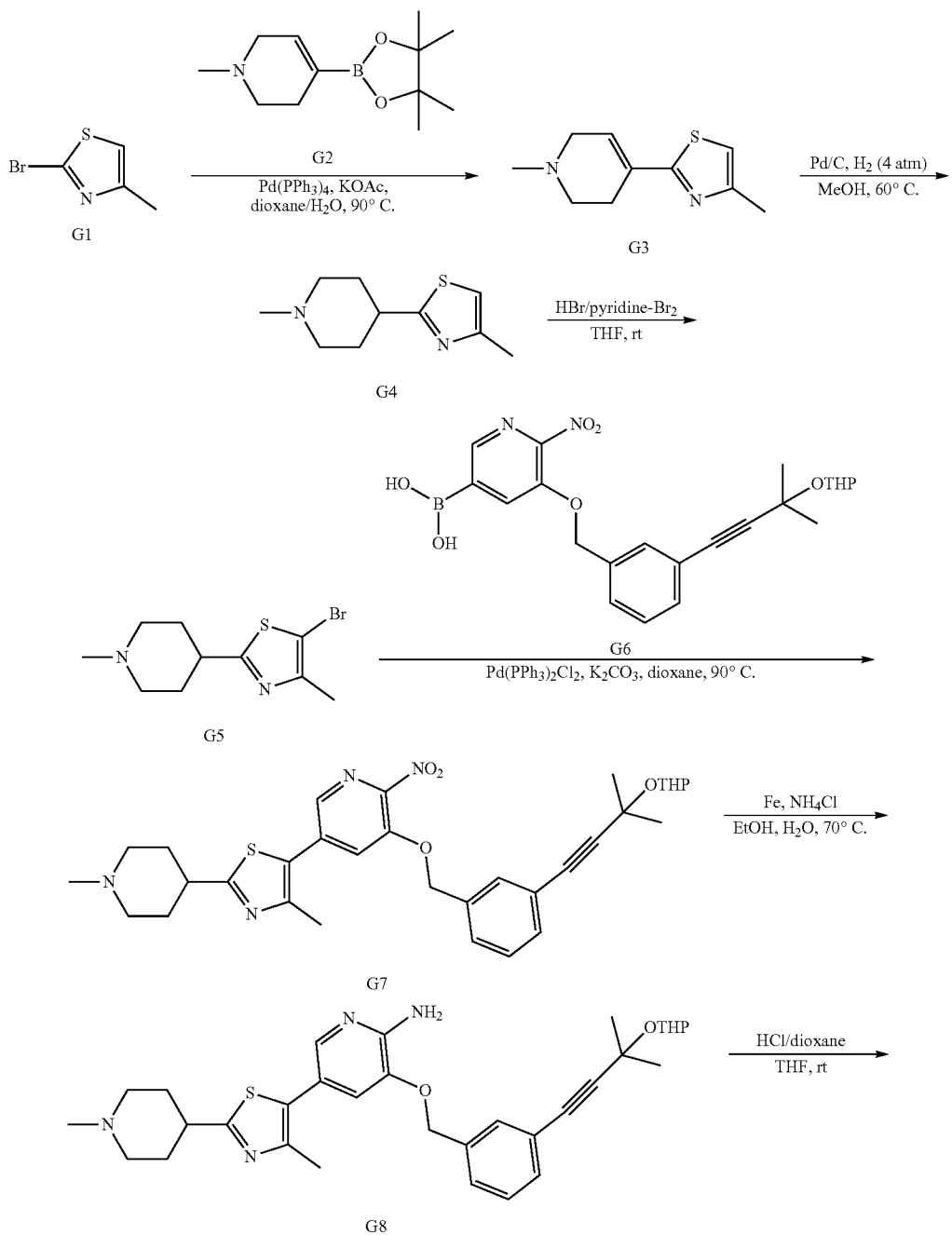

-continued

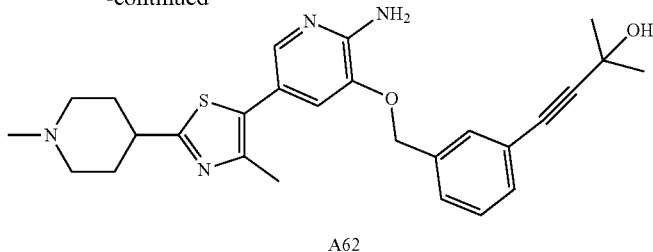

A62

Compound G3: To a solution of compound G1 (3 g, 16.8 mmol), compound G2 (4.5 g, 20.2 mmol), tetrakis(triphenylphosphine)palladium (0) (1.96 g, 1.7 mmol) in 1,4-dioxane (120 mL) was added potassium acetate (3.3 g, 33.6 mmol) and the reaction was stirred at 100° C. for 16 hours under nitrogen atmosphere. The reaction mixture was concentrated under reduced pressure. The residue was diluted with water (100 mL), extracted with EtOAc (100 mL×3). The organic layers were washed with brine (100 mL), dried over anhydrous $Na_2SO_4$ and concentrated under vacuum to afford crude product, which was purified by silica gel chromatography (elution gradient: DCM/MeOH, 8/1, v/v). Pure fractions were evaporated to dryness to afford compound G3 (1.6 g) as a brown oil, yield: 40.8%. LCMS: Rt=0.64 min, MS Calcd.: 194.1, MS Found: 194.9 $[M+H]^+$.

Compound G4: To a solution of compound G3 (1.6 g, 8.2 mmol) in methanol (60 mL) was added 10% Pd/C (2 g) and the mixture was stirred at 60° C. for 48 hours under hydrogen atmosphere (0.4 MPa). The reaction mixture was filtered and the filtrate was concentrated under vacuum to afford the desired product (800 mg, crude) as a yellow oil, without further purification for next step. LCMS: Rt=0.83 min, MS Calcd.: 196.1, MS Found: 197.1 $[M+H]^+$.

Compound G5: To a solution of compound G4 (700 mg, 3.57 mmol, crude) in tetrahydrofuran (30 mL) was added pyridinium tribromide (1.26 g, 3.93 mmol), stirred for 4 hours at room temperature. The reaction mixture was diluted with water (50 mL), extracted with EtOAc (50 mL×3). The organic layers were washed with brine (50 mL), dried over anhydrous $Na_2SO_4$ and concentrated under vacuum to afford crude product, which was purified by silica gel chromatography (elution gradient: DCM/MeOH, 10/1, v/v). Pure fractions were evaporated to dryness to afford compound G5 (460 mg) as a yellow solid, yield: 47%. LCMS: Rt=1.13 min, MS Calcd.: 274.0, 276.0, MS Found: 274.9, 276.9 $[M+H]^+$.

Compound G7: To a mixture of compound G5 (0.4 g, 1.46 mmol), compound G6 (704 mg, 1.6 mmol), potassium carbonate (300 mg, 2.2 mmol) in 1,4-dioxane (20 mL) was added bis(triphenylphosphine)palladium(II) chloride (105 mg, 0.15 mmol) and the mixture was stirred for 2 hours at 90° C. under $N_2$. The mixture was cooled to room temperature and diluted with water (30 mL), extracted with EtOAc (30 mL×3). The organic layers were washed with brine (50 mL), dried over anhydrous $Na_2SO_4$ and concentrated under vacuum to afford crude product, which was purified by silica gel chromatography (elution gradient: DCM/MeOH, 5/1, v/v). Pure fractions were evaporated to dryness to afford compound G7 (160 mg) as a pale yellow solid, yield: 18.5%. LCMS: Rt=1.44 min, MS Calcd.: 590.3, MS Found: 590.8 $[M+H]^+$.

Compound G7 was then converted into compound A62 following a reduction and deprotection procedure similar to those described herein. $^1H$ NMR (400 MHz, DMSO-$d_6$): δ ppm 1.47 (s, 6H), 1.66-1.74 (m, 2H), 1.98-2.08 (m, 4H), 2.22 (s, 3H), 2.25 (s, 3H), 2.84-2.90 (m, 3H), 5.20 (s, 2H), 6.06 (s, 2H), 7.10 (s, 1H), 7.33-7.39 (m, 2H), 7.51 (br. s, 2H), 7.59 (s, 1H).

LCMS: Rt=1.14 min, MS Calcd.: 476.2, MS Found: 477.2 $[M+H]^+$.

Example 30 Preparation of Compound A28

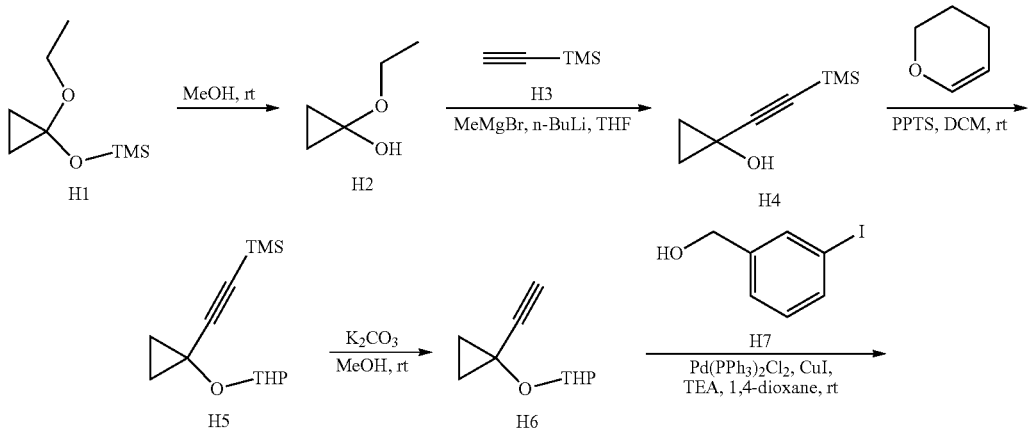

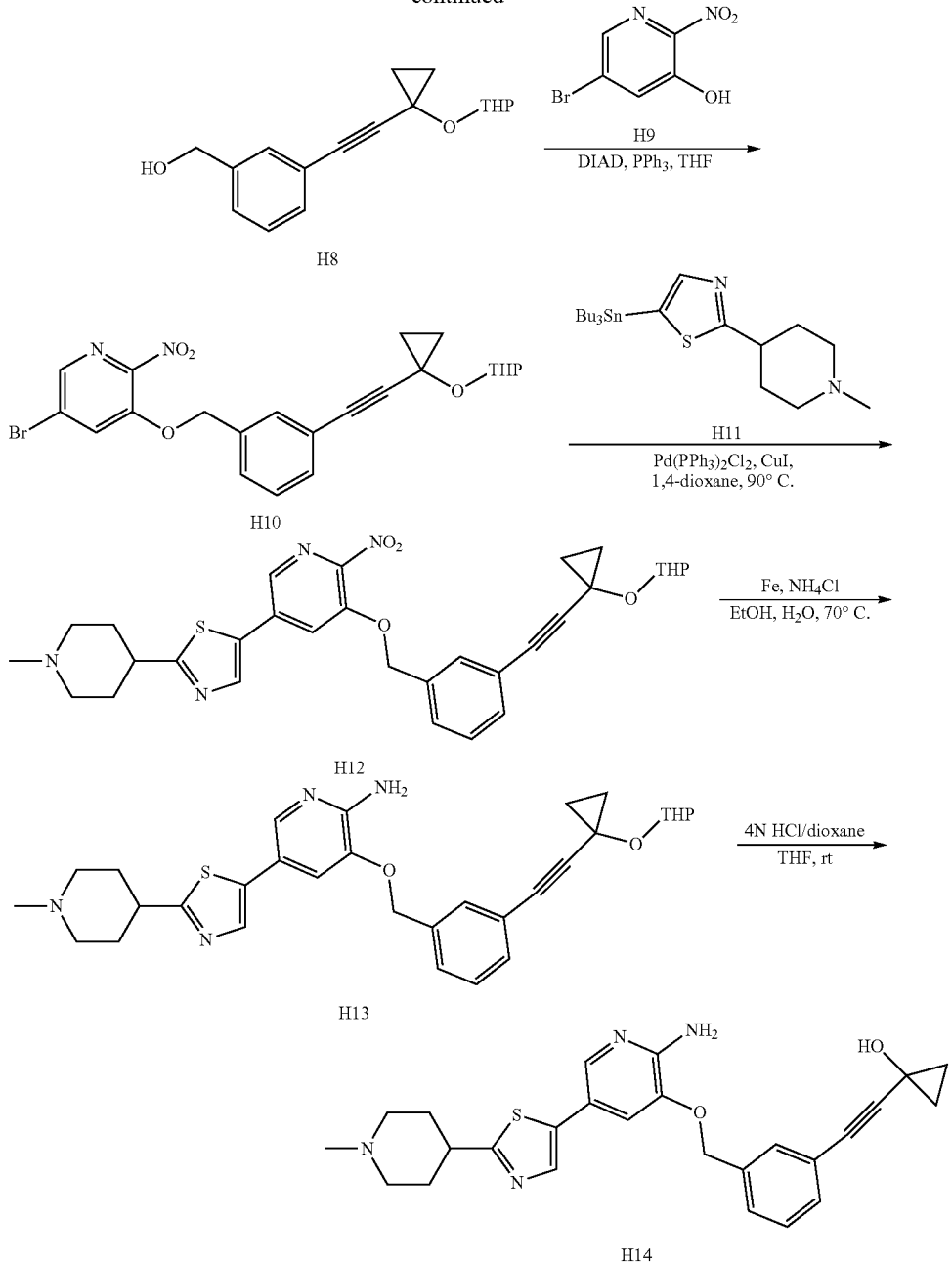

Compound H2: A solution of compound H1 (25 g, 143.6 mmol) in MeOH (70 mL) was stirred at room temperature for 24 hours. The solvent was carefully removed under reduced pressure at room temperature, and the residue was distilled (50 mbar, 65° C.) to provide compound H2 (10.3 g) as a clear, colorless liquid, yield: 70.3%. $^1$H NMR (400 MHz, CDCl$_3$): δ ppm 0.89-0.96 (m, 4H), 1.21 (t, J=7.2 Hz, 3H), 3.76 (q, J=7.1 Hz, 2H), 4.12 (s, 1H).

Compound H4: MeMgBr in ether (3.0 M, 21 mL, 63.2 mmol) at 0° C. was diluted with THF (40 mL). A solution of compound H2 (5 g, 49.0 mmol) in THF (20 mL) was added dropwise via cannula, followed by rinsing with THF (10 mL). The reaction was stirred at 0° C. under N$_2$ for 1 hour. In a separate flask, a solution of compound H3 (6.1 g, 56.8 mmol) in THF (40 mL) at −78° C. was treated with n-BuLi in hexane (2.4 M, 22 mL, 54.9 mmol). The mixture was stirred at −78° C. for 10 min, then added dropwise via cannula over 10 min to the prepared suspension of magnesium 1-ethoxycyclopropanolate bromide. The resulting clear, colorless solution was stirred at 40° C. for 16 hours, then poured into saturated aqueous NH$_4$Cl (100 mL). The phases were separated, and the aqueous layer was extracted with ether (100 mL×3). The combined organic phases were dried over Na$_2$SO$_4$, filtered and concentrated under reduced pressure to afford crude product, which was purified by silica gel chromatography (elution gradient: petroleum ether/EtOAc, 10/1, v/v). Pure fractions were evaporated to dryness to afford compound H4 (5 g) as a clear, colorless liquid, yield: 66.1%. $^1$H NMR (400 MHz, CDCl$_3$): δ ppm 0.16 (s, 9H), 0.96-1.04 (m, 2H), 1.04-1.12 (m, 2H), 2.91 (s, 1H).

Compound H5: To a solution of compound H4 (2.0 g, 13.0 mmol) and PPTS (35 mg) in THF (25 mL) was added 3,4-dihydro-2H-pyran (1.4 g, 16.5 mmol). The mixture was stirred at room temperature under N$_2$ for 16 hours. The mixture was concentrated under vacuum to afford crude product, which was purified by silica gel chromatography (elution gradient: petroleum ether/EtOAc, 5/1, v/v). Pure fractions were evaporated to dryness to afford compound H5 (2.5 g) as a yellow oil, yield: 80.8%. $^1$H NMR (400 MHz, CDCl$_3$): δ ppm 0.16 (s, 9H), 0.94-1.12 (m, 3H), 1.21-1.31 (m, 1H), 1.47-1.65 (m, 4H), 1.68-1.86 (m, 2H), 3.49-3.61 (m, 1H), 3.89 (t, J=9.9 Hz, 1H).

Compound H6: To a solution of compound H5 (2.5 g, 10.5 mmol) in MeOH (20 mL) was added K$_2$CO$_3$ (146 mg, 1.05 mmol). The mixture was stirred at room temperature under N$_2$ for 3 hours. The mixture was concentrated under vacuum to afford crude product, which was purified by silica gel chromatography (elution gradient: petroleum ether/EtOAc, 5/1, v/v). Pure fractions were evaporated to dryness to afford compound H6 (1.5 g) as a yellow oil, yield: 85.7%. $^1$H NMR (400 MHz, CDCl$_3$): δ ppm 0.99-1.10 (m, 3H), 1.25-1.32 (m, 1H), 1.45-1.67 (m, 4H), 1.71-1.82 (m, 2H), 2.39 (s, 1H), 3.54-3.58 (m, 1H), 3.86-3.91 (m, 1H), 5.00-5.04 (m, 1H).

Compound H8: To a solution of compound H6 (1.4 g, 8.4 mmol), compound H7 (1.9 g, 8.4 mmol), bis(triphenylphosphine)palladium(II) chloride (590 mg, 0.84 mmol) and cuprous iodide (480 mg, 2.52 mmol) in 1,4-dioxane (20 mL) was added TEA (4 mL). The mixture was stirred at room temperature under N$_2$ for 16 hours. The mixture was concentrated under reduced pressure to afford a crude product, which was purified by silica gel chromatography (elution gradient: petroleum ether/EtOAc, 8/1, v/v). Pure fractions were evaporated to dryness to afford compound H8 (1.9 g) as a yellow oil, yield: 83.3%. LCMS: Rt=1.59 min, MS Calcd.: 272.1, MS Found: 294.9 [M+Na]$^+$.

Compound H8 was then converted into compound A28 via a series of transformations under procedures similar to those described herein. $^1$H NMR (300 MHz, DMSO-d$_6$): δ ppm 0.96 (d, J=5.9 Hz, 4H), 1.64-1.75 (m, 2H), 1.97-2.05 (m, 4H), 2.18 (s, 3H), 2.79-2.92 (m, 3H), 5.18 (s, 2H), 6.05 (s, 2H), 6.29 (s, 1H), 7.30-7.39 (m, 3H), 7.48-7.51 (m, 2H), 7.73 (s, 1H), 7.84 (s, 1H). LCMS: Rt=1.13 min, MS Calcd.: 460.2, MS Found: 460.8 [M+H]$^+$.

Example 31 Preparation of Compound A68

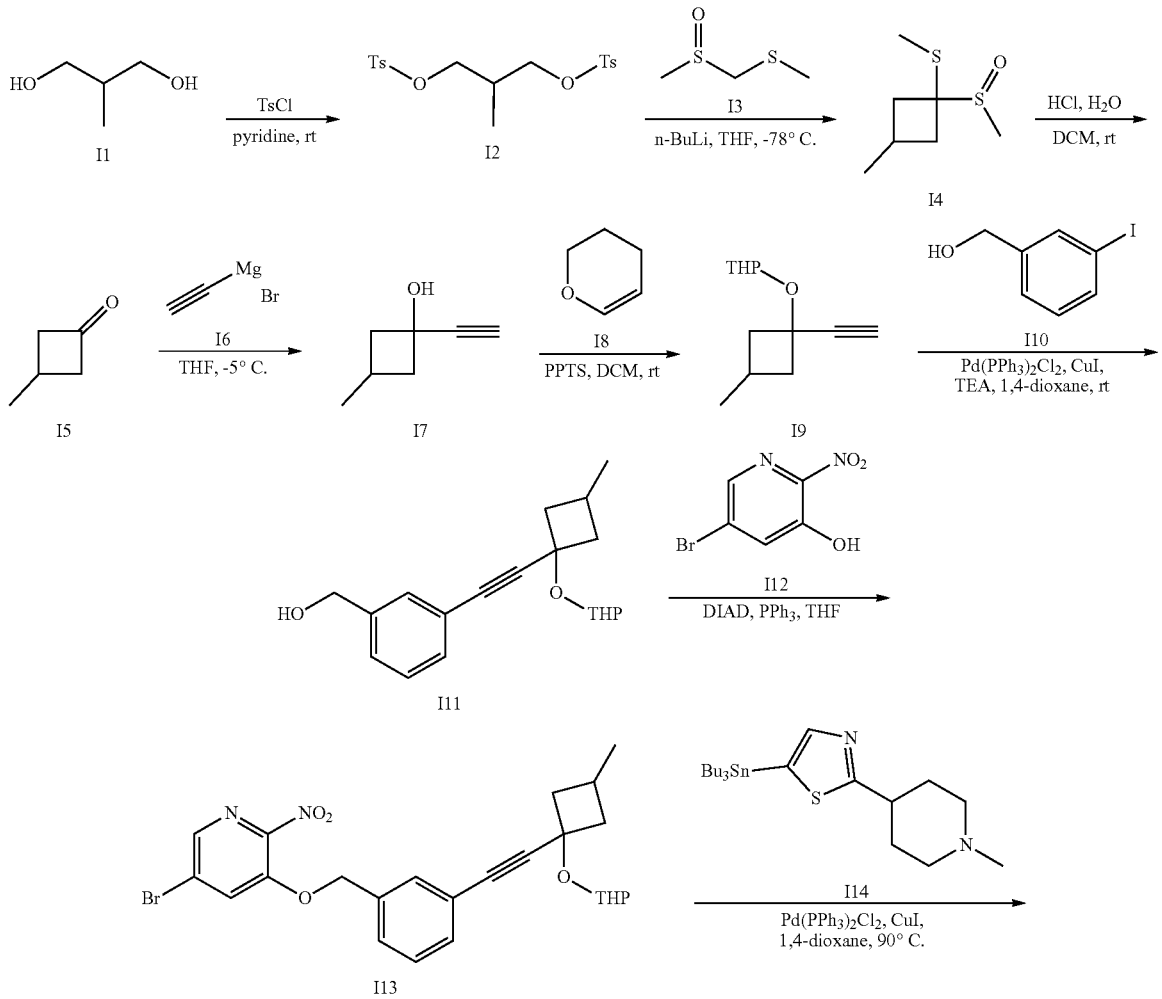

-continued

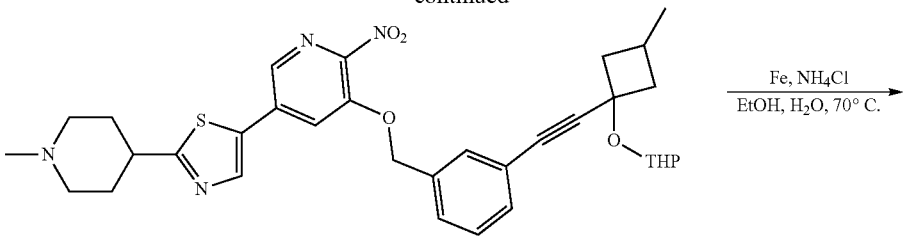

I15

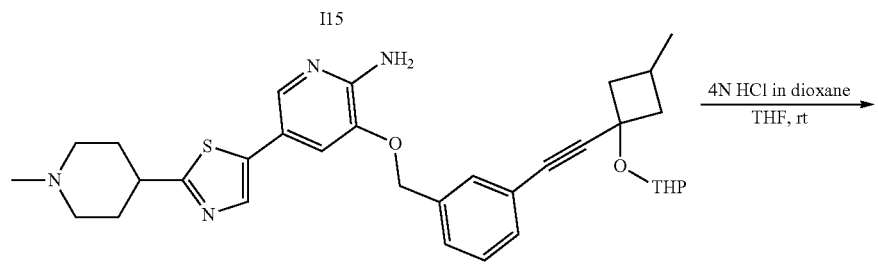

I16

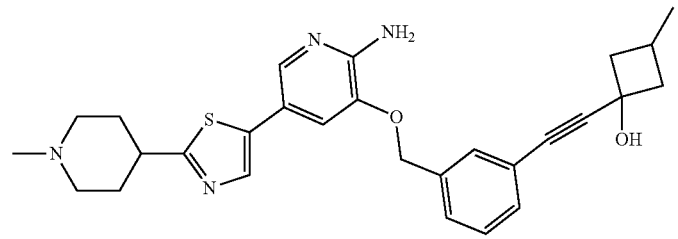

A68

Compound I2: To a solution of compound I1 (20 g, 222 mmol) in pyridine (200 mL) was added tosyl chloride (106 g, 555 mmol) at 0° C. The mixture was stirred at room temperature for 24 hours. The mixture was concentrated under reduced pressure to afford a crude product, which was purified by silica gel chromatography (elution gradient: petroleum ether/EtOAc, 3/1, v/v). Pure fractions were evaporated to dryness to afford compound I2 (41 g) as a yellow oil, yield: 46.4%. $^1$H NMR (400 MHz, CDCl$_3$): δ ppm 0.93 (d, J=6.7 Hz, 3H), 1.98-2.20 (m, 1H), 2.33 (s, 6H), 3.92 (d, J=4.0 Hz, 4H), 7.37 (d, J=4.8 Hz, 4H), 7.77 (d, J=4.6 Hz, 4H). LCMS: Rt=1.64 min, MS Calcd.: 398.1, MS Found: 398.7 [M+H]$^+$.

Compound I4: To a solution of compound I3 (20 g, 161.3 mmol) in THF (150 mL) was added n-BuLi (67.2 mL, 161.3 mmol, 2.4 M in hexane) dropwise at −78° C. under N$_2$. The mixture was stirred at −30° C. for 2 hours. Then compound I2 (32.1 g, 80.6 mmol) in THF (150 mL) was added dropwise at −78° C. The resulting mixture was stirred at room temperature for 16 hours. The mixture was quenched with saturated ammonium chloride (200 mL), extracted with EtOAc (200 mL×3). The organic layers were dried over anhydrous Na$_2$SO$_4$ and concentrated under vacuum to afford crude product, which was purified by silica gel chromatography (elution gradient: petroleum ether/EtOAc, 5/1, v/v). Pure fractions were evaporated to dryness to afford compound I4 (10 g) as a yellow oil, yield: 69.7%.

Compound I5: To a solution of compound I4 (10 g, 56.2 mmol) in DCM (30 mL) was added concentrated HCl (30 mL). The mixture was stirred at room temperature for 6 hours. The mixture was diluted with DCM (30 mL), the organic layer was separated and used for next step without any further purification.

Compound I7: In a 500 mL round-bottom flask was placed ethynylmagnesium bromide (321 mL, 160.5 mmol, 0.5 M in THF) was added a solution of compound I5 in DCM (60 mL) dropwise at −5° C. The mixture was stirred at −5° C. for 3 hours. The mixture was concentrated under vacuum to afford crude product, which was purified by silica gel chromatography (elution gradient: petroleum ether/EtOAc, 3/1, v/v). Pure fractions were evaporated to dryness to afford compound I7 (640 mg) as a yellow oil. The overall yield of 2 steps: 10.3%. $^1$H NMR (300 MHz, CDCl$_3$): δ ppm 1.12 (d, J=6.6 Hz, 3H), 1.82-1.90 (m, 2H), 2.08-2.25 (m, 2H), 2.50 (s, 1H), 2.57-2.64 (m, 2H).

Compound I9: To a solution of compound I7 (640 mg, 5.8 mmol) and PPTS (70 mg) in THF (20 mL) was added 3,4-dihydro-2H-pyran (978 mg, 11.6 mmol). The mixture was stirred at room temperature under N$_2$ for 16 hours. The mixture was diluted with DCM (30 mL), washed with saturated NaHCO$_3$ aqueous solution (30 mL), water (30 mL) and brine (30 mL). The organic layer was dried over anhydrous Na$_2$SO$_4$ and concentrated under vacuum to afford compound I9 (900 mg, crude) as a yellow oil. The product was used directly without any further purification.

Compound I11: To a solution of compound 9 (900 mg, 4.6 mmol), compound I10 (1.1 g, 4.6 mmol), bis(triphenylphosphine)palladium(II) chloride (323 mg, 0.46 mmol) and cuprous iodide (263 mg, 1.38 mmol) in 1,4-dioxane (15 mL) was added TEA (3 mL). The mixture was stirred at room temperature under N$_2$ for 6 hours. The mixture was concentrated under reduced pressure to afford a crude product, which was purified by silica gel chromatography (elution gradient: petroleum ether/EtOAc, 8/1, v/v). Pure fractions were evaporated to dryness to afford compound I11 (1.3 g)

as a yellow oil, yield: 93.5%. LCMS: Rt=1.71 min, MS Calcd.: 300.2, MS Found: 323.1 [M+Na]+.

Compound I11 was then converted into compound A68 via a series of transformations under procedures similar to those described herein. ¹H NMR (400 MHz, DMSO-d₆): δ ppm 1.09 (d, J=6.6 Hz, 3H), 1.66-1.86 (m, 4H), 1.96-2.04 (m, 4H), 2.11-2.17 (m, 1H), 2.18 (s, 3H), 2.53-2.58 (m, 2H), 2.80-2.92 (m, 3H), 5.23 (s, 2H), 5.85 (s, 1H), 6.08 (s, 2H), 7.35-7.43 (m, 3H), 7.53-7.58 (m, 2H), 7.77 (d, J=1.9 Hz, 1H), 7.88 (s, 1H). LCMS: Rt=1.09 min, MS Calcd.: 488.2, MS Found: 488.8 [M+H]+.

Compound J2: Ethynylmagnesium bromide (0.5 M in THF, 20 mmol, 40 mL) was cooled down to 0° C. under nitrogen. Then compound J1 (1.5 g, 20 mmol) was added slowly and the reaction was stirred at 0° C. for 1 h. After completion, the reaction was quenched with NH₄Cl aqueous solution and extracted with Et₂O (20 mL×2). The organic layer was combined, dried over sodium sulfate and concentrated to afford compound J2 (2.4 g, crude) as a brown oil. ¹H NMR (400 MHz, CDCl₃): δ 1.51 (d, J=2.2 Hz, 3H), 2.51 (s, 1H), 4.28 (dd, J=48.0, 9.0 Hz, 1H), 4.40 (dd, J=48.0, 9.0 Hz, 1H).

Compound J4: Compound J2 (2.4 g, 24 mmol) and compound J3 (3.6 g, 15 mmol) were dissolved in 10 mL 1,4-dioxane and 2 mL triethylamine. Then dichlorobis(tri- Example 32 Preparation of Compound A74

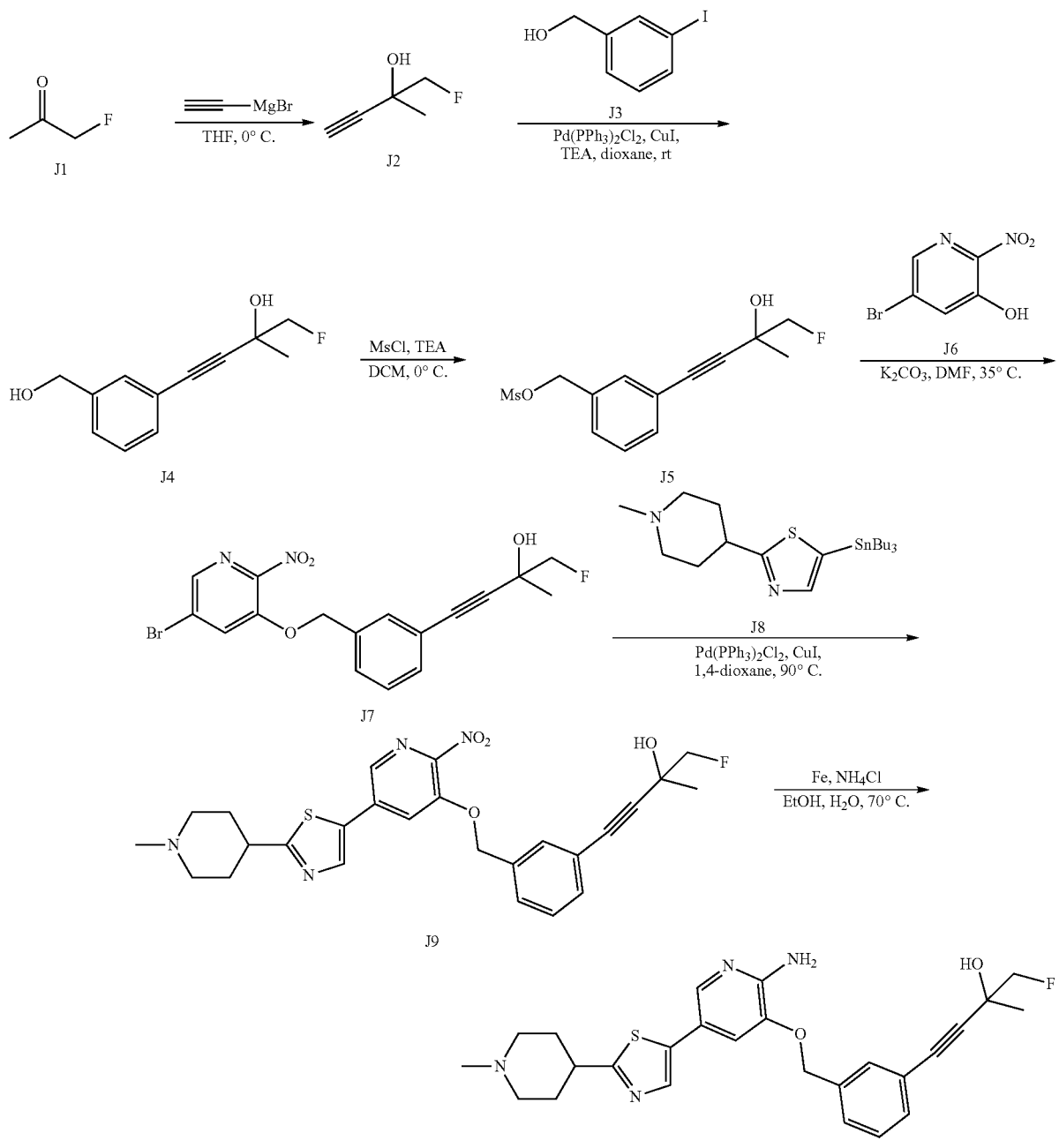

phenyl-phosphine)palladium(II) (2.5 g, 3.6 mmol), cuprous iodide (1.4 g, 7.2 mmol) were added. The reaction was stirred at room temperature for 16 h under nitrogen. After completion, the reaction was purified on silica-gel column (DCM/MeOH, 20/1, v/v) to afford compound J4 as an orange oil, 1.7 g, 40% yield over two steps. $^1$H NMR (400 MHz, DMSO-d$_6$): δ 1.46 (d, J=2.0 Hz, 3H), 4.24-4.40 (m, 2H), 4.49 (d, J=5.4 Hz, 2H), 5.26 (t, J=5.4 Hz, 1H), 5.91 (s, 1H), 7.25-7.38 (m, 4H). LCMS: Rt=1.30 min, MS Calcd.: 208.1, MS Found: 190.9 [M−H$_2$O+H]$^+$.

Compound J5: Compound J4 (1.7 g, 8.2 mmol) was dissolved in 20 mL DCM and triethyl amine (2.5 g, 25 mmol). Then methanesulfonyl chloride (1.5 g, 13 mmol) was added at 0° C. The reaction was stirred at 0° C. for 1 h. The reaction was monitored by TLC, quenched with 20 mL NaHCO$_3$ aqueous solution and extracted with ethyl acetate (15 mL×2). The organic layers were combined, dried over sodium sulfate and concentrated to afford compound J5 as a yellow oil, 2.2 g (crude).

Compound J7: Compound J5 (2.2 g, crude) and potassium carbonate (1.9 g, 14 mmol) was dissolved in 20 mL N,N-dimethylformamide. Then compound J6 (1.8 g, 8.4 mmol) was added and the reaction was stirred at room temperature for 16 h. After completion, the reaction was purified on silica-gel column (DCM/MeOH, 100/1, v/v) to afford compound J7 as an orange oil, 1.3 g, 39% yield over two steps. LCMS: Rt=1.62 min, MS Calcd.: 408.0, 410.0, MS Found: 430.6, 432.7 [M+Na]$^+$.

Compound J7 was then converted into compound A74 via a series of transformations under procedures similar to those described herein. $^1$H NMR (400 MHz, DMSO-d$_6$): δ 1.46 (d, J=2.0 Hz, 3H), 1.65-1.77 (m, 2H), 1.96-2.04 (m, 4H), 2.18 (s, 3H), 2.79-2.94 (m, 3H), 4.32 (dd, J=48.0, 9.0 Hz, 1H), 4.38 (dd, J=48.0, 9.0 Hz, 1H), 5.22 (s, 2H), 5.94 (s, 1H), 6.08 (s, 2H), 7.33-7.44 (m, 3H), 7.54-7.58 (m, 2H), 7.76 (d, J=2.0 Hz, 1H), 7.87 (s, 1H). LCMS: Rt=1.13 min, MS Calcd.: 480.2, MS Found: 480.8 [M+H]$^+$.

Example 33 Preparation of Compound A77

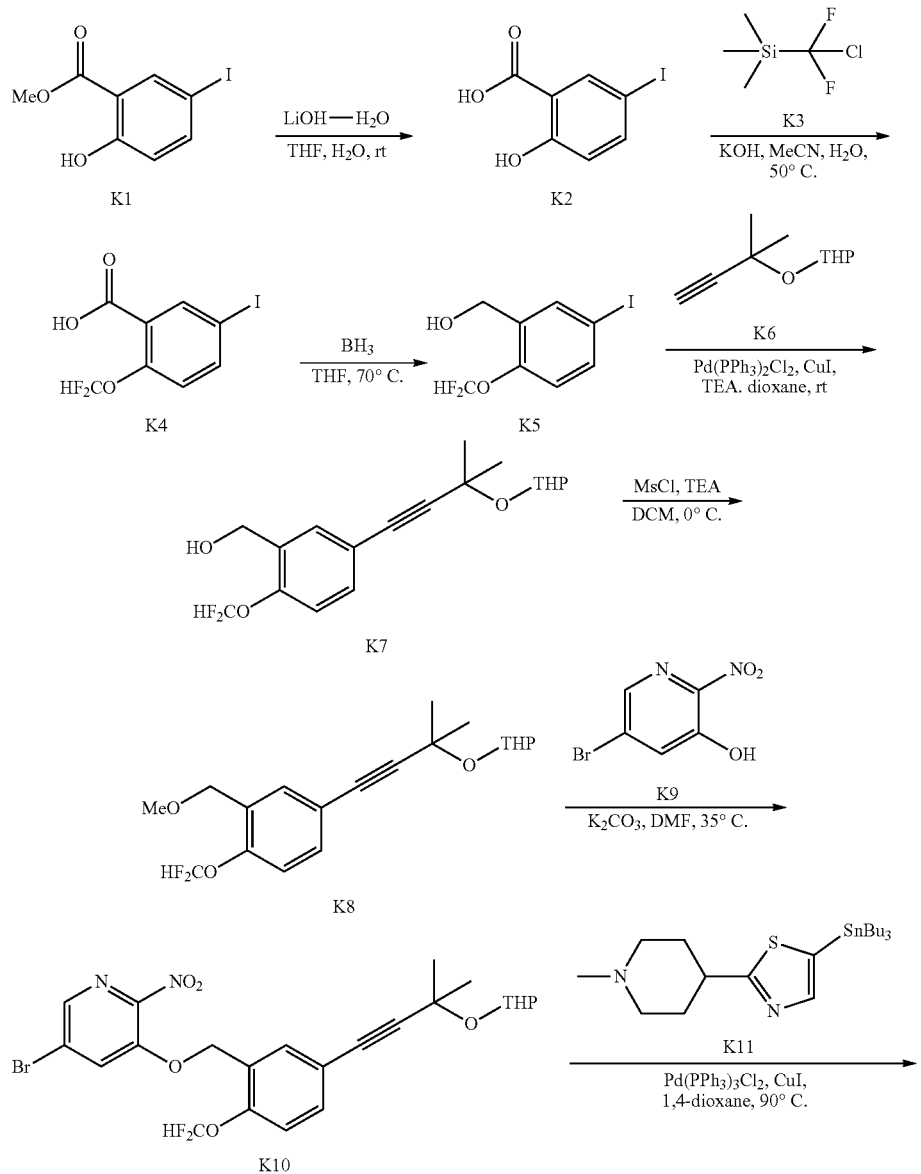

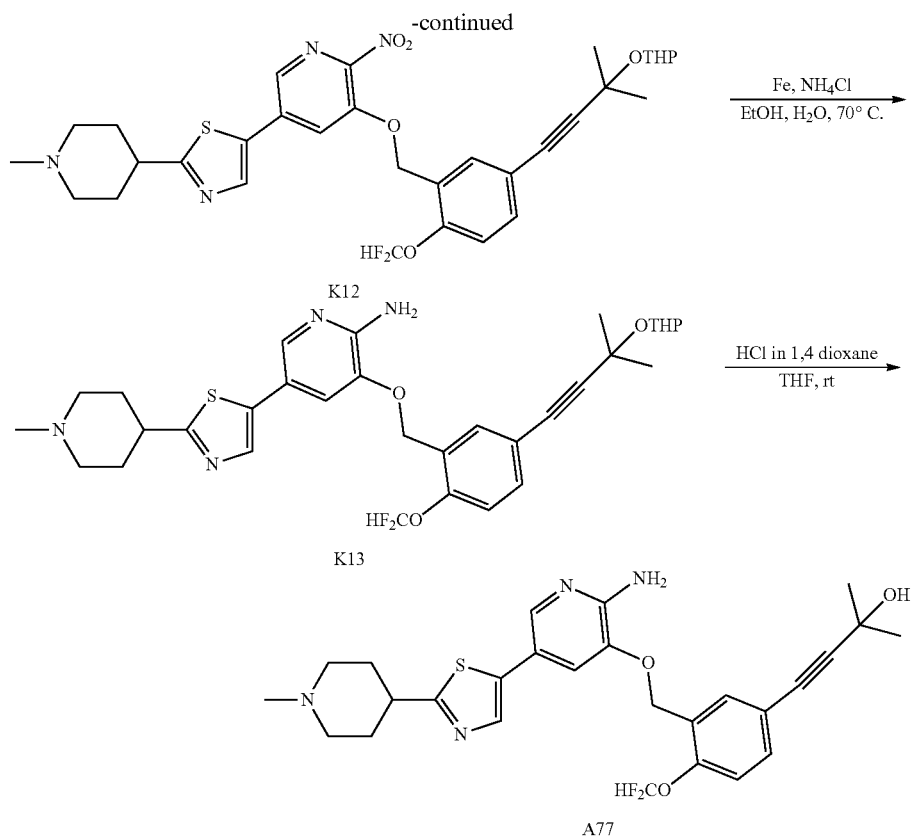

Compound K2: To a solution of compound K1 (3.8 g, 13.67 mmol) in tetrahydrofuran (20 mL) and water (20 mL) was added lithium hydroxide (1.7 g, 41.00 mmol). The mixture was stirred at room temperature for 16 hours. The mixture was adjusted to pH=2 with hydrochloric acid solution (2N), extracted with ethyl acetate (50 mL×3). The combined organic layers were dried over anhydrous sodium sulfate and concentrated under vacuum to afford compound K2 (3.6 g) as a white solid, yield: 100%. $^1$H NMR (400 MHz, DMSO-$d_6$): δ ppm 6.82 (d, J=8.8 Hz, 1H), 7.79 (dd, J=8.8, 2.4 Hz, 1H), 8.03 (d, J=2.4 Hz, 1H).

Compound K4: To a solution of compound K2 (2 g, 7.58 mmol) in acetonitrile (20 mL) was added compound K3 (3 g, 18.94 mmol) and potassium hydroxide aqueous solution (25%, 34.09 mmol). The mixture was stirred at 50° C. for 5 hours. The mixture was diluted with water (20 mL) and adjusted to pH=2 with hydrochloric acid (2N), extracted with ethyl acetate (50 mL×3). The combined organic layers were dried over anhydrous sodium sulfate and concentrated under vacuum to afford crude product, which was purified by silica gel chromatography (elution gradient: dichloromethane/methanol, 10/1, v/v) to afford compound K4 (3.2 g, crude). LCMS: Rt=1.49 min, MS Calcd.: 313.9, MS Found: 312.6 [M−H]$^−$.

Compound K5: To a solution of compound K4 (3.2 g, crude) in anhydrous tetrahydrofuran (20 mL) was added BH$_3$-THF (1M in THF, 23 mL, 23 mmol) at 0° C.

The mixture was stirred at 70° C. under N$_2$ for 6 hours. The mixture was quenched with MeOH (10 mL) and concentrated in vacuo to compound K5 (2.9 g, crude). The product was used directly without any further purification.

Compound K5 was then used as an intermediate for the synthesis of compound A77, through similar procedures described herein. $^1$H NMR (400 MHz, DMSO-$d_6$): δ ppm 1.46 (s, 6H), 1.68-1.77 (m, 2H), 2.01-2.11 (m, 4H), 2.23 (s, 3H), 2.86-2.97 (m, 3H), 5.18 (s, 2H), 6.07 (s, 2H), 7.26 (d, J=8.4 Hz, 1H), 7.36 (d, J=1.6 Hz, 1H), 7.48 (dd, J=8.4, 2.0 Hz, 1H), 7.33 (t, J=73.6 Hz, 1H), 7.67 (d, J=2.0 Hz, 1H), 7.80 (d, J=2.0 Hz, 1H), 7.89 (s, 1H). LCMS: Rt=1.25 min, MS Calcd.: 528.2, MS Found: 528.8 [M+H]$^+$.

Example 34 Preparation of Compound A78

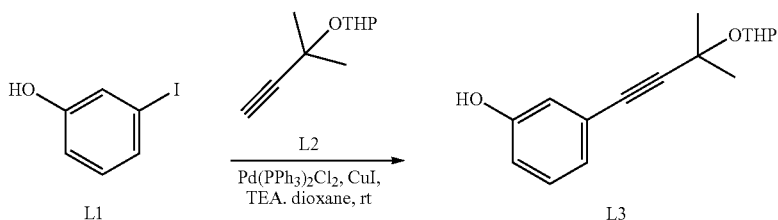

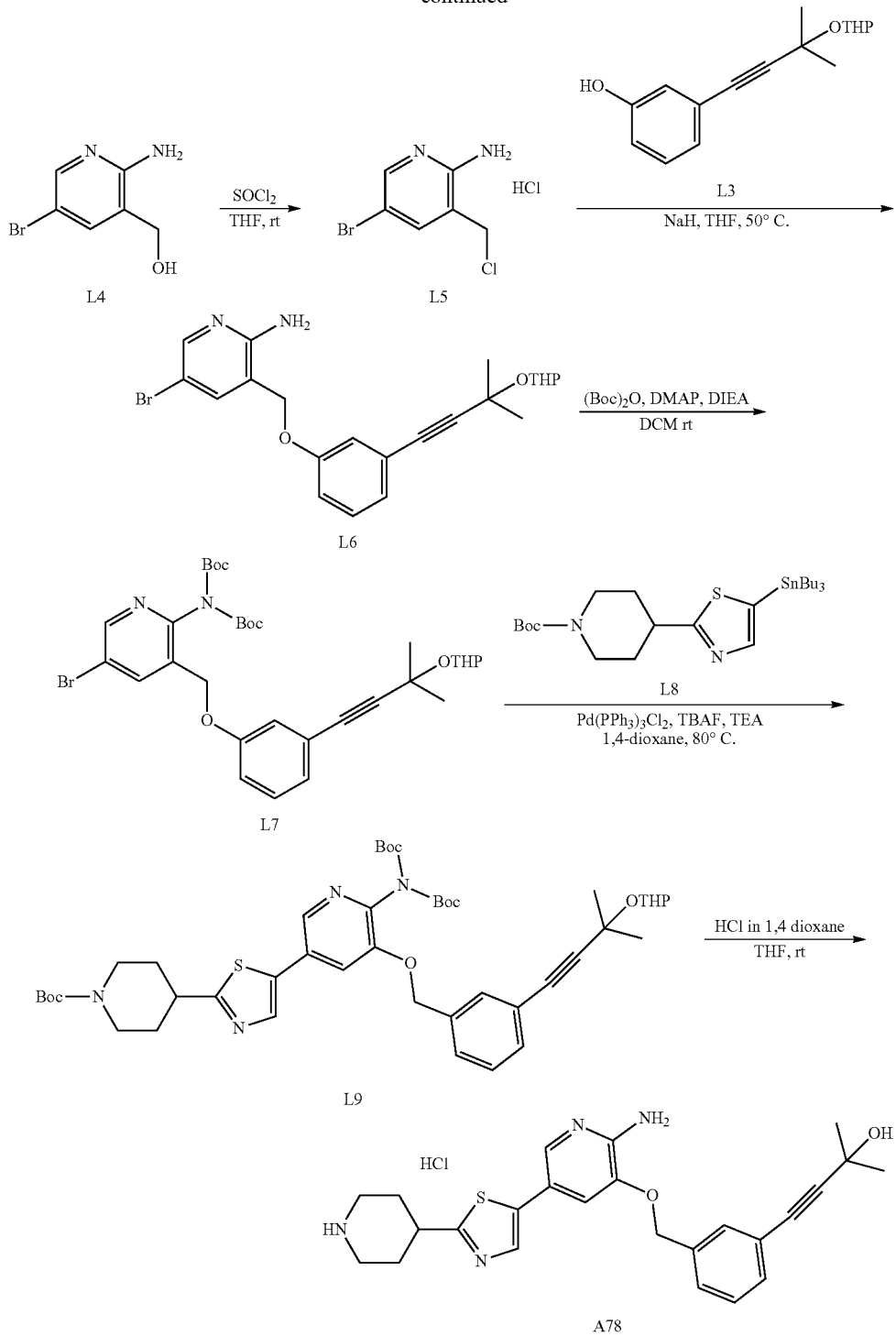

Compound L3: To a solution of compound L1 (5.0 g, 22.7 mmol), compound L2 (4.6 g, 6.8 mmol), bis(triphenylphosphine)palladium(II) chloride (3.16 g, 4.5 mmol) and cuprous iodide (1.3 g, 6.8 mmol) in 1,4-dioxane (100 mL) was added triethyl amine (20 mL) and the mixture was stirred at room temperature for 16 hours under $N_2$. The mixture was added into water (150 mL), extracted with EtOAc (150 mL×3). The organic layers were washed with brine (100 mL), dried over anhydrous $Na_2SO_4$ and concentrated under vacuum to afford crude product, which was purified by silica gel chromatography (elution gradient: petroleum ether/ethyl acetate, 6/1, v/v). Pure fractions were evaporated to dryness to afford compound L3 (6.7 g) as a brown solid, yield: 96.5%.

Compound L5: A mixture of compound L4 (2.5 g, 12.5 mmol) in thionyl chloride (40 mL) was stirred at room temperature for 2 hours. The mixture was concentrated under vacuum to afford crude product, which was added into hexane (30 mL), stirred and filtered to afford compound L5 (2.6 g) as a yellow solid, yield: 90.2%.

Compound L6: To a solution of compound L3 (2.4 g, 9.1 mmol) in THF (120 mL) was added sodium hydride (1.1 g, 27.3 mmol) at 0° C. and the reaction was stirred at room temperature for 30 min. And then compound L5 (2.6 g, 9.1 mmol) was added and the mixture was stirred at 50° C. for 6 hours. The mixture was quenched with water (100 mL), extracted with ethyl acetate (100 mL×3), the organic layers were washed with brine (250 mL), dried over anhydrous $Na_2SO_4$ and concentrated under vacuum to afford crude product, which was purified by silica gel chromatography (elution gradient: petroleum ether/ethyl acetate, 3/1, v/v). Pure fractions were evaporated to dryness to afford compound L6 (630 mg) as a yellow solid, yield: 15.6%.

LCMS: Rt=1.84 min, MS Calcd.: 444.1, 446.1, MS Found: 466.7, 468.7 $[M+Na]^+$.

Compound L7: A solution of compound L6 (400 mg, 0.9 mmol), ditertbutyl dicarbonatein (490 mg, 2.25 mmol), ethyldiisopropylamine (290 mg, 2.25 mmol) in DCM (20 mL) was added 4-dimethylaminopyridine (110 mg, 0.9 mmol) and the reaction was stirred at room temperature for 3 hours. The mixture was added into water (20 mL), extracted with DCM (20 mL×3), the organic layers were washed with brine (50 mL), dried over anhydrous $Na_2SO_4$ and concentrated under vacuum to afford crude product, which was purified by silica gel chromatography (elution gradient: petroleum ether/ethyl acetate, 5/1, v/v). Pure fractions were evaporated to dryness to afford compound L7 (510 mg) as a yellow oil, yield: 87.9%.

LCMS: Rt=2.24 min, MS Calcd.: 644.2, 646.2, MS Found: 666.6, 668.6 $[M+Na]^+$.

Compound L9: To a solution of compound L7 (500 mg, 0.78 mmol), compound L8 (870 mg, 1.56 mmol), bis(triphenylphosphine)palladium(II) chloride (110 mg, 0.16 mmol), TBAF (1M in THF, 0.78 mL, 0.78 mmol) in 1,4-dioxane (20 mL) was added triethyl amine (240 mg, 2.4 mmol) and the reaction was stirred at 80° C. for 3 hours under nitrogen atmosphere. The mixture was concentrated under reduced pressure, the residue was added into water (30 mL), extracted with ethyl acetate (30 mL×3). The organic layers were dried over anhydrous $Na_2SO_4$ and concentrated under vacuum to afford crude product, which was purified by silica gel chromatography (elution gradient: petroleum ether/ethyl acetate, 3/1, v/v). Pure fractions were evaporated to dryness to afford compound L9 (440 mg) as a yellow gum, yield: 66.%.

Compound A78: To a solution of compound L9 (430 mg, 0.52 mmol) in THF (10 mL) was added HCl solution (2 mL, 4 N in 1,4-dioxane) and the reaction was stirred at room temperature for 16 hours. The mixture was concentrated under reduce pressure, adjusted pH=9 with 1N sodium hydroxide, extracted with ethyl acetate (20 mL×3), dried over anhydrous $Na_2SO_4$ and concentrated under vacuum to afford crude product, which was purified by silica gel chromatography (elution gradient: DCM/MeOH, 2/1, v/v). Fractions containing the desired compound were evaporated to dryness to afford compound A78 (58 mg) as a white solid, yield: 23.0%. $^1$H NMR (400 MHz, DMSO-$d_6$): δ ppm 1.46 (s, 6H), 1.89-1.99 (m, 2H), 2.17-2.20 (m, 2H), 2.97-3.04 (m, 2H), 3.30-3.31 (m, 3H), 4.99 (s, 2H), 5.48 (s, 1H), 6.32 (s, 2H), 6.99 (d, J=7.6 Hz, 1H), 7.06-7.09 (m, 2H), 7.30 (t, J=7.6 Hz, 1H), 7.80 (d, J=2.0 Hz, 1H), 7.93 (s, 1H), 8.22 (d, J=2.0 Hz, 1H), 9.01 (br. s, 2H).

LCMS: Rt=1.17 min, MS Calcd.: 448.2, MS Found: 448.8 $[M+H]^+$.

Example 35 Preparation of Compound A82

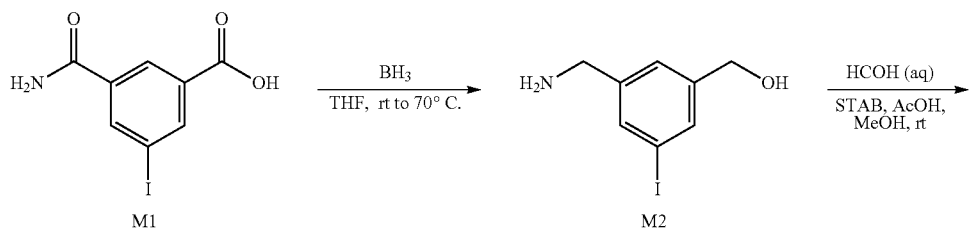

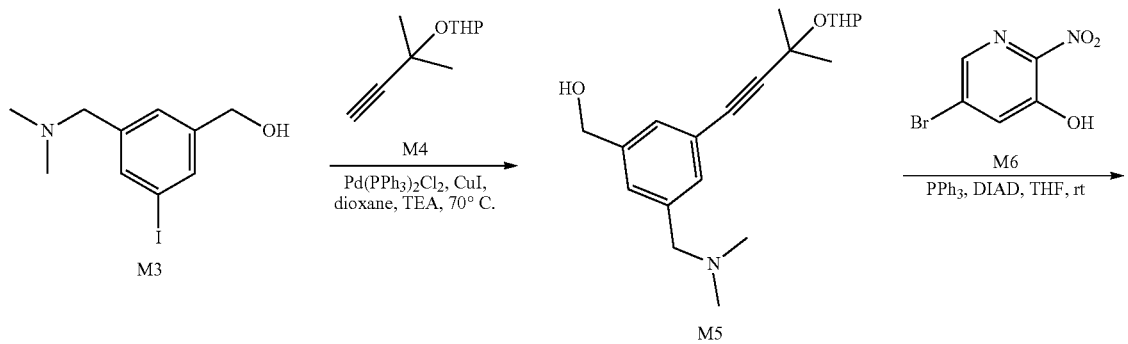

-continued
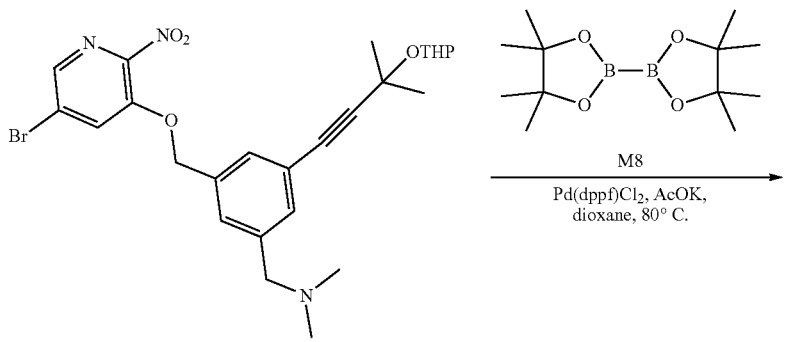
M7
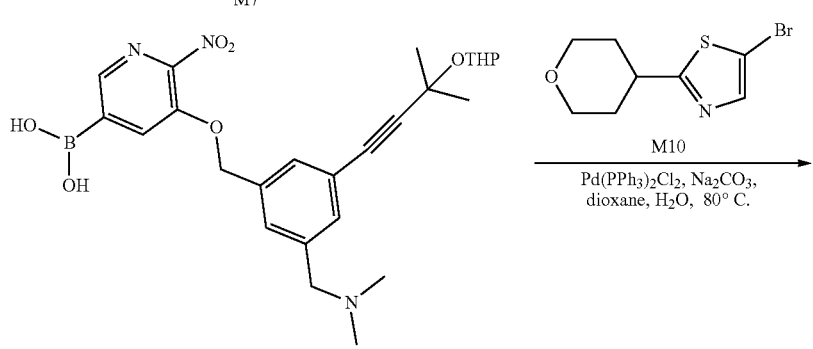
M9
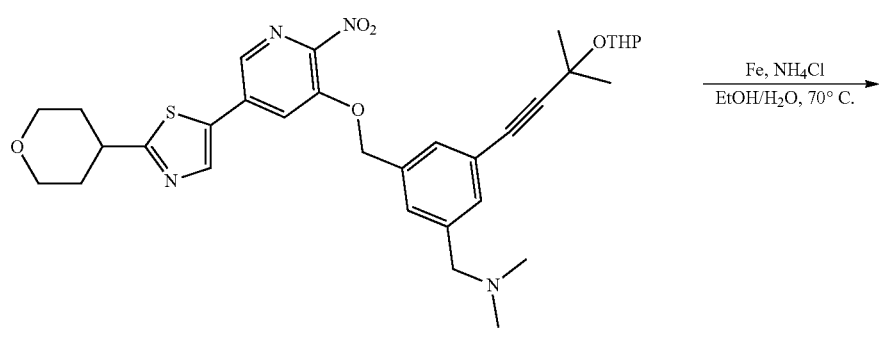
M11
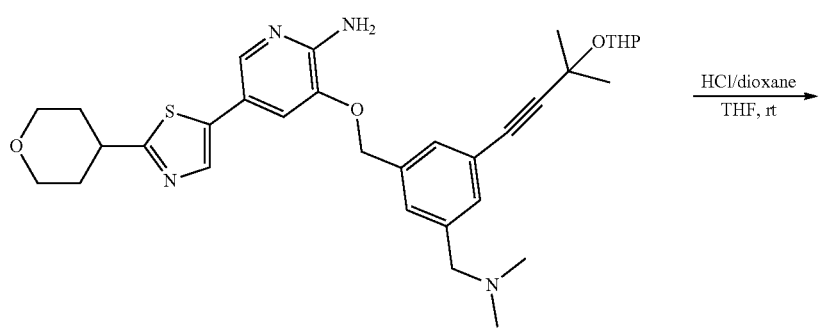
M12

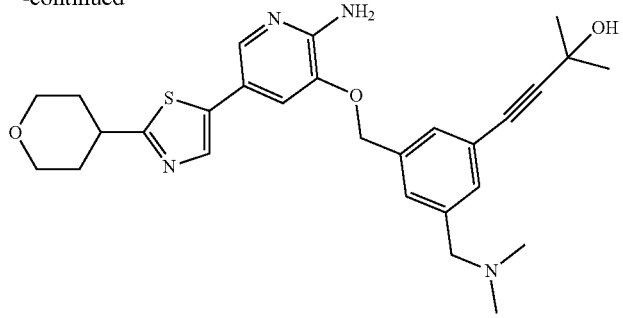

A82

Compound M2: To a solution of compound M1 (5 g, 17.18 mmol) in anhydrous tetrahydrofuran (20 mL) was added BH$_3$-THF (103 mL, 103 mmol, 1M in THF) at 0° C. The mixture was stirred at 70° C. for 16 hours. The mixture was quenched with MeOH (30 mL) and concentrated in vacuo to afford compound M2 (6.6 g, crude) as a yellow oil. The product was used directly without any further purification. LCMS: Rt=0.85 min, MS Calcd.: 263.0, MS Found: 263.8[M+H]$^+$.

Compound M3: To a solution of compound M2 (6.6 g, crude) in MeOH (100 mL) was added formaldehyde (7 g, 85.90 mmol, 30% aqueous solution) and acetic acid (2 mL). The mixture was stirred at room temperature for 1 hour. And then sodium triacetoxyborohydride (7.3 g, 34.36 mmol) was added to the reaction mixture. The mixture was stirred at room temperature for 1 hour. The mixture was concentrated in vacuo to afford a residue. The residue was diluted with water (50 mL), extracted with dichloromethane (100 mL×3). The combined organic layers were dried over anhydrous sodium sulfate and concentrated under vacuum to afford crude product. The crude product was purified by flash chromatography (elution gradient: dichloromethane/methanol, 10/1, v/v) to afford compound M3 (3.8 g) as a yellow oil. The overall yield over 2 steps: 74%. $^1$H NMR (400 MHz, CDCl$_3$): δ ppm 2.24 (s, 6H), 3.38 (s, 2H), 4.61 (s, 2H), 7.29 (s, 1H), 7.57 (s, 1H), 7.60-7.62 (m, 1H). LCMS: Rt=0.89 min, MS Calcd.: 291.0, MS Found: 291.8 [M+H]$^+$.

Compound M5: To a solution of compound M3 (3.7 g, 6.87 mmol), compound M4 (3.2 g, 10.3 mmol), bis(triphenylphosphine)palladium(II) chloride (692 mg, 0.69 mmol) and cuprous iodide (727 mg, 2.06 mmol) in 1,4-dioxane (40 mL) was added triethylamine (8 mL). The mixture was stirred at room temperature under N$_2$ for 16 hours. The mixture was concentrated under reduced pressure to afford a crude product, which was purified by flash chromatography (elution gradient: petroleum dichloromethane/methanol, 10/1, v/v) to afford compound M5 (2.3 g) as a brown oil. LCMS: Rt=1.10 min, MS Calcd.: 331.2, MS Found: 331.9 [M+H]$^+$.

Compound M7: To a solution of compound M5 (1 g, 3.02 mmol), compound M6 (793 mg, 3.62 mmol) and triphenylphosphine (950 mg, 3.62 mmol) in tetrahydrofuran (50 mL) was added diisopropyl azodicarboxylate (732 mg, 3.62 mmol) at 0° C. The mixture was stirred at 0° C. under N$_2$ for 16 hours. The mixture was quenched with water (30 mL), extracted with ethyl acetate (50 mL×2). The combined organic layers were washed with brine (30 mL), dried over anhydrous sodium sulfate and concentrated under vacuum to afford crude product, which was purified by flash chromatography (elution gradient: dichloromethane/methanol, 10/1, v/v) to afford compound 7 (1.1 g) as a yellow oil. LCMS: Rt=1.29 min, MS Calcd.: 531.1, 533.1, MS Found: 531.7, 533.7 [M+H]$^+$.

Compound M9: To a solution of compound M7 (1 g, 1.88 mmol) in 1,4-dioxane (20 mL) was added bis(pinacolato)diboron (954 mg, 3.76 mmol), potassium acetate (553 mg, 5.63 mmol) and bis(triphenylphosphine)palladium(II) chloride (264 mg, 0.38 mmol). The mixture was stirred at 80° C. under N$_2$ for 12 hours. The mixture was cooled to room temperature and concentrated under vacuum to afford crude product (2.1 g). The product was used directly without any further purification. LCMS: Rt=1.34 min, MS Calcd.: 497.2, MS Found: 497.8 [M+H]$^+$.

Compound M9 was then converted into to compound A82 using similar procedures as described herein. $^1$H NMR (400 MHz, DMSO-d$_6$): δ ppm 1.47 (s, 6H), 1.68-1.78 (m, 2H), 1.96-1.99 (m, 2H), 2.29 (s, 6H), 3.20-3.28 (m, 1H), 3.44-3.50 (m, 2H), 3.64 (br. s, 2H), 3.91-3.95 (m, 2H), 5.23 (s, 2H), 5.48 (s, 1H), 6.11 (s, 2H), 7.34-7.35 (m, 2H), 7.47 (s, 1H), 7.52 (s, 1H), 7.78 (d, J=2.0 Hz, 1H), 7.89 (s, 1H). LCMS: Rt=1.06 min, MS Calcd.: 506.2, MS Found: 506.8 [M+H]$^+$.

Following the general synthetic schemes described herein and similar procedures as described above in Examples 1-35, the following compounds were prepared and characterized:

| Compound Code | Compound Structure | Characterization |
|---|---|---|
| A15 | | ¹H NMR (400 MHz, CD₃OD): δ ppm 2.01-2.10 (m, 2H), 2.37 (d, J = 6.8 Hz, 2H), 2.52 (s, 3H), 2.94 (s, 3H), 3.19 (t, J = 12.4 Hz, 2H), 3.47-3.50 (m, 1H), 3.66 (d, J = 6.4 Hz, 2H), 5.84 (s, 1H), 7.81 (s, 1H), 8.21 (d, J = 2.8 Hz, 2H), 8.87 (d, J = 2.8 Hz, 2H). LCMS: Rt = 1.15 min, MS Calcd.: 396.2, MS Found: 397.1 [M + H]⁺. |
| A17 | | ¹H NMR (400 MHz, CD₃OD): δ ppm 1.58 (s, 6H), 2.74 (s, 3H), 5.22 (s, 2H), 7.32 (s, 1H), 7.40 (d, J = 4.3 Hz, 2H), 7.50 (s, 1H), 7.56 (s, 1H), 7.72 (s, 1H), 7.77 (s, 1H). LCMS: Rt = 1.34 min, MS Calcd.: 411.1, MS Found: 411.8 [M + H]⁺. |
| A18 | | ¹H NMR (400 MHz, DMSO-d₆): δ ppm 1.47 (s, 6H), 5.20 (s, 2H), 5.49 (s, 1H), 6.10 (s, 2H), 7.32-7.42 (m, 6H), 7.49-7.53 (m, 5H), 7.70 (s, 1H). LCMS: Rt = 1.51 min, MS Calcd.: 457.1, MS Found: 457.8 [M + H]⁺. |
| A19 | | ¹H NMR (400 MHz, DMSO-d₆): δ ppm 1.47 (s, 6H), 1.68-1.76 (m, 2H), 1.99-2.02 (m, 4H), 2.82-2.94 (m, 3H), 5.24 (s, 2H), 5.49 (s, 1H), 6.06 (s, 2H), 7.28 (t, J = 9.2 Hz, 1H), 7.42-7.46 (m, 2H), 7.69 (d, J = 6.8 Hz, 1H), 7.80 (s, 1H), 7.90 (s, 1H). LCMS: Rt = 1.28 min, MS Calcd.: 480.2, MS Found: 480.8 [M + H]⁺. |
| A20 | | ¹H NMR (400 MHz, DMSO-d₆): δ ppm 0.89 (t, J = 7.2 Hz, 3H), 1.32 (d, J = 3.2 Hz, 3H), 1.47 (s, 6H), 1.62-1.79 (m, 2H), 3.05-3.07 (m, 1H), 5.22 (s, 2H), 5.48 (s, 1H), 6.08 (s, 2H), 7.34-7.42 (m, 3H), 7.54 (s, 2H), 7.77 (s, 1H), 7.86 (s, 1H). LCMS: Rt = 1.48 min, MS Calcd.: 421.2, MS Found: 421.8 [M + H]⁺. |
| A21 | | ¹H NMR (400 MHz, DMSO-d₆): δ ppm 1.35 (d, J = 6.8 Hz, 6H), 1.47 (s, 6H), 3.23-3.30 (m, 1H), 5.24 (s, 2H), 5.49 (s, 1H), 6.05 (s, 2H), 7.28 (t, J = 9.4 Hz, 1H), 7.43-7.46 (m, 2H), 7.69 (d, J = 6.8 Hz, 1H), 7.80 (s, 1H), 7.89 (s, 1H). LCMS: Rt = 1.49 min, MS Calcd.: 425.2, MS Found: 425.9 [M + H]⁺. |

| Compound Code | Compound Structure | Characterization |
|---|---|---|
| A22 | 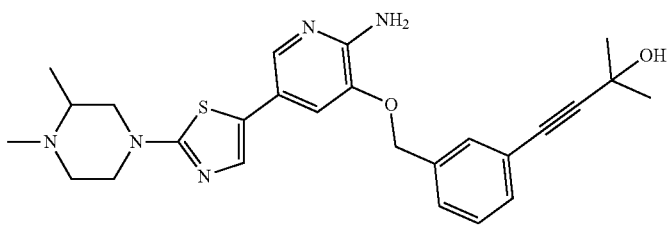 [SMILES: CC1CN(c2ncc(-c3cnc(N)c(OCc4cccc(C#CC(C)(C)O)c4)c3)s2)CCN1C] | ¹H NMR (400 MHz, DMSO-d₆): δ ppm 1.05 (d, J = 3.2 Hz, 3H), 1.47 (s, 6H), 2.14-2.24 (m, 5H), 2.72-2.82 (m, 2H), 3.10-3.15 (m, 1H), 3.65-3.72 (m, 2H), 5.20 (s, 2H), 5.48 (s, 1H), 5.90 (s, 2H), 7.26 (s, 1H), 7.34-7.38 (m, 3H), 7.53-7.55 (m, 2H), 7.60 (s, 1H). LCMS: Rt = 1.12 min, MS Calcd.: 477.2, MS Found: 477.8 [M + H]⁺. |
| A23 | 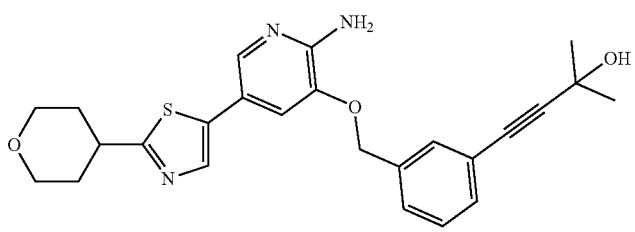 [SMILES: CC(C)(O)C#Cc1cccc(COc2cc(-c3cnc(C4CCOCC4)s3)cnc2N)c1] | ¹H NMR (400 MHz, DMSO-d₆): δ ppm 1.47 (s, 6H), 1.68-1.78 (m, 2H), 1.96-1.99 (m, 2H), 3.20-3.28 (m, 1H), 3.47 (t, J = 11.2 Hz, 2H), 3.93 (d, J = 10.0 Hz, 2H), 5.23 (s, 2H), 5.47 (s, 1H), 6.09 (s, 2H), 7.34-7.43 (m, 3H), 7.54 (m, 2H), 7.78 (s, 1H), 7.90 (s, 1H). LCMS: Rt = 1.29 min, MS Calcd.: 449.2, MS Found: 449.8 [M + H]⁺. |
| A24 | 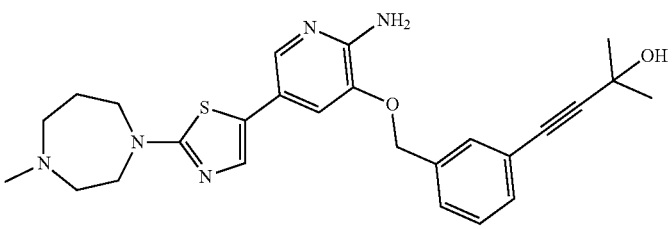 [SMILES: CN1CCCN(c2ncc(-c3cnc(N)c(OCc4cccc(C#CC(C)(C)O)c4)c3)s2)CC1] | ¹H NMR (400 MHz, DMSO-d₆): δ ppm 1.47 (s, 6H), 1.87-1.94 (m, 2H), 2.27 (s, 3H), 2.50 (br. s, 2H), 2.63-2.65 (m, 2H), 3.54 (t, J = 5.8 Hz, 2H), 3.65-3.67 (m, 2H), 5.20 (s, 2H), 5.49 (s, 1H), 5.86 (s, 2H), 7.25 (s, 1H), 7.35 (m, 2H), 7.40 (t, J = 7.8 Hz, 1H), 7.53-7.54 (m, 2H), 7.58 (s, 1H). LCMS: Rt = 1.23 min, MS Calcd.: 477.2, MS Found: 477.9 [M + H]⁺. |
| A25 | 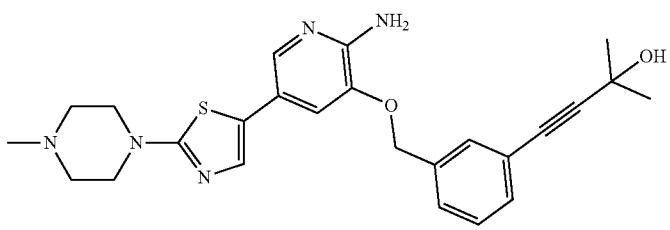 | ¹H NMR (400 MHz, DMSO-d₆): δ 1.46 (s, 6H), 2.24 (s, 3H), 2.41-2.47 (m, 4H), 3.38-3.43 (m, 4H), 5.19 (s, 2H), 5.48 (s, 1H), 5.91 (s, 2H), 7.26 (s, 1H), 7.31-7.41 (m, 3H), 7.50-7.55 (m, 2H), 7.56 (s, 1H). LCMS: Rt = 1.20 min, MS Calcd.: 463.2, MS Found: 463.8 [M + H]⁺. |
| A26 | 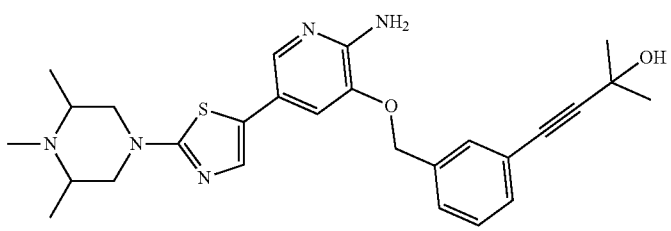 | ¹H NMR (400 MHz, CD₃OD): δ ppm 1.21 (d, J = 6.0 Hz, 6H), 1.58 (s, 6H), 2.37 (s, 3H), 2.47 (s, 2H), 2.90 (t, J = 12.0 Hz, 2H), 3.80 (d, J = 12.8 Hz, 2H), 5.20 (s, 2H), 7.26-7.29 (m, 2H), 7.37-7.44 (m, 2H), 7.49 (s, 1H), 7.55 (s, 1H), 7.60 (s, 1H). LCMS: Rt = 1.03 min, MS Calcd.: 491.2, MS Found: 491.8 [M + H]⁺. |
| A27 | 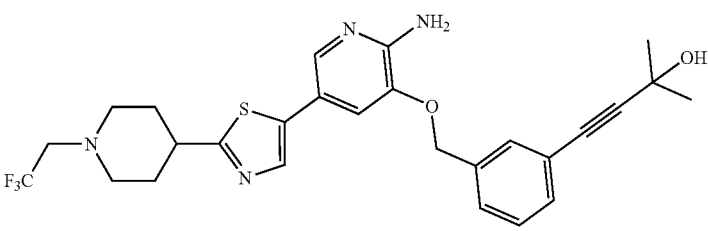 [SMILES: CC(C)(O)C#Cc1cccc(COc2cc(-c3cnc(C4CCN(CC(F)(F)F)CC4)s3)cnc2N)c1] | ¹H NMR (400 MHz, CD₃OD): δ ppm 1.58 (s, 6H), 1.89-1.94 (m, 2H), 2.08-2.12 (m, 2H), 2.56 (t, J = 11.2 Hz, 2H), 2.97-3.06 (m, 1H), 3.09-3.16 (m, 4H), 5.22 (s, 2H), 7.34 (s, 1H), 7.39-7.41 (m, 2H), 7.46-7.53 (m, 1H), 7.56 (s, 1H), 7.76 (s, 1H), 7.79 (s, 1H). LCMS: Rt = 1.27 min, MS Calcd.: 530.2, MS Found: 530.8 [M + H]⁺. |

-continued

| Compound Code | Compound Structure | Characterization |
|---|---|---|
| A29 | 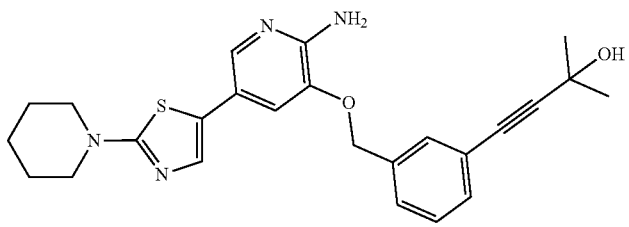 [SMILES: CC(C)(O)C#Cc1cccc(COc2cc(-c3cnc(N4CCCCC4)s3)cnc2N)c1] | ¹H NMR (400 MHz, CDCl₃): δ ppm 1.46 (s, 6H), 1.59 (s, 6H), 3.32 (s, 4H), 5.19 (s, 2H), 5.47 (s, 1H), 5.88 (s, 2H), 7.24 (s, 1H), 7.31-7.41 (m, 3H), 7.50-7.55 (m, 2H), 7.57 (s, 1H). LCMS: Rt = 1.34 min, MS Calcd.: 448.2, MS Found: 448.8 [M + H]⁺. |
| A30 | 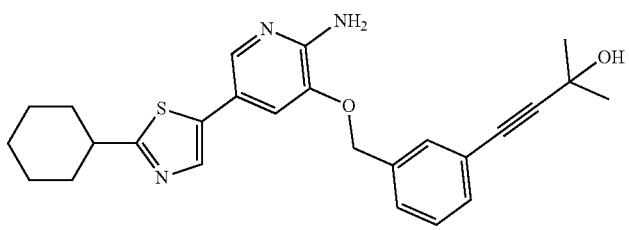 | ¹H NMR (400 MHz, DMSO-d₆): δ ppm 1.24-1.29 (m, 2H), 1.35-1.53 (m, 9H), 1.67-1.70 (m, 1H), 1.77-1.80 (m, 2H), 2.04-2.08 (m, 2H), 2.93-2.98 (m, 1H), 5.22 (s, 2H), 5.47 (s, 1H), 6.07 (s, 2H), 7.35 (br. s, 2H), 7.41 (t, J = 7.6 Hz, 1H), 7.54 (s, 2H), 7.77 (s, 1H), 7.86 (s, 1H). LCMS: Rt = 1.48 min, MS Calcd.: 447.2, MS Found: 447.9 [M + H]⁺. |
| A31 | 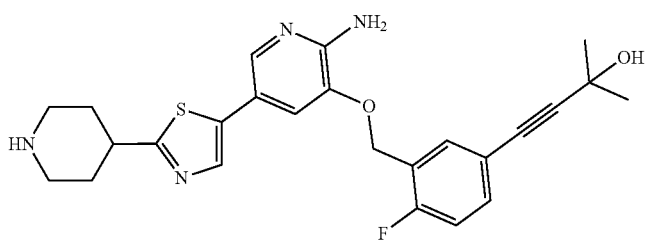 [SMILES: CC(C)(O)C#Cc1ccc(F)c(COc2cc(-c3cnc(C4CCNCC4)s3)cnc2N)c1] | ¹H NMR (400 MHz, DMSO-d₆): δ ppm 1.47 (s, 6H), 1.52-1.61 (m, 2H), 1.94-1.97 (m, 2H), 2.59 (t, J = 12.0 Hz, 2H), 2.99-3.02 (m, 3H), 5.24 (s, 2H), 5.50 (s, 1H), 6.05 (s, 2H), 7.26-7.30 (m, 1H), 7.35-7.50 (m, 2H), 7.69 (d, J = 6.0 Hz, 1H), 7.80 (s, 1H), 7.90 (s, 1H). LCMS: Rt = 1.05 min, MS Calcd.: 466.2, MS Found: 466.8 [M + H]⁺. |
| A33 | 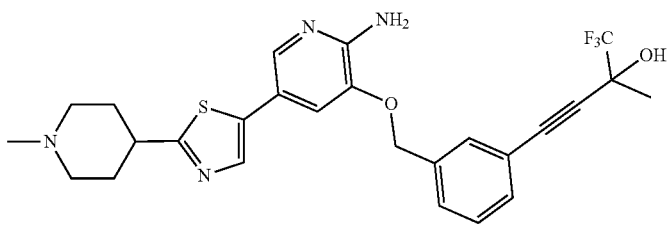 [SMILES: CN1CCC(c2ncc(-c3cnc(N)c(OCc4cccc(C#CC(C)(O)C(F)(F)F)c4)c3)s2)CC1] | ¹H NMR (400 MHz, CD₃OD): δ ppm 1.57 (s, 3H), 2.17-2.36 (m, 4H), 3.03 (s, 3H), 3.25-3.32 (m, 1H), 3.45-3.55 (m, 4H), 4.53 (s, 2H), 7.00 (s, 1H), 7.46- 7.50 (m, 1H), 7.54-7.60 (m, 3H), 7.63 (s, 1H), 7.69 (s, 1H), 8.39 (s, 1H). LCMS: Rt = 1.15 min, MS Calcd.: 516.2, MS Found: 516.8 [M + H]⁺. |
| A44 | 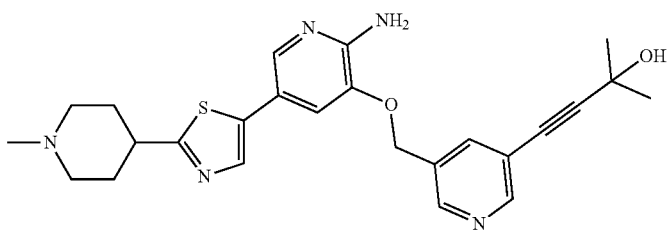 [SMILES: CN1CCC(c2ncc(-c3cnc(N)c(OCc4cncc(C#CC(C)(C)O)c4)c3)s2)CC1] | ¹H NMR (400 MHz, DMSO-d₆): δ ppm 1.49 (s, 6H), 1.67-1.76 (m, 2H), 2.01 (t, J = 9.7 Hz, 4H), 2.19 (s, 3H), 2.82-2.97 (m, 3H), 5.26 (s, 2H), 5.57 (s, 1H), 6.17 (s, 2H), 7.40 (s, 1H), 7.79 (s, 1H), 7.90 (s, 1H), 8.00 (s, 1H), 8.55 (s, 1H), 8.71 (s, 1H). LCMS: Rt = 1.14 min, MS Calcd.: 463.2, MS Found: 463.9 [M + H]⁺. |
| A45 | 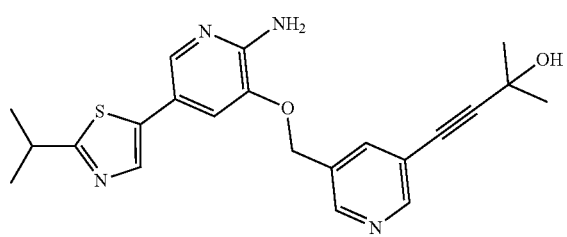 [SMILES: CC(C)c1ncc(-c2cnc(N)c(OCc3cncc(C#CC(C)(C)O)c3)c2)s1] | ¹H NMR (400 MHz, DMSO-d₆): δ ppm 1.35 (d, J = 6.8 Hz, 6H), 1.49 (s, 6H), 3.21-3.32 (m, 1H), 5.26 (s, 2H), 5.58 (s, 1H), 6.17 (s, 2H), 7.41 (s, 1H), 7.80 (s, 1H), 7.89 (s, 1H), 8.00 (s, 1H), 8.56 (s, 1H), 8.72 (s, 1H). LCMS: Rt = 1.34 min, MS Calcd.: 408.2, MS Found: 408.9 [M + H]⁺. |

-continued

| Compound Code | Compound Structure | Characterization |
|---|---|---|
| A46 | | ¹H NMR (400 MHz, DMSO-d₆): δ ppm 0.96-0.98 (m, 4H), 1.69-1.75 (m, 2H), 1.96-2.00 (m, 2H), 3.21-3.28 (m, 1H), 3.44-3.50 (m, 2H), 3.92-3.95 (m, 2H), 5.23 (s, 2H), 6.08 (s, 2H), 6.30 (s, 1H), 7.26-7.30 (m, 1H), 7.43-7.47 (m, 4H), 7.71 (dd, J = 7.2, 2.0 Hz, 1H), 7.80 (d, J = 2.0 Hz, 1H), 7.93 (s, 1H). LCMS: Rt = 1.32 min, MS Calcd.: 465.2, MS Found: 465.8 [M + H]*. |
| A47 | | ¹H NMR (400 MHz, DMSO-d₆): δ ppm 0.96-0.99 (m, 4H), 1.90-2.02 (m, 4BD, 3.46-3.51 (m, 2H), 3.96-3.99 (m, 2H), 3.34-3.42 (m, 1H), 5.18 (s, 2H), 5.67 (s, 2H), 6.30 (s, 1H), 7.34-7.42 (m, 3H), 7.52-7.54 (m, 2H), 7.78 (d, J = 0.8 Hz, 1H), 7.81 (d, J = 2.0 Hz, 1H), 8.13 (s, 1H). LCMS: Rt = 1.27 min, MS Calcd.: 430.2, MS Found: 430.9 [M + H]⁺. |
| A48 | | ¹H NMR (400 MHz, DMSO-d₆): δ ppm 0.97 (dt, J = 4.8, 2.8 Hz, 4H), 1.67-1.77 (m, 2H), 1.98-2.03 (m, 4H), 2.19 (s, 3H), 2.81-2.84 (m, 2H), 2.86-2.91 (m, 1H), 5.23 (s, 2H), 6.07 (s, 2H), 6.32 (s, 1H), 7.25-7.30 (m, 1H), 7.42-7.47 (m, 2H), 7.71 (dd, J = 7.0, 2.1 Hz, 1H), 7.80 (d, J = 1.9 Hz, 1H), 7.91 (s, 1H). LCMS: Rt = 1.18 min, MS Calcd.: 478.2, MS Found: 478.8 [M + H]*. |
| A49 | | ¹H NMR (400 MHz, DMSO-d₆): δ ppm 1.40-1.43 (m, 3H), 1.47 (s, 6H), 1.54-1.57 (m, 1H), 1.76-1.77 (m, 1H), 1.94-1.96 (m, 1H), 2.64-2.70 (m, 1H), 2.98-3.00 (m, 1H), 3.87-3.90 (m, 1H), 5.23 (s, 2H), 5.48 (s, 1H), 6.08 (s, 2H), 7.34-7.35 (m, 2H), 7.36-7.40 (m, 1H), 7.53-7.54 (m, 2H), 7.78 (d, J = 2.0 Hz, 1H), 7.87 (s, 1H). LCMS: Rt = 1.17 min, MS Calcd.: 448.2, MS Found: 448.8 [M + H]⁺. |
| A50 | | ¹H NMR (400 MHz, DMSO-d₆): δ ppm 0.96-1.00 (m, 4H), 1.68-1.78 (m, 2H), 1.96-1.99 (m, 2H), 3.20-3.28 (m, 1H), 3.47 (dt, J = 11.6, 1.6 Hz, 1H), 3.91-3.95 (m, 2H), 5.22 (s, 2H), 6.10 (s, 2H), 6.30 (s, 1H), 7.34-7.42 (m, 3H), 7.52-7.55 (m, 2H), 7.78 (d, J = 2.0 Hz, 1H), 7.90 (s, 1H). LCMS: Rt = 1.31 min, MS Calcd.: 447.2, MS Found: 447.8 [M + H]⁺. |
| A51 | | ¹H NMR (400 MHz, DMSO-d₆): δ ppm 0.95-0.99 (m, 4H), 1.90-2.03 (m, 4H), 3.48 (td, J = 11.6, 2.8 Hz, 2H), 3.96-3.99 (m, 2H), 4.35-4.42 (m, 1H), 5.20 (s, 2H), 5.66 (s, 2H), 6.30 (s, 1H), 7.26-7.30 (m, 1H), 7.40 (d, J = 2.0 Hz, 1H), 7.43-7.47 (m, 1H), 7.70 (dd, J = 7.2, 2.0 Hz, 1H), 7.80 (s, 1H), 7.84 (d, J = 1.6 Hz, 1H), 8.16 (s, 1H). LCMS: Rt = 1.26 min, MS Calcd.: 448.2, MS Found: 448.9 [M + H]⁺. |

| Compound Code | Compound Structure | Characterization |
|---|---|---|
| A52 | 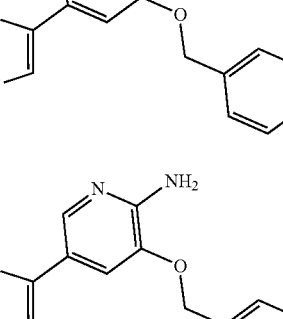 | $^1$H NMR (400 MHz, DMSO-d$_6$): δ ppm 0.98 (dt, J = 4.8, 2.7 Hz, 4H), 1.51-1.61 (m, 2H), 1.93-1.96 (m, 2H), 2.58 (t, J = 11.4 Hz, 2H), 2.99-3.04 (m, 3H), 5.22 (s, 2H), 6.09 (s, 2H), 6.35 (s, 1H), 7.34-7.42 (m, 3H), 7.52-7.55 (m, 2H), 7.77 (d, J = 1.7 Hz, 1H), 7.88 (s, 1H). LCMS: Rt = 1.30 min, MS Calcd.: 446.2, MS Found: 446.9 [M + H]$^+$. |
| A53 | 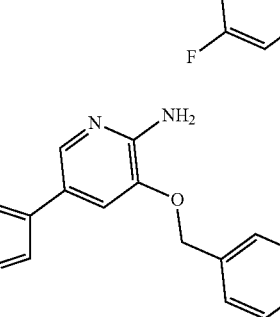 | $^1$H NMR (400 MHz, DMSO-d$_6$): δ ppm 0.98 (d, J = 8.7 Hz, 4H), 1.53-1.61 (m, 2H), 1.94-1.96 (m, 2H), 2.51-2.65 (m, 2H), 2.79-3.15 (m, 3H), 5.23 (s, 2H), 6.06 (s, 2H), 6.35 (s, 1H), 7.25-7.30 (m, 1H), 7.42-7.48 (m, 2H), 7.71 (d, J = 6.0 Hz, 1H), 7.79 (s, 1H), 7.90 (s, 1H). LCMS: Rt = 1.12 min, MS Calcd.: 464.2, MS Found: 464.7 [M + H]$^+$. |
| A54 | 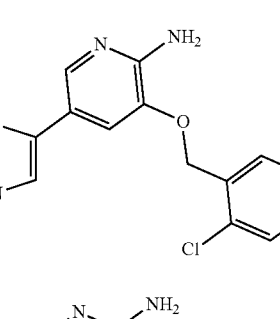 | $^1$H NMR (400 MHz, DMSO-d$_6$): δ ppm 0.93-1.01 (m, 4H), 2.01-2.04 (m, 2H), 2.12-2.14 (m, 2H), 2.89-2.91 (m, 2H), 3.26-3.29 (m, 2H), 4.36 (br. s, 1H), 5.18 (s, 2H), 5.68 (s, 2H), 7.34-7.41 (m, 3H), 7.51-7.53 (m, 2H), 7.80-7.81 (m, 2H), 8.09-8.11 (m, 1H), 8.32 (s, 2H). LCMS: Rt = 1.04 min, MS Calcd.: 429.2, MS Found: 429.9 [M + H]$^+$. |
| A55 | 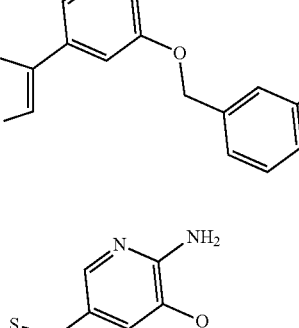 | $^1$H NMR (400 MHz, CDCl$_3$): δ ppm 1.45 (s, 6H), 1.65-1.76 (m, 2H), 1.98-2.04 (m, 4H), 2.18 (s, 3H), 2.79-2.93 (m, 3H), 5.25 (s, 2H), 5.51 (s, 1H), 6.07 (s, 2H), 7.38-7.42 (m, 2H), 7.50-7.54 (m, 1H), 7.71 (d, J = 2.0 Hz, 1H), 7.80 (d, J = 2.0 Hz, 1H), 7.90 (s, 1H). LCMS: Rt = 1.25 min, MS Calcd.: 496.2, MS Found: 496.8 [M + H]$^+$. |
| A56 |  | $^1$H NMR (400 MHz, DMSO-d$_6$): δ ppm 1.46 (s, 6H), 1.68-1.79 (m, 3H), 2.13 (br. s, 1H), 2.74-2.77 (m, 1H), 2.90-2.93 (m, 1H), 3.10-3.13 (d, J = 7.2 Hz, 1H), 3.29 (br. s, 2H), 3.40-3.43 (m, 1H), 5.22 (s, 2H), 6.13 (s, 2H), 7.33-7.42 (m, 3H), 7.53-7.55 (m, 2H), 7.77-7.78 (d, J = 2.0 Hz, 1H), 7.92 (s, 1H), 8.31 (s, 2H). LCMS: Rt = 1.16 min, MS Calcd.: 448.2, MS Found: 448.8 [M + H]$^+$. |
| A57 | | $^1$H NMR (400 MHz, DMSO-d$_6$): δ ppm 1.47 (s, 6H), 1.67-1.76 (m, 2H), 1.99-2.02 (m, 4H), 2.20 (s, 3H), 2.82-2.94 (m, 3H), 5.23 (s, 2H), 5.54 (s, 1H), 6.18 (s, 2H), 7.19 (d, J = 9.2 Hz, 1H), 7.37 (d, J = 12.4 Hz, 2H), 7.48 (d, J = 9.2 Hz, 1H), 7.78 (s, 1H), 7.88 (s, 1H). LCMS: Rt = 1.16 min, MS Calcd.: 480.2, MS Found: 480.8 [M + H]$^+$. |

| Compound Code | Compound Structure | Characterization |
|---|---|---|
| A58 | 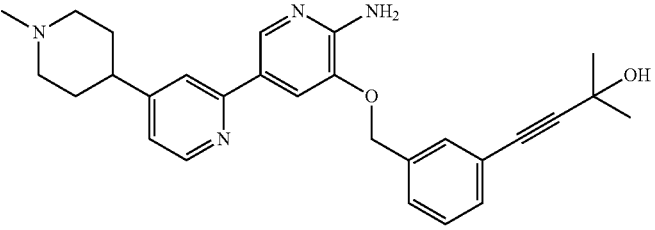 | ¹H NMR (400 MHz, DMSO-d₆): δ ppm 1.47 (s, 6H), 1.81 (br. s, 4H), 2.15 (br. s, 2H), 2.30 (br. s, 3H), 2.57 (s, 1H), 3.00 (br. s, 2H), 5.24 (s, 1H), 6.10 (s, 2H), 7.12 (d, J = 2.4 Hz, 1H), 7.34-7.40 (m, 2H), 7.55-7.57 (m, 2H), 7.73 (s, 1H), 7.78 (s, 1H), 8.24 (s, 1H), 8.34 (s, 1H), 8.46 (d, J = 2.4 Hz, 1H). LCMS: Rt = 1.28 min, MS Calcd.: 456.3, MS Found: 457.2 [M + H]⁺. |
| A59 | 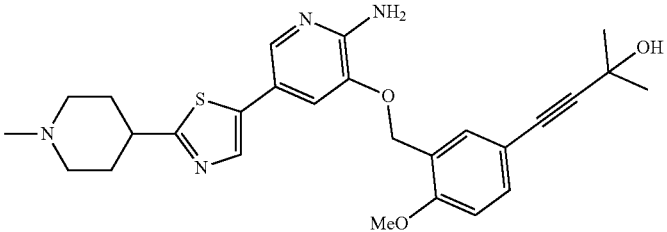 | ¹H NMR (400 MHz, DMSO-d₆): δ ppm 1.45 (s, 6H), 1.67-1.75 (m, 2H), 1.98-2.03 (m, 4H), 2.18 (s, 3H), 2.81-2.93 (m, 3H), 3.88 (s, 3H), 5.14 (s, 2H), 5.43 (s, 1H), 6.03 (s, 2H), 7.07 (d, J = 8.5 Hz, 1H), 7.31 (s, 1H), 7.38 (d, J = 8.5 Hz, 1H), 7.50 (s, 1H), 7.79 (s, 1H), 7.88 (s, 1H). LCMS: Rt = 1.12 min, MS Calcd.: 492.2, MS Found: 492.9 [M + H]⁺. |
| A60 | 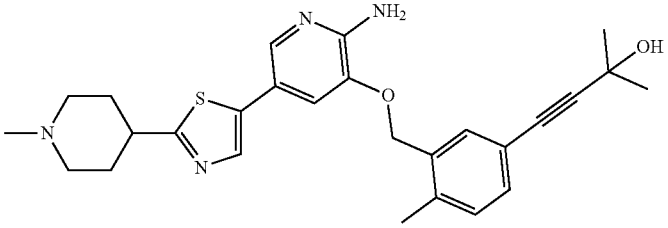 [SMILES: Cc1ccc(C#CC(C)(C)O)cc1COc1cc(-c2cnc(C3CCN(C)CC3)s2)cnc1N] | ¹H NMR (400 MHz, DMSO-d₆): δ ppm 1.46 (s, 6H), 1.69-1.73 (m, 2H), 2.00-2.03 (m, 4H), 2.19 (s, 3H), 2.37 (s, 3H), 2.81-2.93 (m, 3H), 5.19 (s, 2H), 5.46 (s, 1H), 6.02 (s, 2H), 7.23-7.29 (m, 2H), 7.39 (s, 1H), 7.52 (s, 1H) ,7.78 (s, 1H), 7.89 (s, 1H). LCMS: Rt = 1.16 min, MS Calcd.: 476.2, MS Found: 476.9 [M + H]+ |
| A61 | 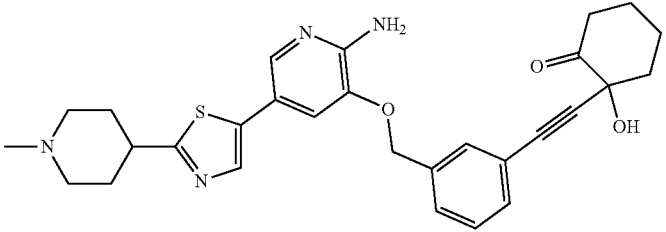 [SMILES: CN1CCC(c2ncc(-c3cnc(N)c(OCc4cccc(C#CC5(O)CCCCC5=O)c4)c3)s2)CC1] | ¹H NMR (400 MHz, DMSO-d₆): δ ppm 1.59-1.67 (m, 1H), 1.69-1.92 (m, 5H), 1.95-2.05 (m, 3H), 2.14 (t, J = 11.2 Hz, 2H), 2.21-2.26 (m, 4H), 2.41 (dt, J = 6.6, 4.0 Hz, 1H), 2.78 (td, J = 13.0, 6.0 Hz, 1H), 2.88-2.96 (m, 3H), 5.23 (s, 2H), 6.10 (s, 2H), 7.37 (s, 1H), 7.42-7.46 (m, 2H), 7.58-7.60 (m, 1H), 7.64 (s, 1H), 7.77 (s, 1H), 7.89 (s, 1H), 8.20 (s, 1H). LCMS: Rt = 1.15 min, MS Calcd.: 516.2, MS Found: 516.8 [M + H]⁺. |
| A63 | 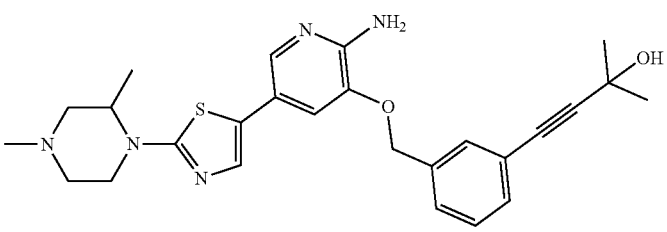 [SMILES: CC1CN(C)CCN1c1ncc(-c2cnc(N)c(OCc3cccc(C#CC(C)(C)O)c3)c2)s1] | ¹H NMR (400 MHz, DMSO-d₆): δ ppm 1.05 (d, J = 3.2 Hz, 3H), 1.47 (s, 6H), 2.14-2.25 (m, 5H), 2.72-2.82 (m, 2H), 3.09-3.15 (m, 1H), 3.65-3.72 (m, 2H), 5.20 (s, 2H), 5.48 (s, 1H), 5.90 (s, 2H), 7.26 (s, 1H), 7.34-7.38 (m, 3H), 7.53-7.54 (m, 2H), 7.60 (s, 1H). LCMS: Rt = 0.31 min, MS Calcd.: 477.2, MS Found: 477.9 [M + H]⁺. |
| A64 | 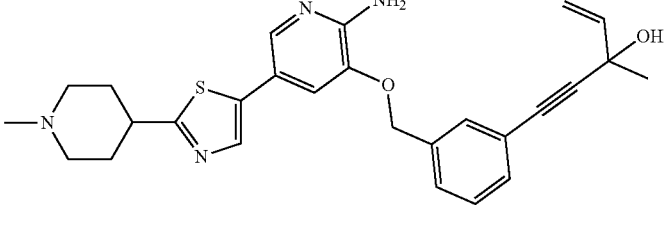 | ¹H NMR (400 MHz, DMSO-d₆): δ ppm 1.51 (s, 3H), 1.67-1.75 (m, 2H), 1.97-2.02 (m, 4H), 2.18 (m, 3H), 2.81-2.88 (m, 2H), 2.88-2.92 (m, 1H), 5.09 (d, J = 8.0 Hz, 1H), 5.23 (s, 2H), 5.43 (d, J = 16.0 Hz, 1H), 5.80 (s, 1H), 5.96-6.03 (m, 1H), 6.09 (s, 2H) ,7.35-7.43 (m, 2H), 7.57 (d, J = 12.0 Hz, 1H), 7.77 (s, 1H), 7.87 (s, 1H). LCMS: Rt = 1.19 min, MS Calcd.: 474.2, MS Found: 474.8 [M + H]⁺. |

-continued

| Compound Code | Compound Structure | Characterization |
|---|---|---|
| A67 | | ¹H NMR (400 MHz, DMSO-d₆): δ ppm 1.34 (d, J = 6.9 Hz, 6H), 1.46 (s, 6H), 3.22-3.29 (m, 1H), 3.90 (s, 2H), 5.27 (s, 2H), 5.46 (s, 1H), 6.07 (s, 2H), 7.37-7.43 (m, 2H), 7.49-7.53 (m, 2H), 7.79 (d, J = 1.9 Hz, 1H), 7.87 (s, 1H). LCMS: Rt = 1.20 min, MS Calcd.: 436.2, MS Found: 436.8 [M + H]⁺. |
| A69 | | ¹H NMR (400 MHz, CD₃OD): δ ppm 1.58 (s, 6H), 1.63-1.68 (m, 2H), 1.98-2.01 (m, 2H), 2.62 (s, 3H), 2.67-2.69 (m, 1H), 2.83-2.95 (m, 9H), 3.10 (t, J = 12.0 Hz, 2H), 4.02 (d, J = 12.4 Hz, 2H), 5.20 (s, 2H), 7.26-7.27 (m, 2H), 7.39-7.40 (m, 2H), 7.48-7.50 (m, 1H), 7.55 (s, 1H), 7.59 (d, J = 1.6 Hz, 1H), 8.51 (s, 1H). LCMS: Rt = 1.21 min, MS Calcd.: 546.3, MS Found: 546.9 [M + H]⁺. |
| A70 | | ¹H NMR (400 MHz, DMSO-d₆): δ ppm 1.33 (s, 3H), 1.35 (s, 3H), 1.47 (s, 6H), 3.23-3.30 (m, 1H), 3.82 (s, 2H), 5.19 (s, 2H), 5.50 (br. s, 1H), 6.10 (s, 2H), 7.36-7.40 (m, 3H), 7.54 (s, 1H), 7.78 (d, J = 1.9 Hz, 1H), 7.87 (s, 1H). LCMS: Rt = 1.26 min, MS Calcd.: 436.2, MS Found: 437.1 [M + H]⁺. |
| A71 | | ¹H NMR (400 MHz, CDCl₃): δ ppm 1.45 (s, 6H), 1.65-1.76 (m, 2H), 1.98-2.09 (m, 4H), 2.21 (s, 3H), 2.31 (s, 3H), 2.81-2.96 (m, 3H), 5.16 (s, 2H), 5.47 (s, 1H), 6.09 (s, 2H), 7.17 (s, 1H), 7.30-7.38 (m, 3H), 7.76 (s, 1H), 7.88 (s, 1H). LCMS: Rt = 1.16 min, MS Calcd.: 476.2, MS Found: 476.9 [M + H]⁺. |
| A72 | | ¹H NMR (400 MHz, DMSO-d₆): δ ppm 1.47 (s, 6H), 1.94-2.02 (m, 1H), 2.28-2.37 (m, 4H), 2.48-2.54 (m, 1H), 2.64-2.68 (m, 2H), 2.82-2.86 (m, 1H), 3.67-3.71 (m, 1H), 5.22 (s, 2H), 5.48 (s, 1H), 6.08 (s, 2H), 7.34-7.42 (m, 3H), 7.54-7.55 (m, 2H), 7.77 (d, J = 2.0 Hz, 1H), 7.84 (s, 1H). LCMS: Rt = 1.13 min, MS Calcd.: 448.2, MS Found: 448.8 [M + H]⁺. |
| A73 | | ¹H NMR (400 MHz, DMSO-d₆): δ ppm 1.46 (s, 6H), 1.93-2.05 (m, 6H), 2.21 (s, 3H), 2.86 (d, J = 5.6 Hz, 2H), 4.04-4.12 (m, 1H), 5.20 (s, 2H), 5.48 (s, 1H), 5.64 (s, 2H), 7.26-7.30 (m, 1H), 7.39-7.42 (m, 1H), 7.43-7.44 (m, 1H), 7.67-7.69 (m, 1H), 7.78 (s, 1H), 7.83 (d, J = 0.8 Hz, 1H), 8.14 (s, 1H). LCMS: Rt = 1.13 min, MS Calcd.: 463.2, MS Found: 463.7 [M + H]⁺. |

-continued

| Compound Code | Compound Structure | Characterization |
|---|---|---|
| A75 | | ¹H NMR (400 MHz, DMSO-d₆): δ ppm 1.48 (s, 6H), 1.61-1.76 (m, 2H), 1.98-2.03 (m, 4H), 2.19 (s, 3H), 2.81-2.93 (m, 1H), 5.19 (s, 2H), 5.59 (br. s, 1H), 6.10 (s, 2H), 7.29-7.36 (m, 2H), 7.57-7.64 (m, 2H), 7.77 (d, J = 2.0 Hz, 1H), 7.88 (s, 1H). LCMS: Rt = 1.33 min, MS Calcd.: 480.2, MS Found: 480.8 [M + H]⁺. |
| A76 | | ¹H NMR (400 MHz, DMSO-d₆): δ ppm 1.48 (s, 6H), 1.67-1.77 (m, 2H), 1.99-2.04 (m, 4H), 2.19 (s, 3H), 2.82-2.95 (m, 3H), 5.31 (s, 2H), 5.58 (s, 1H), 6.04 (s, 2H), 7.34 (d, J = 2.0 Hz, 1H), 7.58-7.60 (m, 1H), 7.79-7.84 (m, 3H), 7.87 (s, 1H). LCMS: Rt = 1.29 min, MS Calcd.: 530.2, MS Found: 530.8 [M + H]⁺. |
| A79 | | ¹H NMR (400 MHz, DMSO-d₆): δ ppm 1.47 (s, 6H), 1.81-1.85 (m, 2H), 1.99-2.01 (m, 2H), 2.63-2.69 (m, 2H), 3.08-3.11 (m, 2H), 4.16-4.23 (m, 1H), 5.19 (s, 2H), 5.66 (s, 2H), 7.33-7.36 (m, 2H), 7.38-7.42 (m, 1H), 7.53-7.54 (m, 2H), 7.76 (d, J = 0.8 Hz, 1H), 7.81 (d, J = 2.0 Hz, 1H), 8.08 (s, 1H). LCMS: Rt = 1.15 min, MS Calcd.: 431.2, MS Found: 431.9 [M + H]⁺. |
| A80 | | ¹H NMR (400 MHz, DMSO-d₆): δ ppm 1.47 (s, 6H), 1.90-2.02 (m, 4H), 3.48 (dt, J = 11.6, 2.4 Hz, 2H), 3.96-3.99 (m, 2H), 4.34-4.42 (m, 1H), 5.19 (s, 2H), 5.48 (s, 1H), 5.67 (s, 2H), 7.34-7.36 (m, 2H), 7.38-7.42 (m, 1H), 7.53-7.55 (m, 2H), 7.78 (d, J = 0.4 Hz, 1H), 7.81 (d, J = 2.0 Hz, 1H), 8.13 (s, 1H). LCMS: Rt = 1.24 min, MS Calcd.: 432.2, MS Found: 432.9 [M + H]⁺. |
| A81 | | ¹H NMR (400 MHz, DMSO-d₆): δ ppm 1.47 (s, 6H), 1.68-1.78 (m, 2H), 1.98 (dd, J = 12.8, 2.0 Hz, 2H), 2.79 (br. s, 2H), 3.20-3.28 (m, 1H), 3.47 (td, J = 11.5, 1.9 Hz, 2H), 3.74 (s, 2H), 3.92-3.95 (m, 2H), 5.19 (s, 2H), 5.46 (s, 1H), 6.09 (s, 2H), 7.35-7.37 (m, 3H), 7.50 (s, 1H), 7.78 (d, J = 1.8 Hz, 1H), 7.90 (s, 1H). LCMS: Rt = 1.04 min, MS Calcd.: 478.2, MS Found: 478.8 [M + H]⁺. |
| A83 | | ¹H NMR (400 MHz, DMSO-d₆): δ ppm 1.47 (s, 6H), 1.67-1.76 (m, 2H), 1.99-2.05 (m, 4H), 2.19 (s, 3H), 2.83 (d, J = 11.3 Hz, 2H), 2.91 (t, J = 11.6 Hz, 1H), 3.85 (s, 2H), 5.20 (s, 2H), 5.47 (s, 2H), 6.11 (s, 2H), 7.36 (s, 1H), 7.41 (d, J = 7.6 Hz, 2H), 7.55 (s, 1H), 7.78 (s, 1H), 7.89 (s, 1H). LCMS: Rt = 0.89 min, MS Calcd.: 491.2, MS Found: 491.8 [M + H]⁺. |

| Compound Code | Compound Structure | Characterization |
|---|---|---|
| A84 | 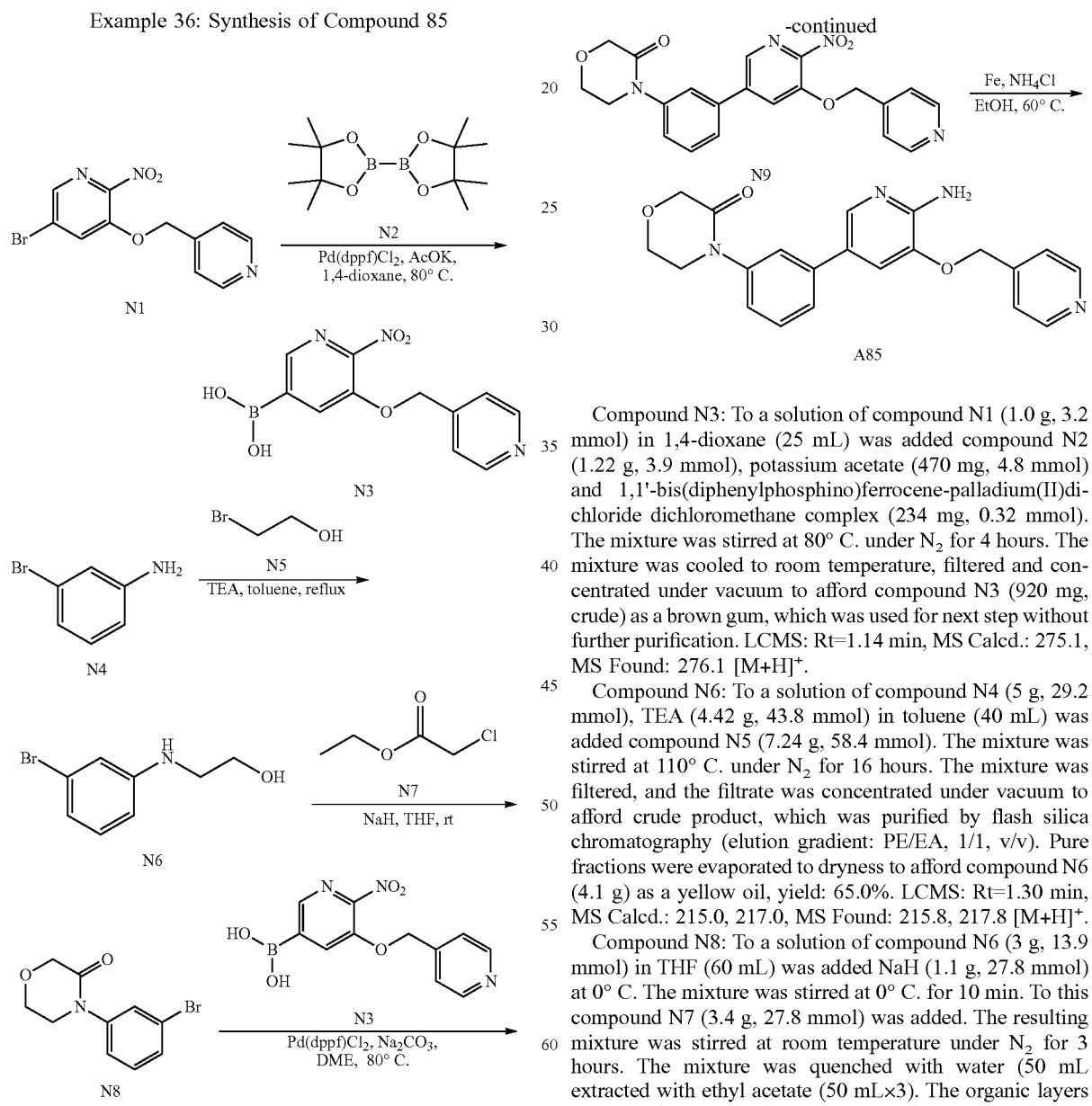 | $^1$H NMR (400 MHz, DMSO-$d_6$): δ ppm 1.46 (s, 6H), 1.68-1.78 (m, 2H), 1.97 (d, J = 13.0 Hz, 2H), 3.21-3.27 (m, 1H), 3.47 (t, J = 10.7 Hz, 2H), 3.90-3.95 (m, 4H), 5.27 (s, 2H), 5.47 (s, 1H), 6.11 (s, 2H), 7.38-7.43 (m, 2H), 7.50 (d, J = 7.9 Hz, 1H), 7.55 (s, 1H), 7.80 (d, J = 1.7 Hz, 1H), 7.90 (s, 1H). LCMS: Rt = 1.01 min, MS Calcd.: 478.2, MS Found: 478.8 [M + H]$^+$. |

Example 36: Synthesis of Compound 85

Compound N3: To a solution of compound N1 (1.0 g, 3.2 mmol) in 1,4-dioxane (25 mL) was added compound N2 (1.22 g, 3.9 mmol), potassium acetate (470 mg, 4.8 mmol) and 1,1'-bis(diphenylphosphino)ferrocene-palladium(II)dichloride dichloromethane complex (234 mg, 0.32 mmol). The mixture was stirred at 80° C. under N$_2$ for 4 hours. The mixture was cooled to room temperature, filtered and concentrated under vacuum to afford compound N3 (920 mg, crude) as a brown gum, which was used for next step without further purification. LCMS: Rt=1.14 min, MS Calcd.: 275.1, MS Found: 276.1 [M+H]$^+$.

Compound N6: To a solution of compound N4 (5 g, 29.2 mmol), TEA (4.42 g, 43.8 mmol) in toluene (40 mL) was added compound N5 (7.24 g, 58.4 mmol). The mixture was stirred at 110° C. under N$_2$ for 16 hours. The mixture was filtered, and the filtrate was concentrated under vacuum to afford crude product, which was purified by flash silica chromatography (elution gradient: PE/EA, 1/1, v/v). Pure fractions were evaporated to dryness to afford compound N6 (4.1 g) as a yellow oil, yield: 65.0%. LCMS: Rt=1.30 min, MS Calcd.: 215.0, 217.0, MS Found: 215.8, 217.8 [M+H]$^+$.

Compound N8: To a solution of compound N6 (3 g, 13.9 mmol) in THF (60 mL) was added NaH (1.1 g, 27.8 mmol) at 0° C. The mixture was stirred at 0° C. for 10 min. To this compound N7 (3.4 g, 27.8 mmol) was added. The resulting mixture was stirred at room temperature under N$_2$ for 3 hours. The mixture was quenched with water (50 mL extracted with ethyl acetate (50 mL×3). The organic layers were dried over anhydrous Na$_2$SO$_4$ and concentrated under vacuum to afford crude product, which was purified by silica gel chromatography (elution gradient: petroleum ether/EtOAc, 1/1, v/v). Pure fractions were evaporated to dryness to afford compound N8 (1.8 g) as a yellow solid, yield:

50.3%. LCMS: Rt=1.27 min, MS Calcd.: 255.0, 257.0, MS Found: 255.8, 257.8 [M+H]$^+$.

Compound N9: To a solution of compound N8 (630 mg, 2.5 mmol) in DME (25 mL) and water (5 mL) was added compound N3 (750 mg, 2.73 mmol), bis(triphenylphosphine)palladium(II) chloride (175 mg, 0.25 mmol) and sodium carbonate (400 mg, 3.75 mmol). The mixture was stirred at 80° C. under N$_2$ for 2 hours. The mixture was cooled to room temperature and diluted with water (30 mL), extracted with dichloromethane (30 mL×3). The combined organic layers were dried over anhydrous sodium sulfate and concentrated under vacuum to afford crude product, which was purified by silica gel chromatography (elution gradient: dichloromethane/methane, 8/1, v/v) to afford compound N9 (370 mg) as a yellow gum, yield: 36.4%. LCMS: Rt=1.11 min, MS Calcd.: 406.1, MS Found: 406.8 [M+H]$^+$.

Compound A85: To a solution of compound N9 (370 mg, 0.91 mmol) in ethanol (15 mL) and water (5 mL) was added ammonium chloride (243 mg, 4.55 mmol) and iron powder (255 mg, 4.55 mmol). The mixture was stirred at 60° C. for 2 hours. The mixture was filtered and concentrated under reduced pressure to afford crude product, which was purified by silica gel chromatography (elution gradient: dichloromethane/methane, 8/1, v/v) to afford compound A85 (90 mg) as a white solid, yield: 26.3%. $^1$H NMR (400 MHz, DMSO-d$_6$): δ ppm 3.80 (t, J=4.8 Hz, 2H), 4.01 (t, J=4.8 Hz, 2H), 4.23 (s, 2H), 5.33 (s, 2H), 6.10 (s, 2H), 7.28-7.30 (m, 1H), 7.43-7.46 (m, 2H), 7.52-7.54 (m, 1H), 7.58-7.62 (m, 3H), 7.93 (s, 1H), 8.60-8.61 (m, 2H).

LCMS: Rt=0.90 min, MS Calcd.: 376.2, MS Found: 376.8 [M+H]$^+$.

Example 37 HPK1 ADP-Glo Enzyme Assay

The buffer used in the enzyme assay contains 5 mM MOPS (pH=7.2), 2.5 mM β-Glycerol Phosphate, 0.4 mM EDTA, 1 mM EGTA, 0.05 mM DTT, 5 mM MgCl$_2$. The compound was dissolved in 100% DMSO at the concentration was 10 mM. The initial concentration of the test was 5 uM, and ten data points were diluted by three-fold gradient, and each point was repeatedly measured twice. The HPK1 protein was purchased from Thermo (Cat. No. PV6355) and diluted to 2× stock solution at the concentration of 10 nM (the final concentration of the enzyme assay was 5 nM). 2.5 μl of 2×HPK1 protein was added to each well of the plate containing the test compound, centrifuged at 1000 rpm for 30 seconds, and then incubated at 25° C. for 15 minutes. MBP protein was purchased from Millipore (Cat. No. 13-110) and ATP was purchased from Sigma (Cat. No. A7699-5G) and the two were formulated into 2× working solutions at concentrations of 4 uM and 80 uM. Added 2.5 μl mixture of 2×MBP and ATP, centrifuged at 1000 rpm for 30 seconds, then incubated at 25° C. for 90 minutes. Then added 5 ul of ADP-Glo™ (Promega, Cat. No. V9102) to the assay plate and incubated at 1000 rpm for 30 minutes at 25° C. for 60 minutes. Finally, 10 ul of the kinase assay reagent (Promega, Cat. No. V9102) was added to the assay plate, centrifuged at 1000 rpm for 30 seconds at 25° C. for 60 minutes, and the fluorescence intensity was determined. Based on the results, the IC$_{50}$ of the compound is calculated. The results of IC$_{50}$ are shown in the following table:

TABLE 1

HPK1 ADP-Glo enzyme assay

| Compound Code | IC$_{50}$ |
|---|---|
| A1 | IC$_{50}$ < 100 nM |
| A2 | 100 nM < IC$_{50}$ < 1000 nM |
| A3 | IC$_{50}$ < 100 nM |
| A4 | 100 nM < IC$_{50}$ < 1000 nM |
| A5 | 100 nM < IC$_{50}$ < 1000 nM |
| A6 | IC$_{50}$ > 1000 nM |
| A7 | IC$_{50}$ < 100 nM |
| A8 | IC$_{50}$ < 100 nM |
| A9 | IC$_{50}$ > 1000 nM |
| A10 | IC$_{50}$ < 100 nM |
| A11 | 100 nM < IC$_{50}$ < 1000 nM |
| A12 | IC$_{50}$ < 100 nM |
| A13 | IC$_{50}$ < 100 nM |
| A14 | 100 nM < IC$_{50}$ < 1000 nM |
| A15 | 100 nM < IC$_{50}$ < 1000 nM |
| A16 | IC$_{50}$ < 100 nM |
| A17 | IC$_{50}$ < 100 nM |
| A18 | 100 nM < IC$_{50}$ < 1000 nM |
| A19 | IC$_{50}$ < 100 nM |
| A20 | IC$_{50}$ < 100 nM |
| A21 | IC$_{50}$ < 100 nM |
| A22 | IC$_{50}$ < 100 nM |
| A23 | IC$_{50}$ < 100 nM |
| A24 | IC$_{50}$ < 100 nM |
| A25 | IC$_{50}$ < 100 nM |
| A26 | IC$_{50}$ < 100 nM |
| A27 | IC$_{50}$ < 100nM |
| A28 | IC$_{50}$ < 100 nM |
| A29 | 100 nM < IC$_{50}$ < 1000 nM |
| A30 | 100 nM < IC$_{50}$ < 1000 nM |
| A31 | IC$_{50}$ < 100 nM |
| A32 | IC$_{50}$ < 100 nM |
| A33 | IC$_{50}$ > 1000 nM |
| A34 | IC$_{50}$ < 100 nM |
| A35 | 100 nM < IC$_{50}$ < 1000 nM |
| A36 | IC$_{50}$ < 100 nM |
| A37 | IC$_{50}$ < 100 nM |
| A38 | IC$_{50}$ > 1000 nM |
| A39 | IC$_{50}$ < 100 nM |
| A40 | IC$_{50}$ < 100 nM |
| A41 | IC$_{50}$ < 100 nM |
| A42 | IC$_{50}$ < 100 nM |
| A43 | 100 nM < IC$_{50}$ < 1000 nM |
| A44 | IC$_{50}$ < 100 nM |
| A45 | 100 nM < IC$_{50}$ < 1000 nM |
| A46 | IC$_{50}$ < 100 nM |
| A47 | IC$_{50}$ < 100 nM |
| A48 | IC$_{50}$ < 100 nM |
| A49 | IC$_{50}$ < 100 nM |
| A50 | IC$_{50}$ < 100 nM |
| A51 | IC$_{50}$ < 100 nM |
| A52 | IC$_{50}$ < 100 nM |
| A53 | IC$_{50}$ < 100 nM |
| A54 | IC$_{50}$ < 100 nM |
| A55 | IC$_{50}$ < 100 nM |
| A56 | IC$_{50}$ < 100 nM |
| A57 | IC$_{50}$ < 100 nM |
| A58 | 100 nM < IC$_{50}$ < 1000 nM |
| A59 | IC$_{50}$ < 100 nM |
| A60 | IC$_{50}$ < 100 nM |
| A61 | 100 nM < IC$_{50}$ < 1000 nM |
| A62 | 100 nM < IC$_{50}$ < 1000 nM |
| A63 | IC$_{50}$ < 100 nM |
| A64 | IC$_{50}$ < 100 nM |
| A65 | IC$_{50}$ < 100 nM |
| A66 | IC$_{50}$ < 100 nM |
| A67 | IC$_{50}$ < 100 nM |
| A68 | IC$_{50}$ < 100 nM |
| A69 | IC$_{50}$ < 100 nM |
| A70 | IC$_{50}$ < 100 nM |
| A71 | IC$_{50}$ < 100 nM |
| A72 | IC$_{50}$ < 100 nM |
| A73 | IC$_{50}$ < 100 nM |
| A74 | IC$_{50}$ < 100 nM |
| A75 | IC$_{50}$ < 100 nM |

TABLE 1-continued

HPK1 ADP-Glo enzyme assay

| Compound Code | IC$_{50}$ |
|---|---|
| A76 | IC$_{50}$ < 100 nM |
| A77 | IC$_{50}$ < 100 nM |
| A78 | 100 nM < IC$_{50}$ < 1000 nM |
| A79 | IC$_{50}$ < 100 nM |
| A80 | IC$_{50}$ < 100 nM |
| A81 | IC$_{50}$ < 100 nM |
| A82 | IC$_{50}$ < 100 nM |
| A83 | IC$_{50}$ < 100 nM |
| A84 | IC$_{50}$ < 100 nM |
| A85 | IC$_{50}$ > 1000 nM |

Example 38. Jurkat E6-1 pSLP-76(Ser376) HTRF Experiment

Jurkat E6-1 cells were purchased from ATCC (Cat. No. TIB-152™) and cultured overnight with RPMI 1640 containing 0.5% FBS, after that 20 µL (10$^7$ cells/mL) cells were added to the experimental plates. Then the test compounds were diluted by three-fold gradient, and 10 different concentrations were prepared, and 5 µl of each was added to the experimental plate, and incubated for 4 hours in 37° C. incubator containing 5% CO$_2$. Then 5 ul of 6× anti-human CD3 antibody (Biolegend, Cat. No. 300432) was added and incubated for 20 minutes in 37° C. incubator containing 5% CO$_2$. Finally, the Phospho-SLP-76 and SLP-76 results were determined using the Cisbio Phospho-SLP-76 and SLP-76 HTRF assay kits (items: 63ADK076PEH and 63ADK077PEH, respectively). Based on the results, the IC$_{50}$ of the compound is calculated. The results of IC$_{50}$ are shown in the following table:

TABLE 2

Jurkat E6-1 pSLP-76(Ser376) HTRF experiment

| Compound Number | IC$_{50}$ |
|---|---|
| A2 | 1000 nM < IC$_{50}$ < 50000 nM |
| A1 | IC$_{50}$ < 1000 nM |
| A3 | IC$_{50}$ < 1000 nM |
| A4 | 1000 nM < IC$_{50}$ < 50000 nM |
| A5 | 1000 nM < IC$_{50}$ < 50000 nM |
| A7 | IC$_{50}$ < 1000 nM |
| A8 | 1000 nM < IC$_{50}$ < 50000 nM |
| A10 | IC$_{50}$ < 1000 nM |
| A11 | 1000 nM < IC$_{50}$ < 50000 nM |
| A12 | IC$_{50}$ < 1000 nM |
| A13 | IC$_{50}$ < 1000 nM |
| A17 | 1000 nM < IC$_{50}$ < 50000 nM |
| A20 | 1000 nM < IC$_{50}$ < 50000 nM |
| A19 | IC$_{50}$ < 1000 nM |
| A21 | IC$_{50}$ < 1000 nM |
| A22 | IC$_{50}$ < 1000 nM |
| A23 | IC$_{50}$ < 1000 nM |
| A24 | IC$_{50}$ < 1000 nM |
| A25 | IC$_{50}$ < 1000 nM |
| A26 | IC$_{50}$ < 1000 nM |
| A27 | 1000 nM < IC$_{50}$ < 50000 nM |
| A28 | IC$_{50}$ < 1000 nM |
| A31 | IC$_{50}$ < 1000 nM |
| A32 | IC$_{50}$ < 1000 nM |
| A34 | IC$_{50}$ < 1000 nM |
| A35 | 1000 nM < IC$_{50}$ < 50000 nM |
| A36 | 1000 nM < IC$_{50}$ < 50000 nM |
| A37 | IC$_{50}$ < 1000 nM |
| A39 | IC$_{50}$ < 1000 nM |
| A40 | IC$_{50}$ < 1000 nM |
| A41 | 1000 nM < IC$_{50}$ < 50000 nM |
| A42 | IC$_{50}$ < 1000 nM |
| A43 | 1000 nMIC$_{50}$ < 50000 nM |
| A44 | 1000 nM < IC$_{50}$ < 50000 nM |
| A45 | 1000 nM < IC$_{50}$ < 50000 nM |
| A46 | IC$_{50}$ < 1000 nM |
| A47 | IC$_{50}$ < 1000 nM |
| A48 | IC$_{50}$ < 1000 nM |
| A49 | IC$_{50}$ < 1000 nM |
| A50 | IC$_{50}$ < 1000 nM |
| A51 | IC$_{50}$ < 1000 nM |
| A52 | IC$_{50}$ < 1000 nM |
| A53 | IC$_{50}$ < 1000 nM |
| A54 | IC$_{50}$ < 1000 nM |
| A55 | IC$_{50}$ < 1000 nM |
| A56 | IC$_{50}$ < 1000 nM |
| A71 | IC$_{50}$ < 1000 nM |
| A57 | IC$_{50}$ < 1000 nM |
| A59 | IC$_{50}$ < 1000 nM |
| A60 | IC$_{50}$ < 1000 nM |
| A63 | IC$_{50}$ < 1000 nM |
| A64 | IC$_{50}$ < 1000 nM |

Example 39. Screening for Candidate Compounds that Enhance Cytotoxicity of CAR-T Cells The following protocol was followed to assess the ability of various compounds to enhance cytotoxicity of CAR-T cells: Incubate CAR-T cell with 100 nM of compounds for 48 hours in a humidified incubator at 37° C. and 5% CO$_2$. Transfer combinations of compound and CAR-T to a plate pre-coated with tumor cells and incubate over 12 hours at 37° C. and 5% CO$_2$. Lyse tumor cells by adding 10×Lysis Solution, and incubate for 30 minutes at 37° C. Centrifuge plate at 500 rpm for 3 minutes. Transfer 50 µl of supernatant from all wells to a fresh 96-well flat-bottom plate. Add 50 µl of Substrate Mix to each well, and incubate 30 minutes at 37° C. Protect the plate from light and incubate for 30 minutes at 37° C. Add 50 µl of Stop Solution to each well. Avoid bubbles, and record the absorbance at 490 nm or 492 nm within 1 hour after adding Stop Solution.

Calculate % cytotoxicity with (Experimental−Effector Spontaneous−Target Spontaneous)/(Target Maximum−Target Spontaneous.

The results are shown in FIG. 1.

Finally, it should be noted that the above embodiments are merely illustrative of the technical solutions of the present invention, and are not intended to be limiting. Although the present invention has been described in detail with reference to the foregoing embodiments, those skilled in the art will understand that the technical solutions described in the foregoing embodiments may be modified, or some or all of the technical features may be equivalently replaced; and the modifications or substitutions do not deviate from the technical solutions of the embodiments of the present invention.

The invention claimed is:
1. A compound of Formula Y or Z, or a pharmaceutically acceptable salt thereof,

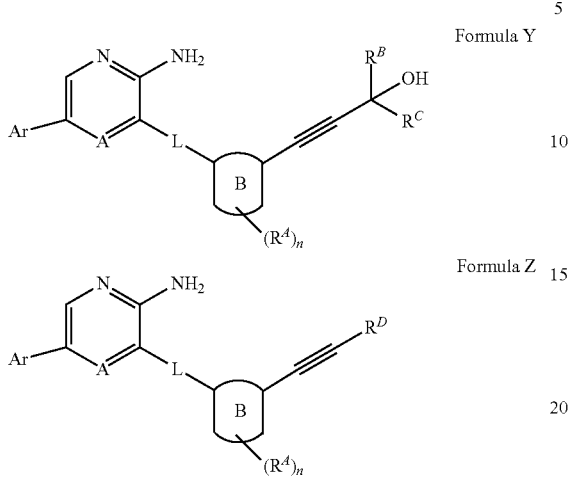

wherein:

A is CH;

Ar is an optionally substituted phenyl or an optionally substituted 5 or 6-membered heteroaryl selected from thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, wherein:

(i) the optionally substituted 5 or 6-membered heteroaryl is optionally substituted with one or more substituents independently selected from alkyl, alkenyl, alkynyl, cycloalkyl, heterocyclyl, aryl, heteroaryl, —O—$R^{100}$, —$NR^{101}R^{102}$, —C(=O)—$R^{103}$, —$NR^{101}$—C(=O)—$R^{103}$, —$NR^{101}$—$SO_2$—$R^{104}$, —$SO_2$—$R^{104}$, —$NR^{101}$—$POR^{105}R^{106}$, —$POR^{105}R^{106}$, —$SR^{107}$, halogen, and —CN, wherein each $R^{100}$ is independently selected from hydrogen, an oxygen protecting group, alkyl, alkenyl, alkynyl, cycloalkyl, heterocyclyl, aryl, and heteroaryl;

each $R^{101}$ or $R^{102}$ is independently selected from hydrogen, a nitrogen protecting group, alkyl, alkenyl, alkynyl, cycloalkyl, heterocyclyl, aryl, and heteroaryl;

each $R^{103}$ is independently selected from hydrogen, alkyl, alkenyl, alkynyl, cycloalkyl, heterocyclyl, aryl, heteroaryl, —O—$R^{100}$ and —$NR^{101}R^{102}$;

each $R^{104}$ is independently selected from hydrogen, alkyl, alkenyl, alkynyl, cycloalkyl, heterocyclyl, aryl, heteroaryl, —O—$R^{100}$ and —$NR^{101}R^{102}$;

each $R^{105}$ or $R^{106}$ is independently selected from hydrogen, alkyl, alkenyl, alkynyl, cycloalkyl, heterocyclyl, aryl, heteroaryl, —O—$R^{100}$ and —$NR^{101}R^{102}$;

each $R^{107}$ is independently selected from hydrogen, a thiol protecting group, alkyl, alkenyl, alkynyl, cycloalkyl, heterocyclyl, aryl, and heteroaryl;

wherein each of the alkyl, alkenyl, alkynyl, cycloalkyl, heterocyclyl, aryl, and heteroaryl is optionally substituted with one or more substituents each independently selected from 1) $C_{1-7}$ alkyl optionally substituted with 1-3 substituents each independently selected from halogen, oxo, —OH or protected OH, optionally substituted $C_{1-4}$ alkoxy, —$NH_2$ or protected $NH_2$, —N($C_{0-4}$ alkyl)($C_{0-4}$ alkyl), optionally substituted $C_{3-6}$ cycloalkyl, optionally substituted phenyl, optionally substituted 5- or 6-membered heteroaryl, and optionally substituted 4-8 membered heterocyclyl; 2) halogen; 3) —OH or protected OH; 4) optionally substituted $C_{1-4}$ alkoxy; 5) —$NH_2$ or protected $NH_2$; 6) —N($C_{0-4}$ alkyl)($C_{0-4}$ alkyl), wherein the alkyl is optionally substituted; 7) optionally substituted $C_{3-6}$ cycloalkyl; 8) optionally substituted phenyl; 9) optionally substituted 5- or 6-membered heteroaryl; and 10) optionally substituted 4-8 membered heterocyclyl; or (ii) when applicable, two adjacent substituents of the optionally substituted 5 or 6-membered heteroaryl form an optionally substituted cycloalkyl, heterocyclyl, aryl, or heteroaryl ring;

L is a linker of formula $J^1$-$J^2$-$J^3$, wherein each of $J^1$, $J^2$, and $J^3$ is independently null, O, S, SO, $SO_2$, C=O, NH, optionally substituted $C_{1-4}$ alkylene, provided that L does not contain O—O, O—N, S—S, N—S, O—S, or N—N bond, and at most one of $J^1$, $J^2$, and $J^3$ is SO, $SO_2$, or C=O;

ring B is an aryl or heteroaryl ring;

n is 0, 1, 2, or 3, as valance permits, each $R^A$ is independently selected from halogen, optionally substituted alkyl, optionally substituted alkenyl, optionally substituted alkynyl, CN, OH, optionally substituted alkoxy, optionally substituted cycloalkyl, optionally substituted cycloalkoxy, optionally substituted aryl, optionally substituted heteroaryl, and optionally substituted heterocyclyl, wherein when applicable, two adjacent $R^A$ can form an optionally substituted cycloalkyl, heterocyclyl, aryl, or heteroaryl ring, $R^B$ and $R^C$ are each independently selected from hydrogen, optionally substituted alkyl, optionally substituted alkenyl, optionally substituted alkynyl, optionally substituted cycloalkyl, optionally substituted heterocyclyl, optionally substituted aryl, and optionally substituted heteroaryl, or $R^B$ and $R^C$ together form an optionally substituted cycloalkyl or an optionally substituted heterocyclyl, $R^D$ is hydrogen, optionally substituted $C_{1-5}$ alkyl, optionally substituted $C_{3-10}$ cycloalkyl, or optionally substituted 4-7 membered heterocyclyl, wherein the triple bond in Formula Y or Z is meta to the linker L; and wherein unless otherwise indicated, (A) the above optionally substituted non-aromatic group is unsubstituted or substituted with 1, 2, or 3 substituents independently selected from F, Cl, —OH, oxo (as applicable), $C_{1-7}$ alkyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-7}$ alkyl and $C_{1-4}$ alkoxy; and (B) the above optionally substituted aromatic group is unsubstituted or substituted with 1, 2, or 3 substituents independently selected from F, Cl, —OH, —CN, $C_{1-7}$ alkyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-7}$ alkyl and $C_{1-4}$ alkoxy.

2. The compound of claim 1, or a pharmaceutically acceptable salt thereof, wherein Ar is thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, which is substituted with one or two substituents, wherein one substituent is selected from

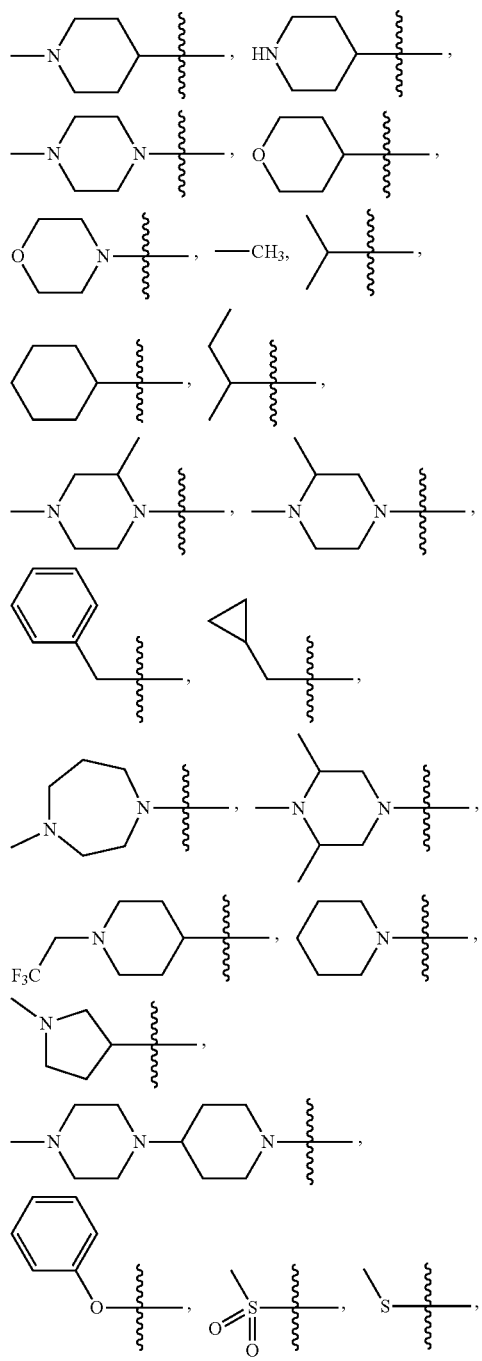

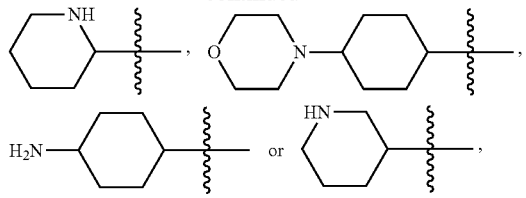

and the other substituent, when exists, is selected from halogen, methyl, ethyl, $NH_2$, or protected $NH_2$.

3. The compound of claim 1, or a pharmaceutically acceptable salt thereof, wherein Ar is

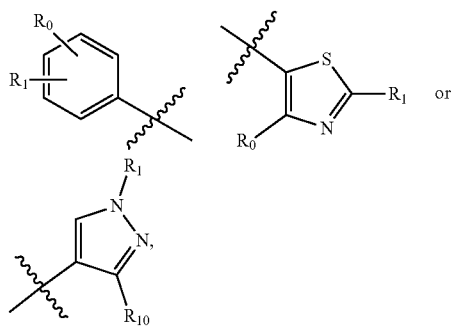

wherein $R_1$ is selected from

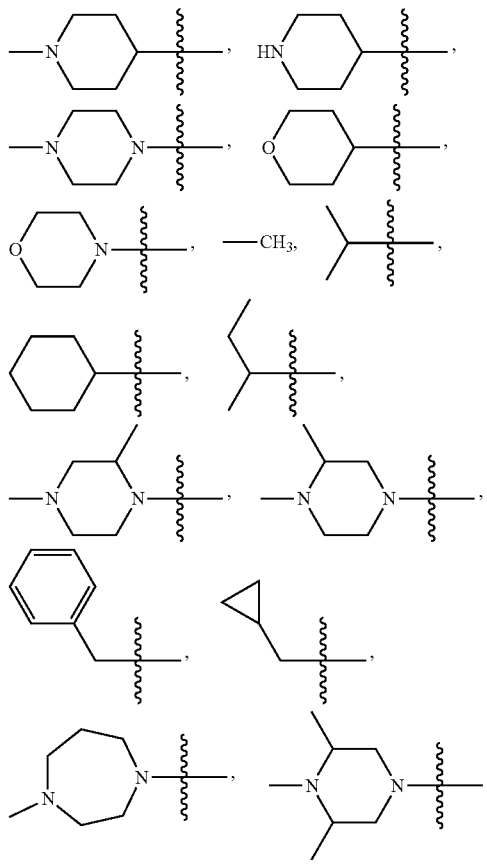

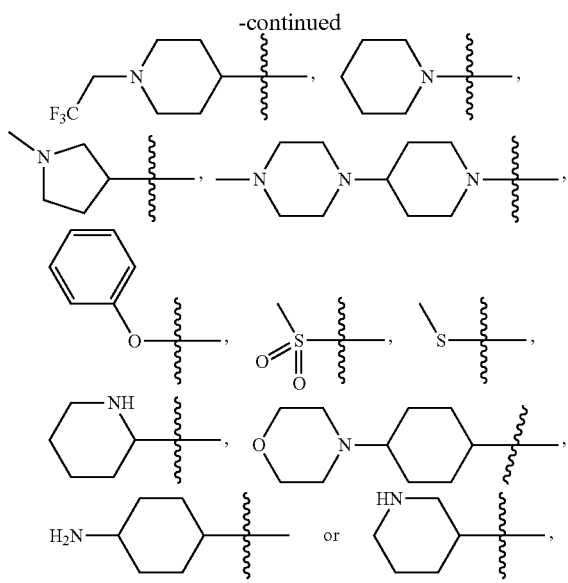

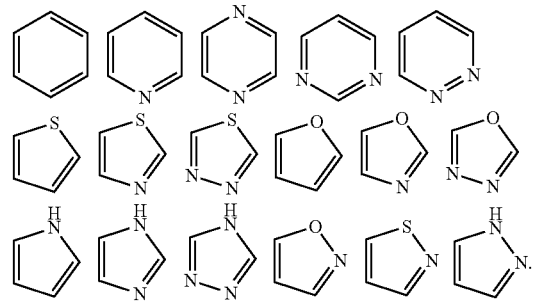

9. The compound of claim 7, or a pharmaceutically acceptable salt thereof, wherein ring B in Formula Y is a 5,5-bicyclic or 5,6-bicyclic heteroaryl ring.

10. The compound of claim 7, or a pharmaceutically acceptable salt thereof, wherein in Formula Y, $R^B$ and $R^C$ are each methyl.

11. The compound of claim 7, or a pharmaceutically acceptable salt thereof, wherein in Formula Y,

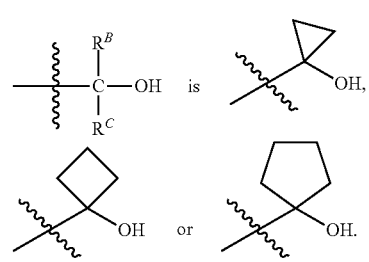

and $R_0$ is selected from hydrogen, methyl, ethyl, $NH_2$, or protected $NH_2$, provided that in

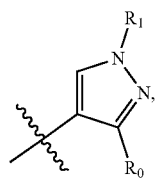

$R_1$ is not a moiety with an N, S, or O attaching point.

4. The compound of claim 1, or a pharmaceutically acceptable salt thereof, wherein L is —O—($C_{1-4}$ alkylene), —S—($C_{1-4}$ alkylene), or $C_{1-4}$ alkylene, wherein each of the $C_{1-4}$ alkylene is optionally substituted with 1-3 substituents selected from F, methyl or fluorine substituted methyl.

5. The compound of claim 1, or a pharmaceutically acceptable salt thereof, wherein L is —O—$CH_2$—, wherein the $CH_2$ is directly attached to ring B.

6. The compound of claim 1, or a pharmaceutically acceptable salt thereof, wherein ring B is a phenyl or pyridinyl ring.

7. The compound of claim 1, or a pharmaceutically acceptable salt thereof, characterized as having the Formula Y.

8. The compound of claim 7, or a pharmaceutically acceptable salt thereof, wherein ring B in Formula Y is selected from:

12. The compound of claim 7, or a pharmaceutically acceptable salt thereof, wherein in Formula Y, n is 0.

13. The compound of claim 7, or a pharmaceutically acceptable salt thereof, wherein in Formula Y, n is 1, and $R^A$ is halogen, $C_{1-7}$ alkyl optionally substituted with one or more substituents each independently selected from halogen and —OH, —CN, —OH, $C_{1-4}$ alkoxyl optionally substituted with 1-3 fluorine, $C_{3-6}$ cycloalkyl optionally substituted with 1 or 2 substituents each independently selected from F and $C_{1-7}$ alkyl, and $C_{3-6}$ cycloalkoxyl optionally substituted with 1 or 2 substituents each independently selected from F and $C_{1-7}$ alkyl.

14. The compound of claim 7, or a pharmaceutically acceptable salt thereof, wherein in Formula Y, L is —O—$CH_2$—, with the $CH_2$ directly attached to ring B.

15. A compound or a pharmaceutically acceptable salt thereof, wherein the compound is selected from:

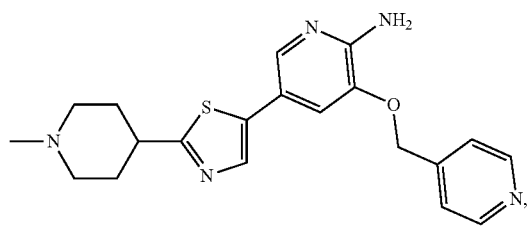

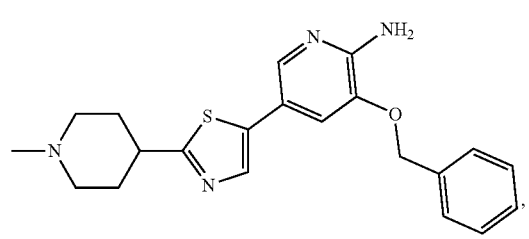

257 258
-continued
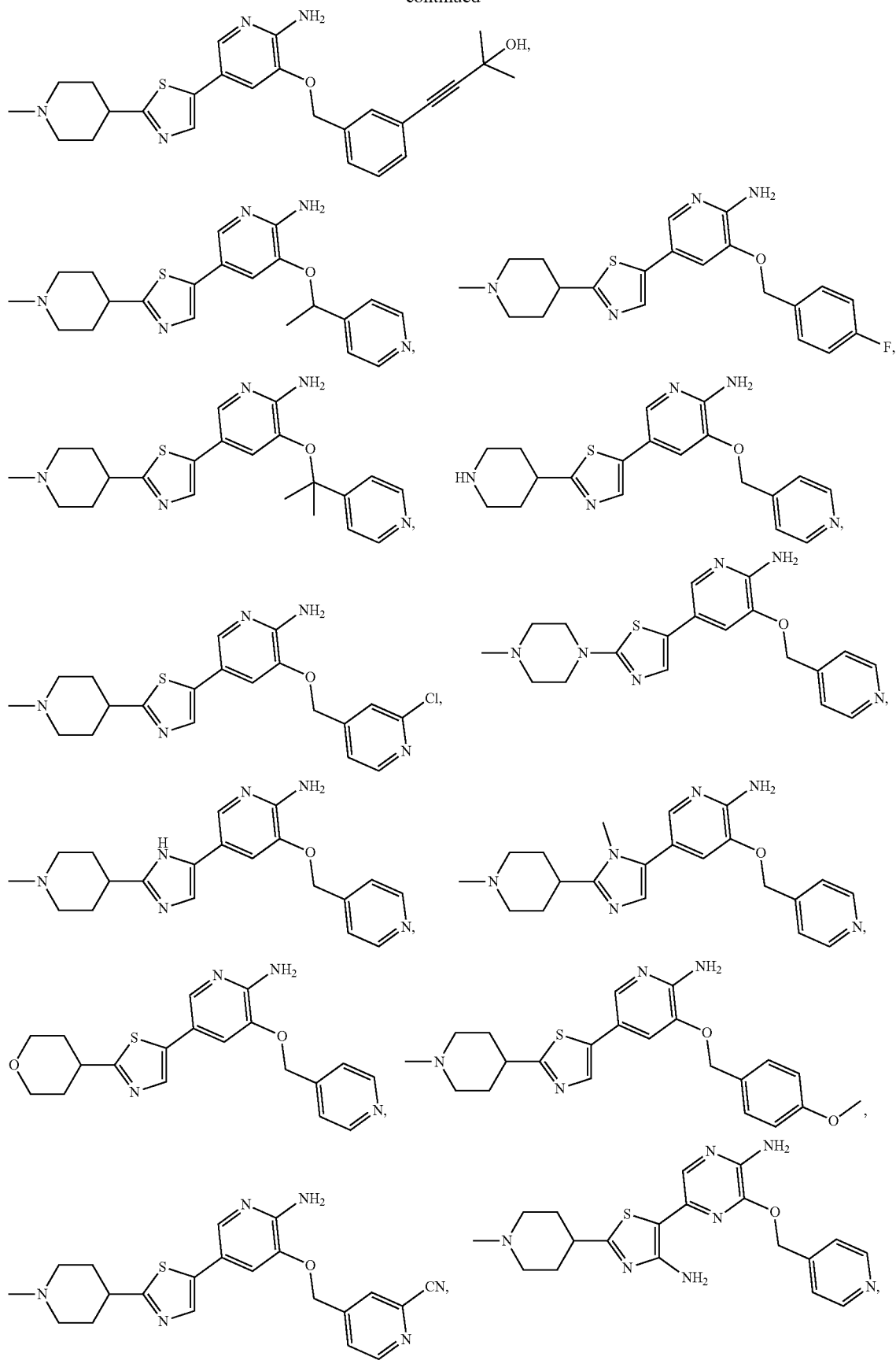

259
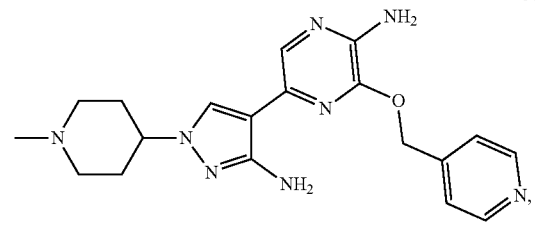
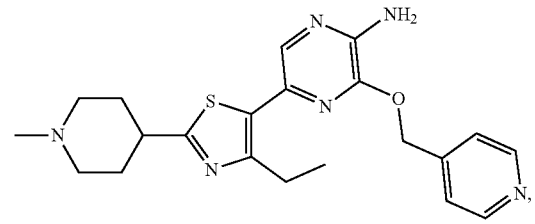
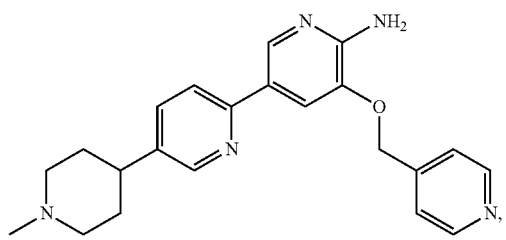
-continued
260
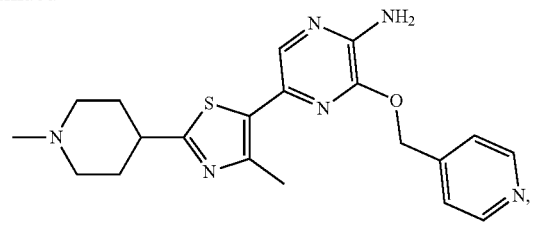
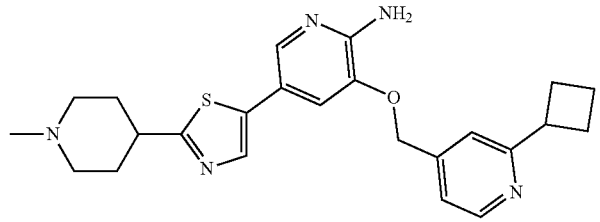
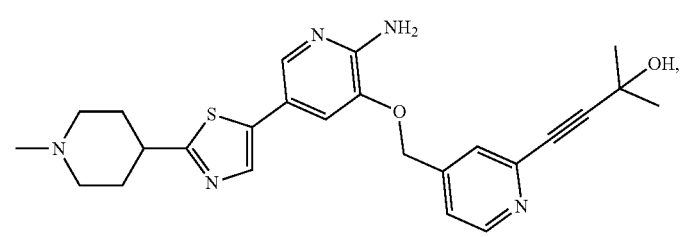
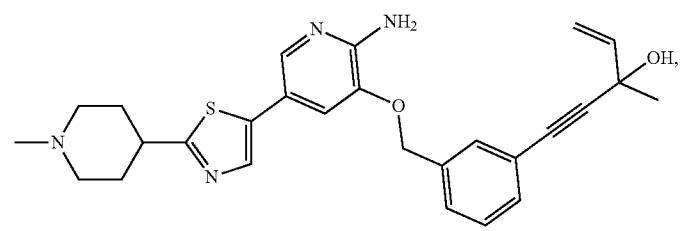
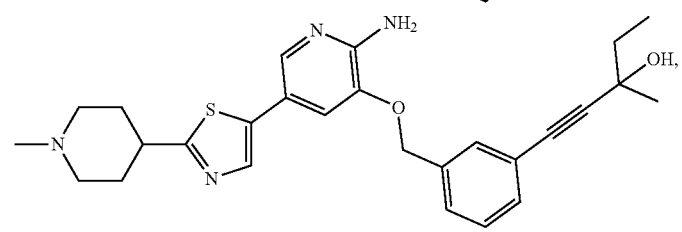
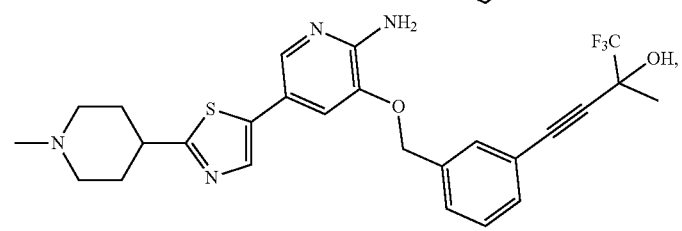
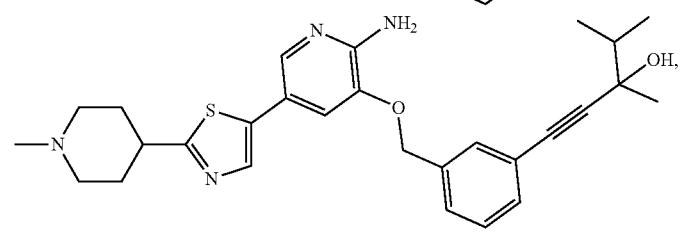

-continued
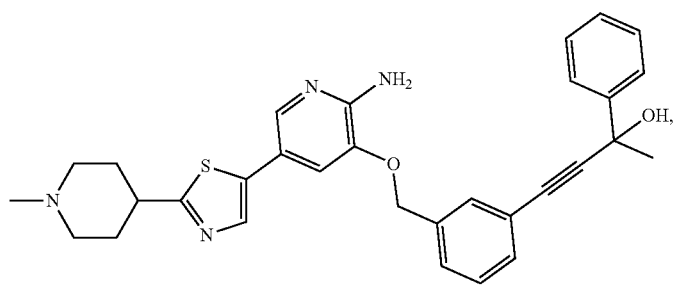
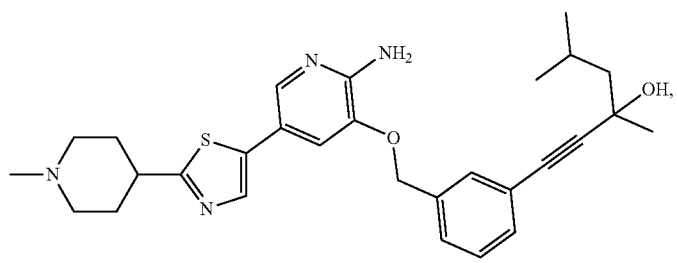
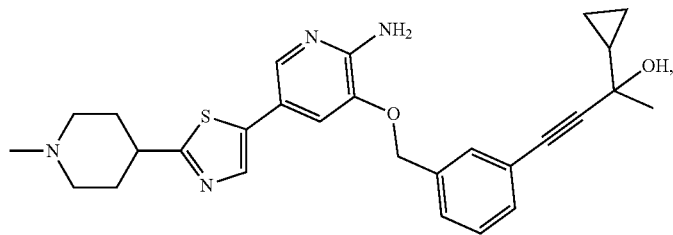
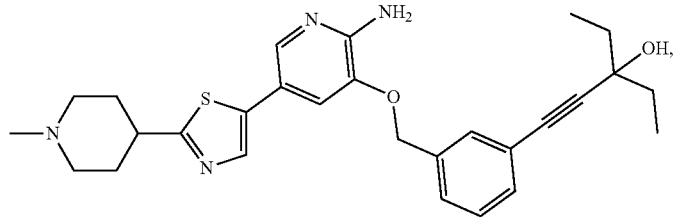
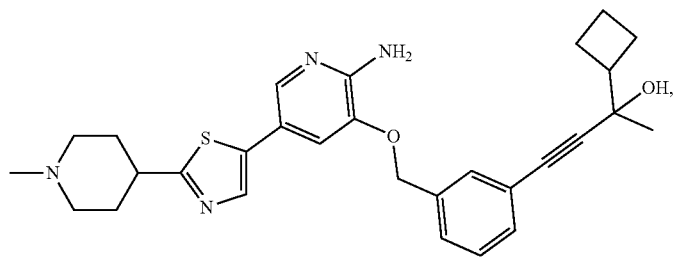
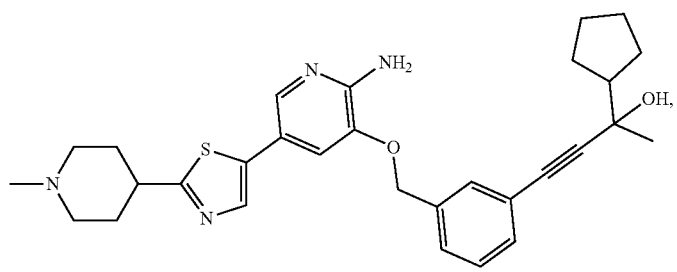

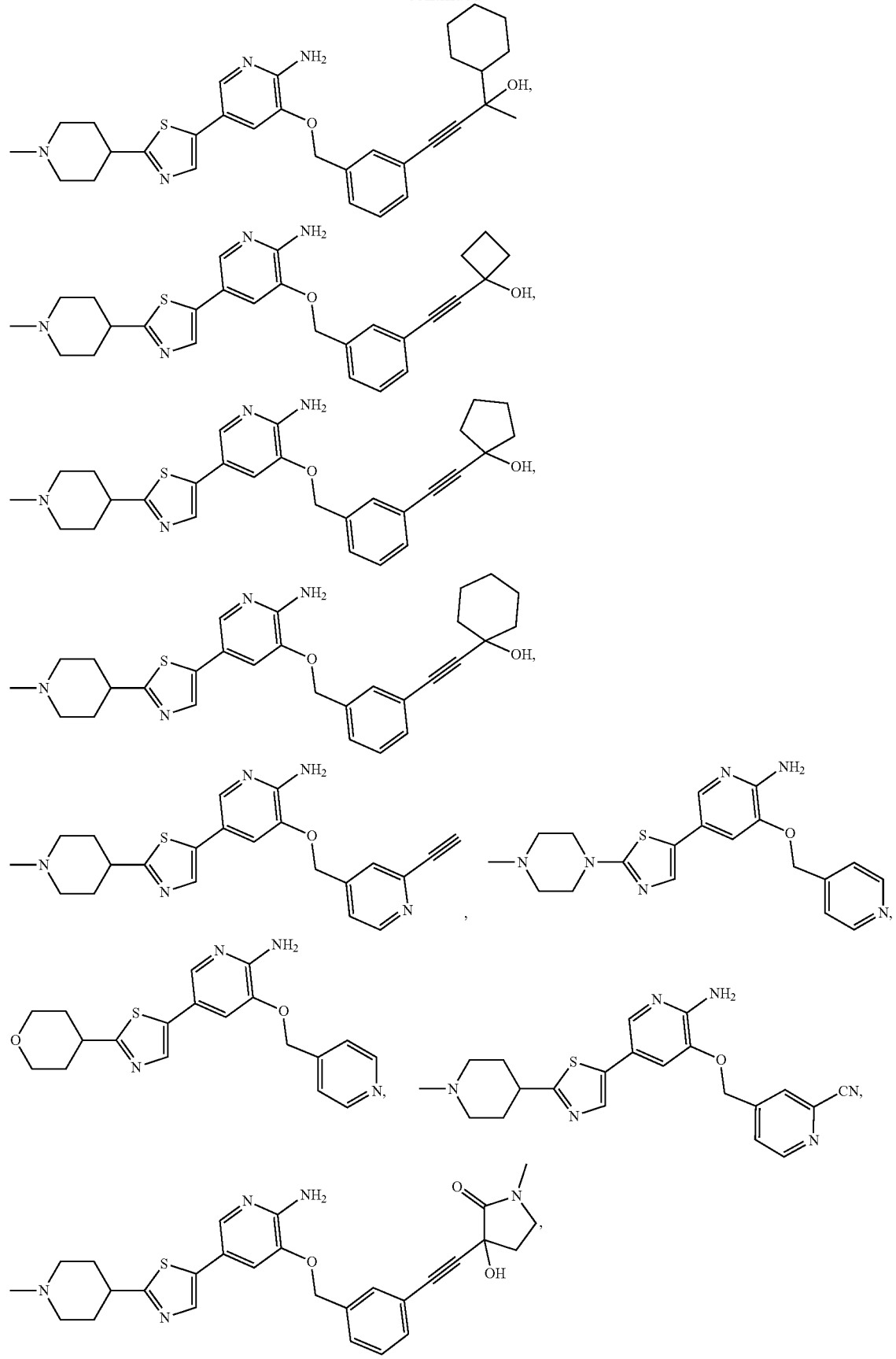

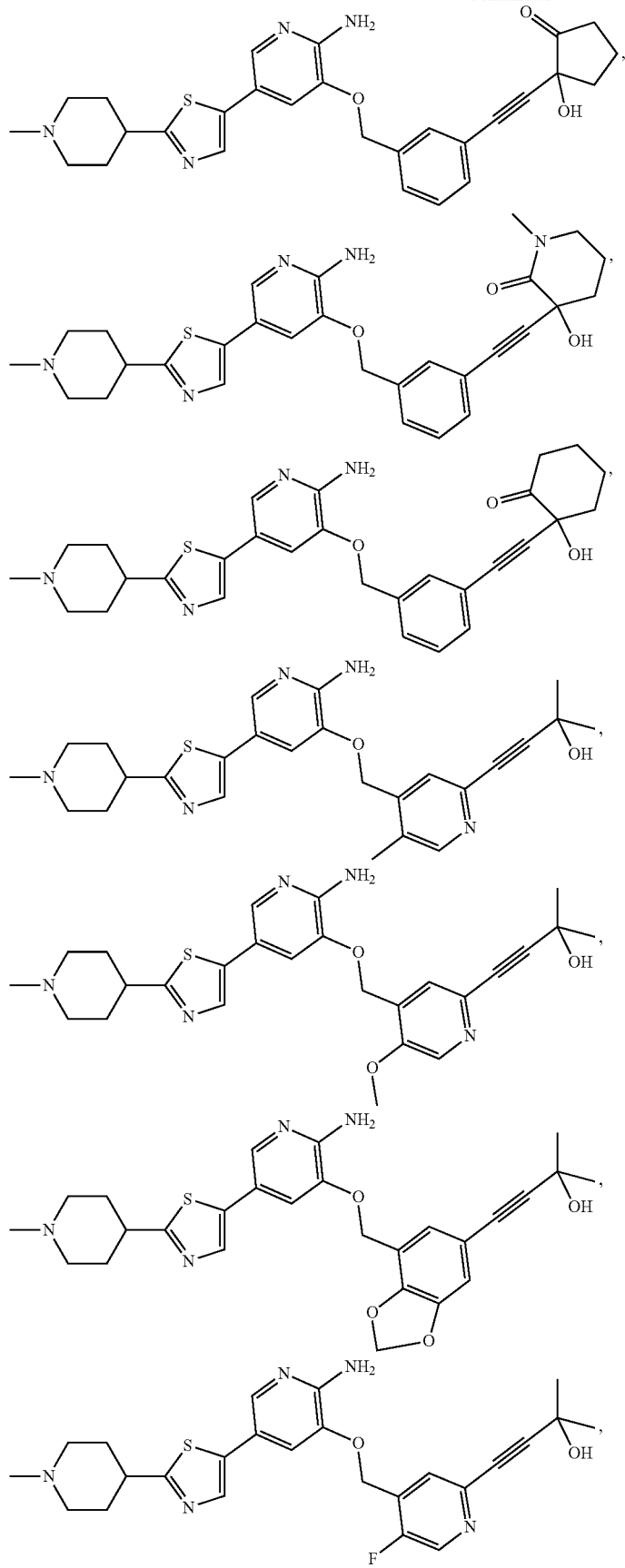

267
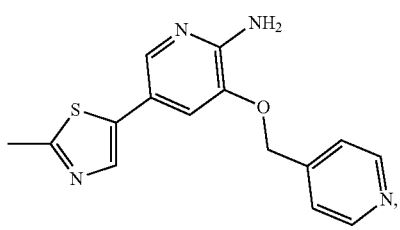
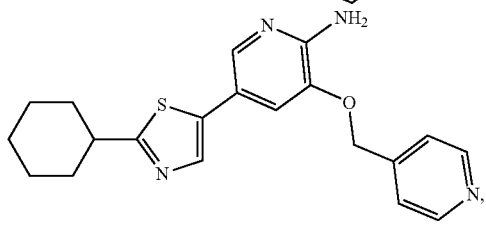
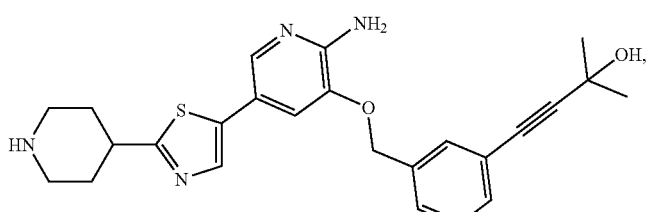
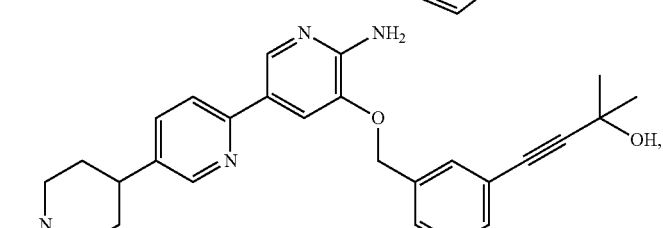
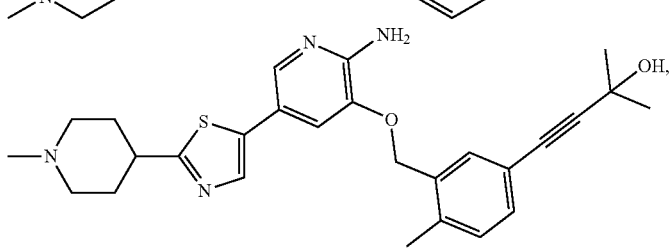
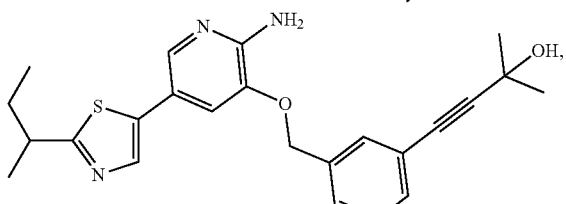
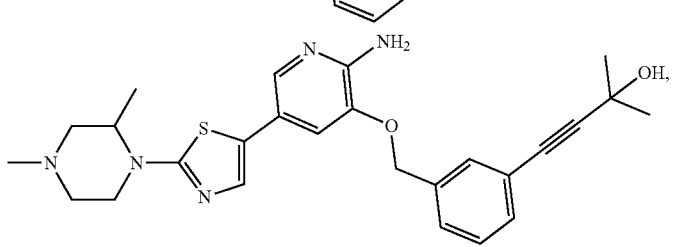
268
-continued
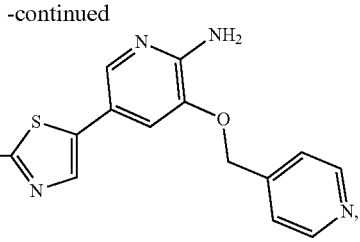
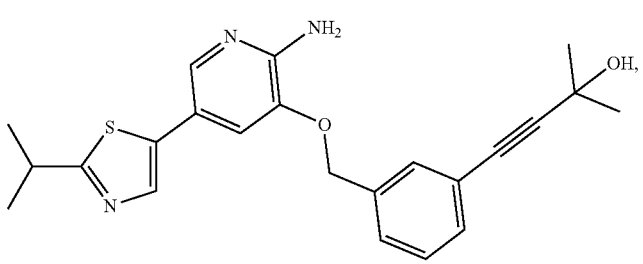

-continued
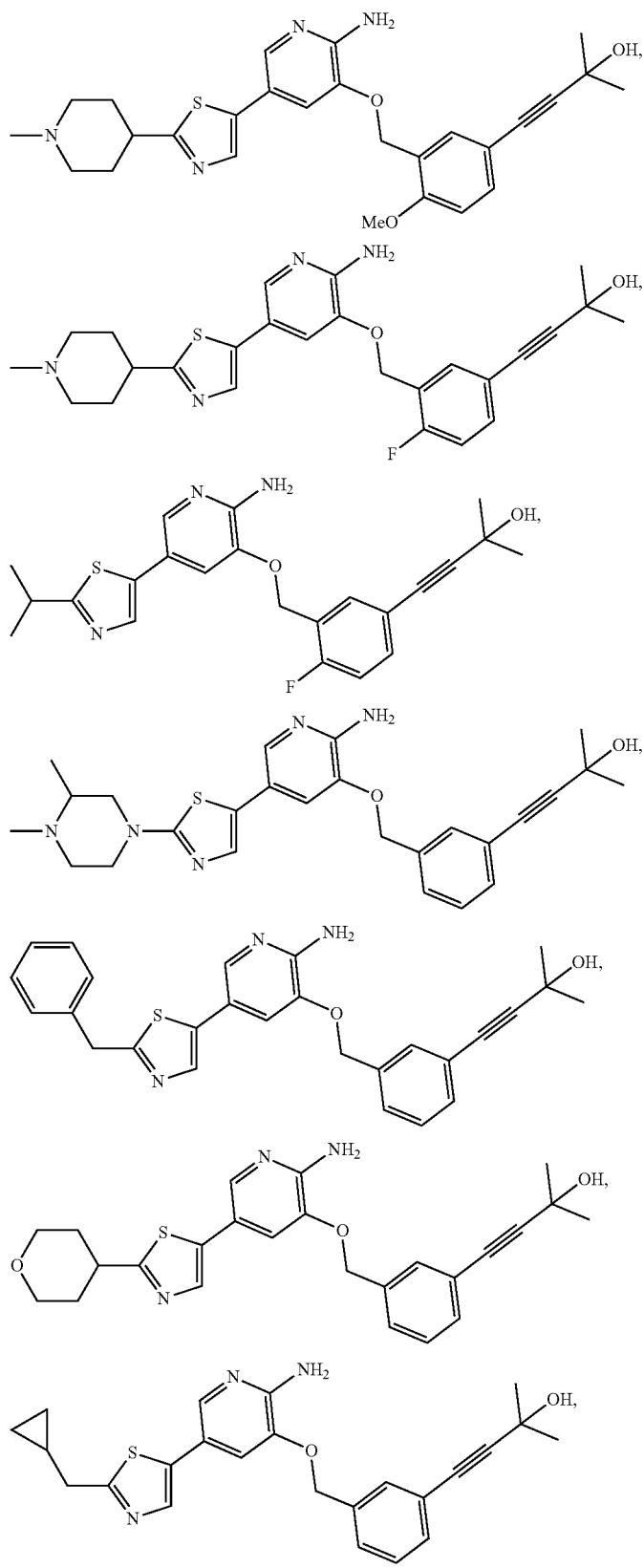

-continued
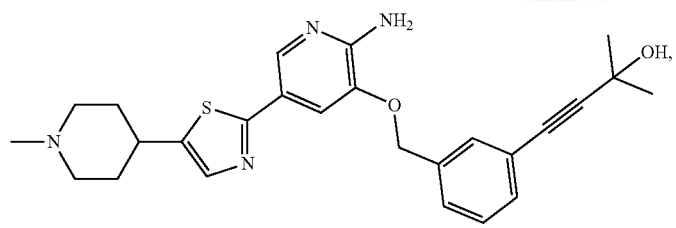
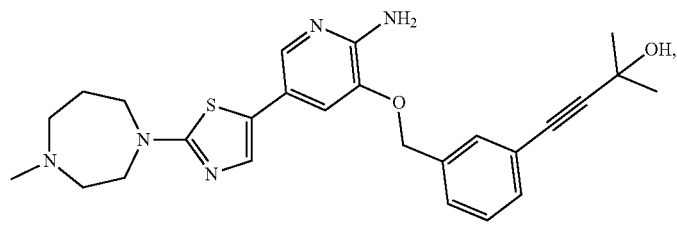
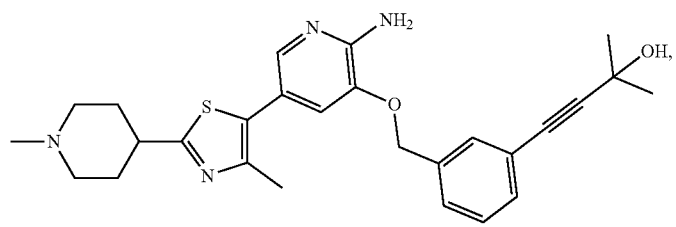
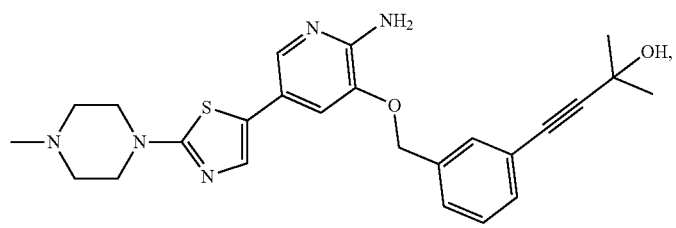
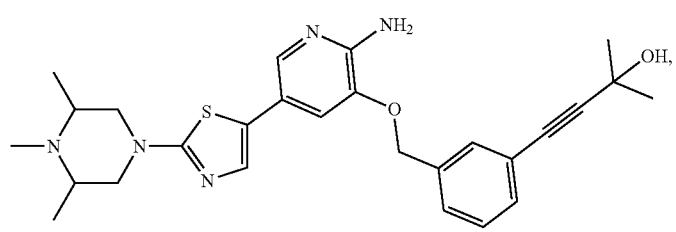
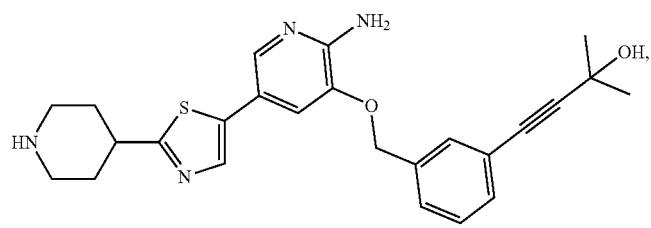
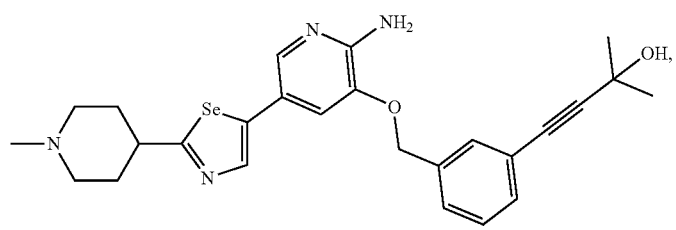

-continued
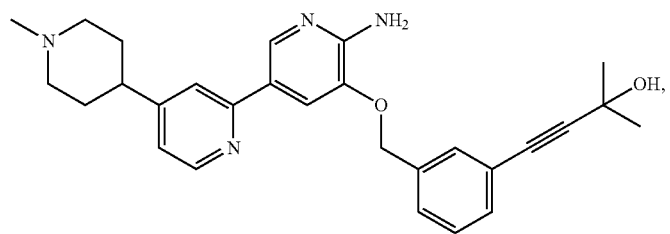
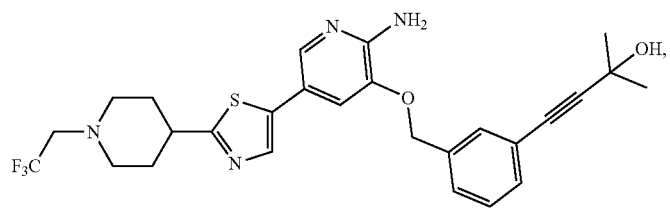
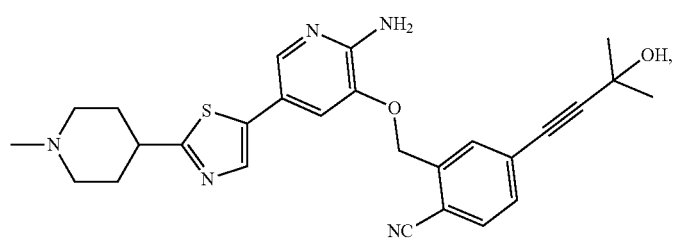
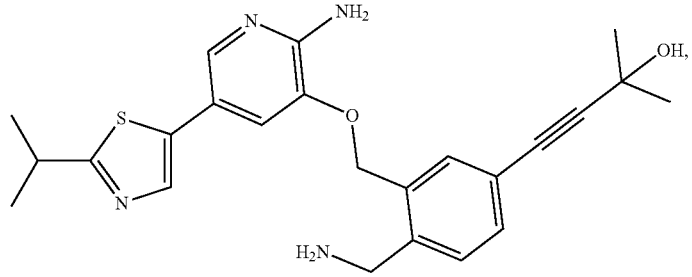
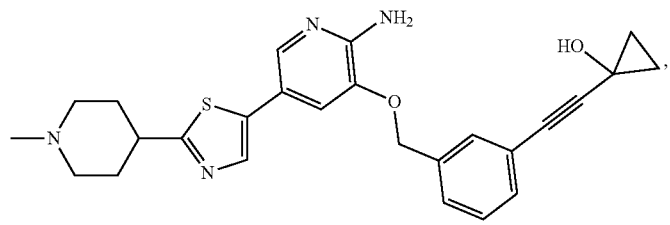
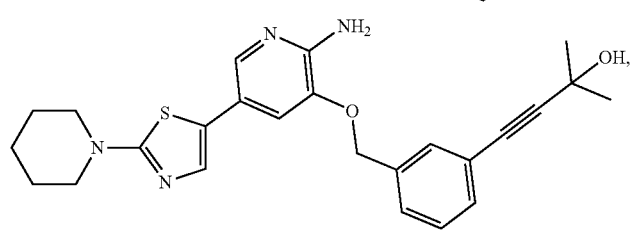
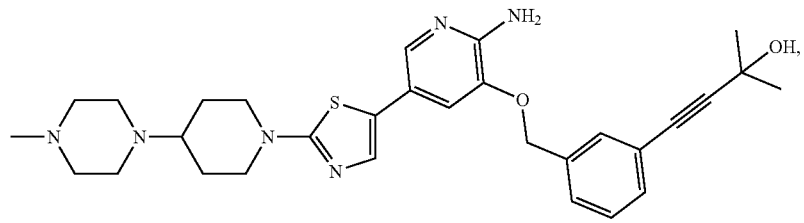

-continued
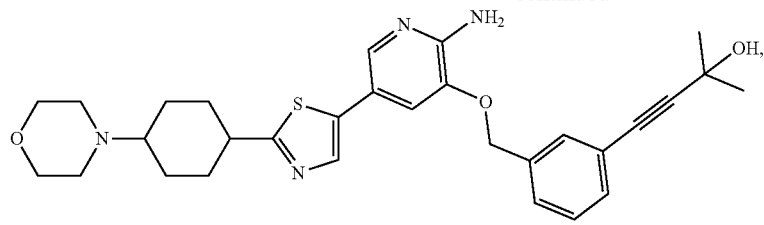
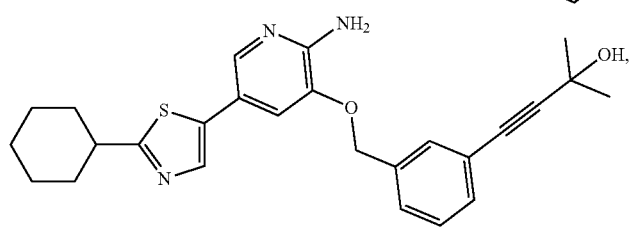
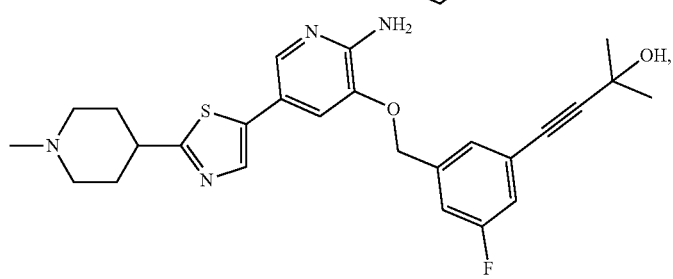
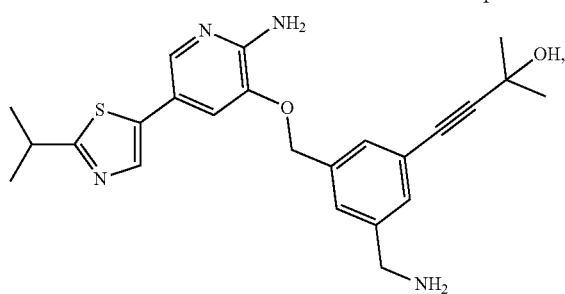
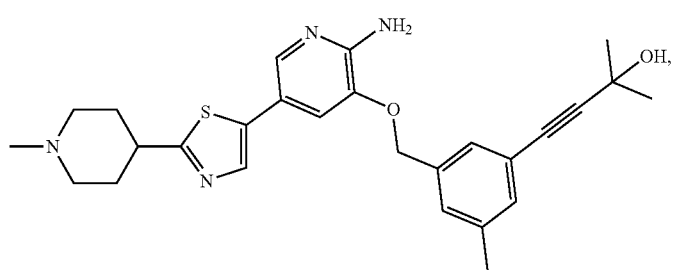 [SMILES: Cc1cc(C#CC(C)(C)O)cc(COc2cc(-c3cnc(C4CCN(C)CC4)s3)cnc2N)c1]
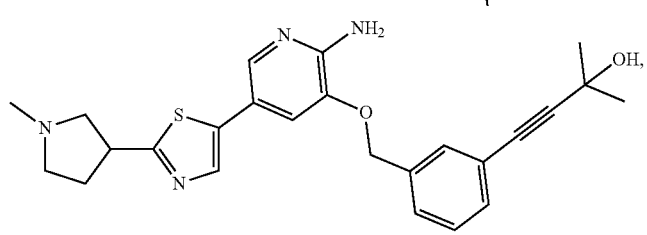
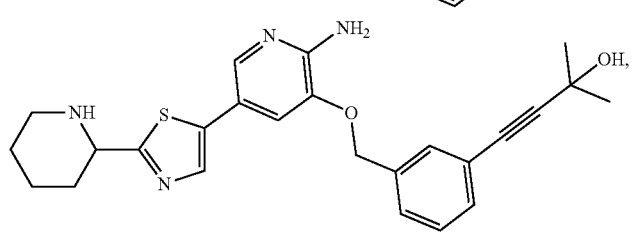

-continued
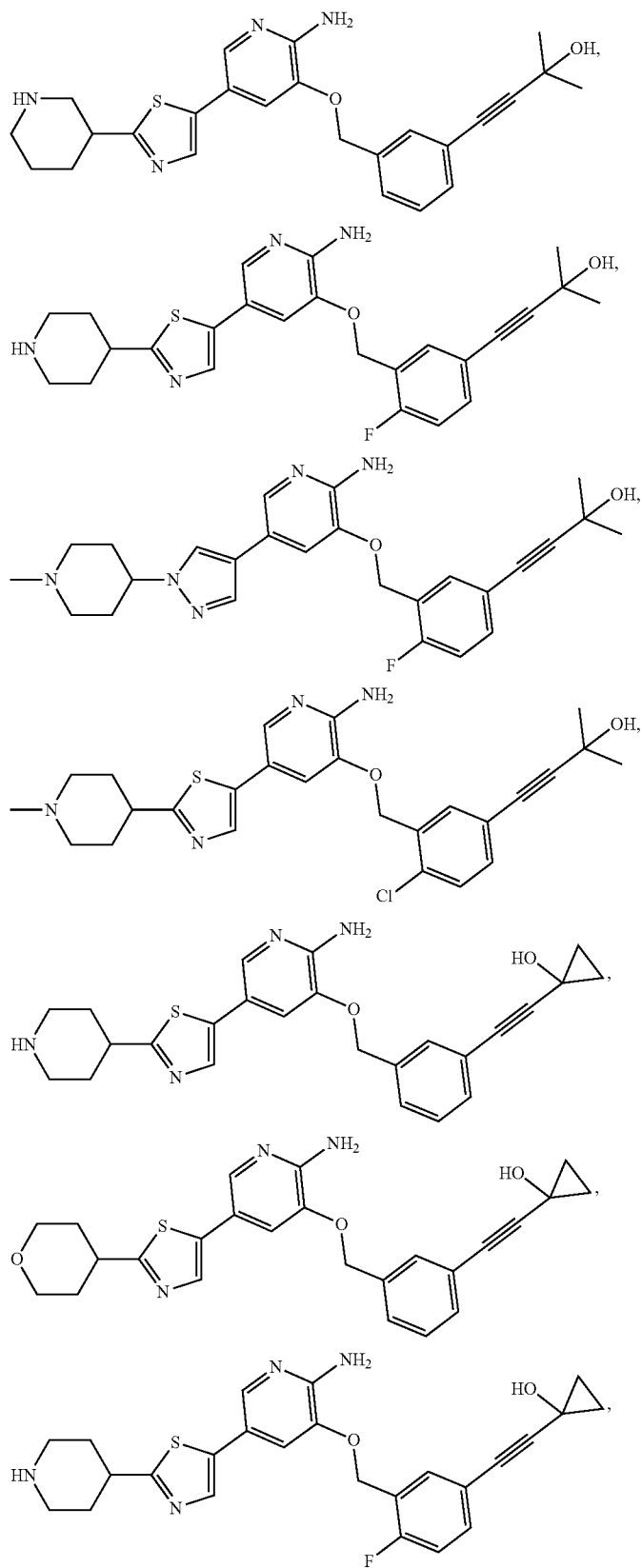

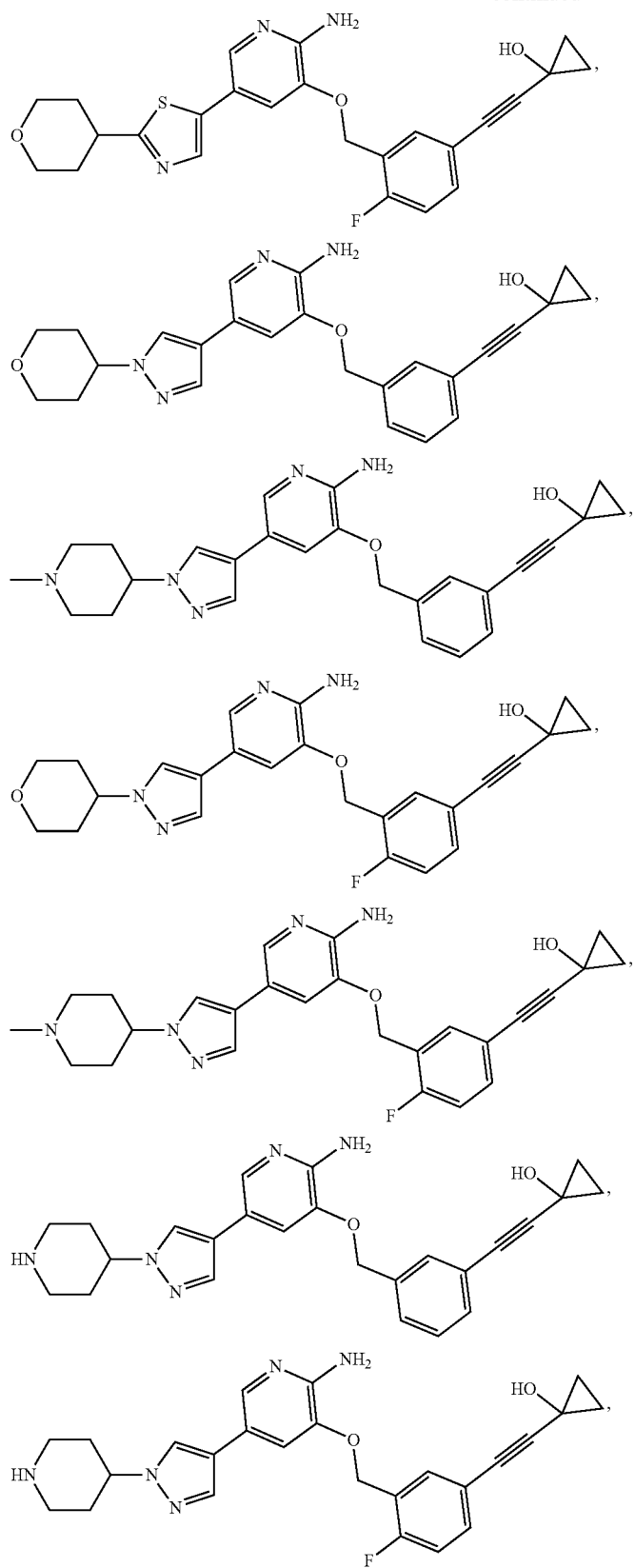

-continued
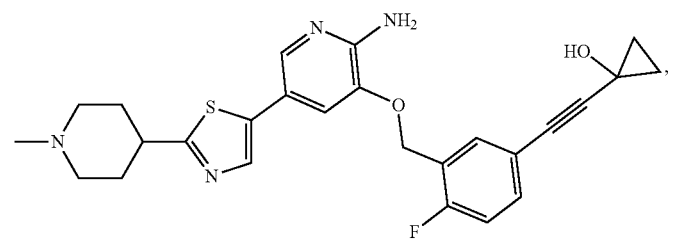
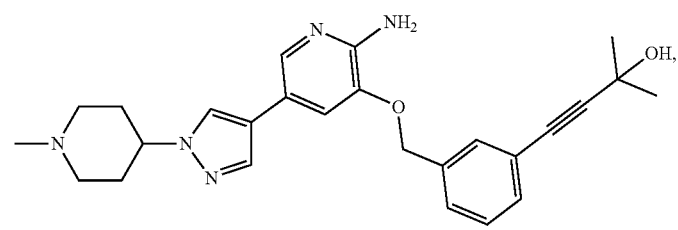
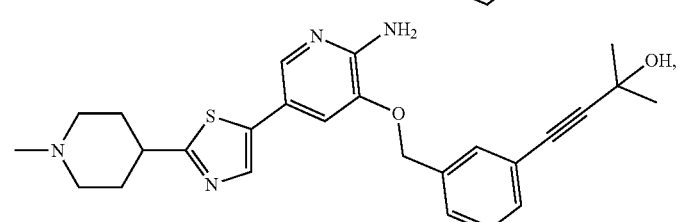
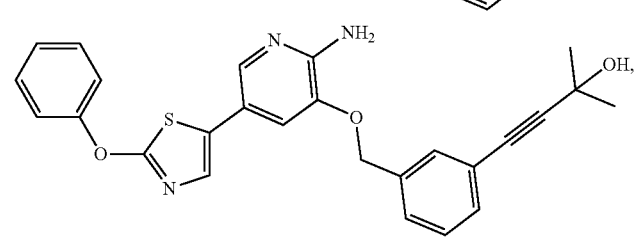
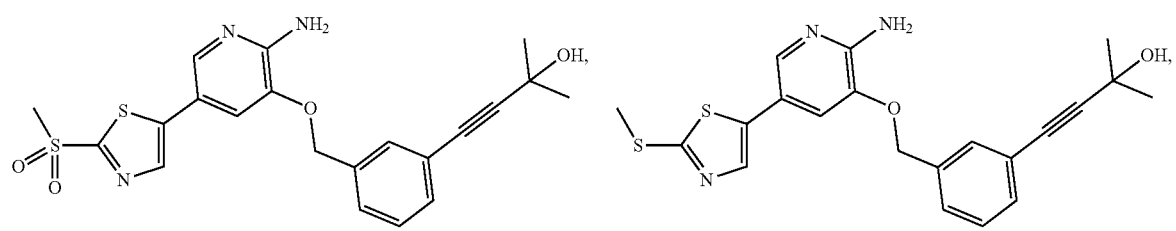
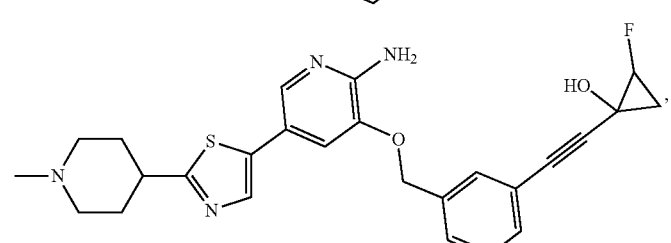
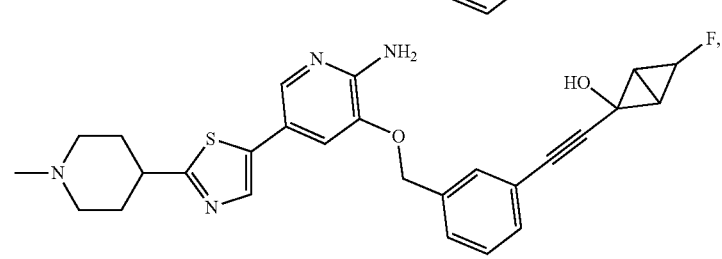

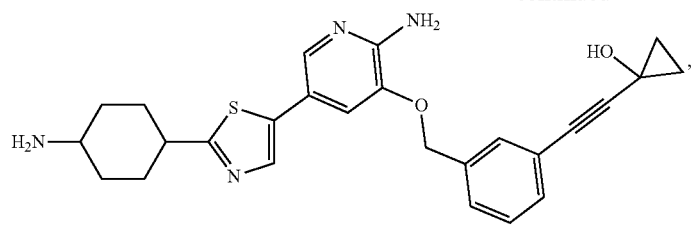
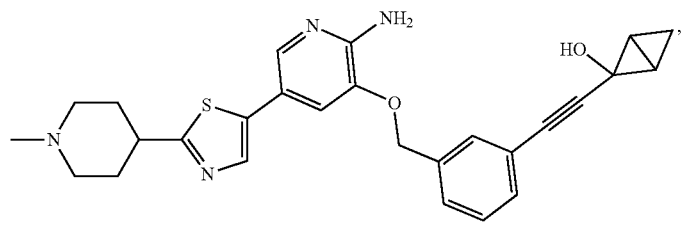
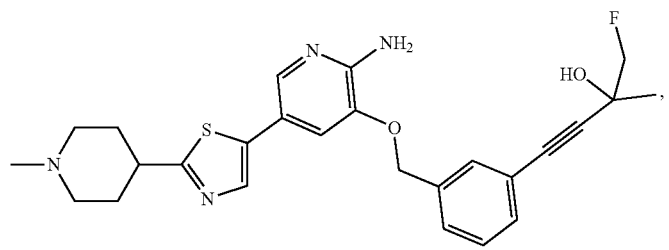
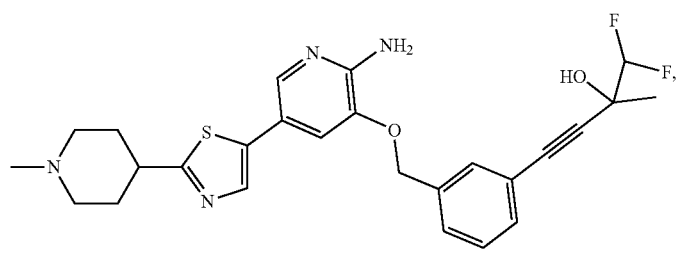
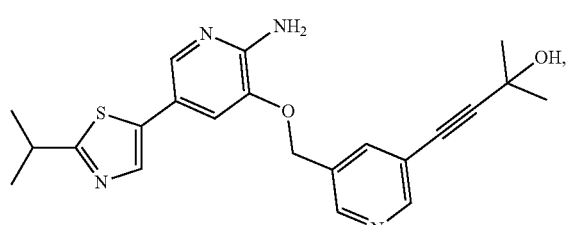
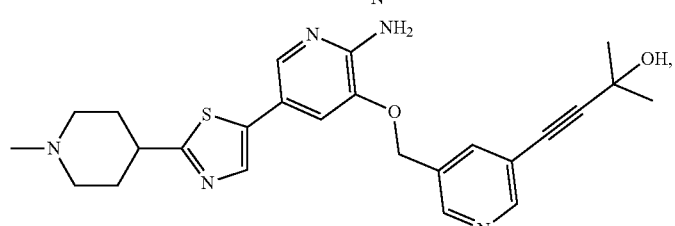
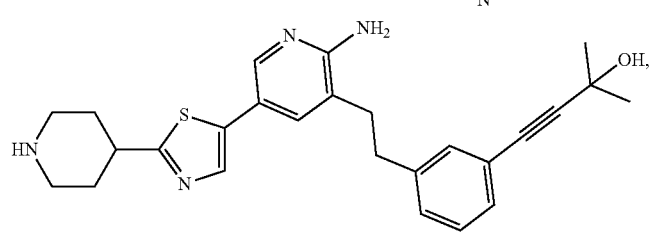

-continued
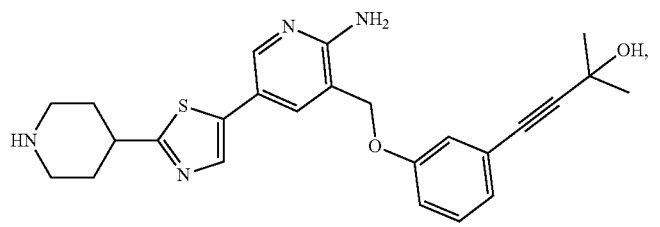
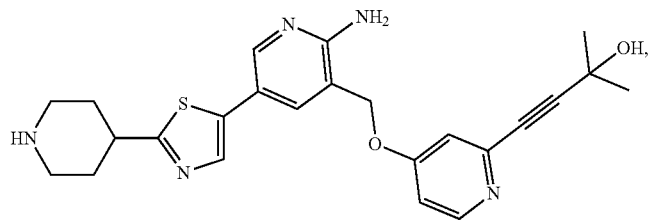
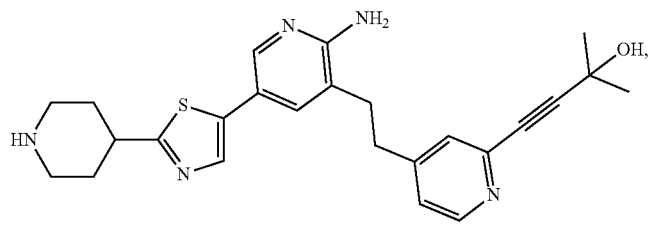
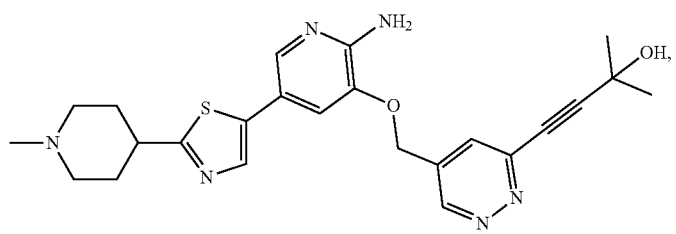
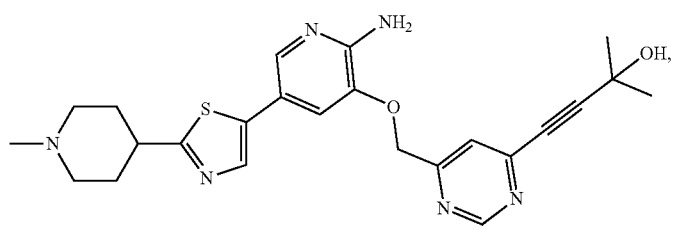
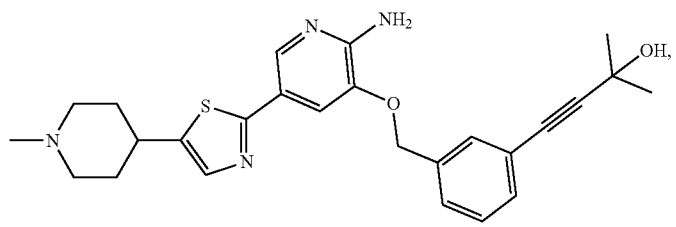
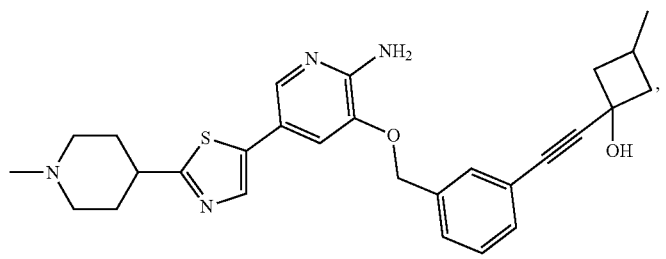

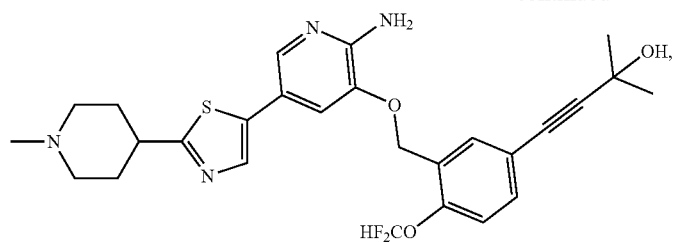 [SMILES: CN1CCC(c2ncc(-c3cnc(N)c(OCc4cc(C#CC(C)(C)O)ccc4C(F)(F)F)c3)s2)CC1]
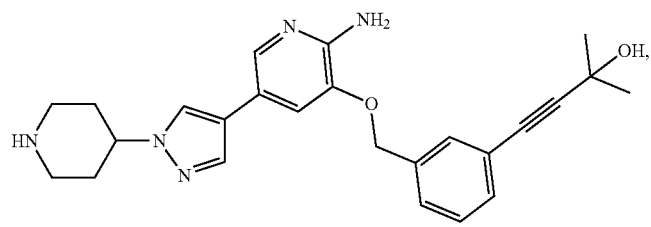 [SMILES: CC(C)(O)C#Cc1cccc(COc2cc(-c3cnn(C4CCNCC4)c3)cnc2N)c1]
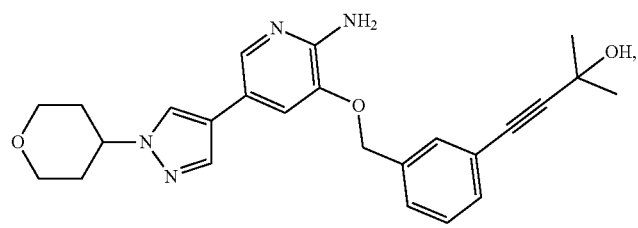
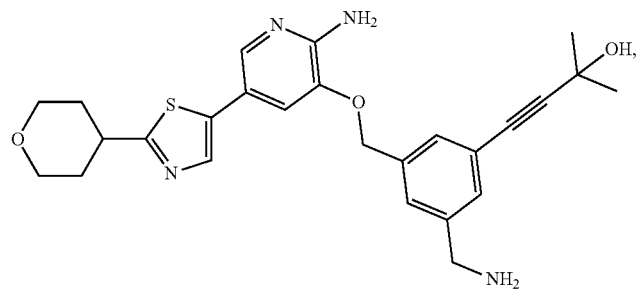 [SMILES: CC(C)(O)C#Cc1cc(CN)cc(COc2cc(-c3cnc(C4CCOCC4)s3)cnc2N)c1]
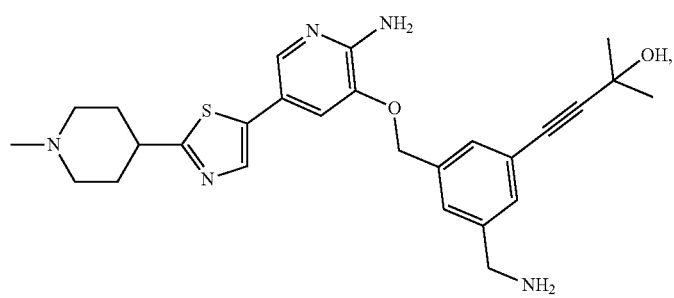 [SMILES: CN1CCC(c2ncc(-c3cnc(N)c(OCc4cc(C#CC(C)(C)O)cc(CN)c4)c3)s2)CC1]
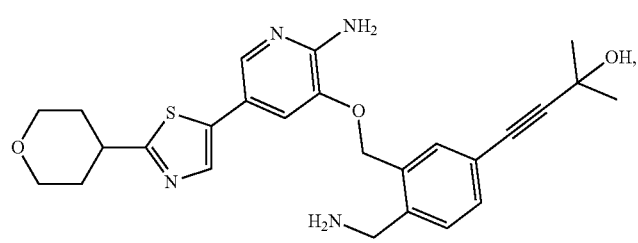

-continued

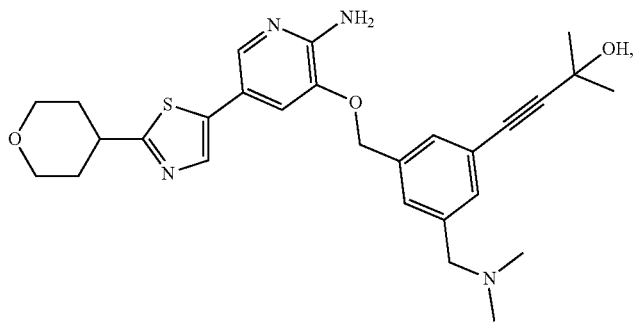

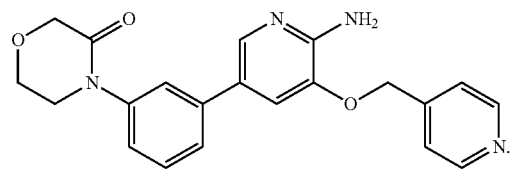

16. A pharmaceutical composition comprising the compound of claim 1 or a pharmaceutically acceptable salt thereof, and optionally a pharmaceutically acceptable excipient.

17. A method of inhibiting HPK1 activity, comprising administering to a subject in need thereof the compound of claim 1 or a pharmaceutically acceptable salt thereof.

18. A method of treating a disease or disorder associated with aberrant activity of HPK1, comprising administering to a subject in need thereof a therapeutically effective amount of the compound of claim 1 or a pharmaceutically acceptable salt thereof.

19. The method of claim 18, wherein the disease or disorder is cancer, metastasis, inflammation, or an autoimmune disease.

20. A method of treating cancer, comprising administering to a subject in need thereof a therapeutically effective amount of the compound of claim 1 or a pharmaceutically acceptable salt thereof.

21. The method of claim 20, wherein the cancer is breast cancer, colorectal cancer, hematological malignancy, lung cancer, melanoma, ovarian cancer, pancreatic cancer, and/or kidney cancer.

22. The compound of claim 7, or a pharmaceutically acceptable salt thereof, wherein in Formula Y, Ar is thiazolyl, oxazolyl, isothiazolyl, isoxazolyl, pyrazolyl, imidazolyl, thiadiazolyl, oxadiazolyl, triazolyl, pyridinyl, pyrimidinyl, pyrazinyl, or pyridazinyl, which is substituted with one or two substituents, wherein one substituent is an optionally substituted 5 or 6-membered heterocyclic ring containing 1 or 2 ring heteroatoms independently selected from S, O, and N, wherein the S and N are optionally oxidized, and the other substituent, if present, is selected from halogen, $C_{1-7}$ alkyl, and —$NR^{101}R^{102}$;
   wherein the 5 or 6-membered heterocyclic ring, when substituted, is substituted with 1-3 substituents each independently selected from 1) halogen; 2) $C_{1-7}$ alkyl optionally substituted with 1-3 fluorine; and 3) 5 or 6-membered heterocyclic ring containing 1 or 2 ring heteroatoms independently selected from S, O, and N, wherein the S and N are optionally oxidized, which is optionally substituted with 1-3 substituents each independently selected from halogen and $C_{1-7}$ alkyl optionally substituted with 1-3 fluorine.

23. The compound of claim 22, or a pharmaceutically acceptable salt thereof, wherein the optionally substituted 5 or 6-membered heterocyclic ring is a ring selected from:

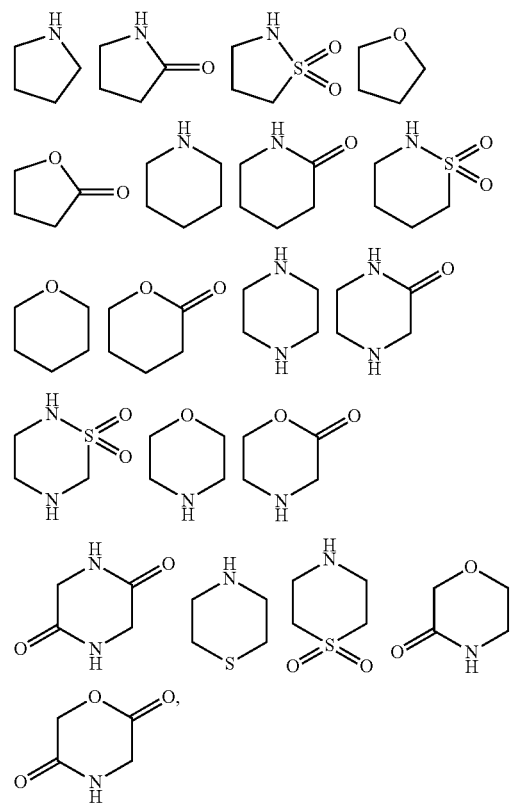

which is unsubstituted or substituted with 1-3 substituents each independently selected from halogen and $C_{1-7}$ alkyl optionally substituted with 1-3 fluorine.

24. The compound of claim 22, or a pharmaceutically acceptable salt thereof, wherein the optionally substituted 5 or 6-membered heterocyclic ring is a ring selected from:

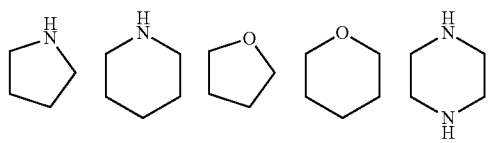

-continued

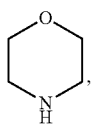

which is unsubstituted or substituted with 1-3 substituents each independently selected from halogen and $C_{1-7}$ alkyl optionally substituted with 1-3 fluorine.

25. The compound of claim 7, or a pharmaceutically acceptable salt thereof, wherein Ar is

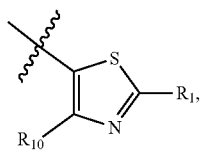

wherein $R_1$ is selected from

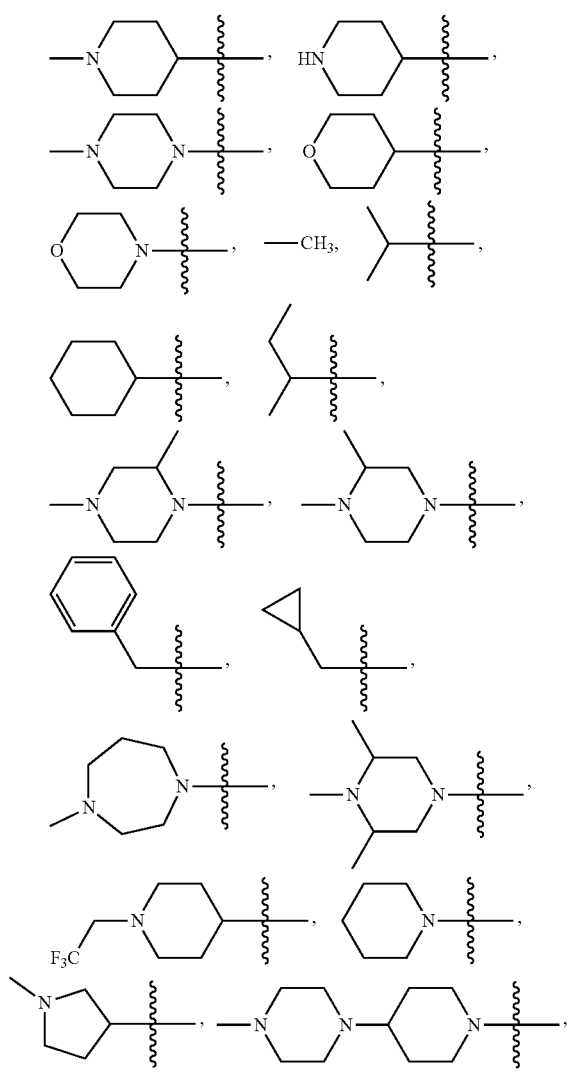

-continued

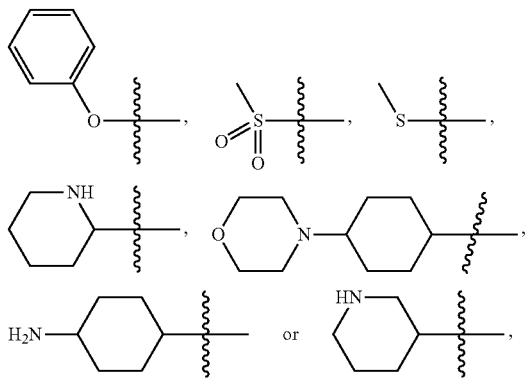

and $R_0$ is selected from hydrogen, methyl, ethyl, $NH_2$, or protected $NH_2$.

26. The compound of claim 22, or a pharmaceutically acceptable salt thereof, wherein L in Formula Y is —O—($C_{1-4}$ alkylene), wherein the $C_{1-4}$ alkylene is optionally substituted with 1-3 substituents selected from F, methyl or fluorine substituted methyl, wherein the $C_{1-4}$ alkylene is directly attached to ring B.

27. The compound of claim 26, or a pharmaceutically acceptable salt thereof, wherein L in Formula Y is —O—CH$_2$—, with the CH$_2$ directly attached to ring B.

28. The compound of claim 26, or a pharmaceutically acceptable salt thereof, wherein ring B in Formula Y is selected from:

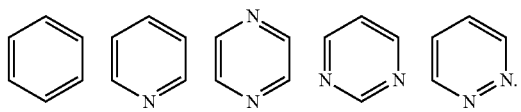

29. The compound of claim 28, or a pharmaceutically acceptable salt thereof, wherein $R^B$ and $R^C$ in Formula Y are each independently selected from hydrogen,

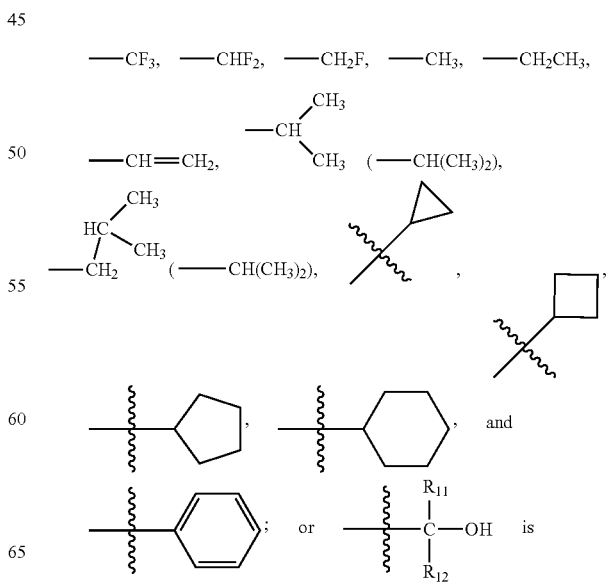

-continued

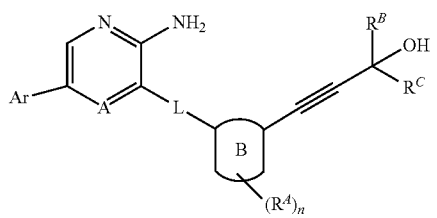

Formula Y wherein:

Ar is

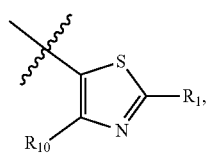

wherein $R_1$ is selected from

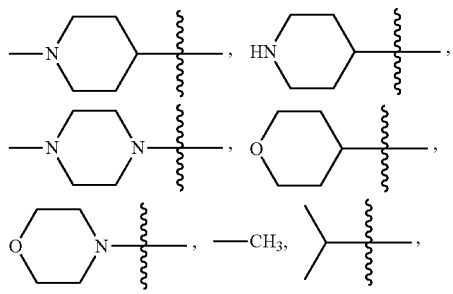

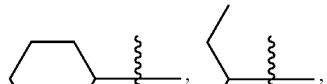

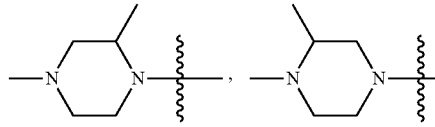

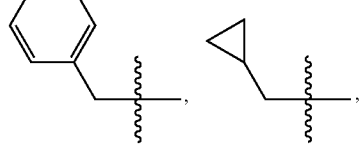

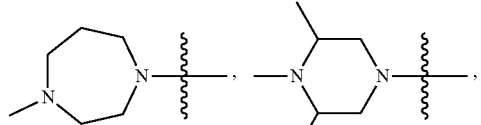

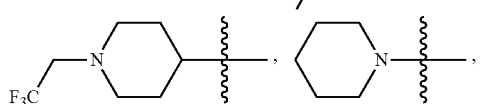

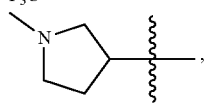

30. The compound of claim 28, or a pharmaceutically acceptable salt thereof, wherein in Formula Y, n is 0.

31. The compound of claim 28, or a pharmaceutically acceptable salt thereof, wherein in Formula Y, n is 1, and $R^A$ is halogen, $C_{1-7}$ alkyl optionally substituted with one or more substituents each independently selected from halogen and —OH, —CN, —OH, $C_{1-4}$ alkoxyl optionally substituted with 1-3 fluorine, $C_{3-6}$ cycloalkyl optionally substituted with 1 or 2 substituents each independently selected from F and $C_{1-7}$ alkyl, and $C_{3-6}$ cycloalkoxyl optionally substituted with 1 or 2 substituents each independently selected from F and $C_{1-7}$ alkyl.

32. A compound, or a pharmaceutically acceptable salt thereof, wherein the compound has a structure according to Formula Y, -continued

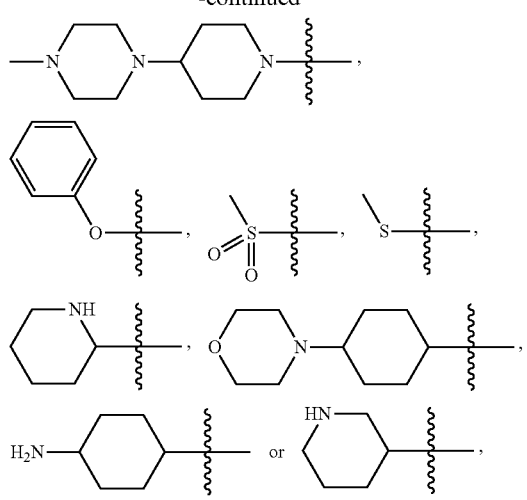

and $R_0$ is selected from hydrogen, methyl, ethyl, $NH_2$, or protected $NH_2$;

L is —O—($C_{1-4}$ alkylene), wherein the $C_{1-4}$ alkylene is optionally substituted with 1-3 substituents selected from F, methyl or fluorine substituted methyl, wherein the $C_{1-4}$ alkylene is directly attached to ring B;

ring B is selected from:

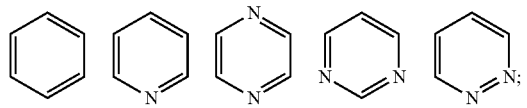

$R^B$ and $R^C$ are each independently selected from hydrogen,

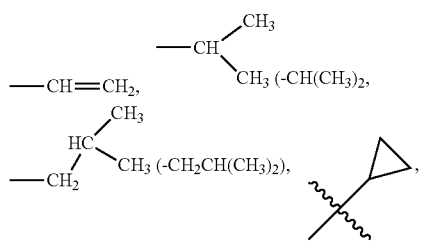

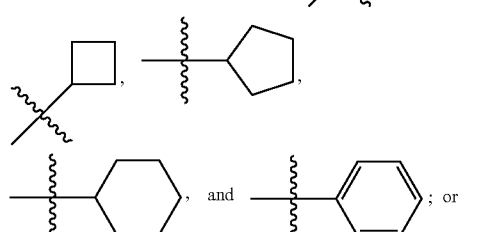

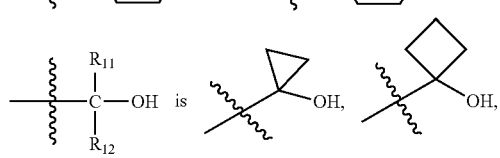

-continued

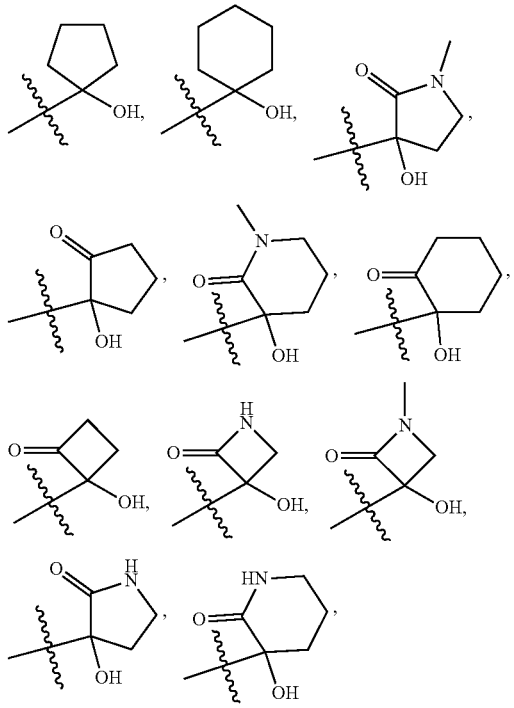

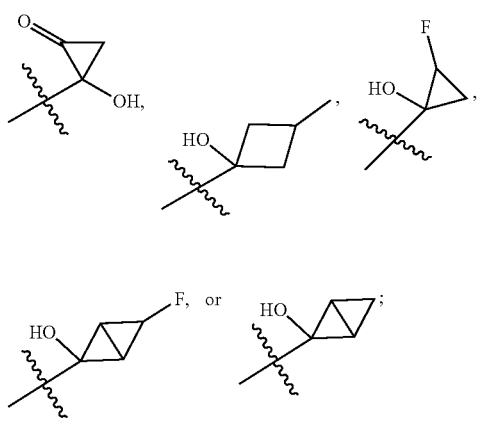

A is CH;

n is 0, or n is 1, and $R^A$ is halogen, $C_{1-7}$ alkyl optionally substituted with one or more substituents each independently selected from halogen, —OH, and $NH_2$, —CN, —OH, $C_{1-4}$ alkoxyl optionally substituted with 1-3 fluorine, $C_{3-6}$ cycloalkyl optionally substituted with 1 or 2 substituents each independently selected from F and $C_{1-7}$ alkyl, and $C_{3-6}$ cycloalkoxyl optionally substituted with 1 or 2 substituents each independently selected from F and $C_{1-7}$ alkyl.

33. The compound of claim 32, or a pharmaceutically acceptable salt thereof, wherein L is —O—$CH_2$—, wherein the $CH_2$ is directly attached to ring B.

34. A compound, or a pharmaceutically acceptable salt thereof, wherein the compound has a structure according to Formula Z:

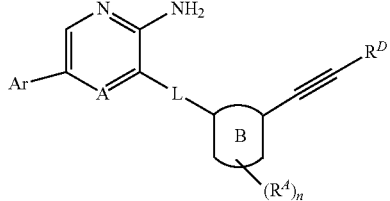

Formula Z wherein in Formula Z,
Ar is

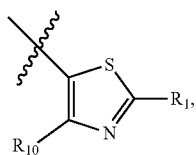

wherein $R_1$ is selected from

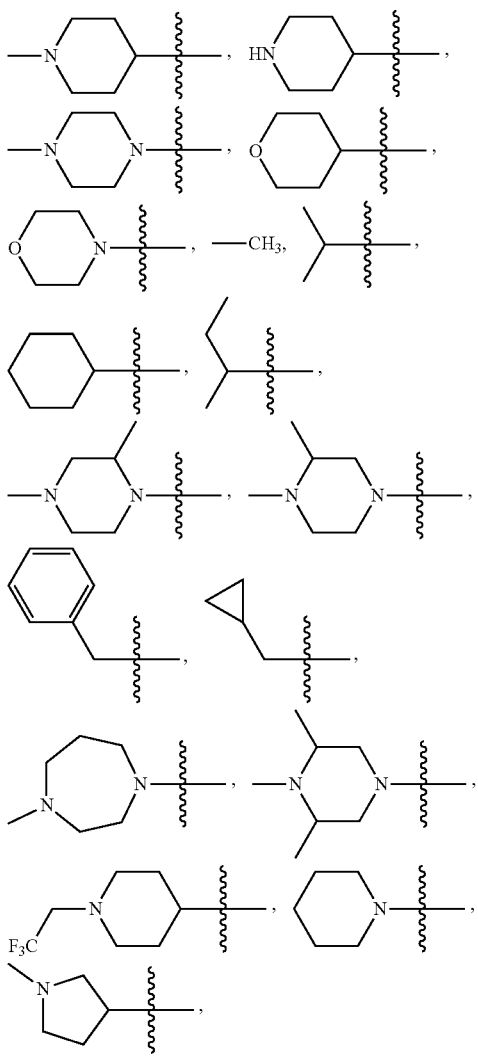

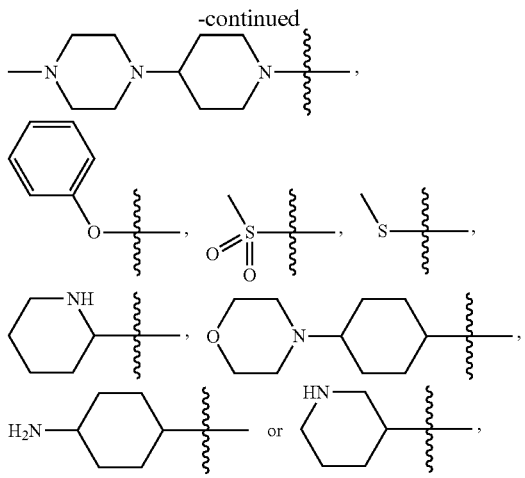

and $R_0$ is selected from hydrogen, methyl, ethyl, $NH_2$, or protected $NH_2$;

L is —O—($C_{1-4}$ alkylene), wherein the $C_{1-4}$ alkylene is optionally substituted with 1-3 substituents selected from F, methyl or fluorine substituted methyl, wherein the $C_{1-4}$ alkylene is directly attached to ring B;

ring B is selected from:

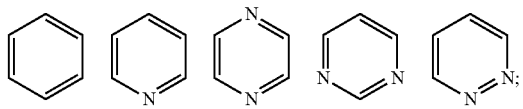

$R^D$ is hydrogen,

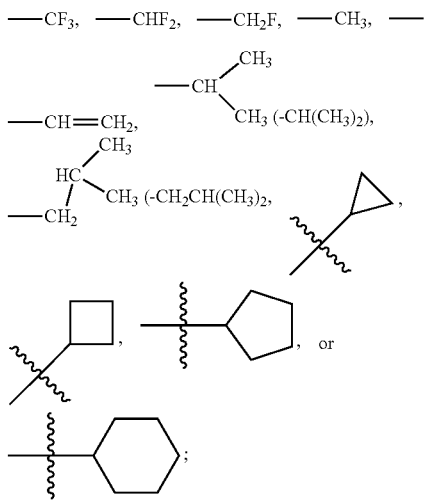

A is CH;
n is 0 or
n is 1, and $R^A$ is halogen, $C_{1-7}$ alkyl optionally substituted with one or more substituents each independently selected from halogen, —OH, and $NH_2$, —CN, —OH, $C_{1-4}$ alkoxyl optionally substituted with 1-3 fluorine, $C_{3-6}$ cycloalkyl optionally substituted with 1 or 2 substituents each independently selected from F and $C_{1-7}$ alkyl, and $C_{3-6}$ cycloalkoxyl optionally substituted with 1 or 2 substituents each independently selected from F and $C_{1-7}$ alkyl.

35. The compound of claim 15, or a pharmaceutically acceptable salt thereof, wherein the compound is selected from:
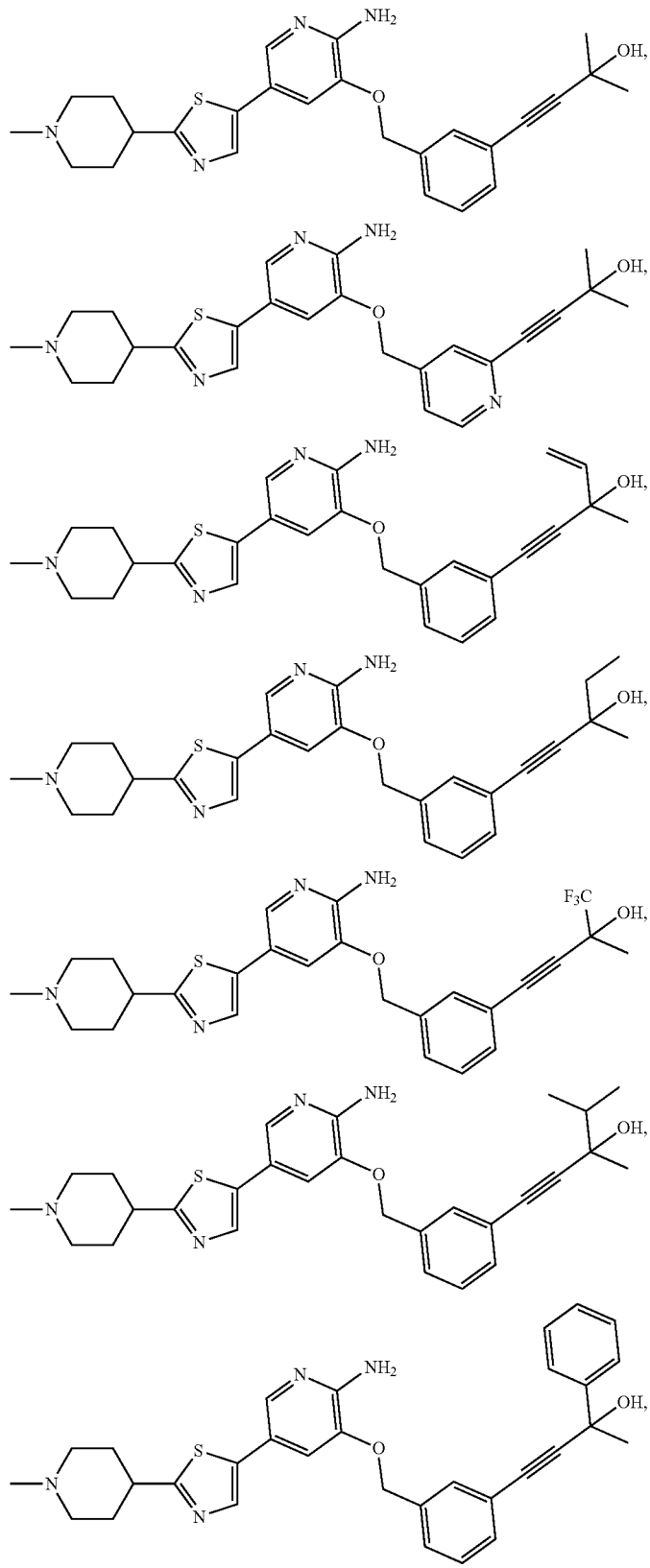

-continued
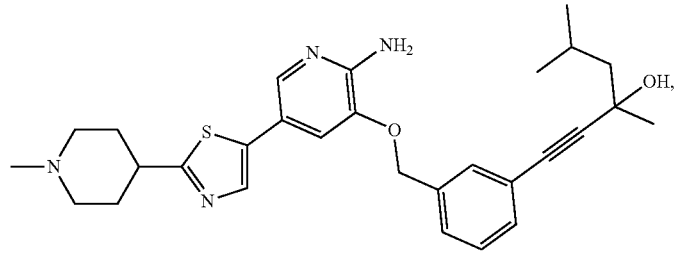
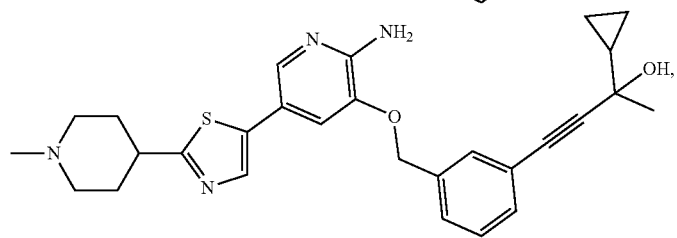
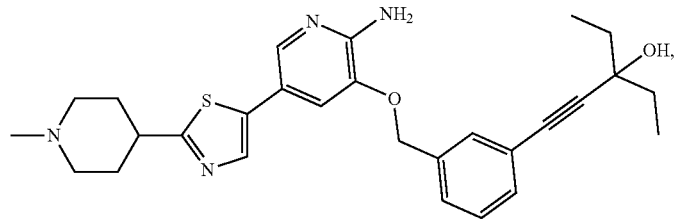
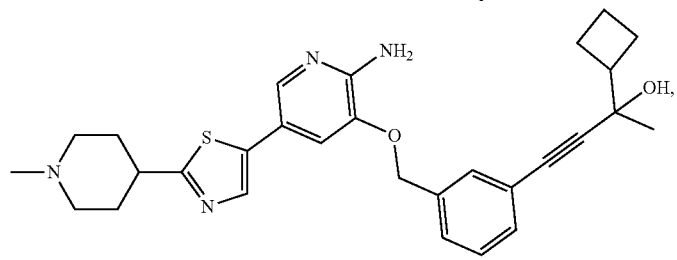
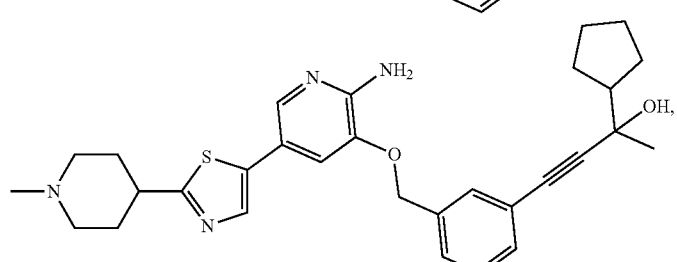
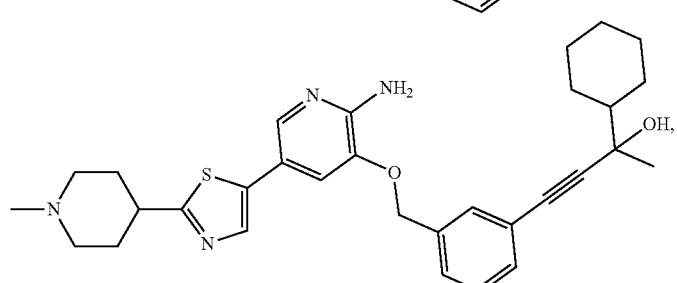
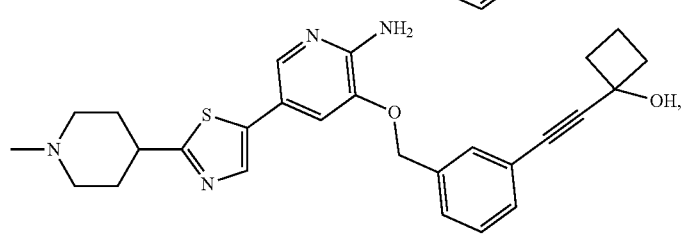

-continued
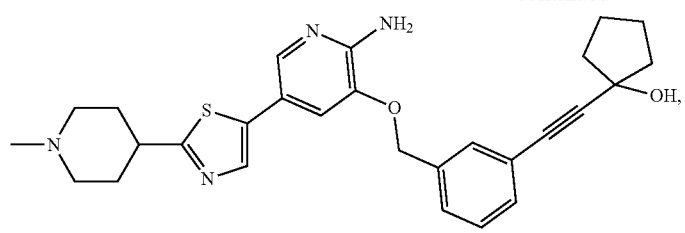
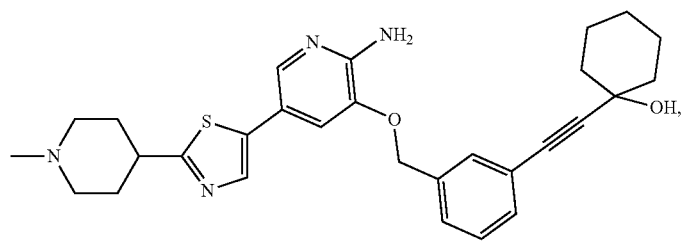
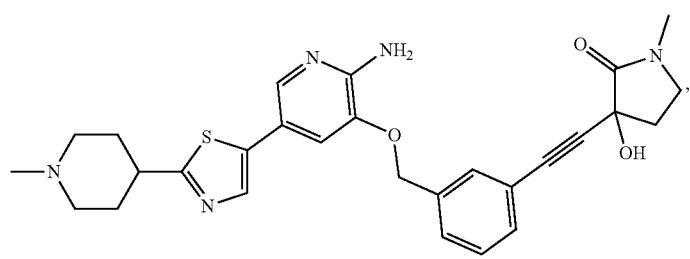
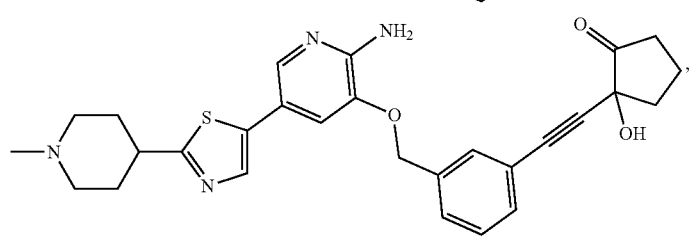
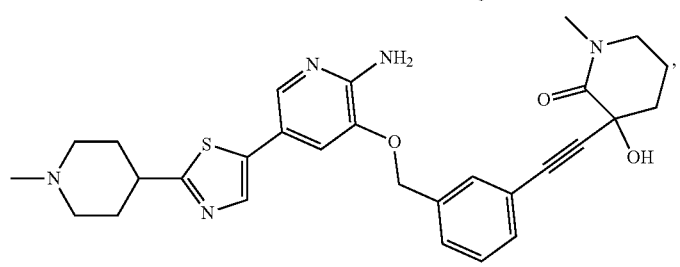
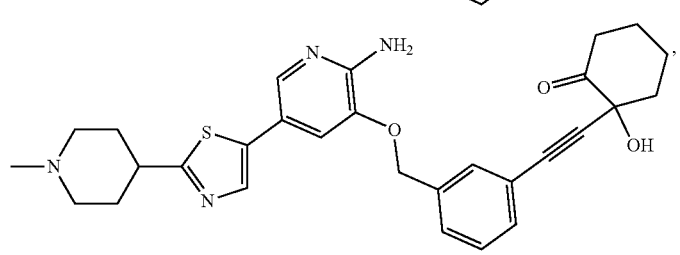
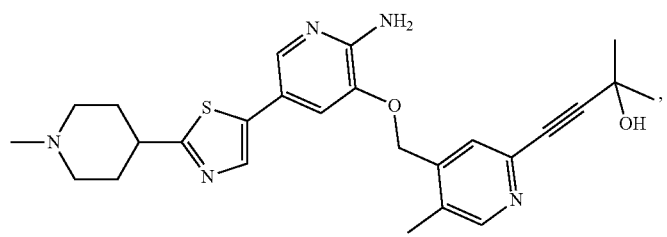

-continued
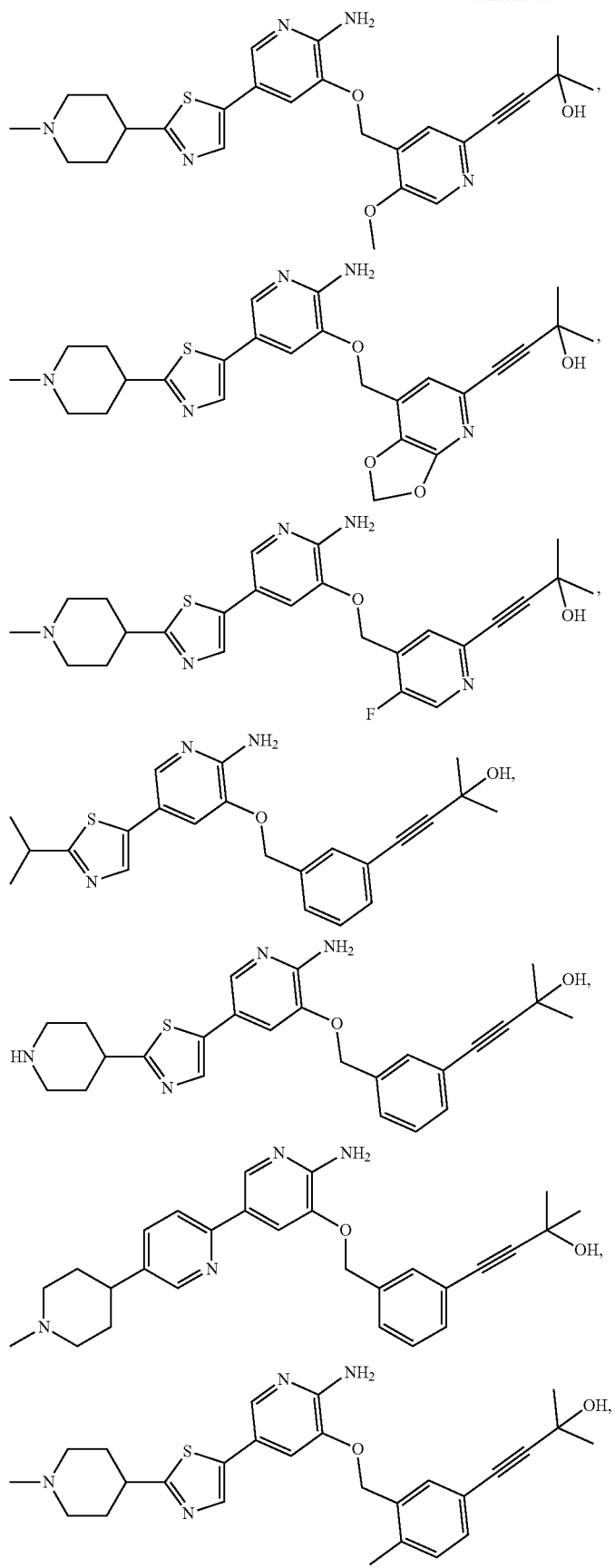

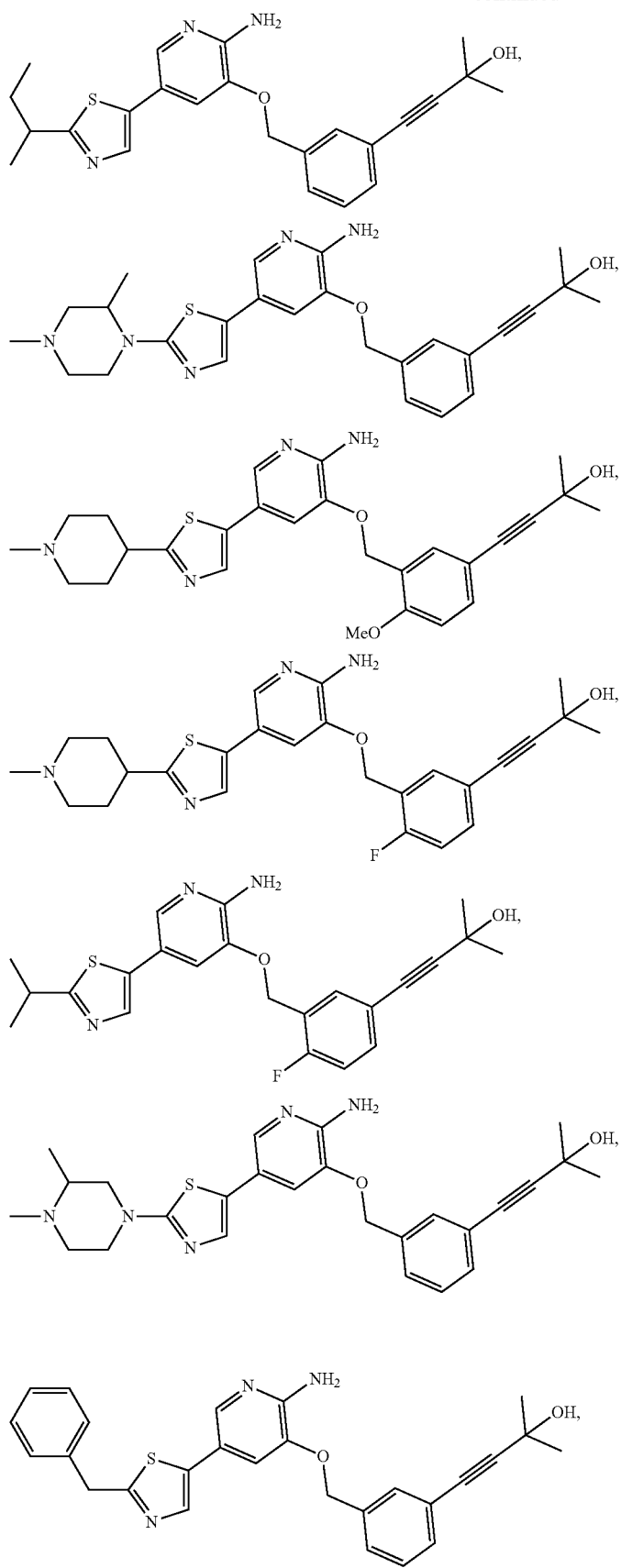

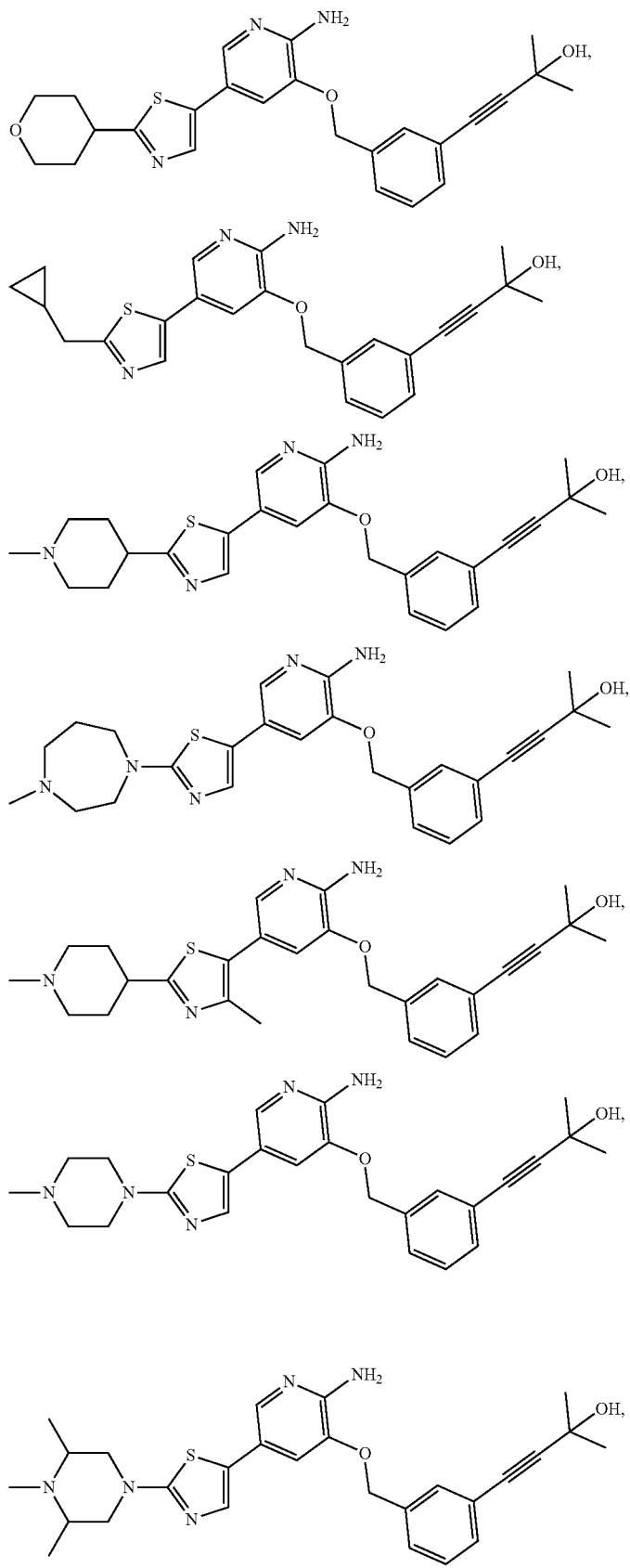

-continued
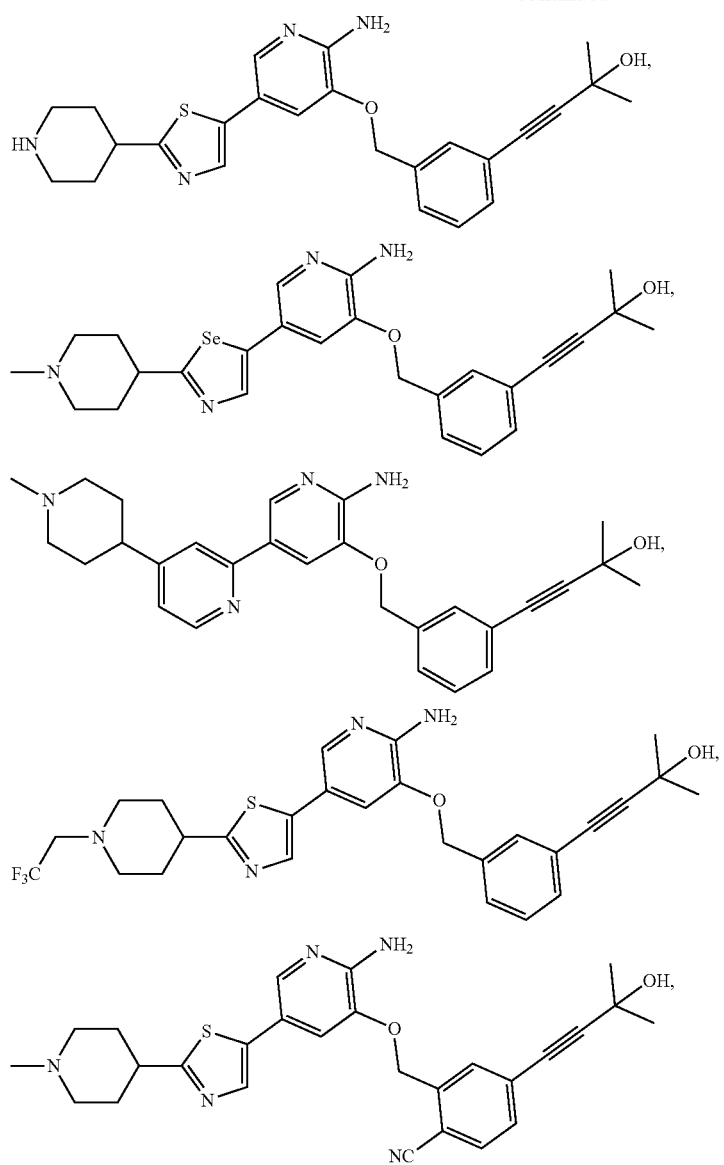
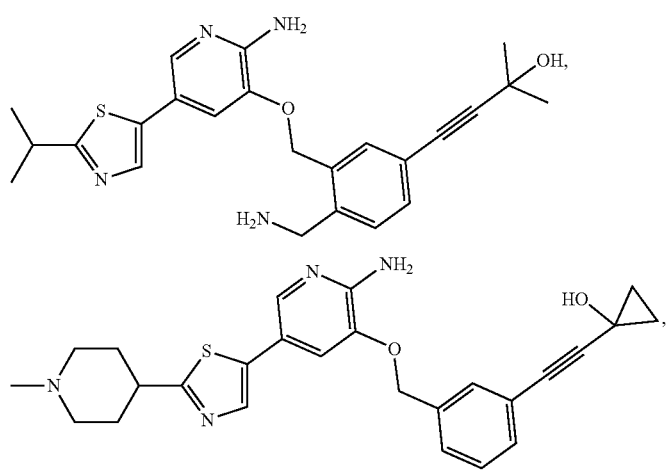

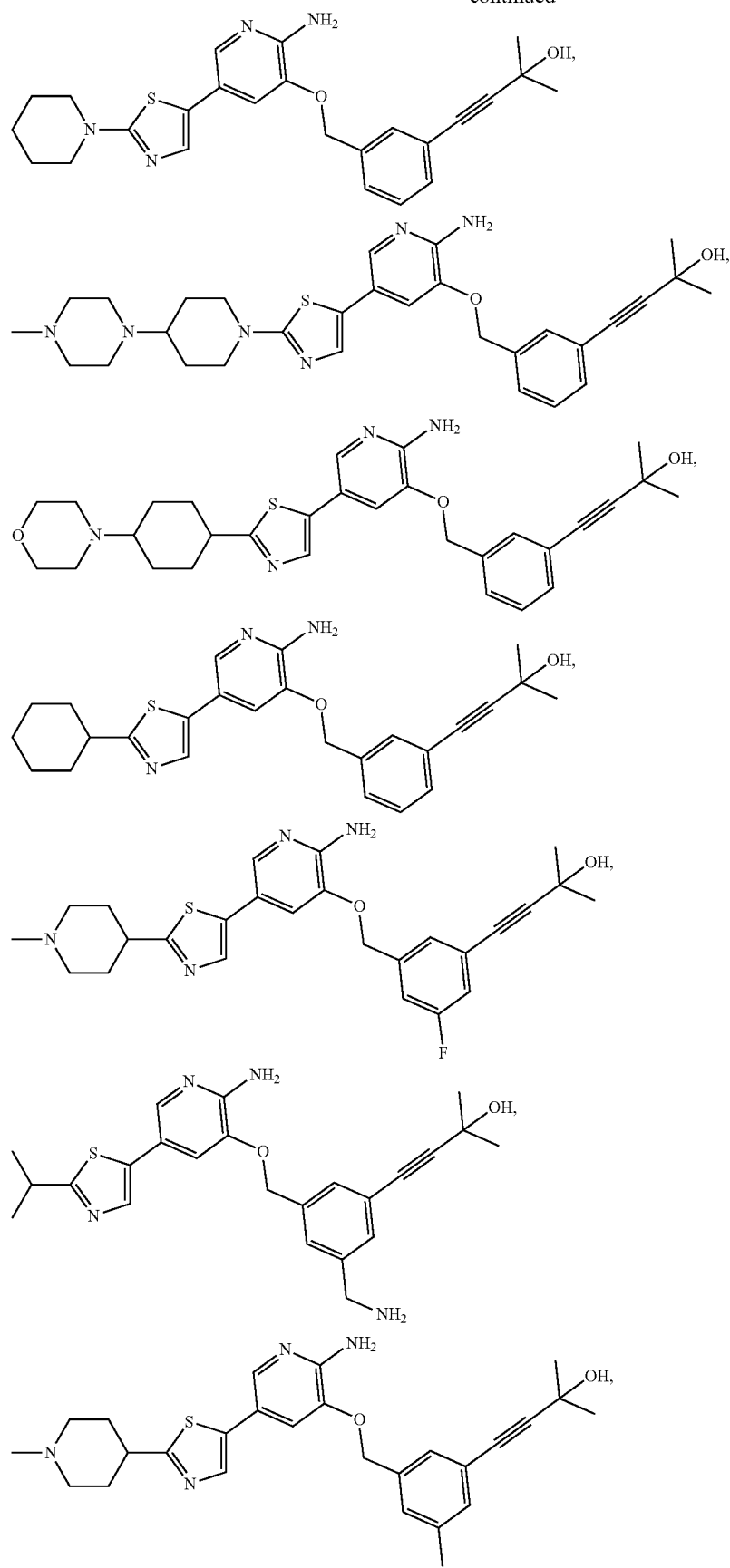

-continued
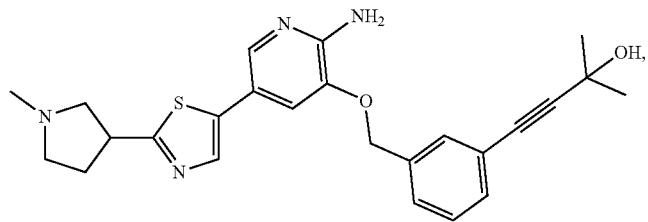
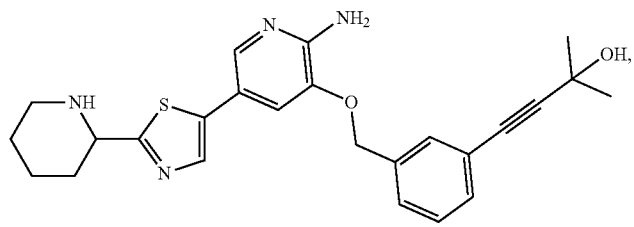
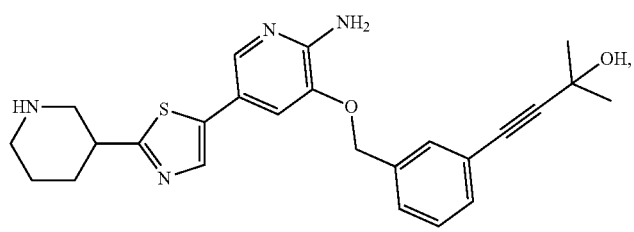
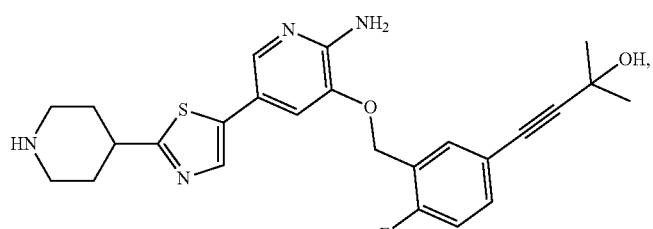
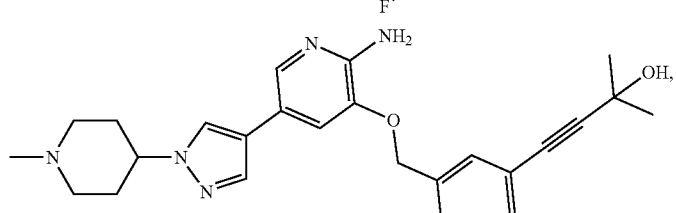
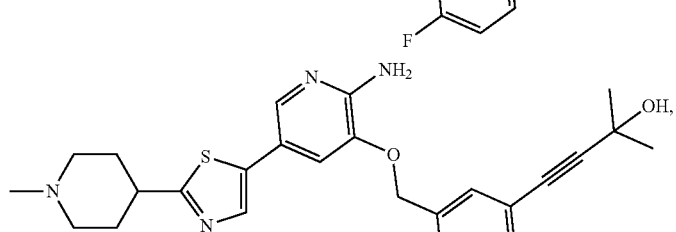
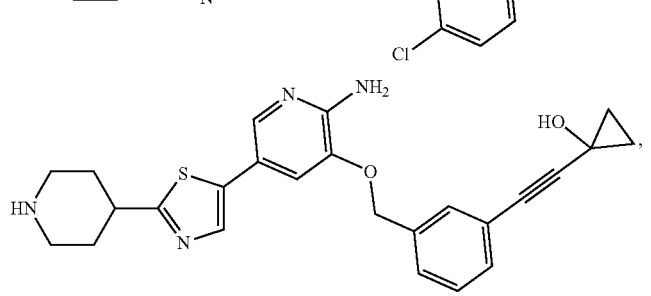

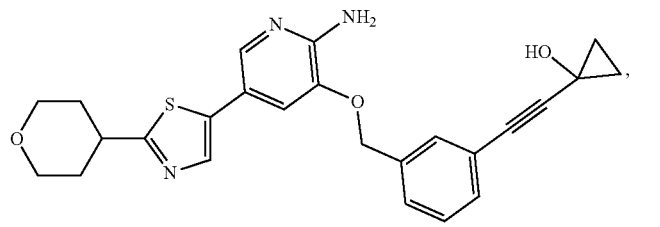
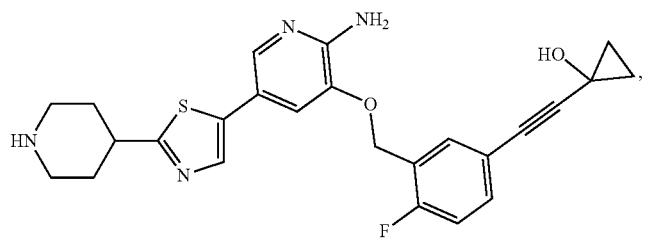
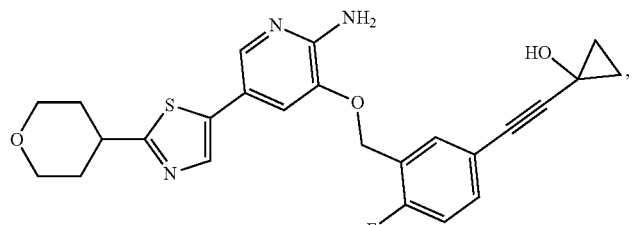
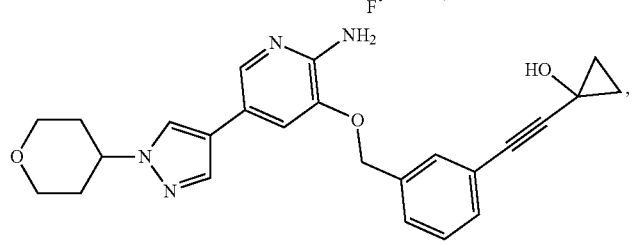
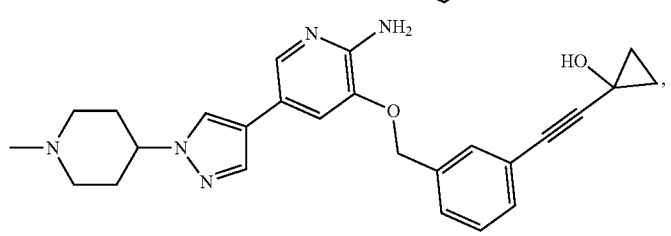
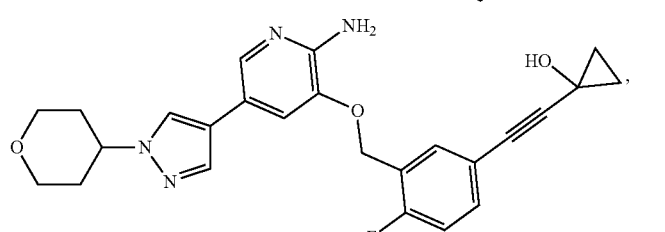
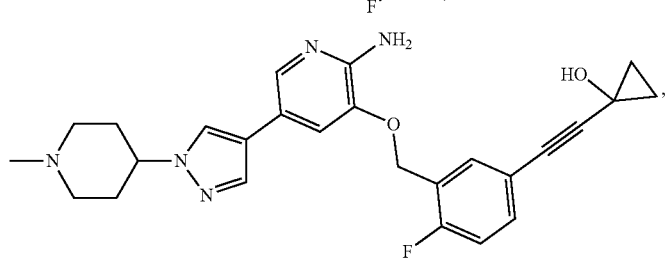

-continued
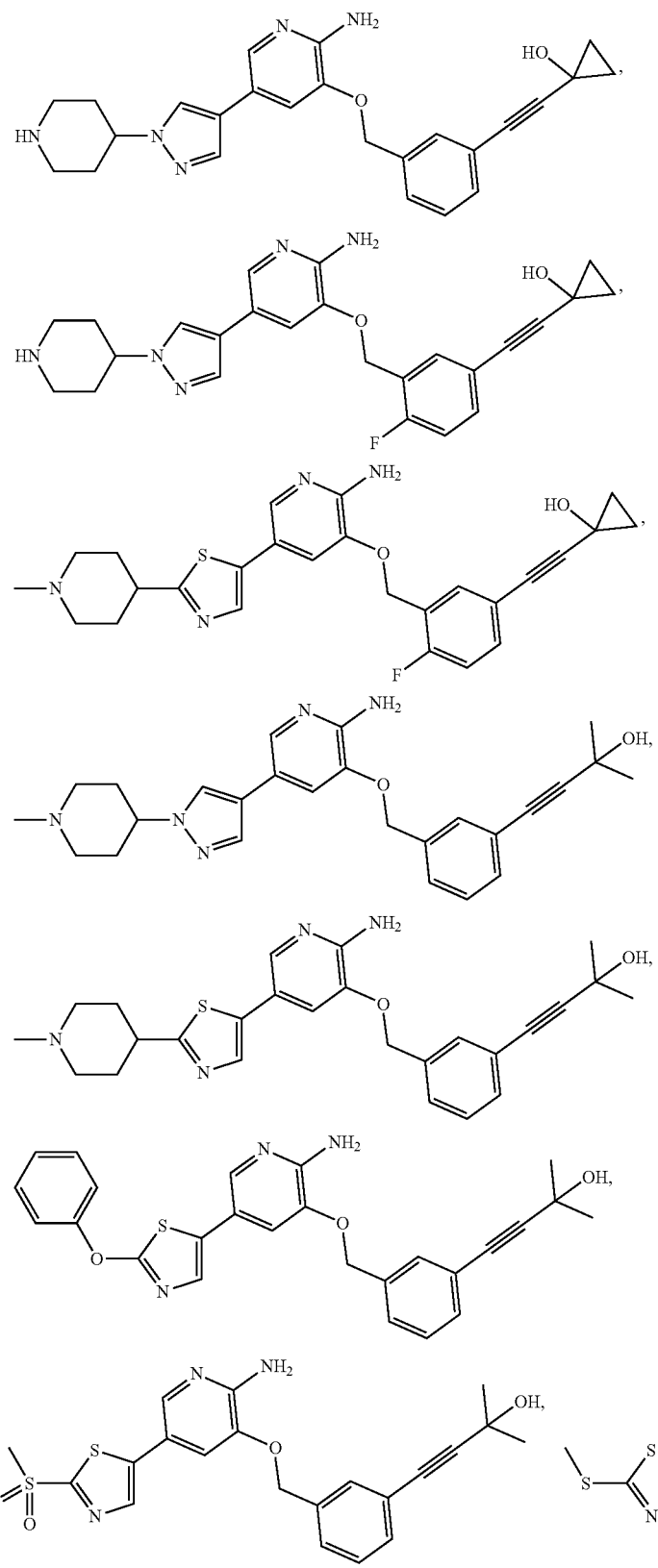

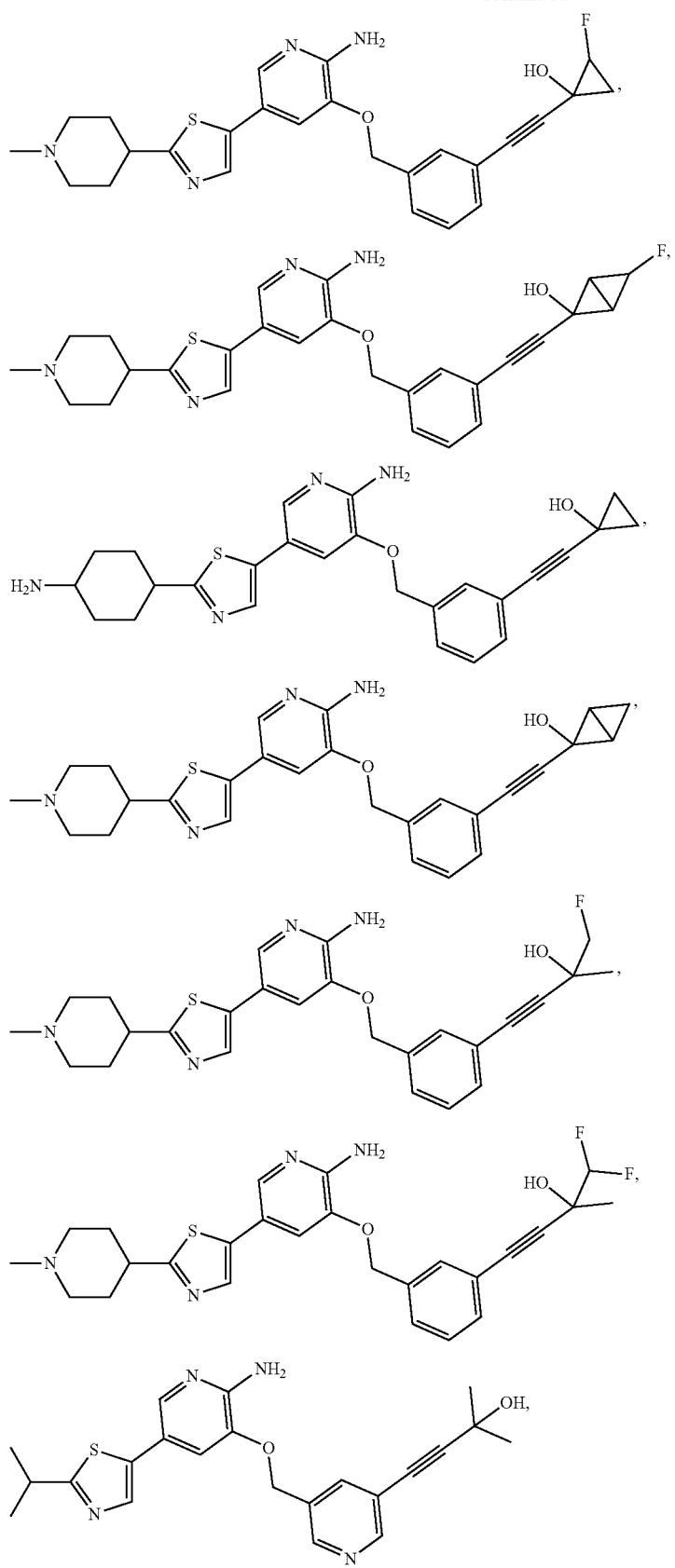

-continued
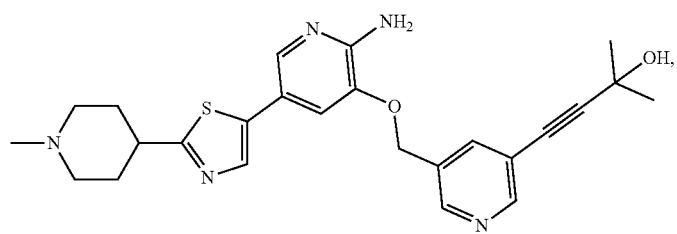
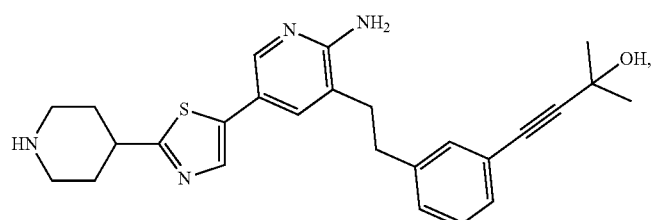
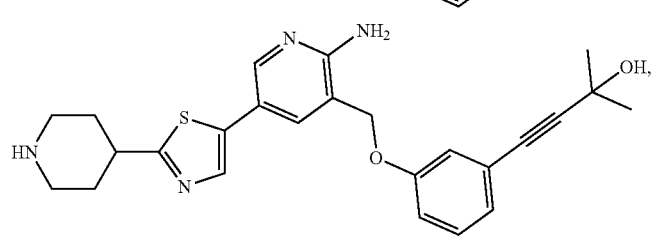
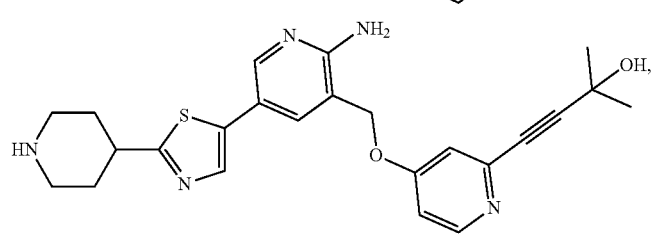
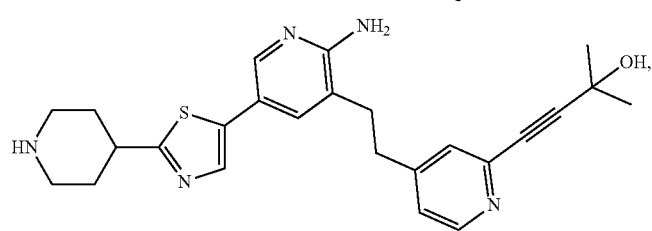
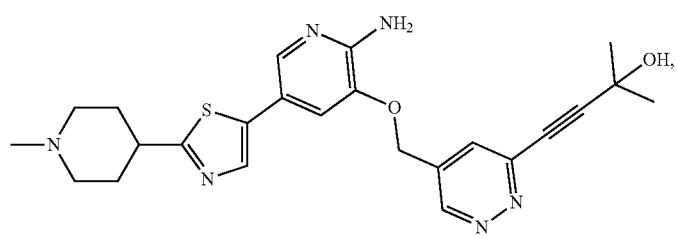
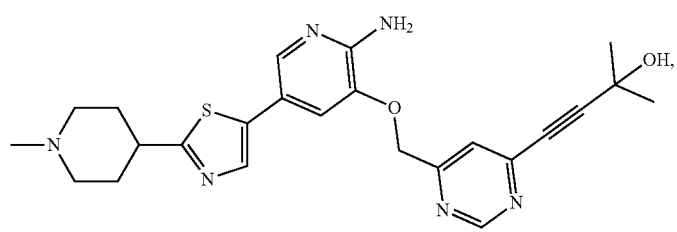

-continued
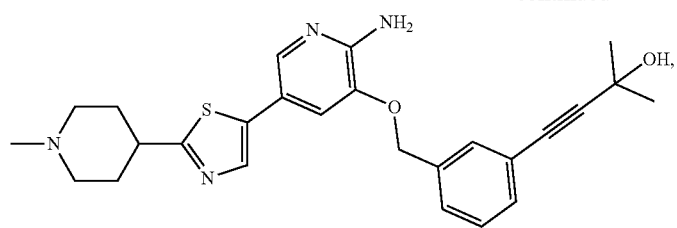
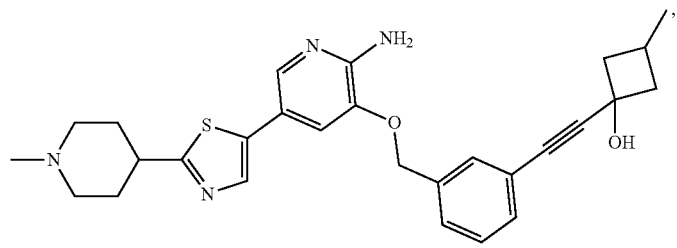
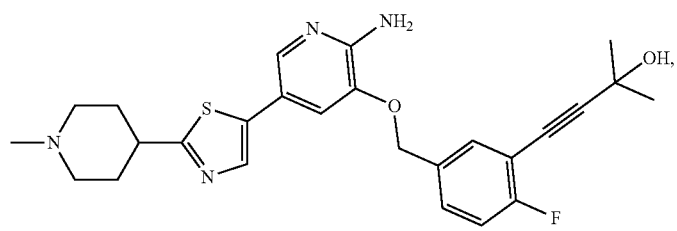
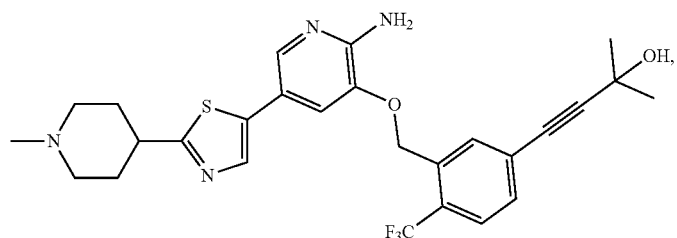
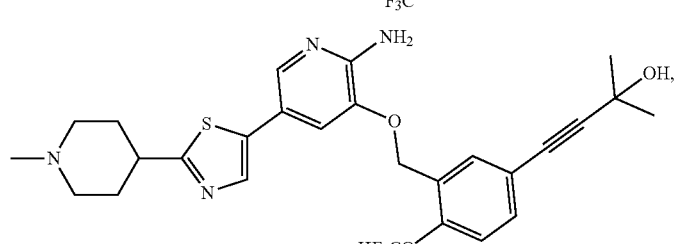
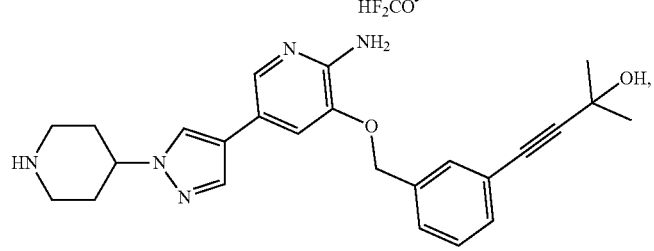
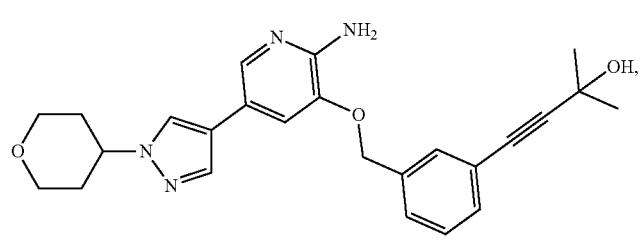

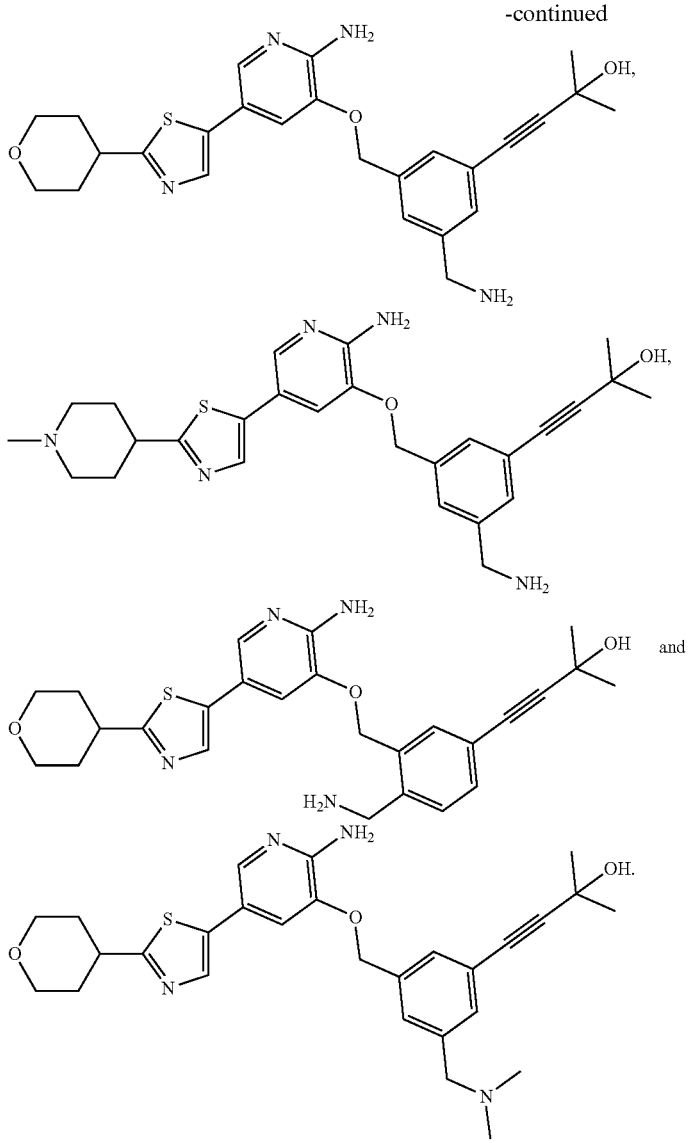
36. A pharmaceutical composition comprising the compound of claim 35 or a pharmaceutically acceptable salt thereof, and optionally a pharmaceutically acceptable excipient.
37. The compound of claim 7, or a pharmaceutically acceptable salt thereof, wherein in Formula Y, $R^B$ and $R^C$ are each independently selected from hydrogen,
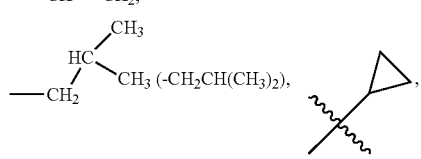
-continued
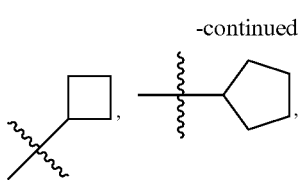
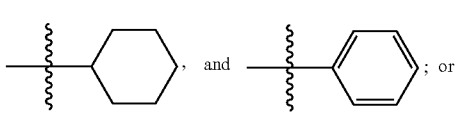; or
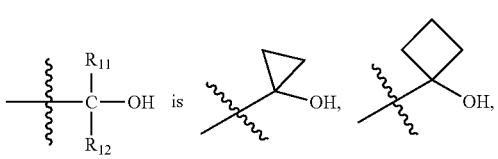

-continued
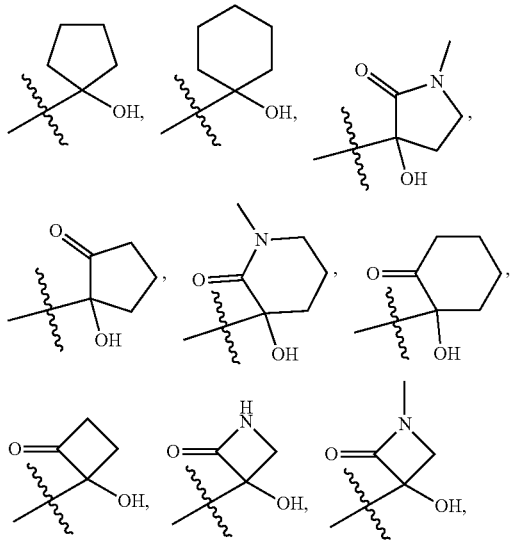
-continued
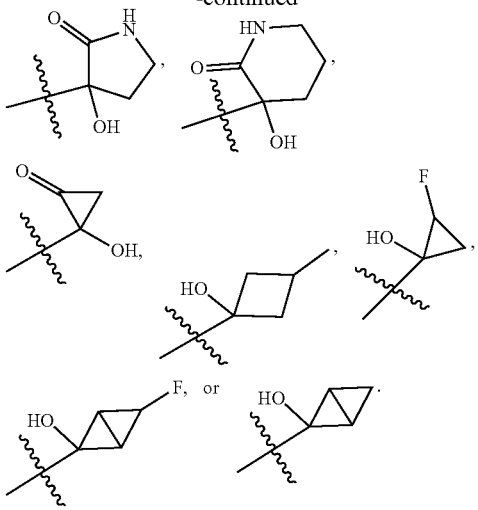
* * * * *